US010370727B2

(12) United States Patent
Nanda et al.

(10) Patent No.: US 10,370,727 B2
(45) Date of Patent: *Aug. 6, 2019

(54) POINT MUTATIONS IN TRK INHIBITOR-RESISTANT CANCER AND METHODS RELATING TO THE SAME

(71) Applicants: Loxo Oncology, Inc., Stamford, CT (US); Array BioPharma, Inc., Boulder, CO (US)

(72) Inventors: Nisha Nanda, Stamford, CT (US); Joshua H. Bilenker, Stamford, CT (US); James F. Blake, Boulder, CO (US); Gabrielle R. Kolakowski, Boulder, CO (US); Barbara J. Brandhuber, Boulder, CO (US); Steven W. Andrews, Boulder, CO (US)

(73) Assignees: Loxo Oncology, Inc., Stamford, CT (US); Array BioPharma, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,174

(22) Filed: Oct. 16, 2017

(65) Prior Publication Data

US 2018/0030548 A1 Feb. 1, 2018

Related U.S. Application Data

(63) Continuation of application No. 15/335,378, filed on Oct. 26, 2016.

(Continued)

(51) Int. Cl.

*C12Q 1/6886* (2018.01)
*A61K 31/5025* (2006.01)

(Continued)

(52) U.S. Cl.

CPC ........ *C12Q 1/6886* (2013.01); *A61K 31/5025* (2013.01); *A61K 31/519* (2013.01);

(Continued)

(58) Field of Classification Search

CPC .......................... A61K 31/5025; A61K 31/519

(Continued)

(56) References Cited

U.S. PATENT DOCUMENTS 5,760,068 A 6/1998 Talley et al.
5,844,092 A 12/1998 Presta et al.

(Continued)

FOREIGN PATENT DOCUMENTS

CN 1938311 3/2007
CN 101119996 2/2008

(Continued)

OTHER PUBLICATIONS

Adriaenssens et al., "Nerve Growth Factor is a Potential Therapeutic Target in Breast Cancer," Cancer Res., 2008, 68(2):346-351.

(Continued)

*Primary Examiner* — San Ming R Hui
(74) *Attorney, Agent, or Firm* — Meunier Carlin & Curfman LLC

(57) ABSTRACT

Provided herein are methods of treating a subject having a cancer, methods of selecting a treatment for a subject having a cancer, methods of selecting a subject having a cancer for a treatment that does not include a Trk inhibitor, methods of determining the likelihood that a subject having a cancer will have a positive response to a treatment with a Trk inhibitor, methods of predicting the efficacy of a Trk inhibitor in a subject having cancer, methods of determining a subject's risk for developing a Trk inhibitor-resistant cancer, and methods of determining the presence of a Trk inhibitor-resistant cancer in a subject, based on the detection of a cell (Continued)

from a sample from the subject that has at least one of the the point mutations in NTRK1 and/or NTRK2 and/or NTRK3.

20 Claims, 15 Drawing Sheets

Specification includes a Sequence Listing.

Related U.S. Application Data

(60) Provisional application No. 62/323,586, filed on Apr. 15, 2016, provisional application No. 62/287,778, filed on Jan. 27, 2016, provisional application No. 62/246,580, filed on Oct. 26, 2015.

(51) Int. Cl.
*A61K 31/519* (2006.01)
*G01N 33/574* (2006.01)

(52) U.S. Cl.
CPC . *G01N 33/57492* (2013.01); *C12Q 2600/106* (2013.01); *C12Q 2600/156* (2013.01); *C12Q 2600/158* (2013.01); *G01N 2800/50* (2013.01); *G01N 2800/52* (2013.01)

(58) Field of Classification Search
USPC .................................................... 514/210.18
See application file for complete search history.

(56) References Cited

U.S. PATENT DOCUMENTS

| | | | |
|---|---|---|---|
| 5,877,016 | A | 3/1999 | Presta et al. |
| 5,910,574 | A | 6/1999 | Presta et al. |
| 6,025,166 | A | 2/2000 | Presta et al. |
| 6,027,927 | A | 2/2000 | Presta et al. |
| 6,153,189 | A | 11/2000 | Presta et al. |
| 7,384,632 | B2 | 6/2008 | Devaux et al. |
| 7,491,794 | B2 | 2/2009 | Blatt et al. |
| 7,550,470 | B2 | 6/2009 | Fraley |
| 7,612,067 | B2 | 11/2009 | Barbosa et al. |
| 7,615,383 | B2 | 11/2009 | Devaux et al. |
| 8,106,167 | B2 | 1/2012 | Wild, Jr. et al. |
| 8,114,989 | B2 | 2/2012 | Wang et al. |
| 8,119,592 | B2 | 2/2012 | Beigelman et al. |
| 8,148,107 | B2 | 4/2012 | MacDonald et al. |
| 8,299,021 | B2 | 10/2012 | Blatt et al. |
| 8,299,057 | B2 | 10/2012 | Lombardi Borgia et al. |
| 8,338,417 | B2 | 12/2012 | Li et al. |
| 8,450,322 | B2 | 5/2013 | Andrews et al. |
| 8,513,263 | B2 | 8/2013 | Haas et al. |
| 8,637,256 | B2 | 1/2014 | Ernst |
| 8,637,516 | B2 | 1/2014 | Fan et al. |
| 8,642,035 | B2 | 2/2014 | Luehrsen |
| 8,673,347 | B2 | 3/2014 | Traversa et al. |
| 8,691,221 | B2 | 4/2014 | Pavane et al. |
| 8,791,123 | B2 | 7/2014 | Allen et al. |
| 8,865,698 | B2 | 10/2014 | Haas et al. |
| 8,911,734 | B2 | 12/2014 | Latham et al. |
| 8,912,194 | B2 | 12/2014 | Ciomei |
| 8,933,084 | B2 | 1/2015 | Andrews |
| 8,946,226 | B2 | 2/2015 | Ciomei et al. |
| 9,102,671 | B2 | 8/2015 | Molteni et al. |
| 9,127,013 | B2 | 9/2015 | Haas et al. |
| 9,187,489 | B2 | 11/2015 | Takeda et al. |
| 9,242,977 | B2 | 1/2016 | Takeuchi et al. |
| 9,447,104 | B2 | 9/2016 | Haas et al. |
| 9,493,476 | B2 | 11/2016 | Andrews et al. |
| 9,676,783 | B2 | 6/2017 | Haas et al. |
| 9,682,979 | B2 | 6/2017 | Allen et al. |
| 9,701,681 | B2 | 6/2017 | Kim et al. |
| 9,718,822 | B2 | 8/2017 | Andrews et al. |
| 9,750,744 | B2 | 9/2017 | Andrews et al. |
| 9,782,414 | B2 | 10/2017 | Arrigo et al. |
| 9,782,415 | B2 | 10/2017 | Allen et al. |
| 2006/0094699 | A1 | 5/2006 | Kampen et al. |
| 2006/0128725 | A1 | 6/2006 | Guzi et al. |
| 2006/0211696 | A1 | 9/2006 | Hibi et al. |
| 2007/0025540 | A1 | 2/2007 | Travis |
| 2007/0042941 | A1 | 2/2007 | Hirashima et al. |
| 2007/0082900 | A1 | 4/2007 | Guzi et al. |
| 2007/0082902 | A1 | 4/2007 | Paruch et al. |
| 2009/0041717 | A1 | 2/2009 | Macdonald et al. |
| 2010/0029633 | A1 | 2/2010 | Allen et al. |
| 2010/0152219 | A1 | 6/2010 | Block et al. |
| 2010/0297115 | A1 | 11/2010 | Blaustein |
| 2011/0166122 | A1 | 7/2011 | Andrews et al. |
| 2011/0195948 | A1 | 8/2011 | Haas et al. |
| 2011/0268725 | A1 | 11/2011 | Shelton |
| 2012/0108568 | A1 | 5/2012 | Allen et al. |
| 2013/0217662 | A1 | 8/2013 | Andrews et al. |
| 2014/0194403 | A1 | 7/2014 | Haas et al. |
| 2014/0227287 | A1 | 8/2014 | Kamohara et al. |
| 2015/0051222 | A1 | 2/2015 | Barbugian et al. |
| 2015/0166564 | A1 | 6/2015 | Allen et al. |
| 2015/0218652 | A1 | 8/2015 | Doebele et al. |
| 2015/0283132 | A1 | 10/2015 | Lim et al. |
| 2015/0306086 | A1 | 10/2015 | Wilcoxen |
| 2016/0000783 | A1 | 1/2016 | Takeuchi et al. |
| 2016/0137654 | A1 | 5/2016 | Arrigo et al. |
| 2016/0251357 | A1 | 9/2016 | Andrews et al. |
| 2016/0272725 | A1 | 9/2016 | Stransky et al. |
| 2017/0107232 | A1 | 4/2017 | Andrews et al. |
| 2017/0112849 | A1 | 4/2017 | Andrews et al. |
| 2017/0114067 | A1 | 4/2017 | Haas et al. |
| 2017/0114068 | A1 | 4/2017 | Andrews et al. |
| 2017/0114069 | A1 | 4/2017 | Allen et al. |
| 2017/0260589 | A1 | 9/2017 | Nanda et al. |
| 2017/0281632 | A1 | 10/2017 | Cox et al. |
| 2017/0283435 | A1 | 10/2017 | Andrews et al. |
| 2017/0296544 | A1 | 10/2017 | Reynolds et al. |
| 2018/0021342 | A1 | 1/2018 | Arrigo et al. |
| 2018/0030549 | A1 | 2/2018 | Nanda et al. |
| 2018/0119228 | A1 | 5/2018 | Nanda et al. |
| 2018/0127427 | A1 | 5/2018 | Haas et al. |
| 2018/0133222 | A1 | 5/2018 | Cox et al. |
| 2018/0140604 | A1 | 5/2018 | Tuch et al. |
| 2018/0142306 | A1 | 5/2018 | Nanda et al. |
| 2018/0207162 | A1 | 7/2018 | Arrigo et al. |

FOREIGN PATENT DOCUMENTS

| | | |
|---|---|---|
| CN | 101208093 | 6/2008 |
| EP | 1873157 | 1/2008 |
| EP | 1948633 | 8/2011 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2013-226108 | 11/2013 |
| JP | 2014-082984 | 5/2014 |
| WO | WO 1998/49167 | 11/1998 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |

(56) References Cited

FOREIGN PATENT DOCUMENTS

| | | | |
|---|---|---|---|
| WO | WO 2005/049033 | | 6/2005 |
| WO | WO 2006/052913 | | 5/2006 |
| WO | WO 2006/087538 | | 8/2006 |
| WO | WO 2006/115452 | | 11/2006 |
| WO | WO 2006/123113 | | 11/2006 |
| WO | WO 2006/131051 | | 12/2006 |
| WO | WO 2006/131952 | | 12/2006 |
| WO | WO 2007/013673 | | 2/2007 |
| WO | WO 2007/015824 | | 2/2007 |
| WO | WO 2007/022999 | | 3/2007 |
| WO | WO 2007/024680 | | 3/2007 |
| WO | WO 2007/025090 | | 3/2007 |
| WO | WO 2007/025540 | | 3/2007 |
| WO | WO 2007/038314 | | 4/2007 |
| WO | WO 2007/044410 | | 4/2007 |
| WO | WO 2007/044449 | | 4/2007 |
| WO | WO 2007/044893 | | 4/2007 |
| WO | WO 2007/048066 | | 4/2007 |
| WO | WO 2007/062805 | | 6/2007 |
| WO | WO 2007/084815 | | 7/2007 |
| WO | WO 2007/102679 | | 9/2007 |
| WO | WO 2007/113000 | | 10/2007 |
| WO | WO 2007/129161 | | 11/2007 |
| WO | WO 2008/016131 | | 2/2008 |
| WO | WO 2008/030579 | | 3/2008 |
| WO | WO 2008/037477 | | 4/2008 |
| WO | WO 2008/052734 | | 5/2008 |
| WO | WO 2008/058126 | | 5/2008 |
| WO | WO 2008/115974 | | 9/2008 |
| WO | WO 2008/116898 | | 10/2008 |
| WO | WO 2008/155421 | | 12/2008 |
| WO | WO 2009/013126 | | 1/2009 |
| WO | WO 2009/052145 | | 4/2009 |
| WO | WO 2009/053442 | | 4/2009 |
| WO | WO 2009/060197 | | 5/2009 |
| WO | WO 2009/092049 | | 7/2009 |
| WO | WO 2009/140128 | | 11/2009 |
| WO | WO 2010/012733 | | 2/2010 |
| WO | WO 2010/033941 | | 4/2010 |
| WO | WO 2010/048314 | * | 4/2010 |
| WO | WO 2010/051549 | | 5/2010 |
| WO | WO 2010/058006 | | 5/2010 |
| WO | WO 2011/006074 | | 1/2011 |
| WO | WO 2011/133637 | | 10/2011 |
| WO | WO 2011/146336 | | 11/2011 |
| WO | WO 2012/024650 | | 2/2012 |
| WO | WO 2012/034091 | | 3/2012 |
| WO | WO 2012/034095 | | 3/2012 |
| WO | WO 2012/116217 | | 8/2012 |
| WO | WO 2012/158413 | | 11/2012 |
| WO | WO 2013/059740 | | 4/2013 |
| WO | WO 2013/074518 | | 5/2013 |
| WO | WO 2013/174876 | | 11/2013 |
| WO | WO 2013/183578 | | 12/2013 |
| WO | WO 2014/036387 | | 3/2014 |
| WO | WO 2014/047572 | | 3/2014 |
| WO | WO 2014/078322 | | 5/2014 |
| WO | WO 2014/078323 | | 5/2014 |
| WO | WO 2014/078325 | | 5/2014 |
| WO | WO 2014/078328 | | 5/2014 |
| WO | WO 2014/078331 | | 5/2014 |
| WO | WO 2014/078372 | | 5/2014 |
| WO | WO 2014/078378 | | 5/2014 |
| WO | WO 2014/078408 | | 5/2014 |
| WO | WO 2014/078417 | | 5/2014 |
| WO | WO 2014/078454 | | 5/2014 |
| WO | WO 2015/017533 | | 2/2015 |
| WO | WO 2015/112806 | | 7/2015 |
| WO | WO 2015/124697 | | 8/2015 |
| WO | WO 2015/175788 | | 11/2015 |
| WO | WO 2016/027754 | | 2/2016 |
| WO | WO 2016/196141 | | 12/2016 |
| WO | WO 2016/196671 | | 12/2016 |
| WO | WO 2017/176744 | | 10/2017 |
| WO | WO 2017/176751 | | 10/2017 |

OTHER PUBLICATIONS

Albaugh et al., "Discovery of GNF-5837, a Selective TRK Inhibitor with Efficacy in Rodent Cancer Tumor Models," ACS Medicinal Chemistry Letters, 2012, 3(2):140-145.

American Cancer Society,"Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.

Asaumi et al., "Expression of neurotrophins and theirreceptors (TRK) during fracture healing," Bone, 2000, 26(6):625-633.

Bardelli et al., "Mutational Analysis of the Tyrosine Kinome in Colorectal Cancers," Science, May 2003, 300(5621):949.

Bardelli, "Mutational analysis of the tyrosine kinome in colorectal cancers," Science, 2003, 300:949.

Bensinger et al., "Transplantation of allogeneic peripheral blood stem cells mobilized by recombinant human granulocyte colony stimulating factor," Stem Cells, Jan. 1996;14(1):90-105.

Bensinger et al., "Transplantation of allogeneic peripheral blood stem cells mobilized by recombinant human granulocyte colony-stimulating factor [see comments].," Blood, Mar. 15, 1995;85(6):1655-8.

Bertrand et al., "The crystal structures of TrkA and TrkB suggest key regions for achieving selective inhibition," Journal of molecular biology, Oct. 26, 2012;423(3):439-53.

Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.

Brodeur, "Neuroblastoma: biological insights into a clinical enigma," Nat. Rev. Cancer, 2003, 3:203-216.

Bruse et al., "Improvements to Bead Based Oligonucleotide Ligation SNP Genotyping Assays," Biotechniques, Nov. 2008, 45:559-571.

Brzezianska et al., "Rearrangements of NTRK1 oncogene in papillary thyroid carcinoma," Neuroendocrinology Letters, 2007, 28(3):221-229.

Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.

Calera et al., "Sunitinib suppress neuroblastoma growth through degradation of MYCN and inhibition of angiogenesis," PLoS One, Apr. 23, 2014;9(4):e95628. doi: 10.1371/journal.pone.0095628. eCollection 2014.

Camoratto et al., "CEP-751 inhibits TRK receptor tyrosine kinase activity in vitro exhibits antitumor activity," Int. J Cancer, Aug. 1997, 72:673-679.

Campos et al., "Enantioselective, palladium-catalyzed alpha-arylation of N-Boc-pyrrolidine," J. Am. Chem Soc., 2006, 128:3538-3539.

Cancer.sanger.ac.uk' [online]. "COSMIC, Catalog of Somatic Mutations in Cancer: Cosmic » Mutation » Overview » NTRK1 p. V321M / c.961G>A," Catalog of Somatic Mutations in Cancer (COSMIC) database, [retrieved on Jul. 17, 2017] Retrived from the Internet: URL<cancer.sanger.ac.uk/cosmic/mutation/overview?id=1259646>, 1 page.

Cancer.sanger.ac.uk' [online]. "COSMIC, Catalog of Somatic Mutations in Cancer: Cosmic » Mutation » Overview » NTRK1 p. D679N / c.2035G>A," Catalog of Somatic Mutations in Cancer (COSMIC) database, [retrieved on Jul. 17, 2017] Retrived from the Internet: URL<cancer.sanger.ac.uk/cosmic/mutation/overview?id=897427>, 1 page.

Cancer.sanger.ac.uk' [online]. "COSMIC, Catalog of Somatic Mutations in Cancer: Cosmic » Mutation » Overview » NTRK3 p. D537Y / c.1609G>T," Catalog of Somatic Mutations in Cancer (COSMIC) database, [retrieved on Jul. 17, 2017] Retrived from the Internet: URL<cancer.sanger.ac.uk/cosmic/mutation/overview?id=966118>, 1 page.

(56) References Cited

OTHER PUBLICATIONS

Cancer.sanger.ac.uk' [online]. "COSMIC, Catalog of Somatic Mutations in Cancer: Cosmic » Mutation » Overview » NTRK3 p. D609V / c.1826A>T," Catalog of Somatic Mutations in Cancer (COSMIC) database, [retrieved on Jul. 17, 2017] Retrived from the Internet: URL:<cancer.sangersactik/cosmic/mutation/overview?id=124878>, 1 page.
Cancer.sanger.ac.uk' [online]. "COSMIC, Catalog of Somatic Mutations in Cancer: Cosmic » Mutation » Overview » NTRK3 p.G 608S / c.1822G>A," Catalog of Somatic Mutations in Cancer (COSMIC) database, [retrieved on Jul. 17, 2017] Retrived from the Internet: URL<cancer.sanger.ac.uk/cosmic/mutation/overview?id=88799>, 1 page.
Cancer.sanger.ac.uk' [online]. "COSMIC, Catalog of Somatic Mutations in Cancer: Cosmic » Mutation » Overview » NTRK3 p. L282M / c.844C>A," Catalog of Somatic Mutations in Cancer (COSMIC) database, [retrieved on Jul. 17, 2017] Retrived from the Internet: URL<cancer.sanger.ac.uk/cosmic/mutation/overview?id=401588>, 1 page.
Cancer.sanger.ac.uk' [online]. "COSMIC, Catalog of Somatic Mutations in Cancer: Cosmic » Mutation » Overview » NTRK3 p. V539M / c.1615G>A," Catalog of Somatic Mutations in Cancer (COSMIC) database, [retrieved on Jul. 17, 2017] Retrived from the Internet: URL<cancer.sanger.ac.uk/cosmic/mutation/overview?id=1708512>, 1 page.
Caria et al., "Cytogenetic and molecular events in adenoma and well-differentiated thyroid follicular-cell neoplasia," Cancer Genet. Cytogenet., 2010, 203:21-29.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Catalog of Somatic Mutations in Cancer (COSMIC) database, cancersanger.ac.uk/cosmic/mutation/.overview?id=1517968, downloaded on May 31, 2016, 2 pages.
Catalog of Somatic Mutations in Cancer (COSMIC) database, cancersangerac.uk/cosmic/mutation/.overview?id=1636266, downloaded on May 31, 2016, 2 pages.
Catalog of Somatic Mutations in Cancer (COSMIC) database, cancersangerac.uk/cosmic/mutation/.overview?id=1688778, downloaded on May 31, 2016, 2 pages.
Catalog of Somatic Mutations in Cancer (COSMIC) database, cancersangerac.ukkosmic/mutation/overview?id=3711772, downloaded on May 31, 2016, 2 pages.
Catalog of Somatic Mutations in Cancer (COSMIC) database, cancersangerac.uk/cosmic/mutation/.overview?id=471203, downloaded on May 31, 2016, 2 pages.
Catalog of Somatic Mutations in Cancer (COSMIC) database, cancersangerac.uk/cosmic/mutation/overview?id=48622, downloaded on May 31, 2016, 2 pages.
Chang-Qi et al., "Brain derived neurotrophic factor (BDNF) contributes to the pain hypersensitivity following surgical incision in the rats," Molecular Pain, 2008, 4:27.
Cherry et al., "Recent kinase and kinase inhibitor X-ray structures: mechanisms of inhibition and selectivity insights," Curr Med Chem. Mar. 2004;11(6):663-73.
Chinese Office Action in Chinese Patent Application No. CN 201180025013.9, dated Apr. 28, 2014, 11 pages.
Chinese Office Action in Chinese Patent Application No. CN201080040095.X, dated Feb. 27, 2015, 8 pages (English translation).
Cho et al., "Expression of mRNA for brain-derived neurotrophic factor in the dorsal root ganglion following peripheral inflammation," Brain Research, 1997, 749:358-362.
Choi et at, "(R)-2-Phernipyrrolidine Substituted imidazopyridazines. A New Class of Potent and Selective Pan-TRK Inhibitors," ACS medicinal chemistry letters, Mar. 19, 2015;6(5):562-7.
Colombian Office Action in Colombian Application No. CO 12-022-116-4, dated Feb. 14, 2014, 8 pages.
Colombian Office Action in Colombian Application No. CO 12-229421-4, dated Jan. 21, 2014, 6 pages.
Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi: 10.1007/s00280-014-2627-1. Epub Nov. 14, 2014.
Cruz, "Lung cancer: epidemiology, etiology and prevention," Clinics in Chest Medicine, 2011, 32(4): 1-61.
Dang et al., "Expression of nerve growth factor receptors is correlated with progression and prognosis of human pancreatic cancer," J. Gastroenterology and Hepatology, 2006, 21(5): 850-858.
Davidson et al., "Expression and activation of the nerve growth factor receptor TrkA in serous ovarian carcinoma," Clin. Cancer Res., 2003, 9(6):2248-2259.
Davies et al., "Resistance to ROS1 inhibition mediated by EGFR pathway activation in non-small cell lung cell," PLoS One, 2013, 8(12):e82236, 13 pages.
Delafoy et al., "Role of nerve growth factor in the trinitrobenzene sulfonic acid-induced colonic hypersensitivity," Pain, 2003, 105:489-497.
Demaria et al., "Development of tumor-infiltrating lymphocytes in breast cancer after neoadjuvant paclitaxel chemotherapy," Clin Cancer Res, Oct. 2001;7(10):3025-30.
Di Mola et al., "Nerve growth factor and Trk high affinity receptor (TrkA) gene expression in inflammatory bowel disease," Gut, 2000, 46(5):670-678.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "An oncogenic NTRK fusion in a soft tissue sarcoma patient with response to the tropomysin-related kinase (TRK) inhibitor LOXO-101," Cancer Discovery, Jul. 2015, 5(10):1049-1057.
Doebele et al., "Phase II Trial of Stereotactic Body Radiation Therapy Combined with Erlotinib for Patients With Limited but Progressive Metastatic Non-Small-Cell Lung Cancer," J. Clin. Oncol., 2014, 32:9 pages.
Dolle et al., "Nerve growth factor-induced migration of endothelial cells," J. Pharmacol Exp Ther, 2005, 315(3):1220-1227.
Dou et al., "Increased nerve growth factor and its receptors in atopic dermatitis: an immunohistochemical study," Archives of Dermatological Research, 2006, 298(1):31-37.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.
Du et al., "Expression of NGF family and their receptors in gastric carcinoma: a eDNA microarray study," World Journal of Gastroenterology, http://www.wjgnet.com/1007-9327/full/v9/i7/1431.htm, Jul. 2003, 9(7):1431-1434.
Duranti et al., "Homologation of Mexiletine alkyl chanin and stereoselective blockade of skelatal muscle sodium channels," Euro. J. Med. Chem., 2000, 35:147-156.
Eguchi et al., "Fusion of ETV6 to neurotrophin-3 receptor TRKC in acute myeloid leukemia with t(12;15)(p13;q25)," Blood, 1999, 93(4):1355-1363.
Endometrial Cancer Gene Database, ecgene.bioinfominzhao org/gene_mutation.cgi?gene=4915, downloaded on May 31, 2016, 13 pages.
Engman et al., "Syngeneic transplant in mantle cell lymphoma: a rare event and review of the literature," Clin Adv Hematol Oncol. May 2009;7(5):321-3.
Essand et al., "Genetically engineered T cells for the treatment of cancer," J Intern Med. Feb. 2013;273(2):166-81. doi: 10.1111/joim.12020.
Estrada-Bemal et al., "Abstract #: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.
Estrada-Bernal et al., "Abstract #: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.

(56) References Cited

OTHER PUBLICATIONS

Euthus et al., "ETV6-NTRK3—Trk-ing the primary event in human secretory breast cancer," Cancer Cell, 2002, 2(5):347-348.
Extended European Search Report in European Application No. 17163978.4, dated Jul. 17, 2017, 5 pages.
Flannery et al., "Immunomodulation: NK cells activated by interferon-conjugated monoclonal antibody against human osteosarcoma," Eur J Cancer Clint Oncol. Jun. 1984;20(6):791-8.
Frattini et al., "The integrated landscape of driver genomic alterations in glioblastoma," Nature Genet., 2013, 45:1141-1149.
Freund-Michel and Frossard, "The nerve growth factor and its receptors in airway inflammatory diseases," Pharmacology & Therapeutics, 2008, 117(1):52-76.
Frey et al., "7-Aminopyrazolo[1,5-a]pyrimidines as potent multitargeted receptor tyrosine kinase inhibitors," J. Med. Chem, Jul. 2008, 51(13):3777-3787.
Gaudet et al., "Allele-specific PCR in SNP genotyping," Methods Mol Biol. 2009;578:415-24. doi: 10.1007/978-1-60327-411-1_26.
Geiger et al., "Functional Characterization of Human Cancer-Derived TRKB Mutations," PLoS ONE, Feb. 17, 2011, 6(2):e16871.
GenBank Accession No. AAB33109.1, "trkB [*Homo sapiens*]," Jul. 27, 1995, 1 page.
GenBank Accession No. AAB33111.1, "trkC [*Homo sapiens*]," Jul. 27, 1995, 1 page.
GenBank Accession No. NM_002529, "high affinity nerve growth factor receptor isoform 2 precursor [*Homo sapiens*]," May 11, 2014, 4 pages.
GenBank Accession No. NM_001007792 "*Homo sapiens* neurotrophic tyrosine kinase, receptor, type 1 (NTRK1), transcript variant 3, mRNA," May 10, 2014, 5 pages.
GenBank Accession No. NM_001012338, "*Homo sapiens* neurotrophic tyrosine kinase, receptor, type 3 (NTRK3), transcript variant 1, mRNA," May 10, 2014, 6 pages.
GenBank Accession No. NM_006180, "*Homo sapiens* neurotrophic tyrosine kinase, receptor, type 2 (NTRK2), transcript variant a, mRNA," May 12, 2014, 9 pages.
GenBank Accession No. NP 001007793, "high affinity nerve growth factor receptor isoform 3 [*Homo sapiens*]," May 10, 2014, 3 pages.
GenBank Accession No. NP_002520 "high affinity nerve growth factor receptor isoform 2 precursor [*Homo sapiens*]," May 11, 2014, 4 pages.
GenBank Accession No. NP_001012338, "NT-3 growth factor receptor isoform a precursor [*Homo sapiens*]," May 10, 2014, 3 pages.
GenBank Accession No. NP_006171, "BDNF/NT-3 growth factors receptor isoform a precursor [*Homo sapiens*]," May 12, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Genevois et al., "Dependence receptor TrkC is a putative colon cancer tumor suppressor," Proc. Nat. Acad. Sci. U.S.A. Feb. 19, 2013, 110(8):3017-3022.
Gimm et al., "Mutation analysis of NTRK2 and NTRK3, encoding 2 tyrosine kinase receptors, in sporadic human medullary thyroid carcinoma reveals novel sequence variants," International Journal of Cancer, Apr. 1, 2001, 92(1):70-74.
Greco et al., "Rearrangements of NTRK1 gene in papillary thyroid carcinoma," Molecular and Cellular Endocrinology, 2010, 321(1):44-49.
Green & Wuts, eds, "Protective Groups in Organic Synthesis," John Wiley & Sons Inc, May 8, 1999.
Gruber-Olipitz et al., "Neurotrophin 3/TrkC-regulated proteins in the human medulloblastoma cell line DAOY," J. Proteome Research, 2008, 7(5):1932-1944.
Gwak et al., "Attenuation of mechanical hyperalgesia following spinal cord injury by administration of antibodies to nerve growth factor in the rat" Neurosci. Lett., 2003, 336:117-120.
Hamdouchi et a l "Imidazo[1,2-b]pyridazines, activity against human picornaviruses: novel nucleus with potent and broad spectrum design, synthesis, and biological evaluation" J Med Chem., Sep. 25, 2003;46(20):4333-4341.
Hansen et al., "Autophagic cell death induced by TrkA receptor activation in human glioblastoma cells," J. of Neurochemistry, 2007, 103:259-275.
Harada et al., "Role and Relevance of TrkB Mutations and Expression in Non-Small Cell Lung Cancer," Clinical Cancer Research, Jan. 17, 2011, 17(9):2638-2645.
Harwood et al., "Experimental organic chemistry—Principles and practice," Experimental Chemistry—Organic Chemistry and Reaction, Jan. 1, 1989, 127-132.
Herzberg et al., "NGF involvement in pain induced by chronic constriction injury of the rat sciatic nerve," Neuroreport, 1997, 8:1613-1618.
Hinrichs et al., "Exploiting the curative potential of adoptive T-cell therapy for cancer," Immunol Rev. Jan. 2014;257(1):56-71. doi: 10.1111/imr.12132.
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.
Howell et al., "Dynamic allele-specific hybridization. A new method for scoring single nucleotide polymorphisms," Nat Biotechnol. Jan. 1999;17(1):87-8.
Hu et al., "Decrease in bladder overactivity with REN1820 in rats with cyclophosphamide induced cystitis," J. Urology, 2005, 173(3):1016-1021.
Hu et al., "Identification of brain-derived neurotrophic factor as a novel angiogenic protein in multiple myeloma" Cancer Genetics and Cytogenetics, 2007, 178:1-10.
Huehls et al., "Bispecific T-cell engagers for cancer immunotherapy,"Immunol Cell Biol. Mar. 2015;93(3):290-6. doi: 10.1038/icb.2014.93. Epub Nov. 4, 2014.
Igaz et al., "Biological and clinical significance of the JAK-STAT pathway; lessons from knockout mice," Inflamm. Res., 2001, 50:435-441.
Ihle et al., "The Roles of Jaks and Stats in Cytokine Signaling," Canc. J. Sci. Am., 1998, 4(1):84-91.
Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
International Preliminary Report on Patentability in International Application No. PCT/US2009/057729, dated Mar. 22, 2011, 7 pages.
International Preliminary Report on Patentability in International Application No. PCT/US2009/061519, dated Apr. 26, 2011, 6 pages.
International Preliminary Report on Patentability in International Application No. PCT/US2010/041538, dated Jan. 10, 2012, 7 pages.
International Preliminary Report on Patentability in International Application No. PCT/US2011/036452, dated Nov. 29, 2012, 6 pages.
International Preliminary Report on Patentability in International Application No. PCT/US2015/060953, dated May 16, 2017, 7 pages.
International Search Report and Written Opinion for International Application No. PCT/US2016/035327, dated Aug. 18, 2016, 15 pages.
International Search Report and Written Opinion in International Application No. PCT/US2009/0161519, dated Feb. 2, 2010, 8 pages.
International Search Report and Written Opinion in International Application No. PCT/US2009/057729, dated Feb. 4, 2010, 10 pages.
International Search Report and Written Opinion in International Application No. PCT/US2010/041538, dated Oct. 1, 2010, 10 pages.

(56) References Cited

OTHER PUBLICATIONS

International Search Report and Written Opinion in International Application No. PCT/US2011/036452, dated Aug. 18, 2011, 9 pages.
International Search Report and Written Opinion in International Application No. PCT/US2015/060953, dated Feb. 8, 2016, 12 pages.
International Search Report and Written Opinion in International Application No. PGT/US2016/058951, dated Feb. 7, 2017, 20 pages.
Isdori et al., "Advancement in high dose therapy and autologous stem cell rescue in lymphoma," World J Stem Cells, Aug. 2015, 7(7):1039-1046.
Iyer et al., "AZ64 inhibits TrkB and enhances the efficacy of chemotherapy and local radiation in neuroblastoma xenografts," Cancer Chemother Pharmacol. Sep. 2012;70(3):477-86. doi: 10.1007/500280-012-1879-x. Epub May 24, 2012.
Iyer, R., "Entrectinib is a potent inhibitor of Trk-driven neuroblastomas in a xenograft mouse model." Cancer letters 372.2 (2016): 179-186. (Year: 2016).
Jaggar et al., "Inflammation of the rat urinary bladder is associated with a referred thermal hyperalgesia which is nerve growth factor dependent," Br. J. Anaesth, 1999, 83:442-448.
Japanese Office Action in Japanese Application No. JP 2013-511239, dated Mar. 4, 2015, 2 pages (English translation).
Jin et al., "TrkC plays an essential role in breast tumor growth and metastasis," Carcinogenesis, 2010, 31(11):1939-1947.
Jones et al., "Recurrent somatic alterations of FGFR1 and NTRK2 in pilocytic astrocytoma," Nature Genetics, 2013, 45:927-932.
Keysar et al., "A patient tumor transplant model of Squamous cell cancer identifies PI3K inhibitors as candidate therapeutics in defined molecular bins," Molecular Oncology, 2013, 7(4):776-790.
Kim et al., "NTRK1 fusion in glioblastoma multiforme," PloS ONE, 2014, 9(3):e91940.
Klijn et al., "A comprehensive transcriptional portrait of human cancer cell lines," Nat Biotechnol., 2015, 33(3):306-312.
Koboldt et al., "The next-generation sequencing revolution and its impact on genomics," Cell, Sep. 26, 2013;155(1):27-38. doi: 10.1016/j.cell.2013.09.006.
Kolokythas et al., "Nerve growth factor and tyrosine kinase a receptor in oral squamous cell carcinoma: is there an association with perineural invasion?" J. Oral Maxillofacial Surgery, 2010, 68(6):1290-1295.
Kremer et al., "The safety and efficacy of a JAK inhibitor in patients with active rheumatoid arthritis: Results of a double-blind, placebo-controlled phase lla trial of three dosage levels of CP-690,550 versus placebo," Arth. & Rheum., 2009, 60:1895-1905.
Kruettgen et al., "The dark side of the NGF family: neurotrophins in neoplasias," Brain Pathology, 2006, 16:304-310.
Lamb et al., "Nerve growth factor and gastric hyperalgesia in the rat," Neurogastrenterol. Motil., 2003, 15:355-361.
Lecht et al., "Angiostatic effects of K252a, a Trk inhibitor, in murine brain capillary endothelial cells," Mol Cell Biochem, Jun. 2010;339(1-2):201-13. doi: 10.1007/s11010-010-0386-9. Epub Feb. 11, 2010.
Leukemia, Wikipedia The Free Encyclopedia, Dec. 8, 2001, https://en.wikipedia.org/Wiki/Leukemia, 15 pages.
Li et al., "Brain derived neurotrophic factor (BDNF) contributes to the pain hypersensitivity following surgical incision in the rats," Molecular Pain, 2008, 4(28):1-11.
Li et al., "Correlation of expressions of GFAP, NT-3, TRK and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "In vivo sensitized and in vitro activated B cells mediate tumor regression in cancer adoptive immunotherapy," J Immunol, Sep. 1, 2009;183(5):3195-203. doi: 10.4049/jimmunol.0803773. Epub Aug. 10, 2009.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "Trk inhibitor attenuates the BDNF/TrkB-induced protection of neuroblastoma cells from etoposide in vitro and in vivo," Cancer Biol. Ther., Feb. 2015, 16(3):477-483.
Linch et al., "Systemic treatment of soft-tissue sarcoma [mdash] gold standard and novel therapies," Nature Reviews Clinical Oncology, 2014, 11(4):187-202.
Lorigan et al., "Phase III trial of two investigational schedules of ifosfamide compared with standard-dose doxombicin in advanced or metastatic soft tissue sarcoma: a European Organisation for Research and Treatment of Cancer Soft Tissue and Bone Sarcoma Group Study," J. Clin Oncol., 2007, 25(21):3144-3150.
Lovly et at, "Inflammatory myofibroblastic tumors harbor multiple potentially actionable kinase fusions," Cancer Discov., 2014, 4(8):889-895.
Ma and Woolf, "The progressive tactile hyperalgesia induced by peripheral inflammation is nerve growth factor dependent," Neuroreport, 1997, 8:807-810.
Marchetti et al., "Frequent mutations in the neurotrophic tyrosine receptor kinase gene family in large cell neuroendocrine carcinoma of the lung," Human Mutation, 2008, 29(5):609-616.
Marras et al., "Genotyping SNPs with molecular beacons," Methods Mol Biol, 2003;212:111-28.
Marras et al., Single Nucleotide Polymorphism: Methods and Protocols. Methods in Molecular Biology, Kwok, P.-Y., Ed., Totowa, NJ, Humana Press, vol. 212, pp. 111-128, 2003.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McCarthy et al., "Tropomyosin receptor kinase inhibitors: a patent update 2009-2013," Expert Opin Ther Pat. Jul. 2014;24(7):731-44. doi: 10.1517/13543776.2014.910195. Epub May 8, 2014.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Corp., 27 pages.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Miranda et al., "Functional characterization of NTRK1 mutations Identified in melanoma," Genes Chromosomes & Cancer, Jun. 26, 2014, 53(10):875-880.
Montagnoli et al., "Anti-proliferative effects of GW441756, a novel inhibitor of NGFreceptor tyrosine kinase a (TRKA), in human sarcoma," Italian Journal of Anatomy and Embryology, Nov. 11, 2010, 115:117.
Nagasubruarnanian et al, "Brief Report: Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.
Nakagawara, "Trk receptor tyrosine kinases: a bridge between cancer and neural development," Cancer Letters, 2001, 169(2):107-114.
Narayanan et al., "Discovery and preclinical characterization of novel small molecule TRK and ROS1 tyrosine kinase inhibitors for the treatment of cancer and inflammation," PLoS One, Dec. 26, 2013;8(12):e83380. doi: 10.1371/journalpone.0083380. eCollection 2013.
National Cancer Institute at the National Institutes of Health, posted on or before Jan. 5, 2000, retrieved on Jan. 13, 2015, http://www.cancer.gov/, 2 pages.

(56) References Cited

OTHER PUBLICATIONS

National Comprehensive Cancer Network, posted on or before Dec. 3, 1998, retrieved on Jan. 13, 2015, http://www.nccn.org/, 1 page.
NCT02050919, "Sorafenib Tosylate, Combination Chemotherapy, Radiation Therapy, and Surgery in Treating Patients With High-Risk Stage ITB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.
NCT02122913, "Oral TRK Inhibitor LOXO-101 for Treatment of Advanced Adult Solid Tumors," ClinicalTrials.gov, First received Apr. 16, 2014, Last Updated Dec. 7, 2015, https://clinicaltrials.gov/ct2/show/NCT02122913.
Ni et al., "siRNA interference with a proliferation-inducing ligand gene in the SGR-7901 gastric carcinoma cell line," Asian Pacific Journal of Cancer Prevention, 2012, 13:1511-1514.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. Biochim Biophys Acta, 1834:2214-2218," Biochim Biophys Acta, Oct. 2013, 1834(10):2213-2218.
Ocgene.bioinfo-niinzhao.org' [online]. "Ovarian Cancer Gene Database, Gene ID: 4914," [retrieved on Jul. 17, 2017] Retrived from the Internet: URL<ocgene.bioinfominzhao.org/gene_mutation.cgi?gene=4914>, 13 pages.
Olivier, "The Invader assay for SNP genotyping," Mutat Res, Jun. 3, 2005;573(1-2):103-10.
O'Shea, "Jaks, STATs, cytokine signal transduction, and immunoregulation: are we there yet?" Immunity, 1997, 7:1-11.
Ovanan Cancer Gene Database, ocgene.bioinfo-minzhao.org/gene_mutation.cgi?gene=4914, downloaded on May 31, 2016, 14 pages.
Ovarian Cancer Gene Database, ocgene.bioinfo-minzhao.org/gene_mutation.cgi?gene=4916, downloaded on May 31, 2016, 21 pages.
Pao, W., et al. "Acquired resistance of lung adenocarcinomas to gefitinib or erlotinib is associated with a second mutation in the EGFR kinase domain," PLoS Med, Feb. 2005, 2(3), e73.
Papatsoris et al., "Manipulation of the nerve growth factor network in prostate cancer," Exper Opin Invest Drugs, 2007, 16(3):303-309.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Pediatric Cancer Gene Database, pedican.bioinfominzhao.org/gene_mutation.cgi?gene=4914, downloaded on May 31, 2016, 6 pages.
Pediatric Cancer Gene Database, peclican.bioinfominzhao.org/gene_mutation.cgi?gene=4915, downloaded on May 31, 2016, 5 pages.
Pediatric Cancer Gene Database, pedican.bioinfominzhao.org/gene_mutation.cgi?gene=4916, downloaded on May 31, 2016, 9 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi: 10.1016/j.bbmt.2015.10.014. Epub Oct. 17, 2015.
Perez-Pinera et al., "The Trk tyrosine kinase inhibitor K252a regulates growth of lung adenocarcinomas," Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Philippines Office Action in Philippines Application No. PH 1/2012/500048, dated May 30, 2014, 2 pages.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Ponsaerts et al., "Cancer immunotherapy using RNA-loaded dendritic cells," Clin. Exp. Immunol., Dec. 2003, 134:378-384.
Pulciani et al., "Oncogenes in solid human tumours," Nature, 1982, 300(5892):539-542.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Raychaudhuri et al., K252a, a high-affinity nerve growth factor receptor blocker, improves psoriasis: an in vivo study using the severe combined immunodeficient mouse-human skin model, J. Investigative Dermatology, 2004, 122(3):812-819.
Reungwetwattana et al., "Targeted therapies in development for non-small cell lung cancer," J Carcinog, Dec. 2013, 12:22, doi: 10.4103/1477-3163.123972. eCollection 2013.
Reuther et al., "Identification and characterization of an activating TrkA deletion mutation in acute myeloid leukemia," Mol. Cell. Biol. 2000, 20:8655-8666.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Ro et al., "Effect of NGF and anti-NGF on neuropathic pain in rats following chronic constriction injury of the sciatic nerve," Pain, 1999, 79:265-274.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Derm. Venereal., 2015, 95:542-548.
Ross et al., "New routes to targeted therapy of intrahepatic cholangiocarcinomas revealed by next-generation sequencing," Oncologist, 2014, 19:235-242.
Russo et al., "Acquired Resistance to the Trk Inhibitor Entrectinib in Colorectal Cancer," Cancer Discovery, Jan. 1, 2016, 6(1):36-44.
Rutkowski et al., "Treatment of advanced dermatofibrosarcoma protuberans with imatinib mesylatc with or without surgical resection,"J. Eur. Acad Delmatol. Venereol., 2011, 25:264-270.
Santoro et al., "Doxorubicin versus CYVADIC versus doxombicin plus ifosfamide in first-line treatment of advanced soft tissue sarcomas: a randomized study of the European Organization for Reasearh and Treatment of Cancer Soft Tissue and Bone Sarcoma Group," J. Clin Oncol., 1995, 13(7):1537-1545.
Saragovi et al., "A TrkA-selective, fast internalizing nerve growth factor-antibody complex induces trophic but not neuritogenic signals," J Biol Chem, Dec. 25, 1998;273(52):34933-34940.
Shaw et al., "Ceritinib in ALK-rearranged non-small-cell lung cancer," N Engl J Med, Mar. 27, 2014;370(13):1189-97. doi: 10.1056/NEJMoa1311107.
Shaw et al., "Crizotinib in ROS1-rearranged non-small-cell lung cancer," N Engl J Med, Nov. 20, 2014;371(21):1963-71. doi: 10.1056/NEJMoa1406766. Epub Sep. 27, 2014.
Shelton et al., "Nerve growth factor mediates hyperalgesia and cachexia in auto-immune arthritis," Pain, 2005, 116:8-16.
Silverman, The Organic Chemistry of Drug Design and Drug Action, Second Edition, 2007, 20-21.
Sleijfer et al., "Prognastic and predictive factors for outcome to firs-line ifosfamide-containing chemotherapy for adult patients with advanced soft tissue saroomas:an exploratory, retrospective analysis on large series from the European Organization for Research and Treatment of Cancer-Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.

(56) References Cited

OTHER PUBLICATIONS

Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Tacconelli et al., "TrkA alternative splicing: a regulated tumor-promoting switch in human neuroblastoma," Cancer Cell, 2004, 6:347-360.
Tafinlar, Highlights of Prescribing Information, GlaxoSmithKline, Jan. 2014, 41 pages.
Tahira et al., "dbQSNP: a database of SNPs in human promoter regions with allele frequency information determined by single-strand conformation polymorphism-based methods," Hum Mutat, Aug. 2005;26(2):69-77.
Taipale et al., "Chaperones as thermodynamic sensors of drug-target interactions reveal kinase inhibitor specifities in living cells," Nat Biotech, 2013, 31(7):630-637.
Taiwan Office Action in Taiwan Application No. 098135670, dated Jan. 20, 2014, 7 pages (with English Translation).
Taiwan Search Report in Taiwan Application No. 098132033, dated Dec. 13, 2013, 1 page (English translation only).
Taiwan Search Report in Taiwan Application No. 105143120, dated Aug. 10, 2017, 6 pages (with English translation).
Theodosiou et al., "Hyperalgesia due to neive damage: role of neive growth factor," Pain, 1999, 81:245-255.
Thiele, "On Trk—the TrkB signal transduction pathway is an increasingly important target in cancer biology," Clinical Cancer Research, 2009, 105(19):5962-5967.
Thompson et al., "Brain-derived neurotrophic factor is an endogenous modulator of nociceptive responses in the spinal cord," Proc.Natl. Acad. Sci. USA, 1999, 96:7714-7718.
Thress et al., "Identification and preclinical characterization of AZ-23, a novel, selective, and orally bioavailable inhibitor of the Trk kinase pathway," Mol Cancer Ther, Jul. 2009;8(7):1818-27. doi: 10.1158/1535-7163.MCT-09-0036. Epub Jun. 9, 2009.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin ," Dermato-Endrocrinology, 2008, 3(1):32-36.
Turtle et al., "Artificial antigen-presenting cells for use in adoptive immunotherapy," Cancer J, Jul.-Aug. 2010;16(4):374-81. doi: 10.1097/PPO.0b013e3181eb33a6.
Vaishnavi et al., "TRKing Down an Old Oncogene in a New Era of Targeted Therapy," Cancer Discovery, Jan. 2015, 5(1):25-34.
Vaishnavi et al., Oncogenic and drug-sensitive NTRK1 rearrangements in lung cancer, Nature Med., 2013, 19:1469-1472.
Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Wadhwa et al., "Expression of the neurotrophin receptors Trk A and Trk B in adult human astrocytoma and glioblastoma," Journal of Biosciences, 2003, 28(2):181-188.
Watch et al., "Role of neurotrophins and neurotrophins receptors in the in vitro invasion and heparanase production of human prostate cancer cells," Clin. Exp. Metastasis, 1999, 17:307-314.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wang et al., "Trk kinase inhibitors as new treatments for cancer and pain," Expert Opin. Ther Patents, Mar. 2009, 19(3):305-319.
Wei et al., "Abstract #2136: Entrectinib is Effective Against the Gatekeeper and Other Emerging Resistance Mutations in NTRK−, ROS1− and ALK− Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wiesner et al., "Kinase fusions are frequent in Spitz tumours and spitzoid melanomas," Nature Comm., 2014, 5:3116.
Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.
Wittwer et al., "High-resolution genotyping by amplicon melting analysis using LCGreen," Clin Chem, Jun. 2003;49(6 Pt 1):853-60.
Woodward, "Bi-allelic SNP genotyping using the TaqMan® assay," Methods Mol Biol., 2014;1145:67-74. doi: 10.1007/978-1-4939-0446-4_6.
Woolf et al., "Letter to Neuroscience: Nerve Growth Factor Contributes to the Generation of Inflammatory Sensory Hypersensitivity," Neuroscience, 1994, 62:327-331.
Wu et al., "The genomic landscape of diffuse intrinsic pontine glioma and pediatric non-brainstem high-grade glioma," Nature Genetics, 2014, 444-450.
Xalkori, Highlights of Prescribing Information, Pfizer Labs, Initial approval 2011, revised Mar. 2016, 20 pages.
Yilmaz et al., "Theraputic targeting of Trk supresses tumor proliferation and enhances cisplatin activity in HNSCC," Cancer Biology and Therapy, 2010, 10(6):644-653.
Yu et al., "Denaturing high performance liquid chromatography: high throughput mutation screening in familial hypertrophic cardiomyopathy and SNP genotyping in motor neurone disease," J Clin Pathol, May 2005;58(5):479-85.
Zage et al., "The selective Trk inhibitor AZ623 inhibits brain-derived neurotrophic factor—mediated neuroblastoma cell proliferation and signaling and is synergistic with topotecan," Cancer, Mar. 2011, 117(6): 1321-1391.
Zahn et al., "Effect of blockade of nerve growth factor and tumor necrosis factor on pain behaviors after plantar incision," J. Pain, 2004, 5:157-163.
Zelboraf, Highlights of Prescribing Information, Genentech USA, Initial Approval 2011, revised Aug. 2015, 18 pages.
Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/journal.pone.0062126. Print 2013.
Zhang et al., "Expression of nerve growth factor receptors and their prognostic value in human pancreatic cancer," Oncology Reports, 2005, 14:161-171.
Zheng et al., "Anchored multiplex PCR for targeted next-generation sequencing," Nature Med., Dec. 2014, 20(12):1479-1486.
Cui et al., "Abstract #MA 07.09: ALK/ROS1/Inhibitor TPX-0005 Effectively Overcomes Clinical Resistance Solvent Front Mutations," Abstracts, Nov. 2017, p. S1829.
Esmo, "TRK Cancer-Causing Mutation Discovered in 1982 Finally Target of Clinical Trials: Matching drugs to long-overlooked oncogene," European Society of Medical Oncology, Jan. 2015, 2 pages.
International Preliminary Report on Patentability in International Application No. PCT/US2016/035327, dated Dec. 14, 2017, 9 pages.
Katayama et al., "Mechanisms of Acquired Crizotinib Resistance in ALKRearranged Lung Cancers," Sci Transl Med, Feb. 2012, 4(120): 120ra17.
McCahon et al., "Non-Resectable Congenital Tumors with the ETV6-NTRK3 Gene Fusion Are Highly Responsive to Chemotherapy," Med. Pediatr. Oncol., May 2003, 40(5):288-292.
Ou et al., "Emergence of novel and dominant acquired EGFR solvent-front mutations at Gly796 (G796S/R) together with C797S/R and L792F/H mutations in one EGFR (L858R/T790M) NSCLC patient who progressed on osimertinib," Lung Cancer, 2017, 108: 22/-231.
Ou et al., "Next-Generation Sequencing Reveals a Novel NSCLC ALK F1174V Mutation and Confirms ALK G1202R Mutation Confers High-Level Resistance to Alectinib (CH5424802/

(56) References Cited

OTHER PUBLICATIONS

RO5424802) in ALK-Rearranged NSCLC Patients Who Progressed on Crizotinib," Journal of Thoracic Oncology, Apr. 2014, 9: 549-553.
Roskoski, Jr. et al., "Classification of small molecule protein kinase inhibitors based upon the structures of their drug-enzyme complexes," Pharmacological Research, 2016, 103: 26-48.
Calabresi and Chabner, Goodman & Gilnnan's The Pharmacological Basis of Therapeutics, 10th ed., 2001, p. 1388, para 2, lines 4-5.
Extended European Search Report in European Application No. 18151233.6, dated Jun. 26, 2018, 6 pages.
Vogelstein and Kinzler, The Genetic Basis of Human Cancer, 2nd ed., 2002, p. 3, col. 1, para 2.
U.S. Appl. No. 14/321,246, filed Jul. 1, 2014, Shelley Allen.
U.S. Appl. No. 15/401,895, filed Jan. 9, 2017, Shelley Allen.
U.S. Appl. No. 15/401,913, filed Jan. 9, 2017, Shelley Allen.
U.S. Appl. No. 15/724,601, filed Oct. 4, 2017, Shelley Allen.
U.S. Appl. No. 13/382,858, filed Jan. 6, 2012, Shelley Allen.
U.S. Appl. No. 13/614,968, filed Sep. 13, 2012, Steven W. Andrews.
U.S. Appl. No. 14/984,353, filed Dec. 30, 2015, Steven W. Andrews.
U.S. Appl. No. 15/401,792, filed Jan. 9, 2017, Steven W. Andrews.
U.S. Appl. No. 15/401,969, filed Jan. 9, 2017, Steven W. Andrews.
U.S. Appl. No. 13/063,894, filed Mar. 14, 2011, Steven W. Andrews.
U.S. Appl. No. 14/575,663, filed Dec. 18, 2014, Steven W. Andrews.
U.S. Appl. No. 15/350,888, filed Nov. 14, 2016, Steven W. Andrews.
U.S. Appl. No. 15/401,839, filed Jan. 9, 2017, Steven W. Andrews.
U.S. Appl. No. 15/401,952, filed Jan. 9, 2017, Steven W. Andrews.
U.S. Appl. No. 15/632,187, filed Jun. 23, 2017, Steven W. Andrews.
U.S. Appl. No. 15/900,019, filed Feb. 20, 2018, Steven W. Andrews.
U.S. Appl. No. 13/698,922, filed Nov. 19, 2012, Steven W. Andrews.
U.S. Appl. No. 13/943,590, filed Jul. 16, 2013, Julia Haas.
U.S. Appl. No. 14/490,460, filed Sep. 18, 2014, Julia Haas.
U.S. Appl. No. 14/596,611, filed Jan. 14, 2015, Julia Haas.
U.S. Appl. No. 14/846,166, filed Sep. 4, 2015, Julia Haas.
U.S. Appl. No. 15/399,389, filed Jan. 5, 2017, Julia Haas.
U.S. Appl. No. 15/860,948, filed Jan. 3, 2018, Julia Haas.
U.S. Appl. No. 13/125,263, filed Apr. 20, 2011, Julia Haas.
U.S. Appl. No. 14/943,014, filed Nov. 16, 2015, Alisha B. Arrigo.
U.S. Appl. No. 15/399,207, filed Jan. 5, 2017, Alisha B. Arrigo.
U.S. Appl. No. 15/706,062, filed Sep. 15, 2017, Alisha B. Arrigo.
U.S. Appl. No. 15/872,769, filed Jan. 16, 2018, Alisha B. Arrigo.
U.S. Appl. No. 15/335,378, filed Oct. 26, 2016, Nisha Nanda.
U.S. Appl. No. 15/785,228, filed Oct. 16, 2017, Nisha Nanda.
U.S. Appl. No. 15/785,218, filed Oct. 16, 2017, Nisha Nanda.
U.S. Appl. No. 15/860,789, filed Jan. 3, 2018, Nisha Nanda.
U.S. Appl. No. 15/579,007, filed Dec. 1, 2017, Tuch et al.
U.S. Appl. No. 15/622,388, filed Jun. 14, 2017, Michael Cox.
U.S. Appl. No. 15/861,017, filed Jan. 3, 2018, Michael Cox.
U.S. Appl. No. 15/622,544, filed Jun. 14, 2017, Mark Reynolds.
Extended European Search Report in European Application No. 17199899.0, dated Feb. 26, 2018, 7 pages.
International Preliminary Report on Patentability in International Application No. PCT/US2016/058951, dated May 11, 2018, 11 pages.
Sun et al., "P-loop conformation governed crizotinib resistance in G2032R-mutated ROS1 tyrosine kinase clues from free energy landscape," PLoS computational biology, Jul. 17, 2014, 10(7): e1003729.

* cited by examiner

*TRK A*

| | $IC_{50}$ (nM) | | |
|---|---|---|---|
| MPRIP-NTRK1 | 15 | TRIM24-NTRK2 | 88.3 |
| V573M | 534.5 | V601G | >2000 |
| F589L | 1999.8 | F617 | -- |
| G595R | | G623S | >2000 |
| G667S | 217.2 | G693S | |
| | | R630K | 45.7 |
| | | Q596E | |

Figure 12

```
NTRK1 486   -----------LQGHIIENPQYFS--------DACVHHIKRRDIVLKWELGEGAFGKVFL 526
NTRK2 490   ------VIIGMTKIPVIENPQYFGITNSQLKPDTFVQHIKRHNIVLKRELGEGAFGKVFL 554
ALK   1083  --------LRTSTIMTDYNPNYCFAGK--TSSISDLKEVPRKNITLIRGLGHGAFGEVYE 1132
ROS1  1908  ------ELRGLAAGVGLANACYAIHTLPTQEEIENLPAFPREKLTLRLLLGSGAFGEVYE 1961
ABL1  199   VHHHSTVADGLITTLHYPAPKRNKPTVYGVSPNYDKWEMERTDITMKHKLGGGQYGEVYE 258
EGFR  680   --------RRLLQERELVEPLTPSGEAPN---QALLRILKETEFKKIKVLGSGAFGTVYK 728

                                                     596 573/601
NTRK1 527   AECHNLLP-EQDKMLVAVKALKEA-SESARQDFQREAELLTMLQHQHIVRFFGVCTEGRP 584
NTRK2 555   AECYNLCP-EQDKILVAVKTLKDA-SDNARKDFHREAELLTNLQHEHIVKFYGVCVEGDP 612
ALK   1133  GQVSGMPN-DPSPLQVAVKTLPEVCSEQDELDFLMEALIISKFNHQNIVRCIGVSLQSLP 1191
ROS1  1962  GTAVDILGVGSGEIKVAVKTLKKGSTDQEKIEFLKEAHLMSKFNHPNILKQLGVCLLNEP 2021
ABL1  259   GVWKK------YSLTVAVKTLKEDTM--EVEEFLKEAAVMKEIKHPNLVQLLGVCTREPP 310
EGFR  729   GLWI--PEGEKVKIPVAIKELREATSPKANKEILDEAYVMASVDNPHVCRLLGICLTSTV 786

                589/617595/623
NTRK1 585   LLMVFEYMRHGDLNRFLRSHGPDAKLLAGGEDVAPGPLGLGQLLAVASQVAAGMVYLAGL 644
NTRK2 613   LIMVFEYMKHGDLNKFLRAHGPDAVLMAEGN--PPTELTQSQMLHIAQQIAAGMVYLASQ 670
ALK   1192  RFILLELMAGGDLKSFLRETRPRPS--------QPSSLAMLDLLHVARDIACGCQYLEEN 1243
ROS1  2022  QYIILELMEGGDLLTYLRKARMATF--------YGPLLTLVDLVDLCVDISKGCVYLERM 2073
ABL1  311   FYIITEFMTYGNLLDYLRECNRQEV--------------NAVVLLYMATQISSAMEYLEKK 357
EGFR  787   QL-ITQLMPFGCLLDYVREHKDNI---------------GSQYLLNWCVQIAKGMNYLEDR 831

            646                         667/693
NTRK1 645   HFVHRDLATRNCLV-----GQGLVVKIGDFGMSRDIYSTDYYRVGGRTMLPIRWMPPESI 699
NTRK2 671   HFVHRDLATRNCLV-----GENLLVKIGDFGMSRDVYSTDYYRVGGHTMLPIRWMPPESI 725
ALK   1244  HFIHRDIAARNCLLTCP--GPGRVAKIGDFGMARDIYRASYYRKGGCAMLPVKWMPPEAF 1301
ROS1  2074  HFIHRDLAARNCLVSVKDYTSPRIVKIGDFGLARDIYKNDYYRKRGEGLLPVRWMAPESL 2133
ABL1  358   NFIHRDLAARNCLV-----GENHLVKVADFGLSRLMTGDTYTAH-AGAKFPIKWTAPESL 411
EGFR  832   RLVHRDLAARNVLV-----KTPQHVKITDFGLAKLLGAEEKEYHAEGGKVPIKWMALESI 886

NTRK1 700   LYRKFTTESDVWSFGVVLWEIFTYGKQPWYQLSNTEAIDCITQGRELERPRACPPEVYAI 759
NTRK2 726   MYRKFTTESDVWSLGVVLWEIFTYGKQPWYQLSNNEVIECITQGRVLQRPRTCPQEVYEL 785
ALK   1302  MEGIFTSKTDTWSFGVLLWEIFSLGYMPYPSKSNQEVLEFVTSGGRMDPPKNCPGPVYRI 1361
ROS1  2134  MDGIFTTQSDVWSFGILIWEILTLGHQPYPAHSNLDVLNYVQTGGRLEPPRNCPDDLWNL 2193
ABL1  412   AYNKFSIKSDVWAFGVLLWEIATYGMSPYPGIDLSQVYELLEKDYRMERPEGCPEKVYEL 471
EGFR  887   LHRIYTHQSDVWSYGVTVWELMTFGSKPYDGIPASEISSILEKGERLPQPPICTIDVYMI 946
```

Figure 13

POINT MUTATIONS IN TRK INHIBITOR-RESISTANT CANCER AND METHODS RELATING TO THE SAME

CROSS-REFERENCE TO RELATED APPLICATIONS

This application is a continuation of U.S. patent application Ser. No. 15/335,378, filed Oct. 26, 2016, which claims priority to U.S. Provisional Application Ser. No. 62/246,580, filed on Oct. 26, 2015, 62/287,778, filed on Jan. 27, 2016, and 62/323,586, filed on Apr. 15, 2016, each of which is herein incorporated by reference in its entirety.

TECHNICAL FIELD

This invention relates to methods of genetics, pharmacogenetics, and cancer biology.

BACKGROUND

Tropomyosin-related kinase (TRK) is a receptor tyrosine kinase family of neurotrophin receptors that are found in multiple tissues types. Three members of the TRK proto-oncogene family have been described: TrkA, TrkB, and TrkC, encoded by the NTRK1, NTRK2, and NTRK3 genes, respectively. The TRK receptor family is involved in neuronal development, including the growth and function of neuronal synapses, memory development, and maintenance, and the protection of neurons after ischemia or other types of injury (Nakagawara, *Cancer Lett.* 169:107-114, 2001).

TRK was originally identified from a colorectal cancer cell line as an oncogene fusion containing 5' sequences from tropomyosin-3 (TPM3) gene and the kinase domain encoded by the 3' region of the neurotrophic tyrosine kinase, receptor, type 1 gene (NTRK1) (Pulciani et al., *Nature* 300:539-542, 1982; Martin-Zanca et al., *Nature* 319:743-748, 1986). TRK gene fusions follow the well-established paradigm of other oncogenic fusions, such as those involving ALK and ROS1, which have been shown to drive the growth of tumors and can be successfully inhibited in the clinic by targeted drugs (Shaw et al., *New Engl. J Med* 371:1963-1971, 2014; Shaw et al., *New Engl. J. Med.* 370:1189-1197, 2014). Oncogenic TRK fusions induce cancer cell proliferation and engage critical cancer-related downstream signaling pathways such as mitogen activated protein kinase (MAPK) and AKT (Vaishnavi et al., *Cancer Discov.* 5:25-34, 2015). Numerous oncogenic rearrangements involving NTRK1 and its related TRK family members NTRK2 and NTRK3 have been described (Vaishnavi et al., *Cancer Disc.* 5:25-34, 2015; Vaishnavi et al., *Nature Med.* 19:1469-1472, 2013). Although there are numerous different 5' gene fusion partners identified, all share an in-frame, intact TRK kinase domain. A variety of different Trk inhibitors have been developed to treat cancer (see, e.g., U.S. Patent Application Publication No. 62/080,374, International Application Publication Nos. WO 11/006074, WO 11/146336, WO 10/033941, and WO 10/048314, and U.S. Pat. Nos. 8,933,084, 8,791,123, 8,637,516, 8,513,263, 8,450,322, 7,615,383, 7,384,632, 6,153,189, 6,027,927, 6,025,166, 5,910,574, 5,877,016, and 5,844,092).

SUMMARY

The present invention is based on the discovery of Trk inhibitor-resistance NTRK1, NTRK2, and NTRK3 mutations. In view of this discovery, provided herein are methods of treating a subject having a cancer, methods of selecting a treatment for a subject having a cancer, methods of selecting a subject having a cancer for a treatment that does not include a Trk inhibitor, methods of determining the likelihood that a subject having a cancer will have a positive response to a treatment with a Trk inhibitor, methods of predicting the efficacy of a Trk inhibitor in a subject having cancer, methods of determining a subject's risk for developing a Trk inhibitor-resistant cancer, and methods of determining the presence of a Trk inhibitor-resistant cancer in a subject. In some embodiments, the methods provided herein are based, in part, on a determination of whether the subject has a cell that has (i) at least one point mutation in a NTRK1 gene that results in the expression of a TrkA protein comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB protein comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC protein comprising a mutation at one or more amino acid position(s) selected from the group consisting of: 545, 570, 596, 601, 617, 623, 624, 628, 630, 675, 685, 686, 696, and 705. Also provided are kits that allow for the detection of at least one of the point mutations in NTRK1 and/or NTRK2 and/or NTRK3.

Detection and identification of a subject having cells having a Trk inhibitor-resistant mutation as described herein (e.g., (i) at least one point mutation in a NTRK1 gene that results in the expression of a TrkA protein comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB protein comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC protein comprising a mutation at one or more amino acid position(s) selected from the group consisting of: 545, 570, 596, 601, 617, 623, 624, 628, 630, 675, 685, 686, 696, and 705) can improve treatment of the subject by, for example, changing the treatment regimen (e.g., changing the Trk inhibitor administered to the subject or adding an additional anticancer agent or anticancer therapy) or by administering a Trk inhibitor that is effective in the presence of a Trk inhibitor-resistant mutation (e.g., one or more of the compounds of Table 5, or a pharmaceutically acceptable salt thereof).

Provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and administering to the identified subject a treatment that does not include a first Trk inhibitor as a monotherapy.

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and administering to the identified subject a treatment that includes one or more compounds of Table 5, or a pharmaceutically acceptable salt thereof.

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and administering to the identified subject a treatment that includes one or more compounds of Table 5, or a pharmaceutically acceptable salt thereof, and another anticancer agent or anticancer therapy.

Also provided herein are methods of treating a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3) that include: administering to the subject a treatment that does not include a first Trk inhibitor as a monotherapy.

Also provided herein are methods of treating a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3) that include administering to the subject a treatment that includes one or more compounds of Table 5, or a pharmaceutically acceptable salt thereof.

Also provided herein are methods of treating a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3) that include administering to the subject a treatment that includes one or more compounds of Table 5, or a pharmaceutically acceptable salt thereof, and another anticancer agent or anticancer therapy.

Also provided herein are methods of treating a subject that include administering a therapeutically effective amount of a treatment that does not include a first Trk inhibitor as a monotherapy, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject that include administering a therapeutically effective amount of a treatment that includes one or more compounds of Table 5, or a pharmaceutically acceptable salt thereof, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject that include administering a therapeutically effective amount of a treatment that includes one or more compounds of Table 5, or a pharmaceutically acceptable salt thereof, and another anticancer agent or anticancer therapy, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering a second Trk inhibitor or a treatment that does not include the first Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering a treatment including one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) administering one or more doses of a first Trk inhibitor to the subject for a period of time; (b) after (a), determining whether a cancer cell in a sample obtained from the subject has (i) at least one point mutation in a NTRK gene that results in the expression of a Trk protein including a mutation at one or more amino acid positions (e.g., a mutation at one or more of the amino acid positions shown in Tables 1, 2, or 3); and (c) administering a treatment including one or more compounds of Table 5, or a pharmaceutically acceptable salt thereof, and another anticancer agent or anticancer therapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer, that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more of the amino acid positions shown in Tables 1, 2, or 3); and (b) administering a second Trk inhibitor or a treatment that does not include the first Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Some embodiments of these methods include administering a second Trk inhibitor or a treatment that does not include the first Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3). Some embodiments of these methods include administering additional doses of the first Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more of the amino acid positions shown in Tables 1, 2, or 3); (b) administering a treatment that includes one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer, that include: (a) determining whether a cancer cell in a sample obtained from a subject having a cancer and previously administered one or more doses of a first Trk inhibitor, has at least one point mutation in a NTRK gene that results in the expression of a Trk protein including a mutation at one or more amino acid positions (e.g., a mutation at one or more of the amino acid positions shown in Tables 1, 2, or 3); (b) administering a treatment that includes one or more compounds of Table 5, or a pharmaceutically acceptable salt thereof, and another anticancer agent or anticancer therapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting a treatment that does not include a first Trk inhibitor as a monotherapy for the identified subject.

Also provided herein are methods of selecting a treatment for a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting a treatment that includes one or more compounds of Table 5, or a pharmaceutically acceptable salt thereof, for the identified subject.

Also provided herein are methods of selecting a treatment for a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting a treatment that includes one or more compounds of Table 5, or a pharmaceutically acceptable salt thereof, and another anticancer agent or anticancer therapy for the identified subject.

Also provided herein are methods of selecting a treatment for a subject having a cancer that include: selecting a treatment that does not include a first Trk inhibitor as a monotherapy for a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer that include: selecting a treatment that includes one or more compounds of Table 5, or a pharmaceutically acceptable salt thereof, for a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer that include: selecting a treatment that includes one or more compounds of Table 5, or a pharmaceutically acceptable salt thereof, and another anticancer agent or anticancer therapy for a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a subject having a cancer for a treatment that does not include a first Trk inhibitor as a monotherapy, that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting the identified subject for a treatment that does not include a first Trk inhibitor as a monotherapy.

Also provided herein are methods of selecting a subject having a cancer for a treatment that includes one or more compounds of Table 5, or a pharmaceutically acceptable salt thereof, that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting the identified subject for a treatment that includes one or more compounds of Table 5, or a pharmaceutically acceptable salt thereof.

Also provided herein are methods of selecting a subject having a cancer for a treatment that includes one or more compounds of Table 5, or a pharmaceutically acceptable salt thereof, and another anticancer agent or anticancer therapy that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting the identified subject for a treatment that includes one or more compounds of Table 5, or a pharmaceutically acceptable salt thereof, and another anticancer agent or anticancer therapy.

Also provided herein are methods of selecting a subject having a cancer for a treatment that does not include a first Trk inhibitor as a monotherapy, that include: selecting a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3), for a treatment that does not include a first Trk inhibitor as a monotherapy.

Also provided herein are methods of selecting a subject having a cancer for a treatment that includes one or more compounds of Table 5, or a pharmaceutically acceptable salt thereof, that include: selecting a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3), for a treatment that includes one or more compounds of Table 5, or a pharmaceutically acceptable salt thereof.

Also provided herein are methods of selecting a subject having a cancer for a treatment that includes one or more compounds of Table 5, or a pharmaceutically acceptable salt thereof, and another anticancer agent or anticancer therapy that include: selecting a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and selecting the identified subject for a treatment that includes one or more compounds of Table 5, or a pharmaceutically acceptable salt thereof, and another anticancer agent or anticancer therapy.

Some embodiments of these methods further include administering the selected treatment to the identified subject.

Some embodiments of these methods further include recording the selected treatment in the identified subject's clinical record (e.g., a computer readable medium). For example, recording that the subject is selected for a treatment that includes one or more compounds of Table 5, or a pharmaceutically acceptable salt thereof. In some embodiments, these methods further include recording that the subject is selected for a treatment that includes one or more compounds of Table 5, or a pharmaceutically acceptable salt thereof, and another anticancer agent or anticancer therapy in the subject's clinical record (e.g., a computer readable medium). In some embodiments, these methods further include recording that the subject is selected for a treatment that does not include a first Trk inhibitor as a monotherapy in the subject's clinical record (e.g., a computer readable medium).

Also provided herein are methods of determining the likelihood that a subject having a cancer will have a positive response to treatment with a first Trk inhibitor as a monotherapy, that include: determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3) has a decreased likelihood of having a positive response to treatment with a first Trk inhibitor as a monotherapy.

Also provided herein are methods of determining the likelihood that a subject having a cancer will have a positive response to treatment that includes one or more compounds of Table 5, or a pharmaceutically acceptable salt thereof, that include: determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3) has an increased likelihood of having a positive response to treatment that includes one or more compounds of Table 5, or a pharmaceutically acceptable salt thereof.

Also provided herein are methods of determining the likelihood that a subject having cancer will have a positive response to treatment with a first Trk inhibitor as a monotherapy, that include: determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3) has a decreased likelihood of having a positive response to treatment with a first Trk inhibitor as a monotherapy.

Also provided herein are methods of determining the likelihood that a subject having cancer will have a positive response to treatment that includes one or more compounds of Table 5, or a pharmaceutically acceptable salt thereof, that include: determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3), has an increased likelihood of having a positive response to treatment including one or more compounds of Table 5, or a pharmaceutically acceptable salt thereof.

Some embodiments of these methods further include: administering a treatment not including a first Trk inhibitor as a monotherapy to the subject determined to have a decreased likelihood of having a positive response to treatment with a first Trk inhibitor as a monotherapy. Some embodiments of these methods further include: administering a treatment including one or more compounds of Table 5, or a pharmaceutically acceptable salt thereof, to the subject determined to have an increased likelihood of having a positive response to treatment including one or more compounds of Table 5, or a pharmaceutically acceptable salt thereof.

Also provided herein are methods of predicting the efficacy of treatment with a first Trk inhibitor as a monotherapy in a subject having cancer, that include: determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and determining that treatment with a first Trk inhibitor as a monotherapy is less likely to be effective in a subject having a cancer cell in a sample obtained from the subject that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of predicting the efficacy of treatment with a treatment including one or more compounds of Table 5, or a pharmaceutically acceptable salt thereof, in a subject having cancer, that include: determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and determining that treatment including one or more compounds of Table 5, or a pharmaceutically acceptable salt thereof, is more likely to be effective in a subject having a cancer cell in a sample obtained from the subject that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of predicting the efficacy of treatment with a first Trk inhibitor as a monotherapy in a subject having cancer, that include: determining that treatment with a first Trk inhibitor as a monotherapy is less likely to be effective in a subject having a cancer cell in a sample obtained from the subject that has at least one point mutation in a NTRK gene that results in the expression of a Trk protein including a mutation at one or more amino acid positions (e.g., a mutation at one or more of the amino acid positions shown in Tables 1, 2, or 3). Some embodiments of these methods further include administering a treatment not including a first Trk inhibitor as a monotherapy to the subject.

Also provided herein are methods of predicting the efficacy of treatment including one or more compounds of Table 5, or a pharmaceutically acceptable salt thereof, in a subject having cancer, that include: determining that treatment including one or more compounds of Table 5, or a pharmaceutically acceptable salt thereof, is more likely to be effective in a subject having a cancer cell in a sample obtained from the subject that has at least one point mutation in a NTRK gene that results in the expression of a Trk protein including a mutation at one or more amino acid positions (e.g., a mutation at one or more of the amino acid positions shown in Tables 1, 2, or 3). Some embodiments of these methods further include administering one or more compound of Table 5, or a pharmaceutically acceptable salt thereof, to the subject.

Also provided herein are methods of selecting a treatment for a subject having a cancer that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) selecting a second Trk inhibitor or a treatment that does not include the first Trk inhibitor of step (a) as a monotherapy for a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) selecting additional doses of the first Trk inhibitor of step (a) for a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) selecting a treatment including one or more compounds of Table 5, or a pharmaceutically acceptable salt thereof, for a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) selecting additional doses of the first Trk inhibitor for a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) selecting a treatment including one or more compounds of Table 5, or a pharmaceutically acceptable salt thereof, and another anticancer agent or anticancer therapy for a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) selecting additional doses of the first Trk inhibitor for a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer that includes: (a) determining whether a cancer cell in a sample obtained from a subject having a cancer and previously administered one or more doses of a first Trk inhibitor, has at least one point mutation in a NTRK gene that results in the expression of a Trk protein including a mutation at one or more amino acid positions (e.g., a mutation at one or more of the amino acid positions shown in Tables 1, 2, or 3); (b) selecting a second Trk inhibitor or a treatment that does not include the first Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) selecting additional doses of the first Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Some embodiments of these methods include selecting a second Trk inhibitor or a treatment that does not include the first Trk inhibitor of step (a) as a monotherapy for a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3). Some embodiments of these methods include selecting additional doses of the first Trk inhibitor of step (a) for a subject having a cancer cell that does not have (at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer, that include: (a) determining whether a cancer cell in a sample obtained from a subject having a cancer and previously administered one or more doses of a first Trk inhibitor, has at least one point mutation in a NTRK gene that results in the expression of a Trk protein including a mutation at one or more amino acid positions (e.g., a mutation at one or more of the amino acid positions shown in Tables 1, 2, or 3); (b) selecting a treatment that includes one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) selecting additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of selecting a treatment for a subject having a cancer, that include: (a) determining whether a cancer cell in a sample obtained from a subject having a cancer and previously administered one or more doses of a first Trk inhibitor, has at least one point mutation in a NTRK gene that results in the expression of a Trk protein including a mutation at one or more amino acid positions (e.g., a mutation at one or more of the amino acid positions shown in Tables 1, 2, or 3); (b) selecting a treatment that includes one or more compounds of Table 5, or a pharmaceutically acceptable salt thereof, and another anticancer agent or anticancer therapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) selecting additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Some embodiments of any of the methods described herein further include recording the selected treatment in the subject's clinical record (e.g., a computer readable medium). Some embodiments of any of the methods described herein further include administering selected treatment to the subject.

In some embodiments of any of the methods described herein, the subject is previously identified or diagnosed as having the cancer.

In some embodiments of the methods described herein, the treatment that does not include a first Trk inhibitor as a monotherapy is selected from a treatment that includes one or more of: surgery, radiation therapy, chemotherapy, immunotherapy, hormone therapy, small molecule drugs targeting other kinases in a Trk-signaling pathway, recombinant antibodies, and stem cell transplant. In some embodiments of the methods described herein, the treatment that does not include a first Trk inhibitor as a monotherapy includes: one or more of surgery, radiation therapy, chemotherapy, immunotherapy, hormone therapy, small molecule drugs targeting other kinases in a Trk-signaling pathway, recombinant antibodies, and stem cell transplant; and one or more Trk inhibitors. In some embodiments of the methods described herein, the treatment that does not include a first Trk inhibitor as a monotherapy includes one or more compounds of Table 5, or a pharmaceutically acceptable salt thereof, as a monotherapy.

Also provided herein are methods of determining a subject's risk for developing a Trk inhibitor-resistant cancer that include: determining whether a cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and identifying a subject having a cell that has at least one point mutation in a NTRK gene that results in the expression of a Trk protein including a mutation at one or more amino acid positions (e.g., a mutation at one or more of the amino acid positions shown in Tables 1, 2, or 3), as having an increased likelihood of developing a Trk inhibitor-resistant cancer. Also provided herein are methods of determining a subject's risk for developing a Trk inhibitor-resistant cancer that include: identifying a subject having a cell that has at least one point mutation in a NTRK gene that results in the expression of a Trk protein including a mutation at one or more amino acid positions (e.g., a mutation at one or more of the amino acid positions shown in Tables 1, 2, or 3), as having an increased likelihood of developing a Trk inhibitor-resistant cancer. Some embodiments of these methods further include confirming a diagnosis of a Trk inhibitor-resistant cancer in a subject determined to have an increased likelihood of developing a Trk inhibitor-resistant cancer.

Also provided herein are methods of determining the presence of a Trk inhibitor-resistant cancer in a subject that include: determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3), has an a Trk inhibitor-resistant cancer. Also provided herein are methods of determining the presence of a Trk inhibitor-resistant cancer in a subject that include: determining that a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3).

In some embodiments of any of the methods described herein, the first Trk inhibitor (e.g., the first Trk inhibitor in step (a)) is selected from the group consisting of: entrectinib (N-[5-(3,5-difluoro-benzyl)-1H-indazol-3-yl]-4-(4-methyl-piperazin-1-yl)-2-(tetrahydro-pyran-4-ylamino)-benzamide); (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; cabozantinib ((N-(4-((6,7-Dimethoxyquinolin-4-yl)oxy)phenyl)-N-(4-fluorophenyl) cyclopropane-1,1-dicarboxamide)); dovatinib (4-amino-5-fluoro-3-[6-(4-methylpiperazin-1-yl)-1H-benzimidazol-2-yl]quinolin-2(1H)-one mono 2-hydroxypropanoate hydrate); belizatinib (4-fluoro-N-(6-((4-(2-hydroxypropan-2-yl)piperidin-1-yl)methyl)-1-((1s,4s)-4-(isopropylcarbamoyl)cyclohexyl)-1H-benzo[d]imidazol-2-yl)benzamide); sitravatinib (N-(3-fluoro-4-((2-(5-(((2-methoxyethyl) amino)methyppyridin-2-yl)thieno[3,2-b]pyridin-7-yl)oxy) phenyl)-N-(4-fluorophenyl)cyclopropane-1,1-dicarboxamide); PLX7486; altiratinib (N-(4-((2-(cyclopropanecarboxamido)pyridin-4-yl)oxy)-2,5-difluorophenyl)-N-(4-fluorophenyl)cyclopropane-1,1-dicarboxamide); AZD7451 ((S)—N-(1-(5-fluoropyrimidin-2-yl)ethyl)-3-(5-isopropoxy-1H-pyrazol-3-yl)-3H-imidazo [4,5-b]pyridin-5-amine). In some embodiments, the first Trk inhibitor (e.g., the first Trk inhibitor in step (a)) is entrectinib. In some embodiments, the first Trk inhibitor (e.g., the first Trk inhibitor in step (a)) is the compound of Formula I:

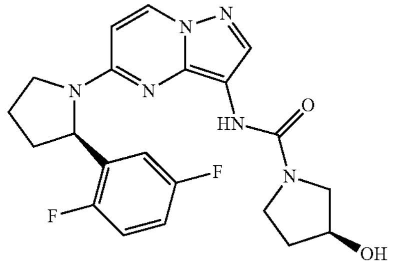 [SMILES: O=C(Nc1cnn2ccc(N3CCC[C@@H]3c3cc(F)ccc3F)nc12)N1CC[C@H](O)C1]

or a hydrogen sulfate salt thereof. In some embodiments, the first Trk inhibitor (e.g., the first Trk inhibitor in step (a)) is a crystalline form of the compound of Formula I or a hydrogen sulfate salt thereof (e.g., a compound of Formula I-HS).

In some embodiments of any of the methods described herein, the second Trk inhibitor is selected from the group consisting of: a (R)-2-phenylpyrrolidine substituted imadazopyridazine, AZD6918, GNF-4256, GTx-186, GNF-5837, AZ623, AG-879, altiratinib, CT327, ARRY-470, AR-772, AR-523, AR-786, AR-256, AR-618, AZ-23, AZD7451, cabozantinib, CEP-701, CEP-751, PHA-739358, dovitinib, entrectinib (N-[5-(3,5-difluoro-benzyl)-1H-indazol-3-yl]-4-(4-methylpiperazin-1-yl)-2-(tetrahydro-pyran-4-ylamino)-benzamide), PLX7486, Gö 6976, GW441756, MGCD516, ONO-5390556, PHA-848125AC, regorafenib, sorafenib, sunitinib, TSR-011, VM-902A, K252a, a 4-aminopyrazolylpyrimidine, and a substituted pyrazolo[1,5-a] pyrimidine compound. In some embodiments of any of the methods described herein, the second Trk inhibitor is selected from the compounds of Table 5, or a pharmaceutically acceptable salt thereof.

In some embodiments of any of the methods described herein, the subject is suspected of having a cancer. In some embodiments of any of the methods described herein, the subject has one or more symptoms of cancer. In some embodiments of any of the methods described herein, the subject is previously identified or diagnosed as having a cancer.

In some embodiments of any of the methods described herein, the step of determining whether a cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3), comprises performing an assay to determine the presence of the at least one point mutation in a NTRK1 gene and/or a NTRK2 gene and/or a NTRK3 gene in a cell in the sample. In some embodiments of any of the methods described herein, the step of determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3), comprises performing an assay to determine the presence of the at least one point mutation in a NTRK1 gene and/or a NTRK2 gene and/or a NTRK3 gene in a cancer cell in the sample. In some embodiments of any of the methods described herein, the assay is selected from the group consisting of: denaturing gradient gel electrophoresis (DGGE), temperature gradient gel electrophoresis (TGGE), temperature gradient capillary electrophoresis, a single strand conformational polymorphism assay, a molecular beacon assay, a dynamic hybridization assay, a PCR-based assay, denaturing high performance liquid chromatography. In some embodiments of any of the methods described herein, the assay includes sequencing a segment of the NTRK1 gene and/or the NTRK2 gene and/or the NTRK3 gene including the at least one point mutation.

In some embodiments of any of the methods described herein, the cancer is selected from the group consisting of: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

In some of embodiments of any of the methods described herein, the at least one point mutation in a NTRK gene that results in the expression of a Trk protein including a mutation at one or more amino acid positions can be selected from (i) at least one point mutation in a NTRK1 gene that results in the expression of a TrkA protein including a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB protein including a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC protein including a mutation at one or more amino acid position(s) selected from the group consisting of: 545, 570, 596, 601, 617, 623, 624, 628, 630, 675, 685, 686, 696, and 705. In some embodiments of any of the methods described herein, the TrkA protein includes one or more of the following amino acid substitutions: G517R, A542V, V573M, F589L, F589C, G595S, G595R, D596V, F600L, F646V, C656Y, C656F, L657V, G667S, G667C, and Y676S. In some embodiments of any of the methods described herein, the TrkB protein includes one or more of the following amino acid substitutions: G545R, A570V, Q596E, Q596P, V601G, F617L, F617C, F617I, G623S, G623R, D624V, R630K, C682Y, C682F, L683V, G693S, and G713S. In some embodiments of any of the methods described herein, the TrkC protein includes one or more of the following amino acid substitutions: G545R, A570V, F617L, G623R, D624V, C685Y, C685F, L686V, and G696A.

Also provided are kits that include: one or more probes that each specifically hybridize to a segment of a NTRK1 gene that encodes a mutation at one of amino acid positions 517, 542, 568, 573, 589, 595, 599, 600, 602, 646, 656, 657, 667, and 676 in TrkA protein; and/or one or more probes that each specifically hybridize to a segment of a NTRK2 gene that encodes a mutation at one of amino acid positions 545, 570, 596, 601, 617, 623, 624, 628, 630, 672, 682, 683, 693, and 702 in TrkB protein; and/or one or more probes that each specifically hybridize to a segment of a NTRK3 gene that encodes a mutation at one or amino acid positions 545, 570, 596, 601, 617, 623, 624, 628, 630, 675, 685, 686, 696, and 705 in TrkC protein. Some embodiments of these kits include: one or more probes that each specifically hybridize to a segment of a NTRK1 gene that encodes a mutation selected from the group consisting of: G517R, A542V, V573M, F589L, F589C, G595S, G595R, D596V, F600L, F646V, C656Y, C656F, L657V, G667S, G667C, and Y676S in TrkA protein; and/or one or more probes that each specifically hybridize to a segment of a NTRK2 gene that encodes a mutation selected from the group consisting of: G545R, A570V, Q596E, Q596P, V601G, F617L, F617C, F617I, G623S, G623R, D624V, R630K, C682Y, C682F, L683V, G693S, and G713S in TrkB protein; and/or one or more probes that each specifically hybridize to a segment of a NTRK3 gene that encodes a mutation selected from the group consisting of: G545R, A570V, F617L, G623R, D624V, C685Y, C685F, L686V, and G696A in TrkC protein. In some embodiments of any of the kits described herein, the one or more probes are labeled with a detectable probe. In some embodiments of any of the kits described herein, the one or more probes are covalently attached to a substrate (e.g., a film, a plate, or a bead).

As used herein, the word "a" before a noun represents one or more of the particular noun. For example, the phrase "a cell" represents "one or more cells."

The term "subject" means a vertebrate, including any member of the class mammalia, including humans, sports or pet animals, such as horse (e.g., race horse) or dog (e.g., race dogs), and higher primates. In some embodiments, the subject is a human.

The term "treating" or "positive response to treatment" means an improvement in the condition of a subject having a cancer, e.g., one or more of a decrease in the size of one or more tumor(s) in a subject, a decrease or no substantial change in the growth rate of one or more tumor(s) in a subject, a decrease in metastasis in a subject, and an increase in the period of remission for a subject (e.g., as compared to the one or more metric(s) in a subject having a similar cancer receiving no treatment or a different treatment, or as compared to the one or more metric(s) in the same subject prior to treatment). Additional metrics for assessing response to a treatment in a subject having a cancer are known in the art.

The term "point mutation" means a change in the nucleotide sequence of a gene that results in a single amino acid change in a protein encoded by the gene. For example, a point mutation in a gene can result in the deletion of a single amino acid in a protein encoded by the gene or can result in the substitution of an amino acid in a wildtype version of the encoded protein with a different amino acid. Non-limiting examples of point mutations in a NTRK1 genes, NTRK2 genes, and NTRK3 genes are described herein.

The phrase "significant level of carcinogen" is meant a level of exposure to a carcinogen that is known to increase (e.g., a statistically significant increase) the likelihood of a subject to develop a cancer (e.g., as compared to a subject that has not been exposed to the same level of exposure or has been exposed to a non-detectable amount of the carcinogen).

As used herein, a "first Trk kinase inhibitor" or "first Trk inhibitor" is a Trk inhibitor as described herein but does not include compounds of Table 5, or a pharmaceutically acceptable salt thereof, as defined herein. As used herein, a "second Trk kinase inhibitor" or a "second Trk inhibitor" is a Trk inhibitor as described herein and includes the compounds of Table 5, or a pharmaceutically acceptable salt thereof, as described herein. When both a first and a second Trk inhibitor are present in a method provided herein, the first and second Trk kinase inhibitors are different.

The term "monotherapy" means the use of a single drug to treat a particular disorder or disease.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 9A is a graph representing the frequency of mutations and the dose of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A) they were isolated from.

FIG. 12 is a table showing the $IC_{50}$ of certain TrkA and TrkB mutations that were identified.

FIG. 13 is an alignment of kinase domains from selected oncogenes with known resistance mutations. In vitro- (green) or patient-derived (yellow) resistance mutations are shown for other drug-targeted kinases for comparison.

DETAILED DESCRIPTION

Figure 1:
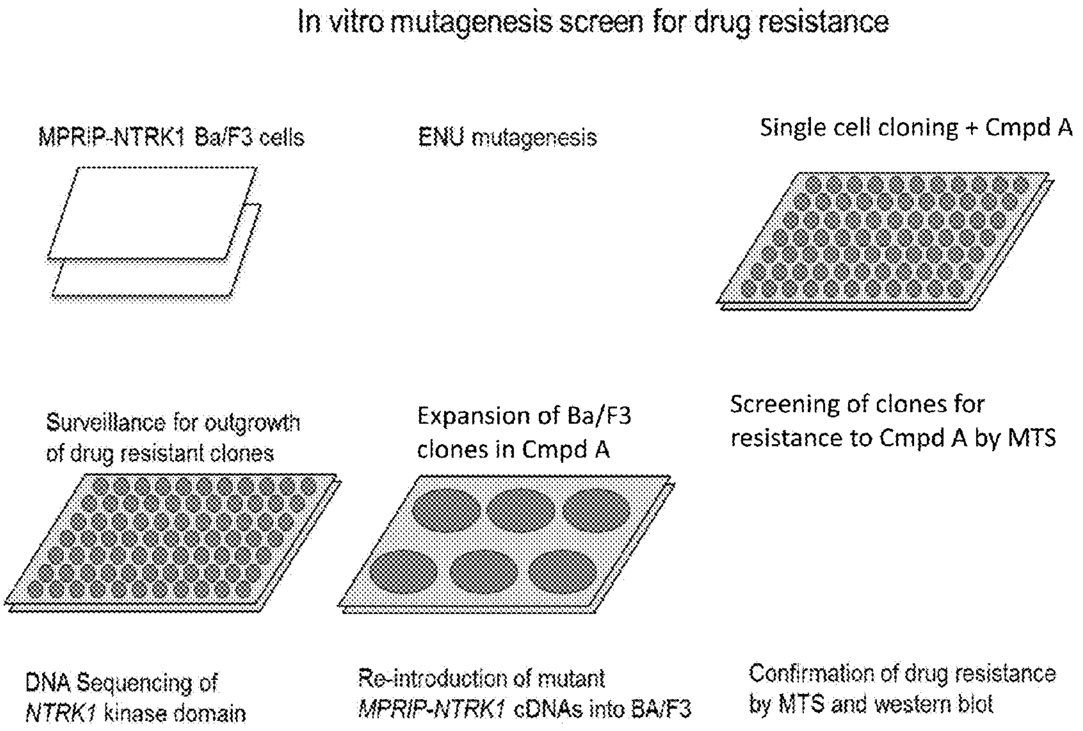
FIG. 1 is a flow chart of the experimental methods used in Example 1.

Trk inhibitor-resistance mutations in a NTRK1 gene, a NTRK2 gene, and a NTRK3 gene were discovered. In view of this discovery, provided herein are methods of treating a subject having a cancer, methods of selecting a treatment for a subject having a cancer, methods of selecting a subject having a cancer for a treatment that does not include a Trk inhibitor, methods of determining the likelihood that a subject having a cancer will have a positive response to a treatment with a Trk inhibitor, methods of predicting the efficacy of a Trk inhibitor in a subject having cancer, methods of determining a subject's risk for developing a Trk inhibitor-resistant cancer, and methods of determining the presence of a Trk inhibitor-resistant cancer in a subject, based on a determination as to whether the subject has a cell that has (i) at least one point mutation in a NTRK1 gene that results in the expression of a TrkA protein including a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB protein including a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC protein including a mutation at one or more amino acid position(s) selected from the group consisting of: 545, 570, 596, 601, 617, 623, 624, 628, 630, 675, 685, 686, 696, and 705. Also provided are kits that allow for the detection of at least one of the point mutations in NTRK1 and/or NTRK2 and/or NTRK3.

Detection and identification of a subject having cells having a Trk inhibitor-resistant mutation as described herein (e.g., (i) at least one point mutation in a NTRK1 gene that results in the expression of a TrkA protein comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB protein comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC protein comprising a mutation at one or more amino acid position(s) selected from the group consisting of: 545, 570, 596, 601, 617, 623, 624, 628, 630, 675, 685, 686, 696, and 705) can improve treatment of the subject by, for example, changing the treatment regimen (e.g., changing the Trk inhibitor administered to the subject or adding an additional anticancer agent or anticancer therapy) or by administering a Trk inhibitor that is effective in the presence of a Trk inhibitor-resistant mutation (e.g., one or more of the compounds of Table 5, or a pharmaceutically acceptable salt thereof).

As can be appreciated in the art, the various aspects described below can be used in any combination without limitation.

Tropomyosin Receptor Kinases (Trks)

Three different NTRK genes have been implicated as having a role in cancer (e.g., through discovery of chromosome translocations resulting in constitutively active Trk fusion proteins): NTRK1, NTRK2, and NTRK3. The NTRK1, NTRK2, and NTRK3 genes encode TrkA, TrkB, and TrkC, respectively.

Non-limiting exemplary amino acid and cDNA sequences for wildtype TrkA are provided below. The exemplary wildtype protein and cDNA sequences provided below can be used to identify a point mutation in a NTRK1 gene or can be used to determine mutation in a TrkA protein caused by a point mutation in a NTRK1 gene, respectively. Additional wildtype protein and cDNA sequences for TrkA are known in the art.

The amino acid positions used to describe the TrkA substitutions herein are based on the wildtype sequence of TrkA of SEQ ID NO: 1. The corresponding amino acid position in the wildtype sequence of another isoform of TrkA (SEQ ID NO: 3) can be identified by performing a sequence alignment between SEQ ID NO: 1 and SEQ ID NO: 3. A similar method (e.g., alignment of SEQ ID NO: 1 to the amino acid sequence of any other isoform of TrkA) can be used to match the amino acid positions of the substitutions in TrkA described herein to the corresponding amino acid position in other isoforms of TrkA known in the art.

Wildtype Human TrkA Protein Isoform A (NP_002520) (SEQ ID NO: 1)

Wildtype Human TrkA cDNA Isoform A (NM_002529) (SEQ ID NO: 2)

Wildtype Human TrkA Protein Isoform B (NP_001007793) (SEQ ID NO: 3)

Wildtype Human TrkA cDNA Isoform B (NM_001007792) (SEQ ID NO: 4)

Alignment of TrkA isoforms (SEQ ID NO: 1 and SEQ ID NO: 3)

```
S1     68  LTELYIENQQHLQHLELRDLRGLGELRNLTIVKSGLRFVAPDAFHFTPRLSRLNLSGNAL 127
           L   YIENQQHLQHLELRDLRGLGELRNLTIVKSGLRFVAPDAFHFTPRLSRLNLSGNAL
S3     38  LAASYIENQQHLQHLELRDLRGLGELRNLTIVKSGLRFVAPDAFHFTPRLSRLNLSGNAL  97
```

-continued

Alignment of TrkA isoforms (SEQ ID NO: 1 and SEQ ID NO: 3)

```
S1    128 ESLSWKTVQGLSLQELVLSGNPLHCSCALRWLQRWEEEGLGGVPEQKLQCHGQGPLAHMP 187
          ESLSWKTVQGLSLQELVLSGNPLHCSCALRWLQRWEEEGLGGVPEQKLQCHGQGPLAHMP
S3     98 ESLSWKTVQGLSLQELVLSGNPLHCSCALRWLQRWEEEGLGGVPEQKLQCHGQGPLAHMP 157

S1    188 NASCGVPTLKVQVPNASVDVGDDVLLRCQVEGRGLEQAGWILTELEQSATVMKSGGLPSL 247
          NASCGVPTLKVQVPNASVDVGDDVLLRCQVEGRGLEQAGWILTELEQSATVMKSGGLPSL
S3    158 NASCGVPTLKVQVPNASVDVGDDVLLRCQVEGRGLEQAGWILTELEQSATVMKSGGLPSL 217

S1    248 GLTLANVTSDLNRKNVTCWAENDVGRAEVSVQVNVSFPASVQLHTAVEMHHWCIPFSVDG 307
          GLTLANVTSDLNRKNVTCWAENDVGRAEVSVQVNVSFPASVQLHTAVEMHHWCIPFSVDG
S3    218 GLTLANVTSDLNRKNVTCWAENDVGRAEVSVQVNVSFPASVQLHTAVEMHHWCIPFSVDG 277

S1    308 QPAPSLRWLFNGSVLNETSFIFTEFLEPAANETVRHGCLRLNQPTHVNNGNYTLLAANPF 367
          QPAPSLRWLFNGSVLNETSFIFTEFLEPAANETVRHGCLRLNQPTHVNNGNYTLLAANPF
S3    278 QPAPSLRWLFNGSVLNETSFIFTEFLEPAANETVRHGCLRLNQPTHVNNGNYTLLAANPF 337

S1    368 GQASASIMAAFMDNPFEFNPEDPIPVSFSPVDTNSTSGDPVEKKDETPFGVSVAVGLAVF 427
          GQASASIMAAFMDNPFEFNPEDPIP      DTNSTSGDPVEKKDETPFGVSVAVGLAVF
S3    338 GQASASIMAAFMDNPFEFNPEDPIP------DTNSTSGDPVEKKDETPFGVSVAVGLAVF 391

S1    428 ACLFLSTLLLVLNKCGRRNKFGINRPAVLAPEDGLAMSLHFMTLGGSSLSPTEGKGSGLQ 487
          ACLFLSTLLLVLNKCGRRNKFGINRPAVLAPEDGLAMSLHFMTLGGSSLSPTEGKGSGLQ
S3    392 ACLFLSTLLLVLNKCGRRNKFGINRPAVLAPEDGLAMSLHFMTLGGSSLSPTEGKGSGLQ 451

S1    488 GHIIENPQYFSDACVHHIKRRDIVLKWELGEGAFGKVFLAECHNLLPEQDKMLVAVKALK 547
          GHIIENPQYFSDACVHHIKRRDIVLKWELGEGAFGKVFLAECHNLLPEQDKMLVAVKALK
S3    452 GHIIENPQYFSDACVHHIKRRDIVLKWELGEGAFGKVFLAECHNLLPEQDKMLVAVKALK 511

S1    548 EASESARQDFQREAELLTMLQHQHIVRFFGVCTEGRPLLMVFEYMRHGDLNRFLRSHGPD 607
          EASESARQDFQREAELLTMLQHQHIVRFFGVCTEGRPLLMVFEYMRHGDLNRFLRSHGPD
S3    512 EASESARQDFQREAELLTMLQHQHIVRFFGVCTEGRPLLMVFEYMRHGDLNRFLRSHGPD 571

S1    608 AKLLAGGEDVAPGPLGLGQLLAVASQVAAGMVYLAGLHFVHRDLATRNCLVGQGLVVKIG 667
          AKLLAGGEDVAPGPLGLGQLLAVASQVAAGMVYLAGLHFVHRDLATRNCLVGQGLVVKIG
S3    572 AKLLAGGEDVAPGPLGLGQLLAVASQVAAGMVYLAGLHFVHRDLATRNCLVGQGLVVKIG 631

S1    668 DFGMSRDIYSTDYYRVGGRTMLPIRWMPPESILYRKFTTESDVWSFGVVLWEIFTYGKQP 727
          DFGMSRDIYSTDYYRVGGRTMLPIRWMPPESILYRKFTTESDVWSFGVVLWEIFTYGKQP
S3    632 DFGMSRDIYSTDYYRVGGRTMLPIRWMPPESILYRKFTTESDVWSFGVVLWEIFTYGKQP 691

S1    728 WYQLSNTEAIDCITQGRELERPRACPPEVYAIMRGCWQREPQQRHSIKDVHARLQALAQA 787
          WYQLSNTEAIDCITQGRELERPRACPPEVYAIMRGCWQREPQQRHSIKDVHARLQALAQA
S3    692 WYQLSNTEAIDCITQGRELERPRACPPEVYAIMRGCWQREPQQRHSIKDVHARLQALAQA 751

S1    788 PPVYLDVLG                                                    796
          PPVYLDVLG
S3    752 PPVYLDVLG                                                    760
```

Non-limiting exemplary amino acid and cDNA sequences for wildtype TrkB are provided below. The exemplary wildtype protein and cDNA sequences provided below can be used to identify a point mutation in a NTRK2 gene or can be used to determine mutation in a TrkB protein caused by a point mutation in a NTRK2 gene, respectively. Additional wildtype protein and cDNA sequences for TrkB are known in the art.

The amino acid positions used to describe the TrkB substitutions herein are based on the wildtype sequence of TrkB of SEQ ID NO: 5. The corresponding amino acid position in the wildtype sequence of another isoform of TrkB can be identified by performing a sequence alignment between SEQ ID NO: 5 and the amino acid sequence of the other isoform of TrkB.

Wildtype Human TrkB Protein Isoform A (AAB33109.1) (SEQ ID NO: 5)

Wildtype Human TrkB cDNA Isoform A (S76473.1) (SEQ ID NO: 6)

Non-limiting exemplary amino acid and cDNA sequences for wildtype TrkC are provided below. The exemplary wildtype protein and cDNA sequences provided below can be used to identify a point mutation in a NTRK3 gene or can be used to determine mutation in a TrkC protein caused by a point mutation in a NTRK3 gene, respectively. Additional wildtype protein and cDNA sequences for TrkC are known in the art.

The amino acid positions used to describe the TrkC substitutions herein are based on the wildtype sequence of TrkC of SEQ ID NO: 7. The corresponding amino acid position in the wildtype sequence of another isoform of TrkC can be identified by performing a sequence alignment between SEQ ID NO: 7 and the amino acid sequence of the other isoform of TrkC.

Wildtype Human TrkC Protein (AAB33111.1) (SEQ ID NO: 7)

Wildtype Human TrkC cDNA (S76475.1) (SEQ ID NO: 8)

NTRK Point Mutations

Point mutations in a NTRK1 gene, a NTRK2 gene, and a NTRK3 gene were discovered in Trk inhibitor-resistant cancer cells. A point mutation in a NTRK1 gene can result in a TrkA protein that includes a substitution of an amino acid in a wildtype version of the TrkA protein with a different amino acid. In other examples, a point mutation in a NTRK1 gene can result in a TrkA protein with a deletion of an amino acid in a wildtype version of the TrkA protein. Exemplary Trk inhibitor-resistance point mutations in TrkA protein are listed in Table 1.

TABLE 1

| Exemplary Trk Inhibitor-Resistance Point Mutations in TrkA Protein |
|---|
| Amino acid position 517 (e.g., G517R) |
| Amino acid position 542 (e.g., A542V) |
| Amino acid position 568 (e.g., Q568x) |
| Amino acid position 573 (e.g., V573M) |
| Amino acid position 589 (e.g., F589L, F589C) |
| Amino acid position 595 (e.g., G595S, G595R[1]) |
| Amino acid position 599 (e.g., D596V) |
| Amino acid position 600 (e.g., F600L) |
| Amino acid position 602 (e.g., R602x) |
| Amino acid position 646 (e.g., F646V) |
| Amino acid position 656 (e.g., C656Y, C656F) |
| Amino acid position 657 (e.g., L657V) |
| Amino acid position 667 (e.g., G667C[1], G667S) |
| Amino acid position 676 (e.g., Y676S) |

The letter "x" when used to describe a mutation of an amino acid at a specific amino acid position means (i) a substitution of the amino acid present at the same amino acid position in the corresponding wildtype protein with a different naturally-occurring amino acid, or (ii) a deletion of the amino acid present at the same amino acid position in the corresponding wildtype protein.

A point mutation in a NTRK2 gene can result in a TrkB protein that includes a substitution of an amino acid in a wildtype version of the TrkB protein with a different amino acid. In other examples, a point mutation in a NTRK2 gene can result in a TrkB protein with a deletion of an amino acid in a wildtype version of the TrkB protein. Exemplary Trk inhibitor-resistance point mutations in TrkB protein are listed in Table 2.

TABLE 2

| Exemplary Trk Inhibitor-Resistance Point Mutations in TrkB Protein |
|---|
| Amino acid position 545 (e.g., G545R) |
| Amino acid position 570 (e.g., A570V) |
| Amino acid position 596 (e.g., Q596E, Q596P) |
| Amino acid position 601 (e.g., V601G) |
| Amino acid position 617 (e.g., F617L, F617C, F617I) |
| Amino acid position 623 (e.g., G623S, G623R) |
| Amino acid position 624 (e.g., D624V) |
| Amino acid position 628 (e.g., F628x) |
| Amino acid position 630 (e.g., R630K) |
| Amino acid position 672 (e.g., F672x) |
| Amino acid position 682 (e.g., C682Y, C682F) |
| Amino acid position 683 (e.g., L683V) |
| Amino acid position 693 (e.g., G693S) |
| Amino acid position 702 (e.g., Y702x) |

The letter "x" when used to describe a mutation of an amino acid at a specific amino acid position means (i) a substitution of the amino acid present at the same amino acid position in the corresponding wildtype protein with a different naturally-occurring amino acid, or (ii) a deletion of the amino acid present at the same amino acid position in the corresponding wildtype protein.

A point mutation in a NTRK3 gene can result in a TrkC protein that includes a substitution of an amino acid in a wildtype version of the TrkC protein with a different amino acid. In other examples, a point mutation in a NTRK3 gene can result in a TrkC protein with a deletion of an amino acid in a wildtype version of the TrkC protein. Exemplary Trk inhibitor-resistance NTRK3 mutations are listed in Table 3.

TABLE 3

| Exemplary Trk Inhibitor-Resistance Point Mutations in TrkC Protein |
|---|
| Amino acid position 545 (e.g., G545R) |
| Amino acid position 570 (e.g., A570V) |
| Amino acid position 596 (e.g., Q596x) |
| Amino acid position 601 (e.g., V601) |
| Amino acid position 617 (e.g., F617x) F617L |
| Amino acid position 623 (e.g., G623R[1]) |
| Amino acid position 624 (e.g., D624V) |
| Amino acid position 628 (e.g., F628x) |
| Amino acid position 630 (e.g., R630x) |
| Amino acid position 675 (e.g., F675x) |
| Amino acid position 685 (e.g., C685Y, C684F) |
| Amino acid position 686 (e.g., L686V) |
| Amino acid position 696 (e.g., G696x) G696A |
| Amino acid position 705 (e.g., Y705x) |

The letter "x" when used to describe a mutation of an amino acid at a specific amino acid position means (i) a substitution of the amino acid present at the same amino acid position in the corresponding wildtype protein with a different naturally-occurring amino acid, or (ii) a deletion of the amino acid present at the same amino acid position in the corresponding wildtype protein.

Non-limiting examples of the specific amino acid positions discovered to have mutations (e.g., substitutions or deletions) in TrkA in Trk inhibitor-resistant cancer cells having a NTRK1 point mutation are listed below. Also listed below are the different specific amino acid mutations (e.g., substitutions) present in TrkA proteins present in Trk inhibitor-resistant cancer cells having a NTRK1 point mutation.

Trk inhibitor-resistant cancer cells were discovered to have point mutations in a NTRK1 gene that result in a TrkA protein that includes one or more (e.g., two, three, four, five, six, seven, eight, nine, ten, eleven, twelve, thirteen, fourteen, or fifteen) amino acid substitutions or deletions at amino acid positions: 517, 542, 568, 573, 589, 595, 599, 600, 602, 646, 656, 657, 667, and 676 (e.g., amino acid positions corresponding to those in wildtype sequence NP_002520 (SEQ ID NO: 1)). Different specific amino acid substitutions present in a TrkA protein generated in a Trk inhibitor-resistant cancer cell include one or more (e.g., two, three, four, five, six, seven, eight, nine, ten, eleven, or twelve) of the following: G517R, A542V, V573M, F589L, F589C, G595S, G595R, D596V, F600L, F646V, C656Y, C656F, L657V, G667S, G667C, and Y676S (e.g., as compared to the wildtype sequence NP_002520 (SEQ ID NO: 1)).

Trk inhibitor-resistant cancer cells were discovered to have point mutations in a NTRK2 gene that result in a TrkB protein that includes one or more (e.g., two, three, four, five, six, seven, eight, nine, ten, eleven, twelve, thirteen, fourteen, or fifteen) amino acid substitutions or deletions at amino acid positions: 545, 570, 596, 601, 617, 623, 624, 628, 630, 672, 682, 683, 693, and 702 (e.g., amino acid positions corresponding to those in wildtype sequence AAB33109.1 (SEQ ID NO: 5)). Different specific amino acid substitutions present in a TrkB protein generated in a Trk inhibitor-resistant cancer cell include one or more (e.g., two, three, four, five, six, seven, eight, nine, eleven, or twelve) of the following: G545R, A570V, Q596E, Q596P, V601G, F617L, F617C, F617I, G623S, G623R, D624V, R630K, C682Y, C682F, L683V, G693S, and G713S (e.g., as compared to the wildtype sequence AAB33109.1 (SEQ ID NO: 5)).

Trk inhibitor-resistant cancer cells were discovered to have point mutations in a NTRK3 gene that result in a TrkC protein that includes one or more (e.g., two, three, four, five, six, seven, eight, nine, ten, eleven, twelve, thirteen, fourteen, or fifteen) amino acid substitutions or deletions at amino acid positions: 545, 570, 596, 601, 617, 623, 624, 628, 630, 675, 685, 686, 696, and 705 (e.g., amino acid positions corresponding to those in a wildtype sequence (SEQ ID NO: 7)). Different specific amino acid substitutions present in a TrkC protein generated in a Trk inhibitor-resistant cancer cell include one or more (e.g., two, three, four, five, six, or seven, or eight) of the following: G545R, A570V, F617L, G623R, D624V, C685Y, C685F, L686V, and G696A (e.g., as compared to the wildtype sequence (SEQ ID NO: 7)).

As one skilled in the art can appreciate, the specific substitutions listed above are exemplary. For example, when a naturally-occurring amino acid at an amino acid position is substituted with a different amino acid, it is understood that an amino acid having a chemically-related amino acid side chain may also be substituted (and detected in a cancer cell). Amino acids that have chemically-related amino acid side chains are listed in Table 4.

TABLE 4

| Chemically Related Amino Acid Side Chains | |
|---|---|
| Positively-Charged Side Chains | Lysine, Arginine, Histidine |
| Negatively-Charged Side Chains | Glutamate and Aspartate |
| Nonpolar and/or Aliphatic Side Groups | Glycine, Alanine, Valine, Leucine, Isoleucine, and Proline |
| Polar, Uncharged Side Groups | Serine, Threonine, Cysteine, Methionine, Asparagine, Glutamine |
| Aromatic Side Chains | Phenylalanine, Tyrosine, and Tryptophan |

Any of the point mutations described herein may result in, e.g., increased catalytic activity of a TrkA kinase or a TrkB kinase or a TrkC kinase. Any of the point mutations described herein may result in, e.g., a decrease in the auto-inhibited conformation of a Trk kinase (e.g., a TrkA kinase or a TrkB kinase or a TrkC kinase). Any of the point mutations described herein may result in, e.g., an increase in the activated conformation of a Trk kinase (e.g., a TrkA kinase or a TrkB kinase or a TrkC kinase). Any of the point mutations described herein may result in, e.g., an altered tertiary structure of a TrkA kinase (as compared to a wildtype TrkA kinase) that decreases binding of a Trk inhibitor to the TrkA kinase, or an altered tertiary structure of a TrkB kinase (as compared to a wildtype TrkB kinase) that decreases binding of a Trk inhibitor to the TrkB kinase, or an altered tertiary structure of a TrkC kinase (as compared to a wildtype TrkC kinase) that decreases binding of a Trk inhibitor to the TrkC kinase. Any of the point mutations described herein may result in, e.g., an increase in the $K_{off}$ rate and/or a decrease in the $K_{on}$ rate of a Trk inhibitor when it interacts with the TrkA protein (as compared to a wildtype TrkA kinase) or the TrkB protein (as compared to a wildtype TrkB kinase) or the TrkC protein (as compared to a wildtype TrkC kinase).

Isolating Genomic DNA from a Biopsy Sample

Methods of isolating genomic DNA from biopsy sample are well known in the art. For example, a number of commercially available kits can be used to isolate genomic DNA from a sample containing mammalian cells (e.g., a biopsy sample). Non-limiting examples of commercially available kits for the isolation of genomic DNA from a sample containing mammalian cells include: ChargeSwitch® gDNA Tissue Kit (Life Technologies), Genomic DNA Isolation Kit (Norgen Biotek Corp., Ontario, Canada), QIAmp DNA FFPE (Qiagen), QIAsymphony DSP DNA kits (Qiagen), REPLI-g Mini Kit (Qiagen), Generation Capture Plate Kit (Qiagen), QI Amp 96 DNA Blood Kit (Qiagen), QIAmp DNA Mini kit (Qiagen), Biosprint 15 DNA Bloot Kit (Qiagen), Biosprint 96 DNA Blood Kit (Qiagen), MagAttract DNA Mini M48 Kit (Qiagen), QIAmp DNA Blood BioRobot 9604 Kit (Qiagen), QIAmp DNA Investigator Kit (Qiagen), QIAmp DNA Micro Kit, Xtreme DNA Isolation Kit (Isohelix; Harrietsham, Kent, UK), DDK DNA Isolation Kit (Isohelix), and XtraClean DNA kit (Isohelix). Genomic DNA can be isolated from a sample (e.g., a biopsy sample) using these and other commercially available genomic DNA isolation kits by following the manufacturer's instructions.

An exemplary method for isolating genomic DNA from a sample (e.g., a biopsy sample) include the steps of: lysing mammalian cells present in the sample, precipitating proteins in the lysate, removing the supernatant, precipitating genomic DNA out of the supernatant, washing the genomic DNA pellet with ethanol, and rehydrating the genomic DNA pellet in a pharmaceutically acceptable buffer (e.g., sterile or filtered water, or a buffered solution).

Assays for Determining the Presence of a Point Mutation

Some of the methods provided herein include a step of performing an assay to determine the presence of (i) at least one (e.g., two, three, four, five, five, six, seven, eight, nine, ten, eleven, twelve, thirteen, fourteen, or fifteen) point mutation in a NTRK1 gene (e.g., any of the point mutations in NTRK1 described herein), and/or (ii) at least one (e.g., two, three, four, five, six, seven, eight, nine, ten, eleven, twelve, thirteen, fourteen, or fifteen) point mutation in a NTRK2 gene, and/or (iii) at least one (e.g., two, three, four, five, six, seven, eight, nine, ten, eleven, twelve, thirteen, fourteen, or fifteen) point mutation in a NTRK3 gene (e.g., any of the point mutations in a NTRK3 gene described herein), in a cell (e.g., cancer cell) in a sample from the subject (e.g., a biopsy sample).

A variety of assays for determining the presence of one or more point mutations in a cell (e.g., a cancer cell) are known in the art. Non-limiting examples of such assays (which can be used in any of the methods described herein) include: denaturing gradient gel electrophoresis (DGGE) (Nollau et al., *Clin. Chem.* 43:1114-1128, 1997), temperature gradient gel electrophoresis (TGGE) (Nollau et al., *Clin. Chem.* 43:1114-1128, 1997), temperature gradient capillary electrophoresis, single strand conformational polymorphism assays (see, e.g., Tahira et al., *Human Mutat.* 26:69-77, 2005), molecular beacon assays (see, e.g., Totowa, N.J., Vol. 212, pp. 111-128, 2003), dynamic hybridization (see, e.g., Howell et al., *Nature Biotechnol.* 17:87-88, 1999), PCR-based assays (e.g., tetraprimer ARMS-PCR (see, e.g., Zhang et al., *Plos One* 8:e62126, 2013), real-time PCR, allele-specific PCR (see, e.g., Gaudet et al., *Methods Mol. Biol.* 578:415-424, 2009), and TaqMan Assay Genotyping (see, e.g., Woodward, *Methods Mol. Biol.* 1145:67-74, 2014, and TaqMan®OpenArray® Genotyping Plates from Life Technologies)), Flap endonuclease assays (also called Invader assays) (see, e.g., Olivier et al., *Mutat. Res.* 573:103-110, 2005), oligonucleotide ligation assays (see, e.g., Bruse et al., *Biotechniques* 45:559-571, 2008), or, denaturing high performance liquid chromatography (see, e.g., Yu et al., *J Clin. Pathol.* 58:479-485, 2005), high-resolution melting of an amplified sequence containing the point mutation (see, e.g., Wittwer et al., *Clinical Chemistry* 49:853-860, 2003), or sequencing (e.g., Maxam-Gilbert sequencing, chain-termination methods, shotgun sequencing, bridge PCR, and next-generation sequencing methods (e.g., massively parallel signature sequencing, polony sequencing, 454 pyrosequencing, Illumina (Solexa) sequencing, SOLiD sequencing, Ion Torrent semiconductor sequence, DNA nanoball sequencing, heliscope single molecule sequencing, and single molecule real-time sequencing)). Additional details and a summary of various next-generation sequencing methods are described in Koboldt et al., *Cell* 155:27-38, 2013.

In some embodiments, the assay used to determine the presence of the (i) at least one point mutation in NTRK1, and/or (ii) at least one point mutation in NTRK2, and/or (iii) at least one point mutation in a NTRK3, includes a PCR assay (e.g., a real-time PCR-assay, e.g., a real-time PCR-based genotyping assay) (with or without a prior pre-amplification step). In some embodiments of any of the methods described herein the assay used to determine the presence of (i) at least one point mutation in NTRK1, and/or (ii) at least one point mutation in NTRK2, and/or (iii) at least one point mutation in NTRK3, is performed using TaqMan®-based sequencing (e.g., TaqMan®-based OpenArray® sequencing, e.g., high throughput TaqMan®-based Open Array® sequencing) (with or without a prior pre-amplification step). Methods for designing primers for use in the assays described herein are well-known in the art. For example, several vendors provide free software for designing forward and reverse primers for use in any of the assays described herein. A forward or reverse primer for use in any of the assays described herein can contain at least 10 (e.g., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). In some examples, a forward or reverse primer used in any of the assays described herein can include a label (e.g., any of the exemplary labels described herein) or can include a contiguous tag sequence (e.g., between about 5 nucleotides and about 25 nucleotides, between about 10 nucleotides and about 25 nucleotides, between about 10 nucleotides and 20 nucleotides, between about 5 nucleotides and about 20 nucleotides) that does not hybridize to a sequence within the subject's genome (e.g., the human genome).

In some embodiments, the assay includes the use of: one or more probes (e.g., detectably labeled probes) that specifically hybridize to one or more segments of a NTRK1 gene that include a point mutation (e.g., any of the point mutations in NTRK1 described herein); and/or one or more probes (e.g., detectable labeled probes) that specifically hybridize to one or more segments of a NTRK2 gene that include a point mutation (e.g., any of the point mutations in NTRK2 described herein); and/or one or more probes (e.g., a detectable labeled probe) that specifically hybridizes to one or more segments of a NTRK3 gene that include a point mutation (e.g., any of the point mutations in NTRK3 described herein). For example, the one or more probes can have 9, 10, 11, 12, 13, 14, 15, 16, 17, 18, 19, 20, 21, 22, 23, 24, 25, 26, 27, 28, 29, 30, 31, 32, 33, 34, or 35 nucleotides. Additional description of the probes that can be used in exemplary assays are described herein.

Subjects

In various embodiments of the methods described herein, the subject can be previously identified or diagnosed as having a cancer (e.g., any of the cancers described herein). A subject can, e.g., be previously identified as having a cancer cell that has at least one point mutation in a NTRK gene that results in the expression of a Trk protein including a mutation at one or more amino acid positions. For example, (i) at least one (e.g., two, three, four, five, six, seven, eight, nine, ten, eleven, twelve, thirteen, fourteen, or fifteen) point mutation in a NTRK1 gene (e.g., any of the NTRK1 point mutations described herein), and/or (ii) at least one (e.g., two, three, four, five, six, seven, eight, nine, ten, eleven, twelve, thirteen, fourteen, or fifteen) point mutation in a NTRK2 gene (e.g., any of the NTRK2 point mutations described herein), and/or (iii) at least one (e.g., two, three, four, five, six, seven, eight, nine, ten, eleven, twelve, thirteen, fourteen, or fifteen) point mutation in a NTRK3 gene (e.g., any of the NTRK3 point mutations described herein). In some embodiments, a subject can be previously identified as having (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation (e.g., substitution) at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., a TrkA protein including one or more (e.g., two, three, four, five, six, seven, eight, nine, ten, eleven, or twelve) of G517R, A542V, V573M, F589L, F589C, G595S, G595R, D596V, F600L, F646V, C656Y, C656F, L657V, G667S, G667C, and Y676S); and/or (ii) at least one (e.g., two, three, four, five, six, seven, eight, nine, ten, eleven, twelve, thirteen, fourteen, or fifteen) point mutation in a NTRK2 gene that results in the expression of a TrkB including a mutation (e.g., substitution) at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 672, 682, 683, 693, and 702 (e.g., a TrkB protein including one or more (e.g., two, three, four, five, six, seven, eight, nine, ten, eleven, or twelve) of G545R, A570V, Q596E, Q596P, V601G, F617L, F617C, F617I, G623S, G623R, D624V, R630K, C682Y, C682F, L683V, G693S, and G713S; and/or (iii) at least one (e.g., two, three, four, five, six, seven, eight, nine, ten, eleven, twelve, thirteen, fourteen, or fifteen) point mutation in a NTRK3 gene that results in the expression of a TrkC protein comprising a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., a TrkC protein including one or more (e.g., two, three, four, five, six, seven, or eight) of G545R, A570V, F617L, G623R, D624V, C685Y, C685F, L686V, and G696A).

In the methods of determining a subject's risk of developing a Trk inhibitor-resistant cancer and the methods of determining the presence of a Trk inhibitor-resistant cancer in a subject, the subject can be an undiagnosed subject, the subject can be identified as having been exposed to a significant level of carcinogen(s), the subject can be suspected of having a cancer (e.g., any of the cancers described herein), the subject can present with one or more (e.g., two, three, four, or five) symptoms of cancer (e.g., any of the symptoms of cancer described herein), and/or the subject is known to an elevated risk of developing a cancer (e.g., a family history of cancer).

In some embodiments, the subject is a pediatric subject.

The term "pediatric subject" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

Cancers

Methods of treating a cancer are provided herein. Point mutations in NTRK1, NTRK2, and NTRK3 were found in Trk inhibitor-resistant cancer cells. Non-limiting examples of cancer (e.g., a Trk-associated cancer) include adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

Additional examples of cancers (e.g., Trk inhibitor-resistant cancer) include: adrenocortical carcinoma, anal cancer, appendix cancer, atypical teratoid/rhabdoid tumor (e.g., central nervous system atypical teratoid/rhabdoid tumor), B-cell cancer, bile duct cancer, bladder cancer, bone cancer (e.g., osteosarcoma and malignant fibrous histiocytoma), brain cancer (e.g., brain and spinal cord tumor, brain stem glioma, central nervous system embryonal tumors, central nervous system germ cell tumors, craniopharyngioma, and ependymoma), breast cancer, bronchogenic carcinoma, bronchus cancer, cancer of hematological tissues, cancer of the oral cavity or pharynx, carcinoid tumor, cervical cancer, childhood cancers, chordoma, chronic lymphocytic leukemia, chronic myeloproliferative neoplasms, colon cancer, colorectal cancer, cutaneous T-cell lymphoma, ductal carcinoma in situ, embryonal tumor, endometrial cancer, esophageal cancer, esthesioneuroblastoma, extracranial germ cell tumor, extragonadal germ cell tumor, extrahepatic bile duct cancer, eye cancer (e.g., retinoblastoma), fallopian tube cancer, fibrosarcoma, fibrous histiocytoma of bone, gallbladder cancer, gastric cancer, gastrointestinal carcinoid tumor, germ cell tumor, gestational trophoblastic disease, glioblastoma multiforme, glioma (e.g., lower-grade glioma), head and neck cancer, heart cancer, histiocytosis, hypopharyngeal cancer, inflammatory myofibroblastic tumors, intrahepatic cholangiocarcinoma, islet cell tumor, kidney cancer (e.g., renal cell cancer), Langerhans cell histiocytosis, large cell neuroendocrine cancer, laryngeal cancer, leukemia (e.g., acute lymphoblastic leukemia, acute myeloid leukemia, chronic myelogenous leukemia, and hairy cell leukemia), lip cancer, liver cancer, lung cancer, Burkitt lymphoma, Hodgkin's lymphoma, and primary central nervous system lymphoma), medulloblastoma, mesothelioma, mouth cancer, multiple myeloma, myelodysplastic syndromes, nasal cavity and paranasal sinus cancer, nasopharyngeal cancer, neoplasm (e.g., a melanocystic neoplasm), nephroma, neuroblastoma, non-small cell lung cancer, oral cancer, oropharyngeal cancer, ovarian cancer, pancreatic cancer, paraganglioma, parathyroid cancer, pediatric glioma, penile cancer, pharyngeal cancer, pheochromocytoma, pilocytic astrocytoma, pituitary tumor, plasma cell neoplasm, primary peritoneal cancer, prostate cancer, rectum carcinoma, salivary gland cancer, sarcoma (e.g., Ewing sarcoma, rhabdomyosarcoma, uterine sarcoma, and undifferentiated sarcoma), secretory breast carcinoma, Sezary syndrome, skin cancer, small bowel cancer, small cell lung cancer, small intestine cancer, Spitz nevi, Spitz tumors, spitzoid melanoma, stomach cancer, squamous cell carcinoma, squamous neck cancer, testicular cancer, throat cancer, thymoma and thymic carcinoma, thyroid carcinoma, urethral cancer, uterine cancer, urinary bladder cancer, vaginal cancer, vulvar cancer, and Wilms tumor.

In some embodiments, the cancer is a pediatric cancer. In some embodiments, the pediatric cancer is a mesenchymal cancer. For example, the mesenchymal cancer can be selected from the group consisting of: pediatric nephroma, congenital fibrosarcoma (CFS), pediatric high-grade glioma (HGG), mesenchymal cancers (infant fibrosarcoma (IF), congenital mesoblastic nephroma, congenital infantile fibrosarcoma (CIFS); pilocytic astrocytoma, brain tumors, pediatic acute leukemia, Ph-like acute lymphoblastic leukemia, cellular congenital mesoblastic nephroma (CMN); infantile fibrosarcoma, pediatric high-grade glioma (HGG), diffuse intrinsic pontine gliomas (DIPGs), non-brainstem HGGs (NBS-HGGs), anaplastic large cell lymphoma (ALCL), non-Hodgkin's lymphoma (NHL), pediatric papillary thyroid carcinoma, soft tissue sarcoma, spitzoid melanoma, pediatric hemangiopericytoma-like sarcoma, spindle cell sarcoma, NOS with myo/haemangiopericytic growth pattern, lung cancer, advanced pediatric solid tumors, neuroectodermal-derived tumors, pediatric colorectal cancer, adrenal neuroblastoma, and central nervous system tumors.

In some embodiments, the pediatric cancer is a fibrosarcoma such as infantile fibrosarcoma.

In some embodiments, the pediatric cancer is a glioma. For example, the pediatric cancer is selected from the group consisting of: pediatric high-grade glioma (HGG), diffuse intrinsic pontine gliomas (DIPGs), and on-brainstem HGGs (NBS-HGGs).

Methods of diagnosing a cancer (e.g., any of the cancers described herein) are known in the art. For example, a health care professional (e.g., a physician) can diagnose a subject as having a cancer by observing one or more symptoms of a cancer in the subject. Non-limiting examples of symptoms of a cancer include fever, fatigue, pain, hyperpigmentation, jaundice, erythema, pruritis, excessive hair growth, long-term constipation, diarrhea, change in the size of stool, pain when urinating, blood in urine, change in bladder function, sore that do not heal, white patches inside the mouth or on tongue, unusual bleeding or discharge, indigestion, trouble swallowing, changes in warts, moles, or freckles, nagging cough, hoarseness, lump or area of thickening that can be felt under skin, weight changes, trouble breathing, discomfort after eating, persistent, unexplained muscle or joint pain, persistent, unexplained fevers and night sweats, and unexplained bruising. The diagnosis of a cancer by a health care profession (e.g., a physician) can also include performing laboratory tests (e.g., urine or blood tests, e.g., complete blood count), imaging tests (e.g., computerized tomography (CT), bone scan, magnetic resonance imaging (MRI), positron emission tomography (PET) scan, ultrasound, and X-ray), and obtaining and/or examining a biopsy sample from the subject.

A Trk inhibitor-resistant cancer cell can have, e.g., an increased rate of growth in the presence of at least one Trk inhibitor (e.g., any of the Trk inhibitors described herein or known in the art) as compared to the rate of growth of a control cell from a control subject having the same type of cancer and not having one or more of the point mutations in a NTRK1 gene described herein or one or more of the point mutations in a NTRK2 gene described herein or a point mutation in a NTRK3 gene described herein, when it is contacted with the at least one Trk inhibitor (e.g., a first Trk inhibitor). One of skill in the art will appreciate that the Trk inhibitor-resistant cancer cell and the control cell are contacted with the same concentration of the at least one Trk inhibitor. For example, rate of growth of the Trk inhibitor-resistant cancer cell is increased about 1% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, about 10%, or about 5%; about 5% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, or about 10%; about 10% to about 100%, about 95%, about 90%, about 85%, about 80%, about 75%, about 70%, about 65%, about 60%, about 55%, about 50%, about 45%, about 40%, about 35%, about 30%, about 25%, about 20%, or about 15%; about 15% to about 100%, about 95%, about 90%, about 85%, about 80%, about 75%, about 70%, about 65%, about 60%, about 55%, about 50%, about 45%, about 40%, about 35%, about 30%, about 25%, or about 20%; about 20% to about 100%, about 95%, about 90%, about 85%, about 80%, about 75%, about 70%, about 65%, about 60%, about 55%, about 50%, about 45%, about 40%, about 35%, about 30%, or about 25%; about 25% to about 100%, about 95%, about 90%, about 85%, about 80%, about 75%, about 70%, about 65%, about 60%, about 55%, about 50%, about 45%, about 40%, about 35%, or about 30%; about 30% to about 100%, about 95%, about 90%, about 85%, about 80%, about 75%, about 70%, about 65%, about 60%, about 55%, about 50%, about 45%, about 40%, or about 35%; about 35% to about 100%, about 95%, about 90%, about 85%, about 80%, about 75%, about 70%, about 65%, about 60%, about 55%, about 50%, about 45%, or about 40%; about 40% to about 100%, about 95%, about 90%, about 85%, about 80%, about 75%, about 70%, about 65%, about 60%, about 55%, about 50%, or about 45%; about 45% to about 100%, about 95%, about 90%, about 85%, about 80%, about 75%, about 70%, about 65%, about 60%, about 55%, to about 50%; about 50% to about 100%, about 95%, about 90%, about 85%, about 80%, about 75%, about 70%, about 65%, about 60%, to about 55%; about 55% to about 100%, about 95%, about 90%, about 85%, about 80%, about 75%, about 70%, about 65%, or about 60%; about 60% to about 100%, about 95%, about 90%, about 85%, about 80%, about 75%, about 70%, or about 65%; about 65% to about 100%, about 95%, about 90%, about 85%, about 80%, about 75%, or about 70%; about 70% to about 100%, about 95%, about 90%, about 85%, about 80%, to about 75%; about 75% to about 100%, about 95%, about 90%, about 85%, or about 80%; about 80% to about 100%, about 95%, about 90%, or about 85%; about 85% to about 100%, about 95%, or about 90%; about 90% to about 100% or about 95%; or about 95% to about 100% (as compared to the rate of growth of a control cell from a control subject having the same type of cancer and not having one or more of the point mutations in a NTRK1 gene described herein or one or more of the point mutations in a NTRK2 gene described herein or one or more of the point mutations in a NTRK3 gene described herein, when it is contacted with the at least one Trk inhibitor).

In some embodiments, a Trk inhibitor-resistant cancer can be resistant to treatment with (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (or a polymorph thereof), but the Trk inhibitor-resistant cancer is still sensitive to a treatment including one or more compounds of Table 5, or a pharmaceutically acceptable salt thereof. In some embodiments, a Trk inhibitor-resistant cancer can be resistant to treatment with entrectinib, but the Trk inhibitor-resistant cancer is still sensitive to a treatment including one or more compounds of Table 5, or a pharmaceutically acceptable salt thereof.

A Trk inhibitor-resistant cancer in a subject can have, e.g., an increased rate of growth of a solid tumor when the subject is treated with at least one Trk inhibitor (e.g., a first Trk inhibitor) as compared to the rate of growth of a control solid tumor in a control subject treated with the at least one Trk inhibitor and having the same type of cancer and not having one or more of the point mutations in a NTRK1 gene described herein or one or more of the point mutations in a NTRK2 gene described herein or a point mutation in a NTRK3 gene described herein). One of skill in the art will appreciate that the subject and the control subject are administered the same concentration of the at least one Trk inhibitor. For example, rate of growth of the solid tumor in a subject having a Trk inhibitor-resistant cancer and administered at least one Trk inhibitor is increased about 1% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, about 10%, or about 5%; about 5% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, or about 10%; about 10% to about 100%, about 95%, about 90%, about 85%, about 80%, about 75%, about 70%, about 65%, about 60%, about 55%, about 50%, about 45%, about 40%, about 35%, about 30%, about 25%, about 20%, or about 15%; about 15% to about 100%, about 95%, about 90%, about 85%, about 80%, about 75%, about 70%, about 65%, about 60%, about 55%, about 50%, about 45%, about 40%, about 35%, about 30%, about 25%, or about 20%; about 20% to about 100%, about 95%, about 90%, about 85%, about 80%, about 75%, about 70%, about 65%, about 60%, about 55%, about 50%, about 45%, about 40%, about 35%, about 30%, or about 25%; about 25% to about 100%, about 95%, about 90%, about 85%, about 80%, about 75%, about 70%, about 65%, about 60%, about 55%, about 50%, about 45%, about 40%, about 35%, or about 30%; about 30% to about 100%, about 95%, about 90%, about 85%, about 80%, about 75%, about 70%, about 65%, about 60%, about 55%, about 50%, about 45%, about 40%, or about 35%; about 35% to about 100%, about 95%, about 90%, about 85%, about 80%, about 75%, about 70%, about 65%, about 60%, about 55%, about 50%, about 45%, or about 40%; about 40% to about 100%, about 95%, about 90%, about 85%, about 80%, about 75%, about 70%, about 65%, about 60%, about 55%, about 50%, or about 45%; about 45% to about 100%, about 95%, about 90%, about 85%, about 80%, about 75%, about 70%, about 65%, about 60%, about 55%, to about 50%; about 50% to about 100%, about 95%, about 90%, about 85%, about 80%, about 75%, about 70%, about 65%, about 60%, to about 55%; about 55% to about 100%, about 95%, about 90%, about 85%, about 80%, about 75%, about 70%, about 65%, or about 60%; about 60% to about 100%, about 95%, about 90%, about 85%, about 80%, about 75%, about 70%, or about 65%; about 65% to about 100%, about 95%, about 90%, about 85%, about 80%, about 75%, or about 70%; about 70% to about 100%, about 95%, about 90%, about 85%, about 80%, to about 75%; about 75% to about 100%, about 95%, about 90%, about 85%, or about 80%; about 80% to about 100%, about 95%, about 90%, or about 85%; about 85% to about 100%, about 95%, or about 90%; about 90% to about 100% or about 95%; or about 95% to about 100% (as compared to the rate of growth of a solid tumor in a control subject having the same type of cancer and not having one or more of the point mutations in a NTRK1 gene described herein or one or more of the point mutations in a NTRK2 gene described herein or a point mutation in a NTRK3 gene described herein, and administered the same at least one Trk inhibitor).

A Trk inhibitor-resistant cancer in a subject can have, e.g., a decreased rate of apoptosis in a solid tumor when the subject is treated with at least one Trk inhibitor (e.g., a first Trk inhibitor) as compared to the rate of apoptosis of a control solid tumor in a control subject treated with the at least one Trk inhibitor and having the same type of cancer and not having one or more of the point mutations in a NTRK1 gene described herein or one or more of the point mutations in a NTRK2 gene described herein or one or more point mutations in a NTRK3 gene described herein). One of skill in the art will appreciate that the subject and the control subject are administered the same concentration of the at least one Trk inhibitor. For example, rate of apoptosis of the solid tumor in a subject having a Trk inhibitor-resistant cancer and administered at least one Trk inhibitor is decreased about 1% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, about 10%, or about 5%; about 5% to about 100%, about 95%, about 90%, about 85%, about 80%, about 75%, about 70%, about 65%, about 60%, about 55%, about 50%, about 45%, about 40%, about 35%, about 30%, about 25%, about 20%, about 15, or about 10%; about 10% to about 100%, about 95%, about 90%, about 85%, about 80%, about 75%, about 70%, about 65%, about 60%, about 55%, about 50%, about 45%, about 40%, about 35%, about 30%, about 25%, about 20%, or about 15%; about 15% to about 100%, about 95%, about 90%, about 85%, about 80%, about 75%, about 70%, about 65%, about 60%, about 55%, about 50%, about 45%, about 40%, about 35%, about 30%, about 25%, or about 20%; about 20% to about 100%, about 95%, about 90%, about 85%, about 80%, about 75%, about 70%, about 65%, about 60%, about 55%, about 50%, about 45%, about 40%, about 35%, about 30%, or about 25%; about 25% to about 100%, about 95%, about 90%, about 85%, about 80%, about 75%, about 70%, about 65%, about 60%, about 55%, about 50%, about 45%, about 40%, about 35%, or about 30%; about 30% to about 100%, about 95%, about 90%, about 85%, about 80%, about 75%, about 70%, about 65%, about 60%, about 55%, about 50%, about 45%, about 40%, or about 35%; about 35% to about 100%, about 95%, about 90%, about 85%, about 80%, about 75%, about 70%, about 65%, about 60%, about 55%, about 50%, about 45%, or about 40%; about 40% to about 100%, about 95%, about 90%, about 85%, about 80%, about 75%, about 70%, about 65%, about 60%, about 55%, about 50%, or about 45%; about 45% to about 100%, about 95%, about 90%, about 85%, about 80%, about 75%, about 70%, about 65%, about 60%, about 55%, to about 50%; about 50% to about 100%, about 95%, about 90%, about 85%, about 80%, about 75%, about 70%, about 65%, about 60%, to about 55%; about 55% to about 100%, about 95%, about 90%, about 85%, about 80%, about 75%, about 70%, about 65%, or about 60%; about 60% to about 100%, about 95%, about 90%, about 85%, about 80%, about 75%, about 70%, or about 65%; about 65% to about 100%, about 95%, about 90%, about 85%, about 80%, about 75%, or about 70%; about 70% to about 100%, about 95%, about 90%, about 85%, about 80%, to about 75%; about 75% to about 100%, about 95%, about 90%, about 85%, or about 80%; about 80% to about 100%, about 95%, about 90%, or about 85%; about 85% to about 100%, about 95%, or about 90%; about 90% to about 100% or about 95%; or about 95% to about 100% (as compared to the rate of apoptosis in a solid tumor in a control subject having the same type of cancer and not having one or more of the point mutations in a NTRK1 gene described herein or one or more of the point mutations in a NTRK2 gene described herein or one or more point mutations in a NTRK3 gene described herein, and administered the same at least one Trk inhibitor).

Exemplary methods of determining the presence of a Trk inhibitor-resistant cancer in a subject are provided herein.

Trk Inhibitors

A variety of Trk inhibitors are known in the art. The ability of a Trk inhibitor to act as a Trk inhibitor may be tested using one or both of the assays described in Examples A and B in U.S. Pat. No. 8,513,263, which is incorporated herein by reference.

A Trk inhibitor can have an $IC_{50}$ of about 0.1 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, about 60 nM, about 40 nM, about 20 nM, about 10 nM, or about 5 nM; about 1 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, about 60 nM, about 40 nM, about 20 nM, about 10 nM, or about 5 nM; about 5 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, about 60 nM, about 40 nM, about 20 nM, or about 10 nM; about 10 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, about 60 nM, about 40 nM, or about 20 nM; about 20 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, about 60 nM, or about 40 nM; about 40 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 80 nM, or about 60 nM; about 60 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, or about 80 nM; about 80 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, to about 100 nM; about 100 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, or about 150 nM; about 150 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, or about 200 nM; about 200 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, or about 250 nM; about 250 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, or about 300 nM; about 300 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, about 400 nM, or about 350 nM; about 350 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, about 450 nM, or about 400 nM; about 400 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, about 500 nM, or about 450 nM; about 450 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, about 550 nM, or about 500 nM; about 500 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, about 600 nM, or about 550 nM; about 550 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, about 650 nM, or about 600 nM; about 600 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, about 700 nM, or about 650 nM; about 650 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, about 750 nM, or about 700 nM; about 700 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, about 800 nM, or about 750 nM; about 750 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, about 850 nM, or about 800 nM; about 800 nM to about 50 μM, about 45 μM, about 40 μM, about 35 μM, about 30 μM, about 25 μM, about 20 μM, about 15 μM, about 10 μM, about 5 μM, about 1 μM, about 950 nM, about 900 nM, or about 850 nM; about 850 nM to about 50 μM, about 45 μM, about 40 μM, about 35 μM, about 30 μM, about 25 μM, about 20 μM, about 15 μM, about 10 μM, about 5 μM, about 1 μM, about 950 nM, or about 900 nM; about 900 nM to about 50 μM, about 45 μM, about 40 μM, about 35 μM, about 30 μM, about 25 μM, about 20 μM, about 15 μM, about 10 μM, about 5 μM, about 1 μM, or about 950 nM; about 950 nM to about 50 μM, about 45 μM, about 40 μM, about 35 μM, about 30 μM, about 25 μM, about 20 μM, about 15 μM, about 10 μM, about 5 μM, or about 1 μM; about 1 μM to about 50 μM, about 45 μM, about 40 μM, about 35 μM, about 30 μM, about 25 μM, about 20 μM, about 15 μM, about 10 μM, or about 5 μM; about 5 μM to about 50 μM, about 45 μM, about 40 μM, about 35 μM, about 30 μM, about 25 μM, about 20 μM, about 15 μM, or about 10 μM; about 10 μM to about 50 μM, about 45 μM, about 40 μM, about 35 μM, about 30 μM, about 25 μM, about 20 μM, or about 15 μM; about 15 μM to about 50 μM, about 45 μM, about 40 μM, about 35 μM, about 30 μM, about 25 μM, or about 20 μM; about 20 μM to about 50 μM, about 45 μM, about 40 μM, about 35 μM, about 30 μM, or about 25 μM; about 25 μM to about 50 μM, about 45 μM, about 40 μM, about 35 μM, or about 30 μM; about 30 μM to about 50 μM, about 45 μM, about 40 μM, or about 35 μM; about 35 μM to about 50 μM, about 45 μM, or about 40 μM; about 40 μM to about 50 μM or about 45 μM; or about 45 μM to about 50 μM. In some embodiments, the Trk inhibitor also inhibits one or both of TrkB and TrkC, in addition to TrkA.

A Trk inhibitor can bind to one or more of the sites on TrkA: the extracellular cysteine-rich region (domain 1), the extracellular leucine rich region (domain 2), the extracellular cysteine-rich region (domain 3), the extracellular immunoglobulin-like region (domain 4), the extracellular immunoglobulin-like region (domain 5), the transmembrane region, the intracellular kinase domain, an amino acid in the active site, the ATP-binding pocket, the tyrosine substrate binding site, the activation loop (e.g., the DFG motif of the activation loop), the kinase insert domain (KID) region (e.g., amino acids 603 to 623), the hinge region of the kinase, the α-C helix in the catalytic domain, the N-lobe lysine responsible for the stabilization of the α phosphate of the ATP substrate, the C-terminus (see, e.g., Bertrand et al., *J. Mol. Biol.* 423:439-453, 2012), the α-D helix in the C-terminus, the α-E helix in the C-terminus, an amino acid in the kinase domain that interacts with a ligand in the ATP binding site (see, e.g., Cherry et al., *Curr. Med. Chem.* 11:663-673, 2004). For example, a Trk inhibitor can bind to domain 5 or the intracellular kinase domain of a TrkA.

Non-limiting examples of Trk inhibitors are described below.

An example of a Trk inhibitor is a (e.g., crystalline form of, a liquid formulation including) the compound of Formula I:

I

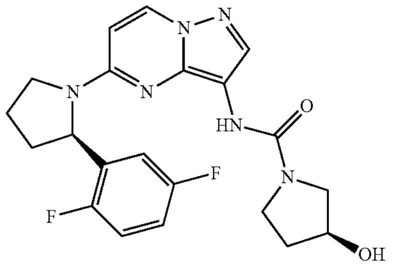

or a pharmaceutically acceptable salt thereof. Another example of a Trk inhibitor is a crystalline form including the hydrogen sulfate salt of the compound of Formula I in a stable polymorph form, referred to as crystalline form (Formula I-HS), which may be characterized, for example, by its X-ray diffraction pattern (see, U.S. Patent Application Ser. Nos. 62/080,374 and 14/943,014, both of which are herein incorporated by reference in their entirety). Additional physical properties of a Trk inhibitor of Formula I and methods of making a Trk inhibitor of Formula I are described in U.S. Patent Application Ser. Nos. 62/080,374 and 14/943,014 (both of which are herein incorporated by reference in its their entirety). In some embodiments, the compound of Formula I is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate or a polymorph thereof.

In some embodiments, crystalline form (I-HS) is characterized by having XRPD diffraction peaks (2θ degrees) at 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, crystalline form (I-HS) is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

In some embodiments, the crystalline form exhibits an onset to maximum of about 193 to about 205° Celsius, as measured by differential scanning calorimetry. In some embodiments, the crystalline form (I-HS) exhibits a heat of melting of about 2.415 mW, as measured by differential scanning calorimetry.

In some embodiments, the Trk inhibitor is selected from the group consisting of: (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; (R)—N-cyclopropyl-5-(2-(5-fluoropyridin-3-yl)pyrrolidin-1-yl)pyrazolo[1,5-a]pyrimidine-3-carboxamide; (6R,13S)-9-fluoro-13-methyl-2,11,15,19,20,23-hexaazapentacyclo[15.5.2.17, 11.02,6.020,24]pentacosa-1(23),7,9,17(24), 18,21-hexaene-16,25-dione; and (6R)-9-fluoro-15-methyl-2,11,16,20,21, 24-hexaazapentacyclo [16.5.2.02,6.07,12.021,25] pentacosa-1(24),7,9,11,18(25),19,22-heptaen-17-one.

Non-limiting examples of Trk inhibitors are described in U.S. Pat. No. 8,513,263 and International Publication No. WO 2010/048314 both of which are incorporated by reference in their entireties herein, and include a compound of Formula I:

I

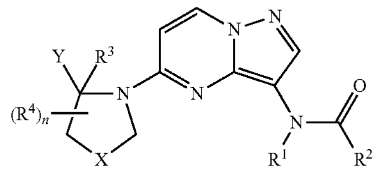

or a pharmaceutically acceptable salt thereof, wherein:

$R^1$ is H or (1-6C alkyl);

$R^2$ is $NR^bR^c$, (1-4C)alkyl, (1-4C)fluoroalkyl, $CF_3$, (1-4C) hydroxyalkyl, -(1-4C alkyl)hetAr$^1$, -(1-4C alkyl)$NH_2$, -(1-4C alkyl)NH(1-4C alkyl), -(1-4C alkyl)N(1-4C alkyl)$_2$, hetAr$^2$, hetCyc$^1$, hetCyc$^2$, phenyl which is optionally substituted with $NHSO_2$(1-4C alkyl), or (3-6C)$^e$cycloalkyl which is optionally substituted with (1-4C alkyl), CN, OH, OMe, $NH_2$, NHMe, $N(CH_3)_2$, F, $CF_3$, $CO_2$(1-4C alkyl), $CO_2H$, C(═O)$NR^eR^f$ or C(═O)$OR^g$;

$R^b$ is H or (1-6C alkyl);

$R^c$ is H, (1-4C)alkyl, (1-4C)hydroxyalkyl, hetAr$^3$, or phenyl, wherein said phenyl is optionally substituted with one or more substituents independently selected from halogen, CN, $CF_3$ and —O(1-4C alkyl), or $NR^bR^c$ forms a 4 membered heterocyclic ring having a ring nitrogen atom wherein said heterocyclic ring is optionally substituted with one or more substituents independently selected from halogen, OH, (1-4C alkyl), (1-4 C)alkoxy, —OC(═O)(1-4C alkyl), $NH_2$, —NHC(═O)O(1-4C alkyl) and (1-4C)hydroxyalkyl, or $NR^bR^c$ forms a 5-6 membered heterocyclic ring having a ring heteroatom which is nitrogen and optionally having a second ring heteroatom or group selected from N, O and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(═O)O(1-4C alkyl) and oxo, or $NR^bR^c$ forms a 7-8 membered bridged heterocyclic ring having a ring nitrogen atom and optionally having a second ring heteroatom selected from N and O, wherein said ring is optionally substituted with $CO_2$(1-4C alkyl);

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4 C)alkoxy, and NH(1-4C alkyl);

hetCyc$^1$ is a carbon-linked 4-6 membered azacyclic ring optionally substituted with one or more substituents independently selected from (1-4C alkyl), and $CO_2$(1-4C alkyl);

hetCyc$^2$ is a pyridinone or pyridazinone ring which is optionally substituted with a substituent selected from (1-4C)alkyl;

hetAr$^3$ is a 5-6 membered heteroaryl ring having 1-2 ring heteroatoms independently selected from N and O and optionally substituted with one or more substituents independently selected from (1-4C)alkyl;

$R^e$ is H or (1-4C)alkyl;

$R^f$ is H, (1-4C)alkyl, or (3-6C)cycloalkyl;

or $NR^eR^f$ forms a 5-6-membered azacyclic ring optionally having an additional ring heteroatom selected from N and O, wherein the azacyclic ring is optionally substituted with OH;

$R^g$ is H or (1-6C)alkyl;

Y is (i) phenyl optionally substituted with one or more substituents independently selected from halogen, (1-4C) alkoxy, $CF_3$ and $CHF_2$, or (ii) a 5-6 membered heteroaryl ring having a ring heteroatom selected from N and S, wherein said heteroaryl ring is optionally substituted with one or more halogen atoms;

X is null, —$CH_2$—, —$CH_2CH_2$—, —$CH_2O$— or —$CH_2NR^d$—;

$R^d$ is H or (1-4C alkyl);

$R^3$ is H or (1-4C alkyl);

each $R^4$ is independently selected from halogen, (1-4C) alkyl, OH, (1-4C)alkoxy, $NH_2$, NH(1-4C alkyl) and $CH_2OH$; and n is 0, 1, 2, 3, 4, 5 or 6.

For example, a Trk inhibitor can include one or more compounds selected from the group consisting of:

(R)—N-(5-(2-(2,5-difluorophenyl)pyrrolidin-1-yl)pyrazolo[1,5-a]pyrimidin-3-yl)-3-hydroxyazetidine-1-carboxamide;

N-(5-(2-(3-fluorophenyl)-2-methylpyrrolidin-1-yl)pyrazolo[1,5-a]pyrimidin-3-yl)-3-hydroxyazetidine-1-carboxamide;

(R)-1-(5-(2-(2,5-difluorophenyl)pyrrolidin-1-yl)pyrazolo[1,5-a]pyrimidin-3-yl)-3-phenylurea;

(R)—N-(5-(2-(2-(difluoromethyl)-5-fluorophenyl)pyrrolidin-1-yl)pyrazolo[1,5-a]pyrimidin-3-yl)-3-hydroxyazetidine-1-carboxamide;

(R)—N-(5-(2-(3-fluorophenyl)pyrrolidin-1-yl)pyrazolo[1,5-a]pyrimidin-3-yl)-1-methyl-6-oxo-1,6-dihydropyridazine-3-carboxamide;

(S)—N-(5-((R)-2-(2,5-difluorophenyl)pyrrolidin-1-yl)pyrazolo[1,5-a]pyrimidin-3-yl)-3-hydroxypyrrolidine-1-carboxamide;

(3R,4R)—N-(5-((R)-2-(2,5-difluorophenyl)pyrrolidin-1-yl) pyrazolo[1,5-a]pyrimidin-3-yl)-3,4-dihydroxypyrrolidine-1-carboxamide;

(S)—N-(5-((R)-2-(2-chloro-5-fluorophenyl)pyrrolidin-1-yl) pyrazolo[1,5-a]pyrimidin-3-yl)-3-methylpiperazine-1-carboxamide;

(R)—N-(5-(2-(2,5-difluorophenyl)pyrrolidin-1-yl)pyrazolo [1,5-a]pyrimidin-3-yl)-3-hydroxy-3-methylazetidine-1-carboxamide;

(R)—N-(5-(2-(3-fluorophenyl)pyrrolidin-1-yl)pyrazolo[1,5-a]pyrimidin-3-yl)-3-hydroxyazetidine-1-carboxamide; and (R)-1-(4-chlorophenyl)-3-(5-(2-(2,5-difluorophenyl)pyrrolidin-1-yl)pyrazolo[1,5-a]pyrimidin-3-yl)urea, or a pharmaceutically acceptable salt thereof.

Additional examples of Trk inhibitors are the substituted pyrazolo[1,5-a] pyrimidine compounds described in U.S. Pat. No. 8,791,123 and International Publication No. WO 2011/006074, both of which are herein incorporated by reference in their entireties. For example, Trk inhibitors that are substituted pyrazolo[1,5-a]pyrimidine compounds can have the general formula II:

II

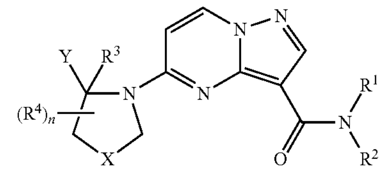

or a salt thereof, wherein:

$R^1$ is H or (1-6C alkyl);

$R^2$ is H, (1-6C)alkyl, -(1-6C)fluoroalkyl, -(1-6C)difluoroalkyl, -(1-6C)trifluoroalkyl, -(1-6C)chloroalkyl, -(2-6C) chlorofluoroalkyl, -(2-6C)difluorochloroalkyl, -(2-6C)chlorohydroxyalkyl, -(1-6C)hydroxyalkyl, -(2-6C) dihydroxyalkyl, -(1-6C alkyl)CN, -(1-6C alkyl)$SO_2NH_2$, -(1-6C alkyl)$NHSO_2$(1-3C alkyl), -(1-6C alkyl)$NH_2$, -(1-6C alkyl)NH(1-4C alkyl), -(1-6C alkyl)N(1-4C alkyl)$_2$, -(1-6C alkyl)NHC(═O)O(1-4C alkyl), -(1-6C alkyl)hetCyc$^1$, -(1-6C alkyl)hetAr$^1$, hetAr$^2$, hetCyc$^2$, —O(1-6C alkyl) which is optionally substituted with halogen, OH or (1-4C)alkoxy, —O(3-6C cycloalkyl), Cyc$^1$, -(1-6C alkyl)(3-6C cycloalkyl), -(1-6C alkyl)(1-4C alkoxy), -(1-6C hydroxyalkyl)(1-4C alkoxy), a bridged 7-membered cycloalkyl ring optionally substituted with (1-6C)hydroxyalkyl, or a bridged 7-8 membered heterocyclic ring having 1-2 ring nitrogen atoms;

or $NR^1R^2$ forms a 4-6 membered azacyclic ring optionally substituted with one or more substituents independently selected from (1-6C)alkyl, OH, $CO_2H$, (1-3C alkyl)$CO_2H$, —O(1-6C alkyl), and (1-6C)hydroxyalkyl;

hetCyc$^1$ is a 5-6 membered heterocyclic ring having 1-2 ring heteroatoms independently selected from N and O, wherein hetCyc$^1$ is optionally substituted with oxo, OH, halogen, or (1-6C)alkyl;

hetCyc$^2$ is a 6 membered carbon-linked heterocyclic ring having 1-2 ring heteroatoms independently selected from N and O, wherein hetCyc$^2$ is optionally substituted with F, $SO_2NH_2$, $SO_2$(1-3C alkyl), or halogen;

hetAr$^1$ is a 5-membered heteroaryl ring having 1-2 ring heteroatoms independently selected from N and O and optionally substituted with (1-4C)alkyl;

hetAr$^2$ is a 5-6 membered heteroaryl ring having 1-2 ring nitrogen atoms and optionally substituted with one or more substituents independently selected from (1-4C)alkyl, (3-6C)cycloalkyl, halogen, and OH;

Cyc$^1$ is a 3-6 membered cycloalkyl ring which is optionally substituted with one or more substituents independently selected from -(1-4C alkyl), —OH, —OMe, —$CO_2H$, -(1-4C alkyl)OH, halogen, and $CF_3$;

Y is (i) phenyl optionally substituted with one or more substituents independently selected from halogen, (1-4C) alkoxy, —$CF_3$, —$CHF_2$, —O(1-4C alkyl)hetCyc$^3$, -(1-4C alkyl)hetCyc$^3$, —O(1-4C alkyl)O(1-3C alkyl) and —O(3-6C dihydroxyalkyl), or (ii) a 5-6 membered heteroaryl ring having a ring heteroatom selected from N and S, wherein the heteroaryl ring is optionally substituted with one or more substituents independently selected from halogen, —O(1-4C alkyl), (1-4C)alkyl, and $NH_2$, or (iii) a pyrid-2-on-3-yl ring optionally substituted with one or more substituents independently selected from halogen and (1-4C)alkyl;

hetCyc$^3$ is a 5-6 membered heterocyclic ring having 1-2 ring heteroatoms independently selected from N and O and optionally substituted with (1-6C)alkyl;

X is —$CH_2$—, —$CH_2CH_2$—, —$CH_2O$—, or —$CH_2NR^d$—;

$R^d$ is H or -(1-4C alkyl);

$R^3$ is H or -(1-4C alkyl);

each $R^4$ is independently selected from halogen, -(1-4C) alkyl, —OH, -(1-4C)alkoxy, —$NH_2$, —NH(1-4C alkyl), and —$CH_2OH$; and n is 0, 1, 2, 3, 4, 5, or 6.

For example, a Trk inhibitor can include one or more compounds selected from the group consisting of:

(R)-5-(2-(2,5-difluorophenyl)pyrrolidin-1-yl)-N-(pyridin-2-yl)pyrazolo[1,5-a]pyrimidine-3-carboxamide;

(R)-5-(2-(2,5-difluorophenyl)pyrrolidin-1-yl)-N-(2-morpholinoethyl)pyrazolo[1,5-a]pyrimidine-3-carboxamide;

N-((2S)-bicyclo[2.2.1]heptan-2-yl)-5-((R)-2-(2,5-difluorophenyl)pyrrolidin-1-yl)pyrazolo[1,5-a]pyrimidine-3-carboxamide;

(R)-5-(2-(2,5-difluorophenyl)pyrrolidin-1-yl)-N-(2-(2-oxoimidazolidin-1-yl)ethyl)pyrazole[1,5-a]pyrimidine-3-carboxamide;

5-((R)-2-(2,5-difluorophenyl)pyrrolidin-1-yl)-N—((R)-2,3-dihydroxypropyl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)—N-tert-butyl-5-(2-(5-fluoropyridin-3-yl)pyrrolidin-1-yl)pyrazolo[1,5-a]pyrimidine-3-carboxamide;

(R)-5-(2-(2,5-difluorophenyl)pyrrolidin-1-yl)pyrazolo[1,5-a]pyrimidine-3-carboxamide;

(R)-5-(2-(5-fluoropyridin-3-yl)pyrrolidin-1-yl)-N-(1-methylcyclobutyl)pyrazolo[1,5-a]pyrimidine-3-carboxamide; and 5-((R)-2-(5-fluoropyridin-3-yl)pyrrolidin-1-yl)-N—((S)-1,1,1-trifluoropropan-2-yl)pyrazolo[1,5-a]pyrimidine-3-carboxamide;

or a pharmaceutically acceptable salt thereof.

Additional examples of Trk inhibitors are the macrocyclic compounds described in U.S. Pat. No. 8,933,084 and International Publication No. WO 2011/146336, both of which are herein incorporated by reference in their entireties. For example, Trk inhibitors that are macrocyclic compounds can have the general formula III:

III

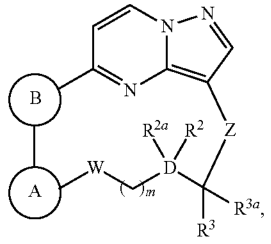

or a pharmaceutically acceptable salt thereof, wherein:

ring A is selected from rings A-I, A-2, and A-3 having the structures:

A-1

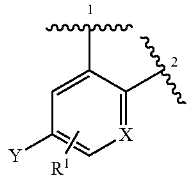

A-2

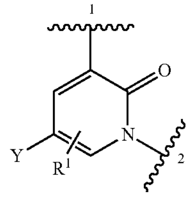

A-3

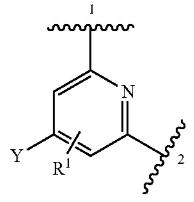

wherein the wavy line labeled 1 indicates the point of attachment of ring A to ring B and the wavy line labeled 2 indicates the point of attachment of ring A to W;

X is N or CH;

Y is H or F;

$R^1$ is H, (1-3C)alkoxy, or halogen;

ring B is selected from rings B-1 and B-2 having the structures:

B-1

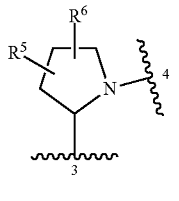

-continued

B-2

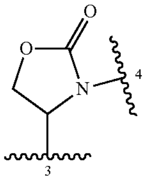

wherein the wavy line labeled 3 indicates the point of attachment to ring A and the wavy line labeled 4 indicates the point of attachment to the pyrazolo[I,5-a]pyrimidine ring of Formula III;

W is O, NH, or $CH_2$, wherein when ring A is A-2, then W is $CH_2$;

m is 0, 1, or 2;

D is carbon, $R^2$ and $R^{2a}$ are independently H, F, (1-3 C)alkyl or OH (provided that $R^2$ and $R^{2a}$ are not both OH), and $R^3$ and $R^{3a}$ are independently H, (1-3 C)alkyl or hydroxy (1-3 C)alkyl, or D is carbon or nitrogen, $R^2$ and $R^3$ are absent, and $R^{2a}$ and $R^{3a}$ together with the atoms to which they are attached form a 5-6 membered heteroaryl ring having 1-2 ring heteroatoms;

Z is *—$NR^{4a}C$(═O)—, *—ONHC(═O)—, *—$NR^{4b}CH_2$— or *—OC(═O)—, wherein the asterisk indicates the point of attachment of Z to the carbon bearing $R^3$;

$R^{4a}$ is H, (I-6C)alkyl, fluoro(I-6C)alkyl, difluoro(I-6C) alkyl, trifluoro(I-6C)alkyl, hydroxy(1-6C alkyl), or dihydroxy(2-6C alkyl);

$R^{4b}$ is H, (1-6C)alkyl, fluoro(1-6C)alkyl, difluoro(1-6C) alkyl, trifluoro(1-6C)alkyl, hydroxy(1-6C alkyl), dihydroxy (2-6C alkyl), (1-6C alkyl)C(O)—, (3-6C cycloalkyl)C (O)—, $Ar^1C(O)$—, $HOCH_2C(O)$—, (1-6C alkyl)sulfonyl, (3-6C cycloalkyl)sulfonyl, $Ar^2(SO_2)$—, $HO_2CCH_2$—, or (1-6C alkyl)NH(CO)—;

$Ar^1$ is phenyl optionally substituted with one or more substituents independently selected from halogen, (1-6C) alkyl, and (1-6C)alkoxy;

$Ar^2$ is phenyl optionally substituted with one or more substituents independently selected from halogen, (1-6C) alkyl, and (1-6C)alkoxy; and $R^5$ and $R^6$ are independently H, halogen, OH, (1-6C)alkyl, or hydroxy(1-6C)alkyl.

For example, a Trk inhibitor can include one or more compounds selected from the group consisting of:

(6R)-9-fluoro-13-oxa-2,11,17,21,22,25-hexaazapentacyclo [$17.5.2.0^{2,6}.0^{7,12}.0^{22,26}$]hexacosa-1(25),7,9,11,19(26),20, 23-heptaen-18-one;

(6R)-9-fluoro-15-hydroxy-13-oxa-2,11,17,21,22,25-hexaazapentacyclo[$17.5.2.0^{2,6}.0^{7,12}.0^{22,26}$]hexacosa-1 (25), 7,9,11,19(26),20,23-heptaen-18-one;

(6R,15R)-9-fluoro-15-hydroxy-13-oxa-2,11,17,21,22,25-hexaazapentacyclo-[$17.5.2.0^{2,6}.0^{7,12}.0^{22,26}$] hexacosa-1 (25),7,9,11,19(26),20,23-heptaen-18-one;

(6R)-9-fluoro-13-oxa-2,11,16,20,21,24-hexaazapentacyclo [$16.5.2.0^{2,6}.0^{7,12}.0^{21,25}$]pentacosa-1(24), 7,9,11,18(25), 19,22-heptaen-17-one;

(6R)-9-fluoro-13-oxa-2,11,18,22,23,26-hexaazapentacyclo [$18.5.2.0^{2,6}.0^{7,12}.0^{23,27}$]heptacosa-1(26), 7,9,11,20(27), 21,24-heptaen-19-one;

(6R,13S)-9-fluoro-13-methyl-2,11,15,19,20,23-hexaazapentacyclo [$15.5.2.1^{7,11}.0^{2,6}.0^{20,24}$]pentacosa-1(23),7,9, 17(24),18,21-hexaene-16,25-dione;

(6R)-9-fluoro-2,11,13,16,20,21,24-heptaazapentacyclo [16.5.2.0$^{2,6}$.0$^{7,12}$.0$^{21,25}$]pentacosa-1(24),7,9,11,18(25), 19,22-heptaen-17-one;

(6R)-9-fluoro-2,11,13,17,21,22,25-heptaazapentacyclo [17.5.2.0$^{2,6}$.0$^{7,12}$.0$^{22,26}$]hexacosa-1(25),7,9,11,19(26),20, 23-heptaen-18-one;

(6R)-9-fluoro-17-methyl-13-oxa-2,11,17,21,22,25-hexaaza-pentacyclo[17.5.2.0$^{2,6}$.0$^{7,12}$.0$^{22,26}$]hexacosa-1(25),7,9,11, 19(26),20,23-heptaen-18-one;

(6R)-9,15,15-trifluoro-13-oxa-2,11,17,21,22,25-hexaaza-pentacyclo[17.5.2.0$^{2,6}$.0$^{7,12}$.0$^{22,26}$]hexacosa-1(25),7,9,11, 19(26),20,23-heptaen-18-one;

(6R)-9-fluoro-2,11,16,20,21,24-hexaazapentacyclo [16.5.2.0$^{2,6}$.0$^{7,12}$.0$^{21,25}$]pentacosa-1(24),7,9,11,18(25), 19,22-heptaen-17-one;

(6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18 (25), 19,22-heptaen-17-one;

(6R)-9-fluoro-(15R)-methyl-2,11,16,20,21,24-hexaazapentacyclo[16.5.2.0$^{2,6}$.0$^{7,12}$.0$^{21,25}$]pentacosa-1(24),7,9,11,18 (25), 19,22-heptaen-17-one;

(6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18 (25), 19,22-heptaen-17-one;

(6R)-9-fluoro-15,15-dimethyl-13-oxa-2,11,17,21,22,25-hexaazapentacyclo [17.5.2.0$^{2,6}$.0$^{7,12}$.0$^{22,26}$] hexacosa-1 (25),7,9,11,19(26),20,23-heptaen-18-one; and (6R)-9-fluoro-15,15-dimethyl-2,11,16,20,21,24-hexaaza-pentacyclo[16.5.2.0$^{2,6}$.0$^{7,12}$.0$^{21,25}$]pentacosa-1(24),7,9, 11,18(25), 19,22-heptaen-17-one;

or a pharmaceutically acceptable salt thereof.

Additional examples of Trk inhibitors are the substituted imidazo[1,2-b]pyridazine compounds described in U.S. Pat. No. 8,450,322 and International Publication No. WO 2010/033941, both of which are herein incorporated by reference in their entireties. For example, Trk inhibitors that are substituted imidazo[1,2B]pyridazine compounds can have the general formula

IV

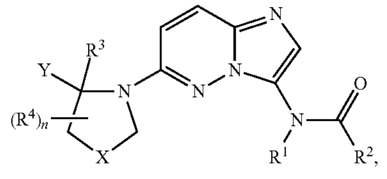

or a pharmaceutically acceptable salt thereof, wherein:

$R^1$ is H or (1-6C alkyl);

$R^2$ is $NR^bR^c$, (1-4C)alkyl, (1-4C)fluoroalkyl, $CF_3$, (1-4C) hydroxyalkyl, -(1-4C alkyl)hetAr$^1$, -(1-4C alkyl)NH(1-4C alkyl), hetAr$^2$, hetCyc$^1$, hetCyc$^2$, phenyl which is optionally substituted with $NHSO_2$(1-4C alkyl), or (3-6C)cycloalkyl which is optionally substituted with (1-4C alkyl), CN, OH, $CF_3$, $CO_2$(1-4C alkyl) or $CO_2H$;

$R^b$ is H or (1-6C alkyl);

$R^c$ is H, (1-4C)alkyl, (1-4C)hydroxyalkyl, hetAr$^3$, or phenyl, wherein said phenyl is optionally substituted with one or more substituents independently selected from halogen, CN, $CF_3$ and —O(1-4C alkyl), or $NR^bR^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(═O)(1-4C alkyl), $NH_2$, —NHC(═O)O(1-4C alkyl), and (1-4C)hydroxyalkyl, or $NR^bR^c$ forms a 5-6 membered heterocyclic ring having a ring heteroatom which is nitrogen and optionally having a second ring heteroatom or group selected from N, O, and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(═O)O(1-4C alkyl), and oxo, or $NR^bR^c$ forms a 7-8 membered bridged heterocyclic ring having 1-2 ring nitrogen atoms and optionally substituted with $CO_2$(1-4C alkyl);

hetAr$^1$ is a 5-membered heteroaryl ring having 1-3 ring nitrogen atoms;

hetAr$^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4 C)alkoxy, and NH(1-4C alkyl);

hetCyc$^1$ is a carbon-linked 4-6 membered azacyclic ring optionally substituted with one or more substituents independently selected from (1-4C alkyl), $CO_2H$ and $CO_2$(1-4C alkyl);

hetCyc$^2$ is a pyridinone or pyridazinone ring substituted with a substituent selected from (1-4C)alkyl;

hetAr$^3$ is a 5-6 membered heteroaryl ring having 1-2 ring heteroatoms independently selected from N and O and optionally substituted with one or more substituents independently selected from (1-4C)alkyl;

Y is a phenyl ring optionally substituted with one or more substituents independently selected from halogen, (1-4C) alkoxy, $CF_3$ and $CHF_2$, or a 5-6 membered heteroaryl ring having a ring heteroatom selected from N and S;

X is null, —$CH_2$—, —$CH_2CH_2$—, —$CH_2O$—, or —$CH_2NR^d$—;

$R^d$ is H or (1-4C alkyl);

$R^3$ is H or (1-4C alkyl);

each $R^4$ is independently selected from halogen, (1-4C) alkyl, OH, (1-4 C)alkoxy, $NH_2$, NH(1-4C alkyl), and $CH_2OH$; and n is 0, 1, 2, 3, 4, 5, or 6.

Additional examples of Trk inhibitors are the substituted pyrazolo[1,5-a]pyrimidine compounds described in WO 10/048314, herein incorporated by reference in its entirety. For example, Trk inhibitors that are substituted pyrazolo[1,5-a]pyrimidine compounds can have the general formula V:

V

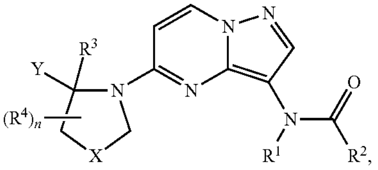

or a pharmaceutically acceptable salt thereof, wherein:

$R^1$ is H or (1-6C alkyl);

$R^2$ is $NR^bR^c$, (1-4C)alkyl, (1-4C)fluoroalkyl, $CF_3$, (1-4C) hydroxyalkyl, -(1-4C alkyl)hetAr$^1$, -(1-4C alkyl)$NH_2$, -(1-4C alkyl)NH(1-4C alkyl), -(1-4C alkyl)N(1-4C alkyl)$_2$, hetAr$^2$, hetCyc$^t$, hetCyc$^2$, phenyl which is optionally substituted with $NHSO_2$(1-4C alkyl), or (3-6C)cycloalkyl which is optionally substituted with (1-4C alkyl), CN, OH, OMe, $NH_2$, NHMe, $N(CH_3)_2$, F, $CF_3$, $CO_2$(1-4C alkyl), $CO_2H$, C(═O)$NR^eR^f$ or C(═O)$OR^g$;

$R^b$ is H or (1-6C alkyl);

$R^c$ is H, (1-4C)alkyl, (1-4C)hydroxyalkyl, $hetAr^3$, or phenyl, wherein said phenyl is optionally substituted with one or more substituents independently selected from halogen, CN, $CF_3$, and —O(1-4C alkyl), or $NR^bR^c$ forms a 4 membered heterocyclic ring having a ring nitrogen atom, wherein said heterocyclic ring is optionally substituted with one or more substituents independently selected from halogen, OH, (1-4C alkyl), (1-4 C)alkoxy, —OC(═O)(1-4C alkyl), $NH_2$, —NHC(═O)O(1-4C alkyl), and (1-4C)hydroxyalkyl, or $NR^bR^c$ forms a 5-6 membered heterocyclic ring having a ring heteroatom which is nitrogen and optionally having a second ring heteroatom or group selected from N, O, and $SO_2$, wherein the heterocyclic ring is optionally substituted with one or more substituents independently selected from OH, halogen, $CF_3$, (1-4C)alkyl, $CO_2$(1-4C alkyl), $CO_2H$, $NH_2$, NHC(═O)O(1-4C alkyl), and oxo, or $NR^bR^c$ forms a 7-8 membered bridged heterocyclic ring having a ring nitrogen atom and optionally having a second ring heteroatom selected from N and O, wherein the ring is optionally substituted with $CO_2$(1-4C alkyl);

$hetAr^1$ is a 5-membered heteroaryl ring having 1-3 ring nitrogen atoms;

$hetAr^2$ is 5-6 membered heteroaryl ring having at least one nitrogen ring atom and optionally having a second ring heteroatom independently selected from N and S, wherein said heteroaryl ring is optionally substituted with one or more substituents independently selected from (1-4C alkyl), halogen, -(1-4 C)alkoxy and NH(1-4C alkyl);

$hetCyc^1$ is a carbon-linked 4-6 membered azacyclic ring optionally substituted with one or more substituents independently selected from (1-4C alkyl) and $CO_2$(1-4C alkyl);

$hetCyc^2$ is a pyridinone or pyridazinone ring which is optionally substituted with a substituent selected from (1-4C)alkyl;

$hetAr^3$ is a 5-6 membered heteroaryl ring having 1-2 ring heteroatoms independently selected from N and O and optionally substituted with one or more substituents independently selected from (1-4C)alkyl;

$R^e$ is H or (1-4C)alkyl;

$R^f$ is H, (1-4C)alkyl, or (3-6C)cycloalkyl;

or $NR^eR^f$ forms a 4-6-membered azacyclic ring optionally having an additional ring heteroatom selected from N and O, wherein the azacyclic ring is optionally substituted with OH;

$R^g$ is H or (1-6C)alkyl;

Y is (i) phenyl optionally substituted with one or more substituents independently selected from halogen, (1-4C) alkoxy, $CF_3$, and $CHF_2$, or (ii) a 5-6 membered heteroaryl ring having a ring heteroatom selected from N and S, wherein said heteroaryl ring is optionally substituted with one or more halogen atoms;

X is null, —$CH_2$—, —$CH_2CH_2$—, —$CH_2O$—, or —$CH_2NR^d$—;

$R^d$ is H or (1-4C alkyl);

$R^3$ is H or (1-4C alkyl);

each $R^4$ is independently selected from halogen, (1-4C) alkyl, OH, (1-4 C)alkoxy, $NH_2$, NH(1-4C alkyl), and $CH_2OH$; and n is 0, 1, 2, 3, 4, 5, or 6.

For example, a Trk inhibitor can include one or more compounds selected from the group consisting of:

(R)-5-(2-(2,5-difluorophenyl)pyrrolidin-1-yl)-N-(pyridin-2-yl)pyrazolo[1,5-a]pyrimidine-3-carboxamide;

(R)-5-(2-(2,5-difluorophenyl)pyrrolidin-1-yl)-N-(2-morpholinoethyl)pyrazolo[1,5-a]pyrimidine-3-carboxamide;

N-((2S)-bicyclo[2.2.1]heptan-2-yl)-5-((R)-2-(2,5-difluorophenyl)pyrrolidin-1-yl)pyrazolo[1,5-a]pyrimidine-3-carboxamide;

(R)-5-(2-(2,5-difluorophenyl)pyrrolidin-1-yl)-N-(2-(2-oxoimidazolidin-1-yl)ethyl)pyrazole[1,5-a]pyrimidine-3-carboxamide;

5-((R)-2-(2,5-difluorophenyl)pyrrolidin-1-yl)-N—((R)-2,3-dihydroxypropyl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)—N-tert-butyl-5-(2-(5-fluoropyridin-3-yl)pyrrolidin-1-yl)pyrazolo[1,5-a]pyrimidine-3-carboxamide;

(R)-5-(2-(2,5-difluorophenyl)pyrrolidin-1-yl)pyrazolo[1,5-a]pyrimidine-3-carboxamide;

(R)-5-(2-(5-fluoropyridin-3-yl)pyrrolidin-1-yl)-N-(1-methylcyclobutyl)pyrazolo[1,5-a]pyrimidine-3-carboxamide; and 5-((R)-2-(5-fluoropyridin-3-yl)pyrrolidin-1-yl)-N—((S)-1,1,1-trifluoropropan-2-yl)pyrazolo[1,5-a]pyrimidine-3-carboxamide;

or a pharmaceutically acceptable salt thereof.

Additional Trk inhibitors can be found in U.S. Publication No. 2015/0166564 and WO 2012/158413, both of which are incorporated by reference in their entireties herein. For example, a Trk inhibitor can be a compound of Formula I:

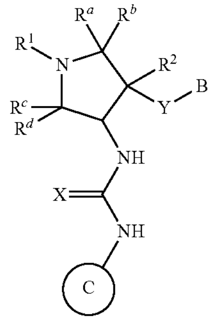

I or stereoisomers, tautomers, or pharmaceutically acceptable salts, solvates or prodrugs thereof, wherein:

the Y—B moiety and the NH—C(═X)—NH moiety are in the trans configuration;

$R^a$, $R^b$, $R^c$ and $R^d$ are independently selected from H and (1-3C)alkyl;

X is O, S or NH;

$R^1$ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluoro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, hydroxycarbonyl(1-3C alkoxy)(1-6C)alkyl, $hetAr^5(CH_2)_{0-1}$, or $Ar^5(CH_2)_{0-1}$;

$R^2$ is H, F, or OH;

Y is a bond, —O— or —$OCH_2$—;

B is Art, $hetAr^1$, 1-6C alkyl or (1-6C)alkoxy;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;

$hetAr^1$ is a 5-6 membered heteroaryl having 1-3 ring heteroatoms independently selected from N, S and O, and optionally substituted with 1-2 groups independently selected form (1-6C)alkyl, halogen, OH, $CF_3$, $NH_2$ and hydroxy(1-2C)alkyl;

Ring C is formula C-1, C-2, or C-3

C-1

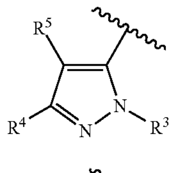

C-2

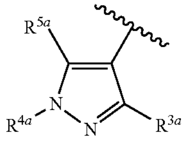

C-3

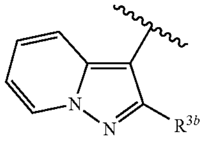

$R^3$ is H, (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more groups independently selected from halogen, (1-6C)alkyl and hydroxymethyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is H, OH, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, amino-carbonyl(1-6C)alkyl, (1-3C)alkylsulfonamido(1-6C)alkyl, sulfamido(1-6C)alkyl, hydroxyl-carbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C)alkoxy trifluoro(1-6C)alkoxy, tetrafluoro(2-6C)alkoxy, pentafluoro(2-6C)alkoxy cyano(1-6C)alkoxy, hydroxy(1-6C)alkoxy, dihydroxy(2-6C)alkoxy, amino(2-6C)alkoxy, aminocarbonyl(1-6C)alkoxy, hydroxycarbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $Ar^4$, $hetCyc^2(O)CH_2$—, (1-4C alkoxycarbonyl)(1-6C)alkoxy, hydroxycarbonyl(1-6C)alkoxy, aminocarbonyl(1-6C)alkoxy, $hetCyc^2$C(═O)(1-6C)alkoxy, hydroxy(1-3C alkoxy)(1-6C)alkoxy, hydroxytrifluoro(1-6C)alkoxy, (1-3 C)alkyl sulfonamido(1-6C)alkoxy, (1-3C)alkylamido(1-6C)alkoxy, di(1-3C alkyl)aminocarboxy, $hetCyc^2$C(═O)O—, hydroxydifluoro(1-6C)alkyl, (1-4C alkylcarboxy)(1-6C)alkyl, (1-6C)alkoxycarbonyl, hydroxycarbonyl, aminocarbonyl, (1-3C alkoxy)amino-carbonyl, $hetCyc^3$, halogen, CN, trifluoromethylsulfonyl, N-(1-3C alkyl)pyridinonyl, N-(1-3C trifluoroalkyl)pyridinonyl, (1-4C alkylsiloxy)(1-6C)alkoxy, isoindoline-1,3-dionyl(1-6C)alkoxy or N-(1-3C alkyl)oxadiazolonyl;

$hetCyc^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

$hetCyc^3$ is a 4-7 membered heterocycle having 1-2 ring heteroatoms independently selected from N and O and optionally substituted with one or more substituents independently selected from F, CN, $CF_3$, (1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

$hetAr^3$ is a 5-membered heteroaryl ring having 1-3 ring atoms independently selected from N, O and S and optionally substituted with (1-6C)alkyl;

$Ar^3$ is phenyl optionally substituted with (1-4C)alkoxy;

$hetAr^4$ is a 5-6 membered heteroaryl ring having 1-3 ring heteroatoms independently selected from N, S and O and optionally substituted with 1-2 substituents independently selected from (1-6C)alkyl, halogen, CN, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoroalkoxy), (1-3C)trifluoroalkyl, and methoxybenzyl; or a 9-10 membered bicyclic heteroaryl having 1-3 ring nitrogen atoms;

$Ar^4$ is phenyl optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—;

$R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(═O)—, (1-6C)alkylthio, phenyl [optionally substituted with one or more groups independently selected from halogen, (1-6C)alkyl and (1-6C)alkoxy], (3-4C)cycloalkyl, amino, aminocarbonyl, or trifluoro(1-3C alky)amido; or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6)acyl, (1-6C)alkyl and oxo, and said sulfur ring atom is optionally oxidized to S(═O) or $SO_2$;

$hetAr^5$ is a 5-6 membered heteroaryl ring having 1-3 ring heteroatoms independently selected from N, O or S, wherein the ring is optionally substituted with one or more substituents independently selected from halogen, (1-6C)alkyl, (1-6C)alkoxy and $CF_3$;

$Ar^5$ is phenyl optionally substituted with one or more groups independently selected from halogen, (1-6C)alkyl, (1-6C)alkoxy, $CF_3O$—, (1-4C)alkoxycarbonyl and aminocarbonyl;

$R^{3a}$ is hydrogen, halogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen;

$R^{3b}$ is hydrogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen;

$R^{4a}$ is hydrogen, (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoroalkoxy)(1-3C)trifluoroalkyl, and methoxybenzyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen, (1-6C)alkyl and hydroxymethyl, or a 5-6 membered heteroaryl ring having 1-3 ring heteroatoms independently selected from N, O and S and optionally substituted with one or more groups independently selected from (1-6C)alkyl and halogen.

Further examples of Trk inhibitors can be found in International Publication No. WO 2014078454, which is incorporated by reference in its entirety herein. For example, a Trk inhibitor can be a compound of Formula I:

I

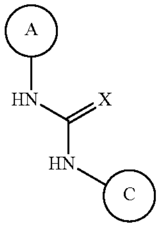

or stereoisomers, tautomers, or pharmaceutically acceptable salts, or solvates thereof, wherein:

X is O, S, NH or N—CN;

Ring A is formula A-1 or A-2

A-1

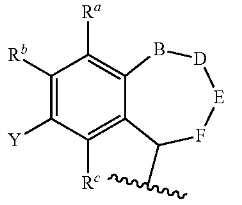

A-2

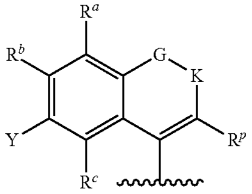

Y is H, halogen, (1-3C alkoxy)(1-6C)alkyl, (1-6C)alkyl [optionally substituted with 1-5 fluoros], cyano(1-6C)alkyl, hydroxy(1-6C)alkyl, dihydroxy(2-6C)alkyl, aminocarbonyl(1-6C)alkyl, (1-6C)alkoxy [optionally substituted with 1-5 fluoros], CN, aminocarbonyl or (1-4C alkoxy)carbonyl;

$R^a$, $R^b$ and $R^c$ are independently selected from H, halogen, (1-3C)alkyl, (1-3C)alkoxy and CN;

B is $NR^1$, O, a bond, $CR^dR^e$, S or $SO_2$;

D is $NR^1$, O, a bond, $CR^fR^8$, S or $SO_2$;

E is $NR^1$, O, a bond, or $CR^hR$\S or $SO_2$;

F is $CR^jR^k$;

provided that the ring formed by B, D, E, and F together with the atoms to which they are attached contains at least five atoms and zero or one of B, D or E is $NR^1$ or O;

G is $CR'''R''$;

K is $NR^1$; $R^1$ is (1-6C)alkyl [optionally substituted with one to five fluoros], (1-6C)cycloalkyl [optionally substituted with one to five fluoros], (1-3C alkoxy)(2-6C)alkyl [optionally substituted with one to five fluoros], (1-6C)alkylC(═O)— or (1-6C alkoxy)C═O—;

$R^d$, $R^e$, $R^f$, $R^g$, $R^h$, R\$R^j$ and $R^k$ are independently H, OH, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], (2-6C)cyanoalkyl, (1-6C)alkoxy [optionally substituted with one to five fluoros], or (1-3C alkoxy)(2-6C)alkoxy [optionally substituted with one to five fluoros], or one of a pair of $R^d$ and $R^e$, or $R^f$ and $R^8$, or $R^h$ and $R^l$, or R* and $R^k$, together with the carbon atom to which they are attached form a (3-6C)cycloalkyl, oxetanyl or azetidinyl ring, or one of a pair of $R^d$ and $R^e$, or $R^f$ and $R^8$, or $R^h$ and $R^1$, or $R^j$ and $R^k$ form an oxo group, and wherein only one of $R^d$ and $R^e$ can be OH and neither is OH if B is connected to a heteroatom, and only one of $R^f$ and $R^8$ can be OH and neither is OH if D is connected to a heteroatom, and only one of $R^h$ and R' can be OH and neither is OH if E is connected to a heteroatom, and only one of $R^j$ and $R^k$ can be OH and neither is OH if F is connected to a heteroatom;

$R'''$ is H, (1-3C)alkyl [optionally substituted with 1-5 fluoros], cyclopropyl or cyclobutyl, and R" is H or (1-3C)alkyl [optionally substituted with 1-5 fluoros], or $R'''$ and $R''$ together form an oxo group;

$R^p$ is H, (1-6C)alkyl [optionally substituted with one to five fluoros], (3-6C)cycloalkyl [optionally substituted with one to five fluoros], (1-3C alkoxy)(2-6C)alkyl [optionally substituted with one to five fluoros], hydroxy(2-6C)alkyl [optionally substituted with one to five fluoros], or (2-6C) cyanoalkyl;

Ring C is formula C-1 or C-2

C-1

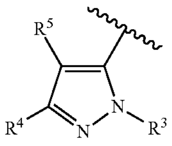

C-2

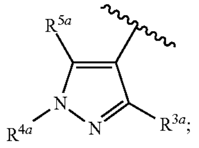

$R^3$ is (1-6C)alkyl, hydroxy(1-6C)alkyl, $Ar^2$, $hetCyc^1$, (3-7C) cycloalkyl, or $hetAr^2$;

$Ar^2$ is phenyl optionally substituted with one or more groups independently selected from halogen and (1-6C)alkyl; $hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro(1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3 C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C)alkoxy, trifluoro(1-6C)alkoxy, tetrafluoro(2-6C)alkoxy, pentafluoro(2-6C)alkoxy, cyano(1-6C)alkoxy, hydroxy(1-6C)alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C) alkyl], $hetAr^4$, $hetAr^4$—O—, $Ar^4$, $hetCyc^2$(O)$CH_2$—, (1-4C alkoxycarbonyl)(1-6C)alkoxy, hydroxycarbonyl(1-6C)alkoxy, aminocarbonyl(1-6C)alkoxy, $hetCyc^2$C(═O)(1-6C)alkoxy, hydroxy(1-3C alkoxy)(1-6C)alkoxy, hydroxytrifluoro(1-6C)alkoxy, (1-3C)alkyl sulfonamido (1-6C)alkoxy, (1-3C)alkylamido(1-6C)alkoxy, di(1-3C alkyl)amino-carboxy, $hetCyc^2$C(═O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, $hetCyc^3$, halogen, CN, trifluoromethylsulfonyl, N-(1-3C alkyl)oxadiazolonyl, $hetAr^5$ or $hetCyc^4$-O—;

hetCyc is a 4-6 membered heterocyclic ring having 1-2 ring heteroatoms independently selected from N and O and optionally substituted with 1-2 groups independently selected from (1-6C)alkyl, (1-4C alkylcarboxy)(1-6C) alkyl, and (1-6C)acyl;

$hetCyc^3$ is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl; $hetAr^3$ is a 5-membered heteroaryl ring having 1-3 ring atoms independently selected from N, O and S and optionally substituted with (1-6C) alkyl;

$Ar^3$ is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy(1-6C)alkyl, trifluoro(1-6C)alkyl, difluoro(1-6C) alkyl, fluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;

$hetAr^5$ is a group selected from the structures:

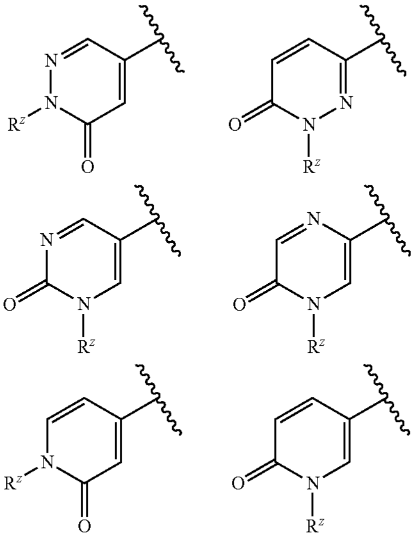

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros;

$hetCyc^4$ is a 7-8 membered bridged heterocycle having a ring nitrogen atom and optionally substituted with one or more groups independently selected from (1-6C)alkyl and halogen;

$Ar^4$ is phenyl optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy (1-4C)alkyl, (1-3C alkoxy)(1-4C)alkyl, (1-4C alkyl)OC (═O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C) alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C) acyl, (1-6C)alkyl and oxo, and said sulfur ring atom is optionally oxidized to S(═O) or $SO_2$;

$R^{3a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is hydrogen, (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

Further examples of Trk inhibitors can be found in International Publication No. WO 2014078417, which is incorporated by reference in its entirety herein. For example, a Trk inhibitor can be a compound of Formula I:

I

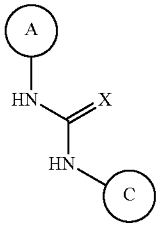

or stereoisomers, tautomers, or pharmaceutically acceptable salts, solvates or prodrugs thereof, wherein:

X is O, S, NH or N—CN;

Ring A is

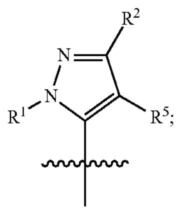

$R^1$ is phenyl optionally substituted with one or more substituents independently selected from halogen and (1-3C) alkyl;

$R^2$ is (1-3C)alkyl [optionally substituted with 1 to 5 fluoros] or (3-4C)cycloalkyl [optionally substituted with one or two fluoros];

$R^6$ is H or $CH_3$; Ring C is formula C-1 or C-2

C-1

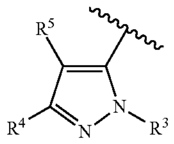

C-2

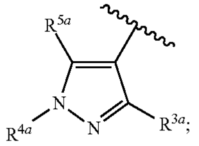

$R^3$ is (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more substituents independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more substituents independently selected from (1-6C)alkyl and halogen; $R^4$ is $hetAr^4$, $hetAr^5$ or hydroxy(1-6C)alkoxy;

$hetAr^4$ is a 5-6 membered heteroaryl ring having 1-3 ring heteroatoms independently selected from N, S and O and substituted with one or more substituents independently selected from (1-6C)alkyl, halogen, CN, hydroxy(1-6C) alkyl, trifluoro(1-6C)alkyl, difluoro(1-6C)alkyl, fluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C) alkoxy, (1-6C)alkylsulfonyl, $NH_2$, (1-6C alkyl)amino, di(1-6C alkyl)amino, (1-3C trifluoroalkoxy), fluoro(1-6C alkyl) amino, difluoro(1-6C alkyl)amino, trifluoro(1-6C alkyl) amino, and (3-4C cycloalkyl)amino;

hetAr[5] is a group selected from the structures:

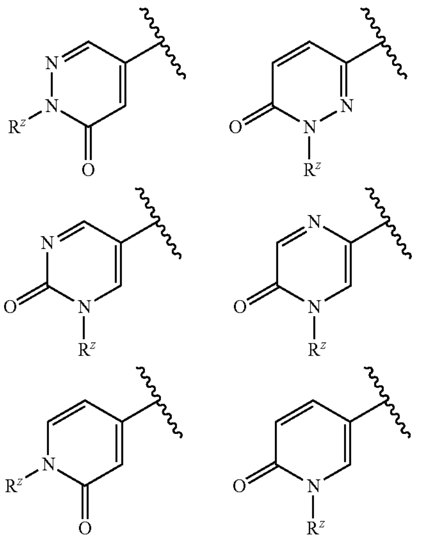

where $R^z$ is (3-4C)cycloalkyl or (1-3C)alkyl (optionally substituted with 1-3 fluoros), wherein each of said hetAr[5] groups is optionally further substituted with one or more substituents independently selected from F and (1-3C)alkyl optionally substituted with 1-3 fluoros;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(═O)—, (1-6C)alkylthio, (3-4C)cycloalkyl, amino, aminocarbonyl, trifluoro(1-3C alkyl)amido, or phenyl (optionally substituted with one or more substituents independently selected from halogen, (1-6C)alkyl and (1-6C) alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C)acyl, (1-6C)alkyl and oxo, and said sulfur ring atom is optionally oxidized to S(═O) or $SO_2$; R is hydrogen, halogen, (1-6C) alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C) alkyl and halogen;

$R^{4a}$ is hydrogen, (1-6C)alkyl, trifluoro(1-6C)alkyl, phenyl [optionally substituted with one or more substituents independently selected from (1-6C)alkyl, halogen, CN, $CF_3$, CF3O—, (1-6C)alkoxy, (1-6Calkyl)OC(═O)—, aminocarbonyl, (1-6C)alkylthio, hydroxy(1-6C)alkyl, (1-6C alkyl) $SO_2$—, HOC(═O)— and (1-3C alkoxy)(1-3C alkyl)OC(═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen.

Additional examples of Trk inhibitors can be found in International Publication No. WO 2014078408, which is incorporated by reference in its entirety herein. For example, a Trk inhibitor can be a compound of Formula I:

I

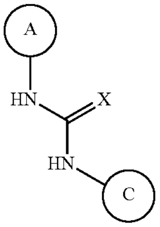

or stereoisomers, tautomers, or pharmaceutically acceptable salts, solvates or prodrugs thereof, wherein:

X is O, S, NH or —N—CN;

Ring A is formula A-1 A-2, A-3 or A-4

A-1

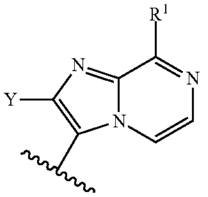

A-2

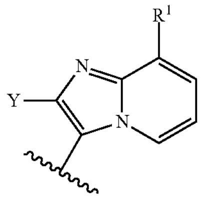

A-3

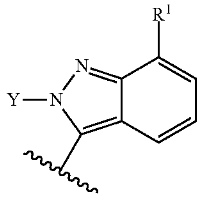

-continued

A-4

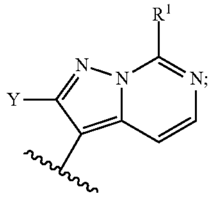

$R^1$ is H, halogen, (1-3C)alkyl [optionally substituted with 1-5 fluoros], (1-3C)alkoxy [optionally substituted with 1-5 fluoros], or (3-5C)cycloalkyl;

Y is $Ar^1$ or $hetAr^1$;

$Ar^1$ is phenyl optionally substituted with one or more substituents independently selected from halogen, (1-3C) alkyl [optionally substituted with 1-5 fluoros], and (1-3C) alkoxy [optionally substituted with 1-5 fluoros];

$hetAr^1$ is pyridyl optionally substituted with one or more substituents independently selected from halogen, (1-3C) alkyl [optionally substituted with 1-5 fluoros], and (1-3C) alkoxy [optionally substituted with 1-5 fluoros];

Ring C is formula C-1 or C-2

C-1

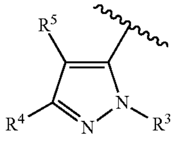

C-2

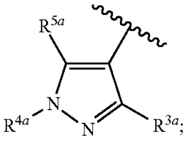

$R^3$ is (1-6C)alkyl, hydroxy(1-6C)alkyl, $Ar^2$, $hetCyc^1$, (3-7C)cycloalkyl, or $hetAr^2$; Ar is phenyl optionally substituted with one or more substituents independently selected from halogen and (1-6C)alkyl; $hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more substituents independently selected from (1-6C)alkyl and halogen;

$R^4$ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C) alkoxy, trifluoro(1-6C)alkoxy, tetrafluoro(2-6C)alkoxy, pentafluoro(2-6C)alkoxy, cyano(1-6C)alkoxy, hydroxy(1-6C) alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2(O)CH_2$—, (1-4C alkoxycarbonyl)(1-6C) alkoxy, hydroxycarbonyl(1-6C)alkoxy, aminocarbonyl(1-6C)alkoxy, $hetCyc^2C(=O)$(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, $hetCyc^2C(=O)O$—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, $hetCyc^3$, halogen, CN, trifluoromethylsulfonyl, N-(1-3C alkyl)oxadiazolonyl, or $hetAr^5$;

hetCyc is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc is a 4-7 membered heterocycle having 1-2 ring heteroatoms independently selected from N and O and optionally substituted with one or more substituents independently selected from F, CN, (1-6C)alkyl, trifluoro(1-6C) alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

$hetAr^3$ is a 5-membered heteroaryl ring having 1-3 ring atoms independently selected from N, O and S and optionally substituted with (1-6C)alkyl; $AT^3$ is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)$CH_2$-(3-6C cycloalkyl)C(=O)—, (1-3C alkoxy)(1-6C)alkyl, (1-6C)alkoxy, (1-6C)alkylsulfonyl, $NH_2$, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

$hetAr^5$ is a group selected from the structures:

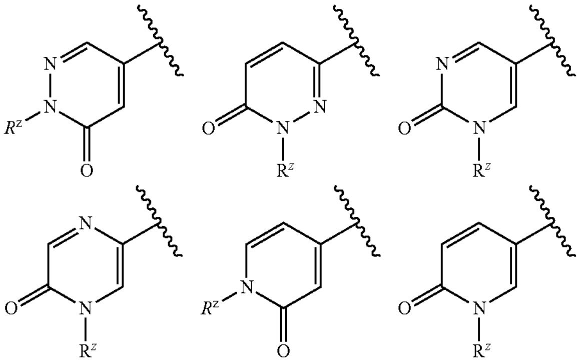

where $R^z$ is (3-4C)cycloalkyl or (1-3C)alkyl (optionally substituted with 1-3 fluoros), wherein each of said $hetAr^5$ groups is optionally further substituted with one or more substituents independently selected from F and (1-3C)alkyl optionally substituted with 1-3 fluoros;

$Ar^4$ is phenyl optionally substituted with one or more substituents independently selected from (1-6C)alkyl, halogen, CN, $CF_3$, $CF_3O$—, (1-6C)alkoxy, (1-6Calkyl)OC (=O)—, aminocarbonyl, (1-6C)alkylthio, hydroxy(1-6C) alkyl, (1-6C alkyl)$SO_2$—, HOC(=O)— and (1-3C alkoxy) (1-3C alkyl)OC(=O)—;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more substituents independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$;

$R^{3a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen;

$R^{4a}$ is hydrogen, (1-6C)alkyl, trifluoro(1-6C)alkyl, phenyl [optionally substituted with one or more substituents independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen.

Further examples of Trk inhibitors can be found in International Publication No. WO 2014078378, which is incorporated by reference in its entirety herein. For example, a Trk inhibitor can be a compound of Formula I:

I

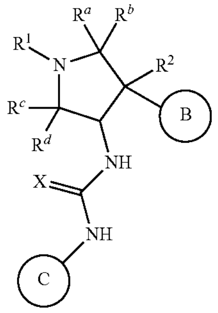

or stereoisomers, tautomers, or pharmaceutically acceptable salts, solvates or prodrugs thereof, wherein:

Ring B and the NH—C(=X)—NH moiety are in the trans configuration;

$R^a$, $R^b$, $R^c$ and $R^d$ are independently selected from H and (1-3C)alkyl, or $R^c$ and $R^d$ are independently selected from H and (1-3C)alkyl, and $R^a$ and $R^b$ together with the atom to which they are attached form a cyclopropyl ring;

X is O, S, NH or N—CN;

$R^1$ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl(1-3C alkoxy)(1-6C)alkyl;

$R^2$ is H, F, or OH;

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; $hetAr^1$ is a 5-6 membered heteroaryl having 1-3 ring heteroatoms independently selected from N, S and O, and optionally substituted with one or more groups independently selected from (1-6C)alkyl, halogen, OH, $CF_3$, $NH_2$ and hydroxy(1-2C)alkyl;

Ring C is selected from formulas C-1 through C-13:

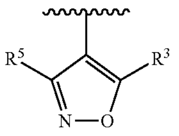

C-1

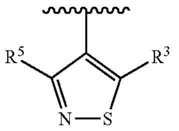

C-2

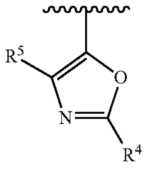

C-3

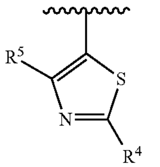

C-4

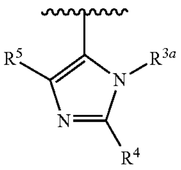

C-5

-continued

C-6

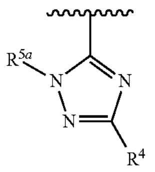

C-7

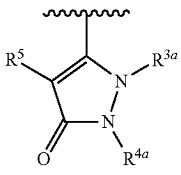

C-8

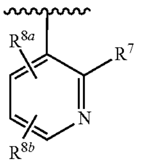

C-9

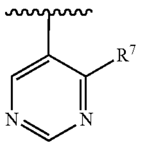

C-10

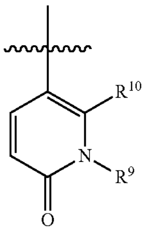

C-11

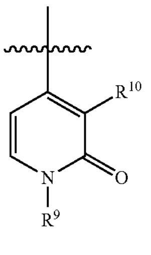

C-12

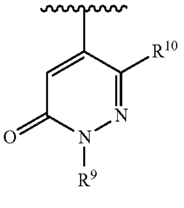

-continued

C-13

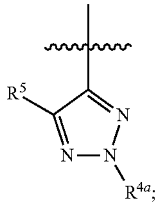

R is H, $NH_2$, CN, halogen, (1-3C)alkyl [optionally substituted with 1 to 3 fluoros], $H_2NC(=O)$—, (1-3Calkyl)NHC(=O)—, di(1-3Calkyl) NHC(=OK hydroxy(1-3C)alkyl, CH3OCH2CH2, (3-4C) cycloalkyl or (1-3C)alkoxy;

$R^{3a}$ is H, (1-3C)alkyl, $CF_3CH_2CH_2$, $HCF_2CH_2CH_2$, $H_2FCCH_2CH_2$, $CF_3CH_2$, $HOCH_2CH_2$, $MeOCH_2CH_2$, or (3-4C)cycloalkyl;

$R^4$ is H, OH, (1-6C)alkyl [optionally substituted with 1-5 fluoros], cyano(1-6C)alkyl, hydroxy(1-6C)alkyl, dihydroxy (2-6C)alkyl, (1-3C alkoxy)(1-6C)alkyl, amino(1-6C)alkyl, aminocarbonyl(1-6C)alkyl, (1-3C)alkylsulfonamido(1-6C) alkyl, sulfamido(1-6C)alkyl, hydroxycarbonyl(1-6C)alkyl, hetAr$^3$(1-6C)alkyl, Ar$^3$(1-6C)alkyl, (1-6C)alkoxy [optionally substituted with 1-5 fluoros], cyano(1-6C)alkoxy, hydroxy(1-6C)alkoxy, dihydroxy(2-6C)alkoxy, amino(2-6C)alkoxy, hydroxyl-carbonyl(1-6C)alkoxy, hetCyc (1-6C) alkoxy, hetAr$^3$(1-6C)alkoxy, Ar$^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], hetAr$^4$, hetAr$^4$—O—, Ar$^4$, hetCyc$^2$(O)$CH_2$—, (1-4C alkoxycarbonyl)(1-6C)alkoxy, hydroxycarbonyl(1-6C)alkoxy, aminocarbonyl(1-6C)alkoxy, hetCyc$^2$C(=O)(1-6C)alkoxy, hydroxy(1-3C alkoxy)(1-6C)alkoxy, hydroxytrifluoro(1-6C)alkoxy, (1-3C)alkylsulfonamido(1-6C)alkoxy, (1-3C) alkylamido(1-6C)alkoxy, di(1-3C alkyl)amino-carboxy, hetCyc C(=O)O—, hydroxydifluoro(1-6C)alkyl, (1-4C alkylcarboxy)(1-6C)alkyl, (1-6C)alkoxycarbonyl, hydroxylcarbonyl, aminocarbonyl, (1-3C alkoxy)aminocarbonyl, hetCyc, halogen, CN, trifluoromethylsulfonyl, N-(1-3C alkyl) oxadiazolonyl, or hetAr$^5$;

$R^{4a}$ is H, (1-6C)alkyl, $CF_3CH_2CH_2$, $HCF_2CH_2CH_2$, $H_2FCCH_2CH_2$, $CF_3CH_2$, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, hetAr$^3$(1-6C)alkyl, Ar$^3$(1-6C)alkyl, (3-6C)cycloalkyl [optionally substituted with F, OH, (1-6C alkyl), (1-6C) alkoxy, or (1-3C alkoxy)(1-6C)alkyl], hetAr$^4$, Ar$^4$, hydroxydifluoro(1-6C)alkyl, (1-4C alkylcarboxy)(1-6C)alkyl, hetCyc$^3$, N-(1-3C alkyl)oxadiazolonyl, or hetAr$^5$;

hetCyc is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl;

hetCyc is a 4-7 membered heterocycle having 1-2 ring heteroatoms independently selected from N and O and optionally substituted with one or more substituents independently selected from F, CN, (1-6C)alkyl, trifluoro(1-6C) alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

hetAr is a 5-membered heteroaryl ring having 1-3 ring atoms independently selected from N, O and S and optionally substituted with (1-6C)alkyl;

Ar is phenyl optionally substituted with (1-4C)alkoxy;

$hetAr^4$ is independently a 5-6 membered heteroaryl ring having 1-3 ring heteroatoms independently selected from N, S and O and optionally substituted with one or more substituents independently selected from (1-6C)alkyl [optionally substituted with 1-3 fluoros], halogen, CN, hydroxy (1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

$hetAr^5$ is a group selected from the structures:

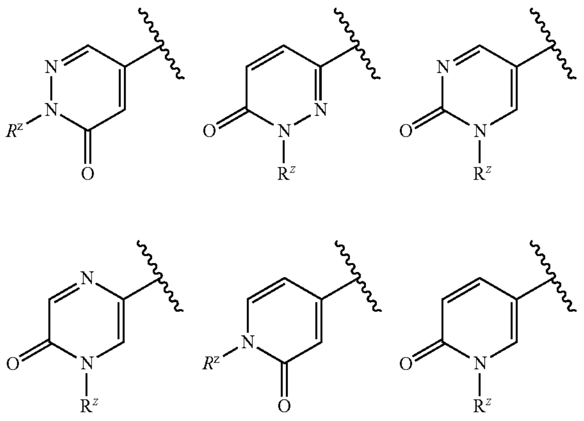

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros;

$Ar^4$ is phenyl optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl) OC(═O)—;

$R^5$ is H, (1-6C)alkyl [optionally substituted with 1-5 fluoros], halogen, CN, (1-4C)alkoxy, hydroxy(1-4C)alkyl, (1-3C alkoxy)(1-4C)alkyl, (1-4C alkyl)OC(═O)—, (1-6C) alkylthio, (3-4C)cycloalkyl, amino, aminocarbonyl, trifluoro(1-3C alkyl)amido, or phenyl [optionally substituted with one or more groups independently selected from halogen, (1-6C)alkyl and (1-6C)alkoxy];

$R^{5a}$ is H, (1-6C)alkyl, $CF_3CH_2CH_2$, $HCF_2CH_2CH_2$, $H_2FCCH_2CH_2$, $CF_3CH_2$, hydroxy(1-4C)alkyl, (1-3C alkoxy)(1-4C)alkyl, (3-4C)cycloalkyl, or phenyl [optionally substituted with one or more groups independently selected from halogen, (1-6C)alkyl and (1-6C)alkoxy];

R is (1-6C)alkyl, (3-6C)cycloalkyl, or phenyl [optionally substituted with one or more groups independently selected from halogen, (1-6C)alkyl, (1-6C)alkoxy, (3-4C)cycloalkyl, amino, aminocarbonyl, and trifluoro(1-3C)alkylamido];

$R^{8a}$ and $R^{8b}$ are independently H, halogen, CN, $NH_2$, (1-6C)alkyl [optionally substituted with 1-5 fluoros], (1-6C) alkoxy, (1-3C alkoxy)(1-6C)alkyl, (1-3C alkoxy)(1-6C) alkoxy, (1-6C alkyl)sulfonyl, (3-6C cycloalkyl)sulfonyl, (3-4C)cycloalkyl, amino, (1-6Calkyl)NH—, phenyl [optionally substituted with (1-6C alkyl)$SO_2$—] or $hetAr^4$, wherein only one of $R^{8a}$ and $R^{8b}$ can be phenyl [optionally substituted with (1-6C alkyl)$SO_2$—] or $hetAr^4$;

$R^9$ is H, (1-6C)alkyl, $CF_3CH_2$—, $CF_3CH_2CH_2$—, (1-3Calkoxy)(1-6C)alkyl or (3-4C)cycloalkyl; and $R^{10}$ is (3-6C)cycloalkyl or phenyl [optionally substituted with one or more substituents independently selected from halogen, (1-6C)alkyl, (1-6C)alkoxy, (3-4C)cycloalkyl, amino, aminocarbonyl and trifluoro(1-3C alkyl)amido].

Additional examples of Trk inhibitors can be found in International Publication No. WO 2014078372, which is incorporated by reference in its entirety herein. For example, a Trk inhibitor can be a compound of Formula I:

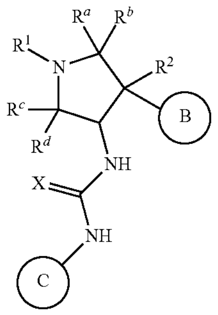

I or stereoisomers, tautomers, or pharmaceutically acceptable salts, solvates or prodrugs thereof, wherein:

Ring B and the NH—C(═X)—NH moiety are in the trans configuration;

$R^a$, $R^b$, $R^c$ and $R^d$ are independently selected from H and (1-3C)alkyl, or $R^c$ and $R^d$ are independently selected from H and (1-3C)alkyl, and $R^a$ and $R^b$ together with the atom to which they are attached form a cyclopropyl ring;

X is O, S, NH or N—CN;

$R^1$ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3C)alkylamino(1-3C)alkyl, (1-4C) alkoxycarbonyl(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl(1-3C alkoxy)(1-6C)alkyl;

$R^2$ is H, F, or OH;

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; $hetAr^1$ is a 5-6 membered heteroaryl having 1-3 ring heteroatoms independently selected from N, S and O, and optionally substituted with one or more groups independently selected from (1-6C)alkyl, halogen, OH, $CF_3$, $NH_2$ and hydroxy(1-2C)alkyl;

Ring C is selected from formulas C-1 through C-9

C-1

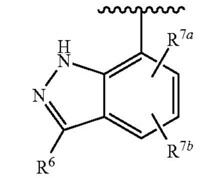

C-2

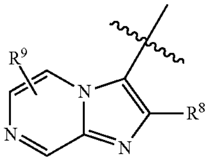

C-3

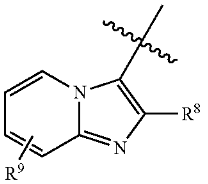

C-4

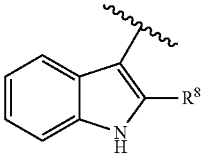

C-5

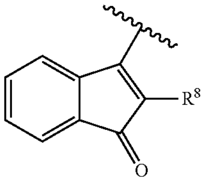

C-6

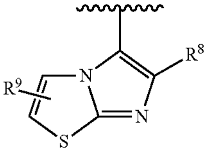

C-7

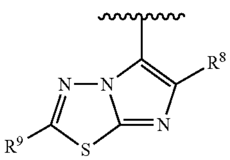

C-8

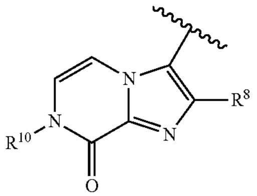

-continued

C-9

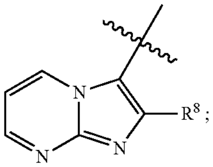

R is H, halogen, or phenyl [optionally substituted with one or more substituents independently selected from halogen and (1-3C)alkyl];

$R^{7a}$ and $R^{7b}$ are independently H, (1-6C)alkyl, or phenyl [optionally substituted with one or more substituents independently selected from halogen and (1-3C)alkyl], wherein only one of $R^{7a}$ and $R^{7b}$ can be phenyl optionally substituted with one or more substituents independently selected from halogen and (1-3C)alkyl;

$R^8$ is phenyl optionally substituted with one or more substituents independently selected from halogen, (1-3C) alkyl and (3-6C)cycloalkyl;

$R^9$ is H, halogen, (1-6C)alkyl [optionally substituted with one to five fluoros] or (1-6C)alkoxy; and $R^{10}$ is H or (1-6C)alkyl.

Further examples of Trk inhibitors can be found in International Publication No. WO 2014078331, which is incorporated by reference in its entirety herein. For example, a Trk inhibitor can be a compound of Formula I-C:

I-C

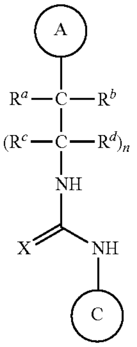

or stereoisomers, tautomers, or pharmaceutically acceptable salts, solvates or prodrugs thereof, wherein:

X is O, S, NH or N—CN;

Ring A is formula A-1 or A-2

A-1

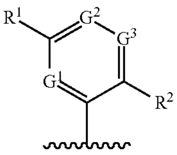

A-2

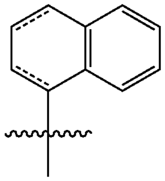

wherein the dashed lines are optional double bonds;

n is 0 or 1 when Ring A is formula A-1, and n is 0 when Ring A is formula A-2;

$G^1$, $G^2$ and $G^3$ are independently $CR^X$ or N, wherein no more than 2 of $G^1$, $G^2$ and $G^3$ can be N;

each $R^x$ is independently H, halogen, (1-4C)alkyl or (1-4C)alkoxy;

$R^1$ is H, halogen, (1-3C)alkoxy(1-3C)alkyl (optionally substituted with 1-5 fluoros), (1-3C alkyl)sulfanyl(1-3C) alkyl (optionally substituted with 1-5 fluoros), (1-3C)alkyl (optionally substituted with 1-5 fluoros), (1-3C)alkoxy (optionally substituted with 1-5 fluoros), (1-3C alkyl)sulfanyl (optionally substituted with 1-5 fluoros), cyano(1-3C)alkyl (optionally substituted with 1-5 fluoros), hydroxy(1-3C) alkyl (optionally substituted with 1-5 fluoros), (1-4C)alkyl (optionally substituted with 1-5 fluoros), $CH_3CH_2NR^y$, $CF_3CH_2NR^y$, $HCF_2CH_2NR^y$, $H_2CFCH_2NR^y$, $CH_3NR^yCH_2$, $R^yR^yNCH_2CH_2$, $R^yR^yNCH_2CFH$, or $R^yR^yNCH_2CF_2$;

each $R^y$ is independently H or methyl;

when n is 0, R is selected from the group consisting of H, halogen, (1-6C)alkyl

[optionally substituted with 1-5 fluoros], (1-6C)alkoxy [optionally substituted with 1-5 fluoros], (1-3C alkoxy)(1-4C)alkyl, (3-6C cycloalkyl)$CH_2O$—, amino(1-3C)alkyl, $CF_3CH_2NHCH_2$, $HCF_2CH_2NHCH_2$, a C5-C8 bridged cycloalkyl, $hetCyc^3$, $hetCyc^aCH_2$, $Cyc^a$, $hetAr^1$ and $Ar^1$, and when n is 1, R is selected from the group consisting of H, halogen, $CF_3$, $F_2CH$, $FCH_2$, methyl and methoxy.

$hetCyc^3$ is a 4-6 membered heterocyclic ring having a ring heteroatom selected from N, O and S and optionally substituted with 1-3 groups independently selected from OH, F, (1-6C)alkoxy or (1-6C)alkyl [optionally substituted with 1-3 fluoros];

$Cyc^a$ is a (3-6C)cycloalkyl optionally substituted with (1-4C)alkoxy, (1-4C)alkyl, F or OH;

$hetAr^1$ is a 5-6 membered heteroaryl having 1-3 ring heteroatoms independently selected from N, S and O, and optionally substituted with 1-2 groups independently selected from (1-6C)alkyl, halogen, OH, $CF_3$, $NH_2$ and hydroxy(1-2C)alkyl;

$Ar^1$ is phenyl optionally substituted with one or more substituents independently selected from halogen, $CF_3$, $CF_3O$—, (1-4C)alkoxy, (1-4C)sulfanyl, hydroxy(1-4C) alkyl, (1-6C)alkyl and CN;

$R^a$ is H, (1-3C)alkyl, cyclopropyl, cyclobutyl, or $CF_3$, and $R^b$ is H, methyl or ethyl, or $R^a$ and $R^b$ together with the carbon atom to which they are attached form a 3-6 membered cycloalkyl ring;

$R^c$ is H, methyl or ethyl $R^d$ is $CF_3CH_2CH_2$, phenyl or phenyl$CH_2$— wherein each phenyl ring is optionally substituted with one or more substituents independently selected from halogen, methoxy and methoxymethyl;

Ring C is formula C-1 or C-2

C-1

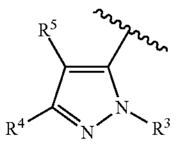

-continued

C-2

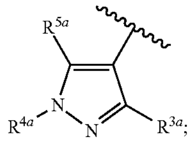

$R^3$ is (1-6C)alkyl, hydroxy(1-6C)alkyl, $Ar^2$, $hetCyc^1$, (3-7C)cycloalkyl, a C5-C8 bridged cycloalkyl, or $hetAr^2$;

$Ar^2$ is phenyl optionally substituted with one or more groups independently selected from halogen and (1-6C) alkyl;

$hetCyc^1$ is a 5-6-membered saturated or partially unsaturated heterocyclic ring having 1-2 ring heteroatoms independently selected from N and O;

hetAr is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C) alkyl, $hetAr^3$(1-6C)alkyl, $Ar^3$(1-6C)alkyl, (1-6C)alkoxy, monofluoro(1-6C)alkoxy, difluoro(1-6C)alkoxy, trifluoro (1-6C)alkoxy, tetrafluoro(2-6C)alkoxy, pentafluoro(2-6C) alkoxy, cyano(1-6C)alkoxy, hydroxy(1-6C)alkoxy, dihydroxy(2-6C)alkoxy, amino(2-6C)alkoxy, hydroxylcarbonyl(1-6C)alkoxy, $hetCyc^2$(1-6C)alkoxy, $hetAr^3$(1-6C) alkoxy, $Ar^3$(1-6C)alkoxy, (1-4C alkoxy)(1-6C)alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2$(O) $CH_2$—, (1-4C alkoxycarbonyl)(1-6C)alkoxy, hydroxycarbonyl(1-6C)alkoxy, aminocarbonyl(1-6C)alkoxy, $hetCyc^2$C (═O)(1-6C)alkoxy, hydroxy(1-3C alkoxy)(1-6C)alkoxy, hydroxytrifluoro(1-6C)alkoxy, (1-3C)alkylsulfonamido (1-6C)alkoxy, (1-3C)alkylamido(1-6C)alkoxy, di(1-3C alkyl)amino-carboxy, $hetCyc^2$C(═O)O—, hydroxydifluoro (1-6C)alkyl, (1-4C alkylcarboxy)(1-6C)alkyl, (1-6C) alkoxycarbonyl, hydroxylcarbonyl, aminocarbonyl, (1-3C alkoxy)aminocarbonyl, $hetCyc^3$, halogen, CN, trifluoromethylsulfonyl, N-(1-3C alkyl)oxadiazolonyl, $hetAr^5$, $Ar^4$—O—, $hetCyc^4$-O—, Cyc'-O—, or aminohydroxy(1-6C) alkoxy; $hetCyc^2$ is a 4-6 membered heterocyclic ring having 1-2 ring heteroatoms independently selected from N and O and optionally substituted with 1-2 groups independently selected from (1-6C)alkyl, 1-4C alkoxy)carbonyl, (1-6C)acyl, halogen and oxo;

hetCyc is a 4-7 membered heterocycle having 1-2 ring heteroatoms independently selected from N and O and optionally substituted with one or more substituents independently selected from F, CN, (1-6C)alkyl, trifluoro (1-6C)alkyl, hydroxy(1-6C)alkyl, (1-3C alkoxy)(1-6C) alkyl, (1-6C)acyl-, (1-6C)alkylsulfonyl, trifluoromethylsulfonyl and (1-4C alkoxy)carbonyl;

$hetCyc^4$ is a 5-8 membered monocyclic, spirocyclic or bridged heterocycle having a ring nitrogen atom and optionally substituted with one or more groups independently selected from (1-6C)alkyl and halogen;

$Cyc^1$ is a 3-6 membered carbocycle optionally substituted with an amino group; $hetAr^3$ is a 5-membered heteroaryl ring having 1-3 ring atoms independently selected from N, O and S and optionally substituted with (1-6C)alkyl;

Ar is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)$CH_2$-(3-6C cycloalkyl)C(═O)—, (1-3C alkoxy)(1-6C)alkyl, (1-6C)alkoxy, (1-6C)alkylsulfonyl, $NH_2$, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

$hetAr^5$ is a group selected from the structures:

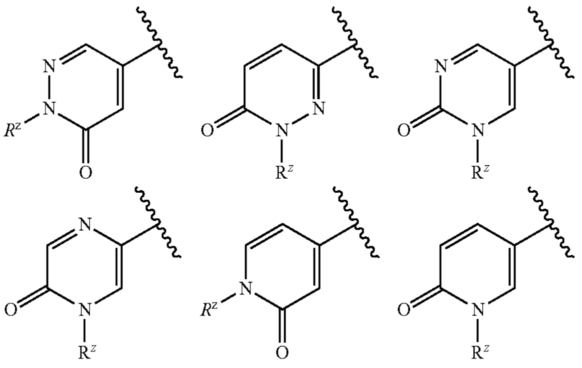

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros;

$Ar^4$ is phenyl optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl) OC(═O)—;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (═O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C)acyl, (1-6C)alkyl and oxo, and said sulfur ring atom is optionally oxidized to S(═O) or $SO_2$;

$R^{3a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is hydrogen, (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl) $SO_2$—, HOC(═O)— and (1-3C alkoxy)(1-3C alkyl)OC (═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

Additional examples of Trk inhibitors can be found in International Publication No. WO 2014078328, which is incorporated by reference in its entirety herein. For example, a Trk inhibitor can be a compound of Formula I-1:

I-1

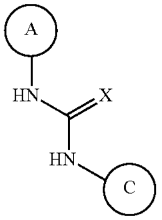

or stereoisomers, tautomers, or pharmaceutically acceptable salts, solvates or prodrugs thereof, wherein:

Ring A is selected from formulas A-1, A-2, A-3 or A-4:

A-1

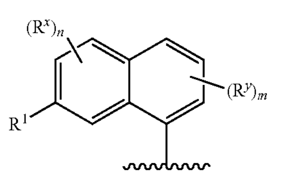

A-2

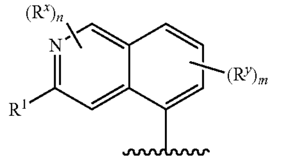

-continued

A-3

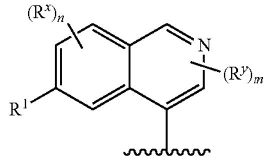

A-4

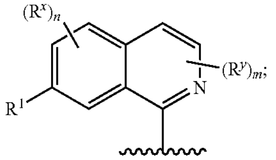

$R^1$ is H, halogen, (1-3C)alkoxy(1-3C)alkyl [optionally substituted with 1-5 fluoros], (1-3C alkyl)sulfanyl(1-3C) alkyl [optionally substituted with 1-5 fluoros], (1-3C)alkoxy [optionally substituted with 1-5 fluoros], (1-3C alkyl)sulfanyl [optionally substituted with 1-5 fluoros], cyano(1-3C) alkyl [optionally substituted with 1-5 fluoros], hydroxy(1-3C)alkyl [optionally substituted with 1-5 fluoros], (1-4C) alkyl [optionally substituted with 1-5 fluoros], $CH_3CH_2NR^a$, $CF_3CH_2NR^a$, $HCF_2CH_2NR^a$, $H_2CFCH_2NR^a$, $CH_3NR^aCH_2$, R^^CHzCHs or R^^CHzCFz;

each $R^a$ is independently H or methyl;

$R^x$ and $R^y$ are independently selected from H, halogen, (1-3C)alkyl [optionally substituted with 1-5 fluoros] or (1-3C)alkoxy [optionally substituted with 1-5 fluoros];

n is 0, 1 or 2;

m is 0, 1 or 2;

X is O, S, NH or N—CN;

Ring C is formula C-1 or C-2

C-1

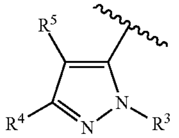

C-2

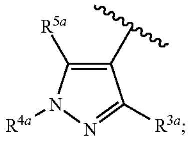

$R^3$ is (1-6C)alkyl, hydroxy(1-6C)alkyl, $Ar^2$, $hetCyc^1$, (3-7C)cycloalkyl, or $hetAr^2$;

Ar is phenyl optionally substituted with one or more groups independently selected from halogen and (1-6C) alkyl;

$hetCyc^1$ is a 5-6-membered saturated or partially unsaturated heterocyclic ring having 1-2 ring heteroatoms independently selected from N and O;

hetAr is a 5-6 membered heteroaryl ring having 1-3 ring heteroatoms independently selected from N, O and S and optionally substituted with one or more groups independently selected from (1-6C)alkyl and halogen;

$R^4$ is OH, (1-6C)alkyl, monofluoro(1-6C)alkyl, difluoro (1-6C)alkyl, trifluoro(1-6C)alkyl, tetrafluro(2-6C)alkyl, pentafluro(2-6C)alkyl, cyano(1-6C)alkyl, hydroxy(1-6C) alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C) alkoxy trifluoro(1-6C)alkoxy, tetrafluoro(2-6C)alkoxy, pentafluoro(2-6C)alkoxy, cyano(1-6C)alkoxy, hydroxy(1-6C) alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2$(O)$CH_2$—, (1-4C alkoxycarbonyl)(1-6C) alkoxy, hydroxycarbonyl(1-6C)alkoxy, aminocarbonyl(1-6C)alkoxy, $hetCyc^2$C(═O)(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, $hetCyc^2$C(═O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, $hetCyc^3$, halogen, CN, trifluoromethylsulfonyl, N-(1-3C alkyl)oxadiazolonyl, or $hetAr^5$;

hetCyc is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl; hetCyc is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)aikyl, (1-3C alkoxy)(1-6C) alkyl, (1-6C)acyl-, (1-6C)alkylsulfonyl, trifluoromethylsulfonyl and (1-4C alkoxy)carbonyl; $hetAr^3$ is a 5-membered heteroaryl ring having 1-3 ring atoms independently selected from N, O and S and optionally substituted with (1-6C)alkyl; $Ar^3$ is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)$CH_2$-(3-6C cycloalkyl)C(═O)—, (1-3C alkoxy)(1-6C)alkyl, (1-6C)alkoxy, (1-6C)alkylsulfonyl, $NH_2$, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

$hetAr^5$ is a group selected from the structures:

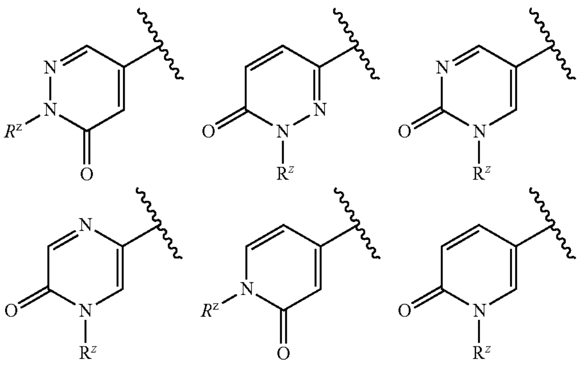

where $R^z$ is (3-4C)cycloalkyl or (1-3C)alkyl (optionally substituted with 1-3 fluoros), wherein each of said hetAr$^5$ groups is optionally further substituted with one or more groups independently selected from F and (1-3C)alkyl optionally substituted with 1-3 fluoros;

$Ar^4$ is phenyl optionally substituted with one or more groups independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl) OC(=O)—;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC (=O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(—O) O—, (1-6C)acyl, (1-6C)alkyl and oxo, and said sulfur ring atom is optionally oxidized to S(=O) or $SO_2$;

$R^{3a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is halogen, (1-6C)alkyl, trifluoro(1-6C)alkyl, (3-6C) cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

Further examples of Trk inhibitors can be found in International Publication No. WO 2014078325, which is incorporated by reference in its entirety herein. For example, a Trk inhibitor can be a compound of Formula I:

I-2

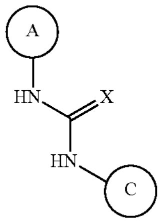

or a stereoisomer, tautomer, or pharmaceutically acceptable salt, solvate or prodrug thereof, wherein:

Ring A is formula A-1, A-2, A-3, A-4, A-5 or A-6

A-1

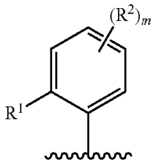

A-2

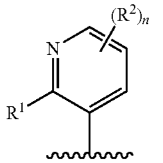

A-3

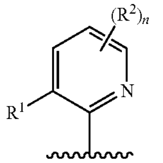

A-4

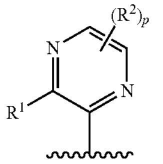

A-5

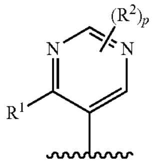

A-6

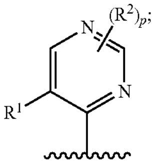

m is 0, 1, 2, 3 or 4;

n is 0, 1, 2 or 3;

p is 0, 1 or 2;

$R^1$ is formula $R^1$-1, $R^1$-2 or $R^1$-3

$R^1$-1

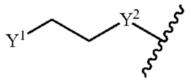

$R^1$-2

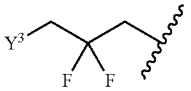

$R^1$-3

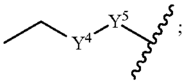

;

$Y^1$ is $CH_3CH_2$—, $CF_3CH_2$—, $CH_3O$—, $F_3CO$—, $F_2CHO$—, $FCH_2O$—, $CH_3S$—, $F_3CS$—, $F_2CHS$—, or $FCH_2S$—;

$Y^2$ is O, S, NH, MeN— or $CH_2$;

$Y^3$ is CH3O—, CH3S—, MeNH— or $Me_2N$—;

$Y^4$ is $CH_2$ and $Y^5$ is S or, or $Y^4$ is S or O and $Y^5$ is $CH_2$;

$R^2$ is halogen, (1-3C)alkyl (optionally substituted with 1-3 fluoros), (1-3C)alkoxy (optionally substituted with 1-3 fluoros), $CH_3OCH_2$— (optionally substituted with 1-3 fluoros), (1-3C alkyl)sulfanyl, di(1-3C)alkylamino, cyclopropyl, cyclobutyl or azetidinyl, wherein each of said cyclopropyl, cyclobutyl and azetidinyl is optionally substituted with 1 to 2 fluoros;

X is O, S, NH or N—CN;

Ring C is formula C-1 or C-2

C-1

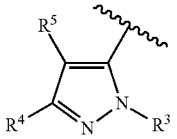

C-2

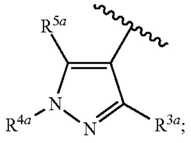

$R^3$ is (1-6C)alkyl, hydroxy(1-6C)alkyl, $Ar^2$, $hetCyc^1$, (3-7C)cycloalkyl, or $hetAr^2$;

$Ar^2$ is phenyl optionally substituted with one or more groups independently selected from halogen and (1-6C) alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is H, OH, (1-6C)alkyl, monofluoro(1-6C)alkyl, difluoro(1-6C)alkyl, trifluoro(1-6C)alkyl, tetrafluro(2-6C) alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C) alkoxy trifluoro(1-6C)alkoxy, tetrafluoro(2-6C)alkoxy, pentafluoro(2-6C)alkoxy cyano(1-6C)alkoxy, hydroxy(1-6C) alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2(O)CH_2$—, (1-4C alkoxycarbonyl)(1-6C) alkoxy, hydroxycarbonyl(1-6C)alkoxy, aminocarbonyl(1-6C)alkoxy, $hetCyc^2C(=O)$(1-6C)alkoxy, hydroxy(1-3C alkoxy)(1-6C)alkoxy, hydroxytrifluoro(1-6C)alkoxy, (1-3C) alkylsulfonamido(1-6C)alkoxy, (1-3C)alkylamido(1-6C) alkoxy, di(1-3C alkyl)amino-carboxy, hetCyc C(=O)O—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, hetCyc halogen, CN, trifluoromethylsulfonyl, N-(1-3C alkyl)oxadiazolonyl, or $hetAr^5$;

$hetCyc^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, (1-6C)acyl and halogen;

$hetCyc^3$ is a 4-7 membered heterocycle having 1-2 ring heteroatoms independently selected from N and O and optionally substituted with one or more substituents independently selected from F, CN, (1-6C)alkyl, trifluoro(1-6C) alkyl, hydroxy(1-6C)alkyl, (1-3C alkoxy)(1-6C)alkyl, (1-6C)acyl-, (1-6C)alkylsulfonyl, trifluoromethylsulfonyl and (1-4C alkoxy)carbonyl;

$hetAr^3$ is a 5-membered heteroaryl ring having 1-3 ring atoms independently selected from N, O and S and optionally substituted with (1-6C)alkyl;

Ar is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)$CH_2$-(3-6C cycloalkyl)C(=O)—, (1-3C alkoxy)(1-6C)alkyl, (1-6C)alkoxy, (1-6C)alkylsulfonyl, $NH_2$, (1-6C alkyl) amino, di(1-6C alkyl)amino, (1-3C trifluoroalkoxy), fluoro (1-6C alkyl)amino, difluoro(1-6C alkyl)amino, trifluoro(1-6C alkyl)amino, and (3-4C cycloalkyl)amino;

$hetAr^5$ is a group selected from the structures:

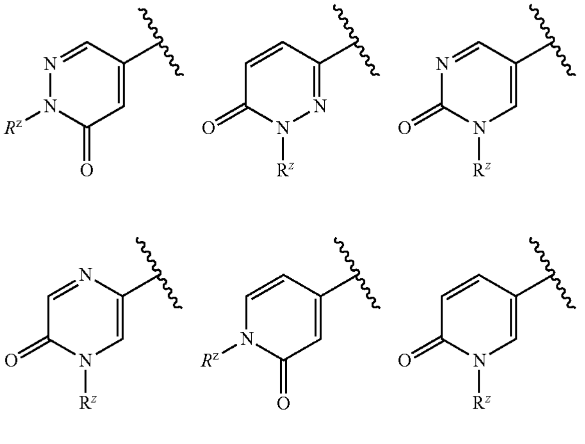

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros; $AT^4$ is phenyl optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(═O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C)acyl, (1-6C)alkyl and oxo, and said sulfur ring atom is optionally oxidized to S(═O) or $SO_2$;

$R^{3a}$ is halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl)$SO_2$—, HOC(═O)— and (1-3C alkoxy)(1-3C alkyl)OC(═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C)alkoxy, (1-6C)alkylsulfonyl, $NH_2$, (1-6C alkyl)amino, di(1-6C alkyl)amino and (1-3C trifluoroalkoxy(1-3 C)trifluoroalkyl; and $R^{5a}$ is (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

Additional examples of Trk inhibitors can be found in International Publication No. WO 2014078323, which is incorporated by reference in its entirety herein. For example, a Trk inhibitor can be a compound of Formula I:

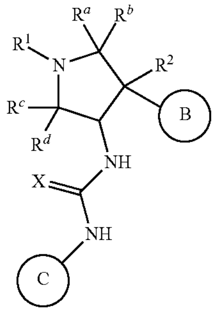

I or stereoisomers, tautomers, or pharmaceutically acceptable salts, solvates or prodrugs thereof, wherein:

Ring B and the NH—C(═X)—NH moiety are in the trans configuration;

$R^a$, $R^b$, $R^c$ and $R^d$ are independently selected from H and (1-3C)alkyl, or $R^o$ and $R^d$ are independently selected from H and (1-3C)alkyl, and $R^a$ and $R^b$ together with the atom to which they are attached form a cyclopropyl ring;

X is O, S, NH, or N—CN;

$R^1$ is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl or hydroxycarbonyl(1-3C alkoxy)(1-6C)alkyl;

$R^2$ is H, F, or OH;

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; $hetAr^1$ is a 5-6 membered heteroaryl having 1-3 ring heteroatoms independently selected from N, S and O, and optionally substituted with one or more substituents independently selected from (1-6C)alkyl, halogen, OH, $CF_3$, $NH_2$ and hydroxy(1-2C)alkyl;

Ring C is

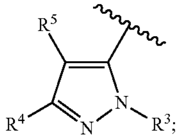

$R^3$ is H, (1-6C)alkyl, hydroxy(1-6C)alkyl, $Ar^2$, $hetCyc^1$, (3-7C)cycloalkyl, $hetAr^2$, or a C5-C8 bridged carbocyclic ring;

$Ar^2$ is phenyl optionally substituted with one or more substituents independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S and optionally substituted with one or more substituents independently selected from (1-6C)alkyl and halogen;

$R^4$ is selected from -6C alkyl)$SO_2$—, (1-6C alkyl)C(═O)— and from the structures:

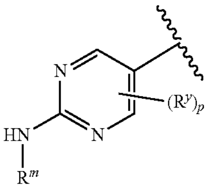
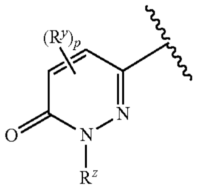
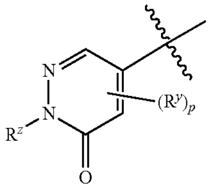
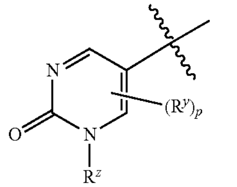
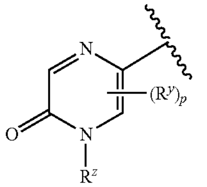
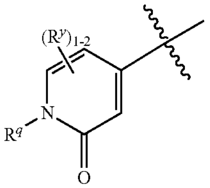
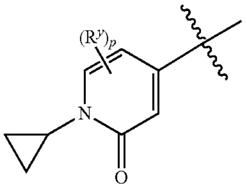
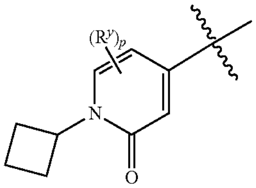
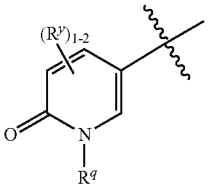
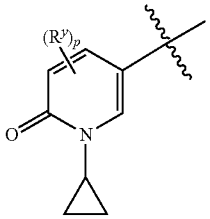
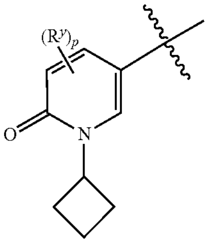
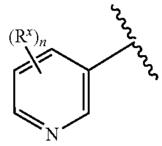
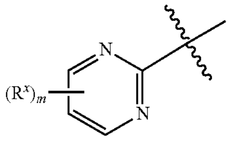
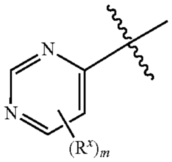
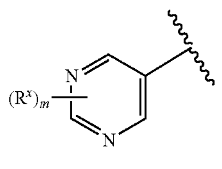
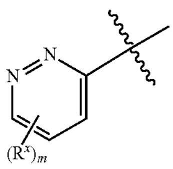

-continued

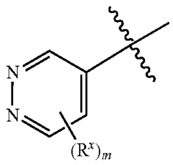
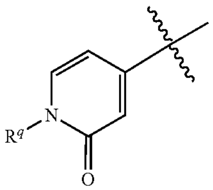
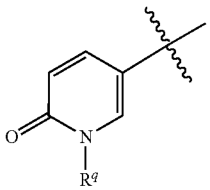
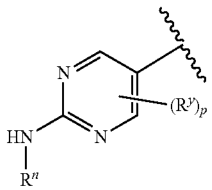
;

$R^m$ is (1-3C)alkyl substituted with 1-3 fluoros, or (3-4C) cycloalkyl;

$R^n$ is (1-3C)alkyl;

$R^4$ is (1-3C)alkyl optionally substituted with 1-3 fluoros;

$R^x$ is (1-6C)alkyl, halogen, CN, hydroxy(1-6C)alkyl, trifluoro(1-6C)alkyl, (3-6C)cycloalkyl, (3-6C cycloalkyl)$CH_2$—, (3-6C cycloalkyl)C(═O)—, (1-3C alkoxy)(1-6C) alkyl, (1-6C)alkoxy, (1-6C)alkylsulfonyl, $NH_2$, (1-6C alkyl) amino, di(1-6C alkyl)amino, trifluoro(1-3C)alkoxy or trifluoro(1-6C)alkyl;

n is 0, 1, 2, 3 or 4;

m is 0, 1, 2 or 3;

$R^y$ is F or (1-3C)alkyl optionally substituted with 1-3 fluoros;

p is 0, 1 or 2;

$R^z$ is (3-4C)cycloalkyl, or (1-3C)alkyl optionally substituted with 1-3 fluoros; and $R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C) alkyl, (1-4C alkyl)OC(═O)—, (1-6C)alkylsulfanyl, phenyl [optionally substituted with one or more substituents independently selected from halogen, (1-6C)alkyl and (1-6C) alkoxy], (3-4C)cycloalkyl, amino, aminocarbonyl, or trifluoro(1-3 C alkyl)amido.

Additional examples of Trk inhibitors can be found in International Publication No. WO 2014078322, which is incorporated by reference in its entirety herein. For example, a Trk inhibitor can be a compound of Formula I:

I

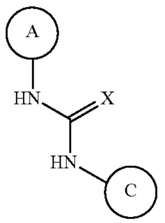

or stereoisomers, tautomers, or pharmaceutically acceptable salts, solvates or prodrugs thereof, wherein:

X is O, S, NH or N—CN;

Ring A is

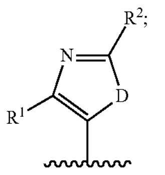

D is O or S;

$R^1$ is phenyl optionally substituted with one or more substituents independently selected from halogen and (1-3C)alkyl;

R is (1-6C)alkyl [optionally substituted with 1 to 5 fluoros] or (3-6C)cycloalkyl [optionally substituted with one or two fluoros];

Ring C is formula C-1 or C-2

C-1

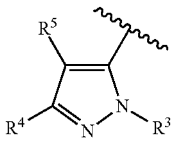

C-2

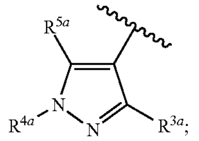

$R^3$ is (1-6C)alkyl, hydroxy(1-6C)alkyl, $Ar^2$, $hetCyc^1$, (3-7C)cycloalkyl, or $hetAr^2$;

Ar is phenyl optionally substituted with one or more groups independently selected from halogen and (1-6C) alkyl;

$hetCyc^1$ is a 5-6-membered saturated or partially unsaturated heterocyclic ring having 1-2 ring heteroatoms independently selected from N and O; $hetAr^2$ is a 5-6 membered heteroaryl ring having 1-3 ring heteroatoms independently selected from N, O and S and optionally substituted with one or more groups independently selected from (1-6C)alkyl and halogen;

$R^4$ is H, OH, (1-6C)alkyl, monofluoro(1-6C)alkyl, difluoro(1-6C)alkyl, trifluoro(1-6C)alkyl, tetrafluro(2-6C) alkyl, pentafluro(2-6C)alkyl, cyano(1-6C)alkyl, hydroxy(1-6C)alkyl, dihydroxy(2-6C)alkyl, (1-3C alkoxy)(1-6C)alkyl, amino(1-6C)alkyl, aminocarbonyl(1-6C)alkyl, (1-3C)alkylsulfonamido(1-6C)alkyl, sulfamido(1-6C)alkyl, hydroxycarbonyl(1-6C)alkyl, $hetAr^3$(1-6C)alkyl, $Ar^3$(1-6C)alkyl, (1-6C)alkoxy, monofluoro(1-6C)alkoxy, difluoro(1-6C) alkoxy, trifluoro(1-6C)alkoxy, tetrafluoro(2-6C)alkoxy, pentafluoro(2-6C)alkoxy, cyano(1-6C)alkoxy, hydroxy(1-6C) alkoxy, dihydroxy(2-6C)alkoxy, amino(2-6C)alkoxy, hydroxyl-carbonyl(1-6C)alkoxy, $hetCyc^2$(1-6C)alkoxy, $hetAr^3$(1-6C)alkoxy, $Ar^3$(1-6C)alkoxy, (1-4C alkoxy)(1-6C) alkoxy, (1-3C alkylsulfonyl)(1-6C)alkoxy, (3-6C)cycloalkyl [optionally substituted with F, OH, (1-6C alkyl), (1-6C) alkoxy, or (1-3C alkoxy)(1-6C)alkyl], $hetAr^4$, $hetAr^4$—O—, $Ar^4$, $hetCyc^2(O)CH_2$—, (1-4C alkoxycarbonyl)(1-6C) alkoxy, hydroxycarbonyl(1-6C)alkoxy, aminocarbonyl(1-6C)alkoxy, $hetCyc^2C(=O)$(1-6C)alkoxy, hydroxy(1-3C alkoxy)(1-6C)alkoxy, hydroxytrifluoro(1-6C)alkoxy, (1-3 C)alkylsulfonamido(1-6C)alkoxy, (1-3 C)alkylamido(1-6C) alkoxy, di(1-3C alkyl)amino-carboxy, $hetCyc^2C(=O)O$—, hydroxydifluoro(1-6C)alkyl, (1-4C alkylcarboxy)(1-6C) alkyl, (1-6C)alkoxycarbonyl, hydroxylcarbonyl, aminocarbonyl, (1-3C alkoxy)aminocarbonyl, hetCyc, halogen, CN, trifluoromethylsulfonyl, N-(1-3C alkyl)oxadiazolonyl, or $hetAr^5$;

$hetCyc^2$ is a 4-6 membered heterocyclic ring having 1-2 ring heteroatoms independently selected from N and O and optionally substituted with 1-2 groups independently selected from (1-6C)alkyl, (1-4C alkylcarboxy)(1-6C)alkyl, and (1-6C)acyl; hetCyc is a 4-7 membered heterocycle having 1-2 ring heteroatoms independently selected from N and O and optionally substituted with one or more substituents independently selected from F, CN, (1-6C)alkyl, trifluoro(1-6C)alkyl, hydroxy(1-6C)alkyl, (1-3C alkoxy)(1-6C) alkyl, (1-6C)acyl-, (1-6C)alkylsulfonyl, trifluoromethylsulfonyl and (1-4C alkoxy)carbonyl;

hetAr is a 5-membered heteroaryl ring having 1-3 ring atoms independently selected from N, O and S and optionally substituted with (1-6C)alkyl;

Ar is phenyl optionally substituted with (1-4C)alkoxy;

$hetAr^4$ is a 5-6 membered heteroaryl ring having 1-3 ring heteroatoms independently selected from N, S and O and optionally substituted with one or more substituents independently selected from (1-6C)alkyl, halogen, CN, hydroxy (1-6C)alkyl, trifluoro(1-6C)alkyl, difluoro(1-6C)alkyl, fluoro(1-6C)alkyl, (3-6C)cycloalkyl, (3-6C cycloalkyl)$CH_2$-(3-6C cycloalkyl)C(O)—, (1-3C alkoxy)(1-6C)alkyl, (1-6C) alkoxy, (1-6C)alkylsulfonyl, $NH_2$, (1-6C alkyl)amino, di(1-6C alkyl)amino, (1-3C trifluoroalkoxy), fluoro(1-6C alkyl) amino, difluoro(1-6C alkyl)amino, trifluoro(1-6C alkyl) amino, and (3-4C cycloalkyl)amino;

$hetAr^5$ is a group selected from the structures:

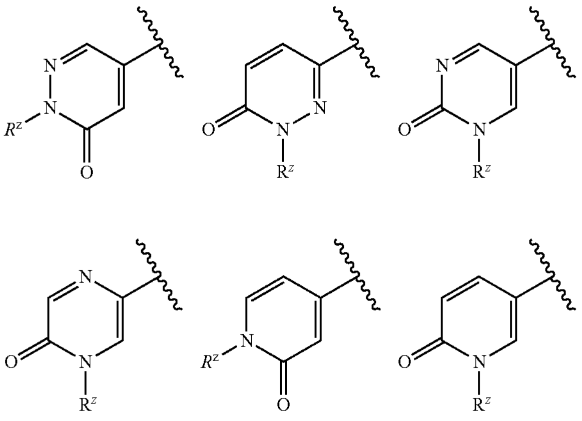

where $R^z$ is (3-4C)cycloalkyl or (1-3C)alkyl (optionally substituted with 1-3 fluoros), wherein each of said $hetAr^5$ groups is optionally further substituted with one or more groups independently selected from F and (1-3C)alkyl optionally substituted with 1-3 fluoros;

$Ar^4$ is phenyl optionally substituted with one or more groups independently selected from (1-6C)alkyl, halogen, CN, $CF_3$, $CF_3O$—, (1-6C)alkoxy, (1-6C alkyl)OC(O)—, aminocarbonyl, (1-6C)alkylthio, hydroxy(1-6C)alkyl, (1-6C alkyl)$SO_2$—, HOC(O)— and (1-3C alkoxy)(1-3C alkyl)OC (=O)—;

$R^5$ is (1-6C)alkyl, monofluoro(1-6C)alkyl, difluoro(1-6C) alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(═O)—, (1-6C)alkylthio, (3-4C)cycloalkyl, amino, aminocarbonyl, trifluoro(1-3C alkyl)amido, or phenyl (optionally substituted with one or more groups independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(═O)O—, (1-6C)acyl, (1-6C)alkyl and oxo, and said sulfur ring atom is optionally oxidized to S(═O) or $SO_2$; $^3$a is hydrogen, halogen, (1-6C) alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen;

$R^{4a}$ is hydrogen, (1-6C)alkyl, trifluoro(1-6C)alkyl, phenyl [optionally substituted with one or more groups independently selected from (1-6C)alkyl, halogen, CN, $CF_3$, $CF_3O$—, (1-6C)alkoxy, (1-6Calkyl)OC(═O)—, aminocarbonyl, (1-6C)alkylthio, hydroxy(1-6C)alkyl, (1-6C alkyl) $SO_2$—, HOC(═O)— and (1-3C alkoxy)(1-3C alkyl)OC(═O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$— (3-6C cycloalkyl)C(═O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C) alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more groups independently selected from (1-6C)alkyl and halogen.

Further examples of Trk inhibitors can be found in International Publication No. WO 2015175788, which is incorporated by reference in its entirety herein. For example, a Trk inhibitor can be a compound 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, or a pharmaceutically acceptable salt thereof. In some embodiments, the compound is a chloride salt.

Exemplary Trk inhibitors include AR-772, AR-786, AR-256, and AR-618.

Non-limiting examples of Trk inhibitors can be found in U.S. Pat. No. 8,299,057 and International Publication No. WO 2009/013126 both of which are incorporated by reference in their entireties. For example, a Trk inhibitor can be a compound of Formula (I):

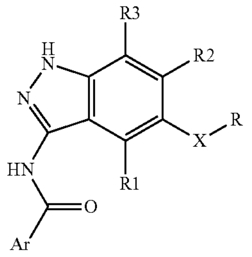

wherein:

X is —$CH_2$—, —CH(OH)—, —CH(OR')— or —C(R'R")—, wherein:

R' is $C_1$-$C_6$ alkyl and R" is hydrogen;

Ar is phenyl, pyrazolyl or pyridyl optionally substituted with one or more substituents independently selected from halogen, nitro, COR4, OR7, NR5R6, $NHSO_2R10$, a straight or branched $C_1$-C6 alkyl optionally substituted by a heterocyclyl, in its turn optionally substituted by a straight or branched $C_1$-$C_6$ alkyl or an heterocyclylalkyl, or a heterocyclyl optionally substituted by a straight or branched $C_1$-$C_6$ alkyl, in its turn optionally substituted by a heterocyclyl or a $C_1$-$C_6$ alkoxycarbonyl, or a $C_1$-$C_6$ dialkylamino:

R4 is NR5R6, or a heterocyclyl, optionally further substituted by a straight or branched $C_1$-$C_6$ alkyl, heterocyclylalkyl, heterocyclyl or a $C_1$-$C_6$ dialkylamino;

R5 and R6 are independently hydrogen, R8R9N—$C_2$-$C_6$ alkyl, R8O—$C_2$-$C_6$alkyl, a straight or branched $C_1$-$C_6$ alkyl optionally further substituted by $C_1$-$C_6$ alkoxy, $C_1$-$C_6$ dialkylamino, halogen, phenyl, hydroxyl or heterocyclyl in its turn optionally substituted by alkyl, $C_3$-$C_6$ cycloalkyl optionally substituted by hydroxyl or trifluoro $C_1$-$C_6$ alkyl, heterocyclyl optionally substituted by $C_1$-$C_6$ alkyl in its turn optionally substituted by halogen or heterocyclyl, $C_1$-$C_6$alkoxycarbonyl, $C_1$-$C_6$ dialkylamino, heterocyclyl, or phenyl, or $R^5$ and $R^6$, taken together with the nitrogen atom to which they are bonded, may form a heterocyclyl group optionally substituted by a straight or branched $C_1$-$C_6$ alkyl, in its turn optionally substituted by a heterocyclyl or a $C_1$-$C_6$ alkoxycarbonyl, a $C_1$-$C_6$ dialkylamino or a heterocyclyl;

$R^7$ is straight or branched $C_1$-$C_6$ alkyl, optionally substituted by $C_1$-$C_6$dialkylamino or heterocyclyl in its turn substituted by $C_1$-$C_6$ alkyl;

R8 and R9 are independently an optionally further substituted straight or branched $C_1$-$C_6$ alkyl;

R10 is an optionally further substituted straight or branched $C_1$-$C_6$ alkyl;

R is phenyl or pyridyl optionally substituted halogen or straight or branched $C_1$-$C_6$ alkyl;

R1, R2 and R3 are hydrogen;

or optical isomers, tautomers or pharmaceutically acceptable salt thereof.

For example, a Trk inhibitor can be entrectinib (N-[5-(3,5-difluoro-benzyl)-1H-indazol-3-yl]-4-(4-methyl-piperazin-1-yl)-2-(tetrahydro-pyran-4-ylamino)-benzamide), or a pharmaceutically acceptable salt thereof. For example, a Trk inhibitor can be a polymorph such as those described in U.S. Publication No. 2015/0051222 or International Publication No. WO 2013/174876, both of which are incorporated by reference in their entireties herein. In some embodiments, a Trk inhibitor can be any disclosed in U.S. Publication No. 2015/0283132, International Publication No. WO 2015/124697, U.S. Pat. No. 8,946,226, International Publication No. WO 2010/012733, U.S. Pat. No. 8,912,194, and International Publication No. WO 2010/058006, all of which are incorporated by reference in their entireties herein.

Additional examples of Trk inhibitors can be found in U.S. Publication No. International Publication No. WO 2015/017533, which is incorporated by reference in its entirety herein.

Further examples of Trk inhibitors can be found in U.S. Publication No. 2016/0272725 and International Publication No. WO 2015/112806, both of which are incorporated by reference in their entirety herein. For example, a Trk inhibitor can be a compound of Formula (I-A):

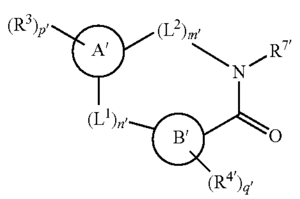

or a pharmaceutically acceptable salt thereof, wherein

Ring A' and Ring B' are each independently a monocyclic or bicyclic aryl or heteroaryl; wherein one of Ring A' and Ring B' is a monocyclic aryl or heteroaryl and the other is a bicyclic heteroaryl; and at least one of Ring A' and Ring B' comprises at least one nitrogen ring member;

each $L^1$ and $L^2$ is independently —C($R^{1'}$)($R^{2'}$)—, —O—, —N($R^{k'}$)—, —S—, —S(O)— or —$S(O)_2$; each $R^1$ and $R^2$ are independently H, deuterium, halogen, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, —$OR^{a'}$, —OC(O)$R^{a'}$, —OC(O)$NR^{a'}R^{b'}$, —OS(O)$R^{a'}$, —OS$(O)_2R^{a'}$, —$SR^{a'}$, —S(O)$R^{a'}$, —$S(O)_2R^{a'}$, —S(O)$NR^{a'}R^{b'}$, —$S(O)_2NR^{a'}$ $R^{b'}$, —OS(O)$NR^{a'}R^{b'}$, —$OS(O)_2NR^{a'}R^{b'}$, —$NR^{a'}R^{b+}$, —$NR^{a'}$C(O)$R^{b'}$, —$NR^{a'}$C(O)$OR^{b'}$, —$NR^{a'}$C(O)$NR^{a'}R^{b'}$, —$NR^{a'}$S(O)$R^{b'}$, —$NR^{a'}S(O)_2R^{b'}$, —$NR^{a'}$S(O)$NR^{a'}R^{b'}$, —$NR^{a'}S(O)_2NR^{a'}R^{b'}$, —C(O)$R^{a'}$, —C(O)$OR^{a'}$, —C(O)$NR^{a'}R^{b'}$, —$PR^{a'}R^{b'}$, —P(O)$R^{a'}R^{b'}$, —$P(O)_2R^{a'}R^{b'}$, —P(O)$NR^{a'}R^{b'}$, —$P(O)_2NR^{a'}R^{b'}$, —P(O)$OR^{a'}$, —$P(O)_2OR^{a'}$, —CN, or —$NO_2$, or $R^{1'}$ and $R^{2'}$ taken together with the carbon or carbons to which they are attached form a $C_{3-6}$cycloalkyl or a 4- to 6-membered heterocycloalkyl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, mono- or bicyclic heteroaryl, 4- to 6-membered heterocycloalkyl is independently optionally substituted by deuterium, halogen, $C_{1-6}$alkyl, $C_{1-6}$haloalkyl, —$OR^{e'}$, —OC(O)$R^{e'}$, —OC(O)$NR^{e'}R^{f'}$, —OS(O)$R^{e'}$, —OS$(O)_2R^{e'}$, —OS(O)$NR^{e'}R^{f'}$, —$OS(O)_2NR^{e'}R^{f'}$, —$SR^{e'}$, —S(O)$R^{e'}$, $S(O)_2R^{e'}$, —S(O)$NR^{e'}R^{f'}$, —$S(O)_2NR^{e'}R^{f'}$, —$NR^{e'}R^{f'}$, —$NR^{e'}$C(O)$R^{f'}$, —$NR^{e'}$C(O)$OR^{f'}$, $NR^{e'}$C(O)$NR^{e'}R^{f'}$, —$NR^{e'}$S(O)$R^{f'}$, —$NR^{e'}S(O)_2R^{f'}$, —$NR^{e'}$S(O)$NR^{e'}R^{f'}$, —$NR^{e'}S(O)_2NR^{e'}R^{f'}$, —C(O)$R^{e''}$, —C(O)$OR^{e'}$, —C(O)$NR^{e'}R^{f'}$, —$PR^{e'}R^{f'}$, —P(O)$R^{e'}R^{f'}$, —$P(O)_2R^{e'}R^{f'}$, —P(O)$NR^{e'}R^{f'}$, —$P(O)_2NR^{e'}R^{f'}$, —P(O)$OR^{e'}$, —$P(O)_2OR^{e'}$, —CN, or —$NO_2$;

each $R^{k'}$ is independently H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl is independently optionally substituted by deuterium, halogen, $C_{1-6}$alkyl, $C_{1-6}$haloalkyl, —$Or^{e'}$, —OC(O)$R^{e'}$, —OC(O)$NR^{e'}R^{f'}$, —OS(O)$R^{e'}$, —$OS(O)_2R^{e'}$, —OS(O)$NR^{e'}R^{f'}$, —OS$(O)_2NR^{e'}R^{f'}$, —$SR^{e'}$, —S(O)$R^{e'}$, $S(O)_2R^{e'}$, —S(O)$NR^{e'}R^{f'}$, —$S(O)_2NR^{e'}$$^{R}$f, —$NR^{e'}R^{f'}$, —$NR^{e'}$C(O)$R^{f'}$, —$NR^{e'}$C(O)$OR^{f'}$, —$NR^{e'}$C(O)$NR^{e'}R^{f'}$, —$NR^{e'}$S(O)$R^{f'}$, —$NR^{e'}S(O)_2R^{f'}$, —$NR^{e'}$S(O)$NR^{e'}R^{f'}$, —$NR^{e'}S(O)_2NR^{e'}R^{f'}$, —C(O)$R^{e'}$, —C(O)$OR^{e'}$, —C(O)$NR^{e'}R^{f'}$, —$PR^{e'}R^{f'}$, —P(O)$R^{e'}R^{f'}$, —$P(O)_2R^{e'}R^{f'}$, —P(O)$NR^{e'}R^{f'}$, —$P(O)_2NR^{e'}R^{f'}$, —P(O)$OR^{e'}$, —$P(O)_2OR^{e'}$, —CN, or —$NO_2$;

each $R^{3'}$ and $R^{4'}$ is independently deuterium, halogen, —$OR^{c'}$, —OC(O)$R^{c'}$, —OC(O)$NR^{c'}R^{d'}$, —OC(=N)$NR^{c'}R^{d'}$, —OS(O)$R^{c'}$, —$OS(O)_2R^{c'}$, —OS(O)$NR^{c'}R^{d'}$, —$OS(O)_2NR^{c'}R^{d'}$, $SR^{c'}$, —S(O)$R^{c'}$, —$S(O)_2R^{c'}$, —S(O)$NR^{c'}R^{d'}$, —$S(O)_2NR^{c'}R^{d'}$, —$NR^{c'}R^{d'}$, —$NR^{c'}$C(O)$R^{d'}$, —$NR^{c'}$C(O)$OR^{d'}$, —$NR^{c'}$C(O)$NR^{c'}R^{d'}$, —$NR^{c'}$C(=N)$NR^{c'}R^{d'}$, —$NR^{c'}$S(O)$R^{d'}$, —$NR^{c'}S(O)_2R^{d'}$, —$NR^{c'}$S(O)$NR^{c'}R^{d'}$, —$NR^{c'}S(O)_2NR^{c'}R^{d'}$, —C(O)$R^{c'}$, —C(O)$OR^{c'}$, —C(O)$NR^{c'}R^{d'}$, —C(=N)$NR^{c'}R^{d'}$, —$PR^{c'}R^{d'}$, —P(O)$R^{c'}R^{d'}$, —$P(O)_2R^{c'}R^{d'}$, —P(O)$NR^{c'}R^{d'}$, —$P(O)_2NR^{c'}R^{d'}$, —P(O)$OR^{c'}$, —$P(O)_2OR^{c'}$, —CN, —$NO_2$, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, or any two $R^{3'}$ groups or any two $R^{4'}$ groups taken together with the ring to which they are attached form a $C_{5-8}$cycloalkyl or a 5- to 8-membered heterocycloalkyl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, mono- or bicyclic heteroaryl $C_{5-8}$cycloalkyl or a 5- to 8-membered heterocycloalkyl is independently optionally substituted by deuterium, halogen, $C_{1-6}$alkyl, $C_{1-6}$haloalkyl, —$OR^{e'}$, —OC(O)$R^{e'}$, —OC(O)$NR^{e'}R^{f'}$, —OS(O)$R^{e'}$, —OS$(O)_2R^{e'}$—OS(O)$NR^{e'}R^{f'}$, —$OS(O)_2NR^{e'}R^{f'}$, —$SR^{e'}$, —S(O)$R^{e'}$, —$S(O)_2R^{e'}$, —S(O)$NR^{e'}R^{f'}$, —$S(O)_2NR^{e'}R^{f'}$, —$NR^{e'}R^{f'}$, —$NR^{e'}$C(O)$R^{f'}$, —$NR^{e'}$C(O)$OR^{f'}$, —$NR^{e'}$C(O)$NR^{e'}R^{f'}$, —$NR^{e'}$S(O)$R^{f'}$, —$NR^{e'}S(O)_2R^{f'}$, —$NR^{e'}$S(O)$NR^{e'}R^{f'}$, —$NR^{e'}S(O)_2NR^{e'}R^{f'}$, —C(O)$R^{e'}$, —C(O)$OR^{e'}$, —C(O)$NR^{e'}R^{f'}$, —$PR^{e'}R^{f'}$, —P(O)$R^{e'}R^{f'}$, —$P(O)_2R^{e'}R^{f'}$, —P(O)$NR^{e'}R^{f'}$, —$P(O)_2NR^{e'}R^{f'}$, —P(O)$OR^{e'}$, —$P(O)_2OR^{e'}$, —CN, or —$NO_2$;

$R^{7'}$ is H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl, wherein each hydrogen atom in $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, or mono- or bicyclic heteroaryl is independently optionally substituted by deuterium, halogen, —$OR^{i'}$, —OC(O)$R^{i'}$, —OC(O)$NR^{i'}R^{j'}$, —OS(O)$R^{i'}$, —$OS(O)_2R^{i'}$, —OS(O)$NR^{i'}R^{j'}$, —OS$(O)_2NR^{i'}R^{j'}$, —$SR^{i'}$, —S(O)$R^{i'}$, —$S(O)_2R^{i'}$, —S(O)$NR^{i'}R^{j'}$, —$S(O)_2NR^{i'}R^{j'}$, —$NR^{i'}R^{j'}$, —$NR^{i'}$C(O)$R^{j'}$, —$NR^{i'}$C(O)$OR^{j'}$, —$NR^{i'}$C(O)$NR^{i'}R^{j'}$, —$NR^{i'}$S(O)$R^{j'}$, —$NR^{i'}S(O)_2R^{j'}$, —$NR^{i'}$S(O)$NR^{i'}R^{j'}$, —$NR^{i'}S(O)_2NR^{i'}R^{j'}$, —C(O)$R^{i'}$, —C(O)$OR^{i'}$, —C(O)$NR^{i'}R^{j'}$, —$PR^{i'}R^{j'}$, —P(O)$R^{i'}R^{j'}$, —$P(O)_2R^{i'}R^{j'}$, —P(O)$NR^{i'}R^{j'}$, —$P(O)_2NR^{i'}R^{j'}$, —P(O)$OR^{i'}$, —$P(O)_2OR^{i'}$, —CN, or —$NO_2$;

each $R^{a'}$, $R^{b'}$, $R^{c'}$, $R^{d'}$, $R^{e'}$, $R^{f'}$, $R^{i'}$ and $R^{j'}$ is independently selected from the group consisting of H, deuterium, $C_{1-6}$alkyl, $C_{2-6}$alkenyl, $C_{2-6}$alkynyl, $C_{3-6}$cycloalkyl, 3- to 7-membered heterocycloalkyl, $C_{6-10}$ aryl, and heteroaryl;

m' is 2, 3, 4, or 5;

n' is 2, 3, or 4;

p' is 0, 1, 2, 3, or 4; and q' is 0, 1, 2, 3, or 4; or a pharmaceutically acceptable salt thereof. Exemplary Trk inhibitors include TPX-0005.

A Trk inhibitor can be one found in U.S. Pat. No. 9,187,489 and International Publication No. WO 2013/

183578, both of which are incorporated by reference in their entireties herein. Exemplary Trk inhibitors include PLX7486 and DS-6051.

Non-limiting examples of Trk inhibitors can be found in U.S. Publication No. 2015/0306086 and International Publication No. WO 2013/074518, both of which are incorporated by reference in their entireties herein. Exemplary Trk inhibitors include TSR-011.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in *ACS Med. Chem. Lett.* 3(2): 140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imadizopyridazines, e.g., (4-((5-chloro-4-(methylamino)-7H-pyrrolo[2,3-d]pyrimidin-2-yl)amino)-3-methoxyphenyl)(morpholino)methanone as described in ACS Med. Chem. Lett. 6(5):562-567, 2015; GTx-186 and others, as described in *PLoS One* 8(12): e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[12,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15):4672-4684, 2008; PHA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5 S,6S,8R)-6-Hydroxy-6-(hydroxymethyl)-5-methyl-7,8,14,15-tetrahydro-5H-16-oxa-4b,8a, 14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2(1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); VSR-902A; all of the references above are incorporated by reference in their entireties herein.

In some embodiments, a Trk inhibitor is selected from the group consisting of:

(6R)-9-fluoro-2,11,15,19,20,23-hexaazapentacyclo[$15.5.2.1^{7,11}.0^{2,6}.0^{20,24}$]pentacosa-1(23),7,9,17(24),18,21-hexaene-16,25-dione;

(6R)-12-oxa-2,16,20,21,24,26-hexaazapentacyclo[$16.5.2.1^{7,11}.0^{2,6}.0^{21,25}$]hexacosa-1(24),7(26),8,10,18(25), 19,22-heptaen-17-one;

(6R)-9-fluoro-13-oxa-2,11,17,21,22,25-hexaazapentacyclo[$17.5.2.0^{2,6}.0^{7,12}.0^{22,26}$]hexacosa-1(25),7,9,11,19(26),20,23-heptaen-18-one;

(6R)-9-fluoro-15-hydroxy-13-oxa-2,11,17,21,22,25-hexaazapentacyclo[$17.5.2.0^{2,6}.0^{7,12}.0^{22,26}$] hexacosa-1(25),7,9,11,19(26),20,23-heptaen-18-one;

(6R,13S)-9-fluoro-13-hydroxy-2,11,15,19,20,23-hexaazapentacyclo-[$15.5.2.1^{7,11}.0^{2,6}.0^{20,24}$]pentacosa-1(23),7,9,17(24),18,21-hexaene-16,25-dione;

(6R,15R)-9-fluoro-15-hydroxy-13-oxa-2,11,17,21,22,25-hexaazapentacyclo-[$17.5.2.0^{2,6}.0^{7,12}.0^{22,26}$] hexacosa-1(25),7,9,11,19(26),20,23-heptaen-18-one;

(6R,13R)-9-fluoro-13-hydroxy-2,11,15,19,20,23-hexaazapentacyclo-[$15.5.2.1^{7,11}.0^{2,6}.0^{20,24}$]pentacosa-1(23),7,9,17(24),18,21-hexaene-16,25-dione;

(6R)-9-fluoro-13-oxa-2,11,16,20,21,24-hexaazapentacyclo[$16.5.2.0^{2,6}.0^{7,12}.0^{21,25}$]pentacosa-1(24),7,9,11,18(25),19,22-heptaen-17-one;

(6R)-9-fluoro-13-oxa-2,11,18,22,23,26-hexaazapentacyclo[$18.5.2.0^{2,6}.0^{7,12}.0^{23,27}$]heptacosa-1(26),7,9,11,20(27),21,24-heptaen-19-one;

(6R)-9-fluoro-2,11,16,20,21,24-hexaazapentacyclo[$16.5.2.1^{7,11}.0^{2,6}.0^{21,25}$]hexacosa-1(24),7,9,18(25),19,22-hexaene-17,26-dione;

(6R)-9-fluoro-2,11,13,16,20,21,24-heptaazapentacyclo [16.5.2.0$^{2,6}$.0$^{7,12}$.0$^{21,25}$]pentacosa-1(24),7,9,11,18(25), 19,22-heptaen-17-one;

(6R)-9-fluoro-2,11,13,17,21,22,25-heptaazapentacyclo [17.5.2.0$^{2,6}$.0$^{7,12}$.0$^{22,26}$]hexacosa-1(25),7,9,11,19(26),20, 23-heptaen-18-one;

(6R)-9-fluoro-13,16-dioxa-2,11,20,21,24-pentaazapentacyclo[16.5.2.0$^{2,6}$.0$^{7,12}$.0$^{21,25}$]-pentacosa-1(24),7,9,11,18 (25), 19,22-heptaen-17-one;

(6R)-9-fluoro-14-oxa-2,11,18,19,22-pentaazapentacyclo [14.5.2.1$^{7,11}$.0$^{2,6}$.0$^{19,23}$]tetracosa-1(22),7,9,16(23), 17,20-hexaene-15,24-dione;

(6R)-9-fluoro-13,16-dioxa-2,11,17,21,22,25-hexaazapentacyclo[17.5.2.0$^{2,6}$.0$^{7,12}$.0$^{22,26}$]hexacosa-1(25),7,9,11,19 (26),20,23-heptaen-18-one;

(6R,13R)-9,13-difluoro-2,11,15,19,20,23-hexaazapentacyclo[15.5.2.1$^{7,11}$.0$^{2,6}$.0$^{20,24}$]pentacosa-1(23), 7,9,17(24), 18,21-hexaene-16,25-dione;

(6R)-9-fluoro-17-methyl-13-oxa-2,11,17,21,22,25-hexaaza-pentacyclo[17.5.2.0$^{2,6}$.0$^{7,12}$.0$^{22,26}$]hexacosa-1(25),7,9,11, 19(26),20,23-heptaen-18-one;

(6R)-9,15,15-trifluoro-13-oxa-2,11,17,21,22,25-hexaaza-pentacyclo[17.5.2.0$^{2,6}$.0$^{7,12}$.0$^{22,26}$]hexacosa-1(25),7,9,11, 19(26),20,23-heptaen-18-one;

(6R)-9-fluoro-13-oxa-2,17,21,22,25-pentaazapentacyclo [17.5.2.0$^{2,6}$.0$^{7,12}$.0$^{22,26}$]hexacosa-1(25),7,9,11,19(26),20, 23-heptaen-18-one;

(6R)-9-fluoro-13-oxa-2,16,20,21,24-pentaazapentacyclo [16.5.2.0$^{2,6}$.0$^{7,12}$.0$^{21,25}$]pentacosa-1(24), 7,9,11,18(25), 19,22-heptaene;

1-[(6R)-9-fluoro-13-oxa-2,16,20,21,24-pentaazapentacyclo [16.5.2.0$^{2,6}$.0$^{7,12}$.0$^{21,25}$]pentacosa-1(24),7,9,11,18(25), 19,22-heptaen-16-yl]ethan-1-one;

1-[(6R)-9-fluoro-13-oxa-2,16,20,21,24-pentaazapentacyclo [16.5.2.0$^{2,6}$.0$^{7,12}$.0$^{21,25}$]pentacosa-1 (24),7,9,11,18(25), 19,22-heptaen-16-yl]-2-hydroxyethan-1-one;

(6R)-9-fluoro-13-oxa-2,17,21,22,25-pentaazapentacyclo [17.5.2.0$^{2,6}$.0$^{7,12}$.0$^{22,26}$]hexacosa-1(25), 7,9,11,19(26),20, 23-heptaene;

(6R)-9-fluoro-16-methanesulfonyl-13-oxa-2,16,20,21,24-pentaazapentacyclo[16.5.2.0$^{2,6}$.0$^{7,12}$.0$^{21,25}$] pentacosa-1 (24),7,9,11,18(25), 19,22-heptaene;

2-[(6R)-9-fluoro-13-oxa-2,16,20,21,24-pentaazapentacyclo [16.5.2.0$^{2,6}$.0$^{7,12}$.0$^{21,25}$]pentacosa-1(24),7,9,11,18(25), 19,22-heptaen-16-yl]acetic acid;

(6R)-9-fluoro-17-methanesulfonyl-13-oxa-2,17,21,22,25-pentaazapentacyclo[17.5.2.0$^{2,6}$.0$^{7,12}$.0$^{22,26}$] hexacosa-1 (25),7,9,11,19(26),20,23-heptaene;

(6R)—N-ethyl-9-fluoro-13-oxa-2,17,21,22,25-pentaaza-pentacyclo[17.5.2.0$^{2,6}$.0$^{7,12}$. 0$^{22,26}$]hexacosa-1(25),7,9, 11,19(26),20,23-heptaene-17-carboxamide;

(6R)—N-ethyl-9-fluoro-13-oxa-2,16,20,2,24-pentaazapentacyclo-[16.5.2.0$^{2,6}$.0$^{7,12}$.0$^{21,25}$]pentacosa-1(24),7,9,11, 18(25), 19,22-heptaene-16-carboxamide;

(6S)-9-fluoro-4,13-dioxa-2,11,17,21,22,25-hexaazapentacyclo[17.5.2.0$^{2,6}$.0$^{7,12}$.0$^{22,26}$]hexacosa-1(25),7(12),8,10, 19(26),20,23-heptaene-3,18-dione;

(6S)-9-fluoro-4,13-dioxa-2,11,16,20,21,24-hexaazapentacyclo [16.5.2.0$^{2,6}$.0$^{7,12}$.0$^{21,25}$]pentacosa-1(24),7(12),8,10, 18(25), 19,22-heptaene-3,17-dione;

(6R)-9-fluoro-2,11,16,20,21,24-hexaazapentacyclo [16.5.2.0$^{2,6}$.0$^{7,12}$.0$^{21,25}$]pentacosa-1(24), 7,9,11,18(25), 19,22-heptaen-17-one;

(6R)-9-fluoro-15-methyl-2,11,16,20,21,24-hexaazapentacyclo[16.5.2.0$^{2,6}$.0$^{7,12}$.0$^{21,25}$]pentacosa-1(24), 7,9,11,18 (25), 19,22-heptaen-17-one;

(6R,13R)-9-fluoro-13-methyl-2,11,15,19,20,23-hexaaza-pentacyclo[15.5.2.1$^{7,11}$.0$^{2,6}$.0$^{20,24}$]pentacosa-1(23),7,9,17 (24), 18,21-hexaene-16,25-dione;

(6R,13S)-9-fluoro-13-methyl-2,11,15,19,20,23-hexaaza-pentacyclo [15.5.2.1$^{7,11}$.0$^{2,6}$.0$^{20,24}$]pentacosa-1(23),7,9, 17(24), 18,21-hexaene-16,25-dione;

(6R)-9-fluoro-15,15-dimethyl-13-oxa-2,11,17,21,22,25-hexaazapentacyclo [17.5.2.0$^{2,6}$.0$^{7,12}$.0$^{22,26}$] hexacosa-1 (25),7,9,11,19(26),20,23-heptaen-18-one;

(6R)-9-fluoro-15,15-dimethyl-2,11,16,20,21,24-hexaaza-pentacyclo[16.5.2.0$^{2,6}$.0$^{7,12}$.0$^{21,25}$]pentacosa-1(24), 7,9, 11,18(25), 19,22-heptaen-17-one;

(6R)-9-fluoro-13-oxa-2,11,16,17,21,25,26,29-octaaza-hexacyclo[21.5.2.0$^{2,6}$.0$^{7,12}$.0$^{16,20}$.0$^{26,30}$]triaconta-1 (29), 7,9,11,17,19,23(30),24,27-nonaen-22-one;

(6R)-9-fluoro-13-oxa-2,11,19,21,25,26,29-heptaazahexacyclo[21.5.2.0$^{2,6}$.0$^{7,12}$.0$^{15,20}$.0$^{26,30}$]triaconta-1(29),7,9,11, 15(20),16,18,23(30),24,27-decaen-22-one;

(6R)-9-fluoro-13,13-dimethyl-2,11,15,19,20,23-hexaaza-pentacyclo [15.5.2.1$^{7,11}$.0$^{2,6}$.0$^{20,24}$]pentacosa-1(23),7,9, 17(24),18,21-hexaene-16,25-dione;

(4R,6R,15S)-9-fluoro-4,15-dihydroxy-13-oxa-2,17,21,22, 25-pentaazapentacyclo [17.5.2.0$^{2,6}$.0$^{7,12}$.0$^{22,26}$]hexacosa-1(25),7(12),8,10,19(26),20,23-heptaen-18-one;

(4R,6S,15 S)-9-fluoro-4,15-dihydroxy-13-oxa-2,17,21,22, 25-pentaazapentacyclo [17.5.2.0$^{2,6}$.0$^{7,12}$.0$^{22,26}$]hexacosa-1(25),7(12),8,10,19(26),20,23-heptaen-18-one;

(4R,6R)-9-fluoro-4-hydroxy-13-oxa-2,17,21,22,25-pentaazapentacyclo [17.5.2.0$^{2,6}$.0$^{7,12}$.0$^{22,26}$]hexacosa-1(25),7 (12),8,10,19(26),20,23-heptaen-18-one;

(4R,6S)-9-fluoro-4-hydroxy-13-oxa-2,17,21,22,25-pentaazapentacyclo [17.5.2.0$^{2,6}$.0$^{7,12}$.0$^{22,26}$] hexacosa-1(25), 7(12),8,10,19(26),20,23-heptaen-18-one;

(4R,6R)-9-fluoro-4-hydroxy-13-oxa-2,16,20,21,24-pentaazapentacyclo [16.5.2.0$^{2,6}$.0$^{7,12}$.0$^{21,25}$] pentacosa-1(24), 7,9,11,18(25), 19,22-heptaen-17-one;

(4R,6S)-9-fluoro-4-hydroxy-13-oxa-2,16,20,21,24-pentaazapentacyclo [16.5.2.0$^{2,6}$.0$^{7,12}$.0$^{21,25}$] pentacosa-1 (24),7,9,11,18(25), 19,22-heptaen-17-one;

(4R,6R,15R)-9-fluoro-4,15-dihydroxy-13-oxa-2,17,21,22, 25-pentaazapentacyclo [17.5.2.0$^{2,6}$.0$^{7,12}$.0$^{22,26}$]hexacosa-1(25),7(12),8,10,19(26),20,23-heptaen-18-one;

(4R,6S,15R)-9-fluoro-4,15-dihydroxy-13-oxa-2,17,21,22, 25-pentaazapentacyclo [17.5.2.0$^{2,6}$.0$^{7,}$1$^{2}$.0$^{22,26}$]hexacosa-1(25),7(12),8,10,19(26),20,23-heptaen-18-one; and (15S)-4,4,9-trifluoro-15-hydroxy-13-oxa-2,17,21,22,25-pentaazapentacyclo[17.5.2.0$^{2,6}$.0$^{7,12}$.0$^{22,26}$]hexacosa-1 (25),7(12),8,10,19(26),20,23-heptaen-18-one, or a pharmaceutically acceptable salt thereof.

In some embodiments, a Trk inhibitor is selected from the group consisting of:

(R)—N-tert-butyl-5-(2-(2,5-difluorophenyl)pyrrolidin-1-yl) pyrazolo[1,5-a]pyrimidine-3-carboxamide;

(R)-5-(2-(2,5-difluorophenyl)pyrrolidin-1-yl)-N-(pyridin-2-yl)pyrazolo[1,5-a]pyrimidine-3-carboxamide;

(R)-5-(2-(2,5-difluorophenyl)pyrrolidin-1-yl)-N-(3-methyl-pyridin-2-yl)pyrazolo[1,5-a]pyrimidine-3-carboxamide;

(R)-5-(2-(2,5-difluorophenyl)pyrrolidin-1-yl)-N-(2-morpholinoethyl)pyrazolo[1,5-a]pyrimidine-3-carboxamide;

(R)-5-(2-(2,5-difluorophenyl)pyrrolidin-1-yl)-N-((5-methylfuran-2-yl)methyl)pyrazolo[1,5-a]pyrimidine-3-carboxamide;

(R)-5-(2-(2,5-difluorophenyl)pyrrolidin-1-yl)-N-(1-methyl-1H-pyrazol-3-yl)pyrazolo[1,5-a]pyrimidine-3-carboxamide;

5-((R)-2-(2,5-difluorophenyl)pyrrolidin-1-yl)-N-((trans)-4-hydroxycyclohexyl)pyrazolo[1,5-a]pyrimidine-3-carboxamide;

(R)-5-(2-(2,5-difluorophenyl)pyrrolidin-1-yl)-N-(1-hydroxy-2-methylpropan-2-yl)pyrazolo[1,5-a]pyrimidine-3-carboxamide;

(R)-5-(2-(2,5-difluorophenyl)pyrrolidin-1-yl)-N-(2-methyl-1-morpholinopropan-2-yl)pyrazolo[1,5-a]pyrimidine-3-carboxamide;

(R)-5-(2-(2,5-difluorophenyl)pyrrolidin-1-yl)-N-methyl-pyrazolo[1,5-a]pyrimidine-3-carboxamide;

(R)-1-(5-(2-(2,5-difluorophenyl)pyrrolidin-1-yl)pyrazolo[1,5-a]pyrimidine-3-carbonyl)piperidine-4-carboxylic acid;

(R)-2-(1-(5-(2-(2,5-difluorophenyl)pyrrolidin-1-yl)pyrazolo[1,5-a]pyrimidine-3-carbonyl)piperidin-4-yl)acetic acid;

(R)—N-cyclopropyl-5-(2-(2,5-difluorophenyl)pyrrolidin-1-yl)pyrazolo[1,5-a]pyrimidine-3-carboxamide;

(R)—N-cyclobutyl-5-(2-(2,5-difluorophenyl)pyrrolidin-1-yl)pyrazolo[1,5-a]pyrimidine-3-carboxamide;

N-((2S)-bicyclo[2.2.1]heptan-2-yl)-5-((R)-2-(2,5-difluorophenyl)pyrrolidin-1-yl)pyrazolo[1,5-a]pyrimidine-3-carboxamide;

(R)-5-(2-(2,5-difluorophenyl)pyrrolidin-1-yl)-N-(1-(hydroxymethyl)cyclopropyl)pyrazolo[1,5-a]pyrimidine-3-carboxamide;

(R)-5-(2-(2,5-difluorophenyl)pyrrolidin-1-yl)-N-(2-hydroxy-2-methylpropyl)pyrazolo[1,5-a]pyrimidine-3-carboxamide;

(5-((R)-2-(2,5-difluorophenyl)pyrrolidin-1-yl)pyrazolo[1,5-a]pyrimidin-3-yl)((S)-3-hydroxypyrrolidin-1-yl)methanone;

(5-((R)-2-(2,5-difluorophenyl)pyrrolidin-1-yl)pyrazolo[1,5-a]pyrimidin-3-yl)((R)-3-hydroxypyrrolidin-1-yl)methanone;

(R)-5-(2-(2,5-difluorophenyl)pyrrolidin-1-yl)-N-(tetrahydro-2H-pyran-4-yl)pyrazolo[1,5-a]pyrimidine-3-carboxamide;

(R)-5-(2-(2,5-difluorophenyl)pyrrolidin-1-yl)-N-((1-methyl-1H-imidazol-4-yl)methyl) pyrazole[1,5-a]pyrimidine-3-carboxamide;

(R)-5-(2-(2,5-difluorophenyl)pyrrolidin-1-yl)-N-((1-methyl-1H-pyrazol-4-yl)methyl)pyrazolo[1,5-a]pyrimidine-3-carboxamide;

(R)-5-(2-(2,5-difluorophenyl)pyrrolidin-1-yl)-N-(2-(1-methyl-1H-imidazol-5-yl)ethyl)pyrazolo[1,5-a]pyrimidine-3-carboxamide;

(R)-5-(2-(2,5-difluorophenyl)pyrrolidin-1-yl)-N-(2-(2-oxoimidazolidin-1-yl)ethyl) pyrazole[1,5-a]pyrimidine-3-carboxamide;

(R)—N-(2-(1H-imidazol-4-yl)ethyl)-5-(2-(2,5-difluorophenyl)pyrrolidin-1-yl)pyrazole [1,5-a]pyrimidine-3-carboxamide;

5-((R)-2-(2,5-difluorophenyl)pyrrolidin-1-yl)-N—((R)-2,3-dihydroxypropyl)pyrazolo[1,5-a]pyrimidine-3-carboxamide;

(R)-5-(2-(2,5-difluorophenyl)pyrrolidin-1-yl)-N,N-dimethylpyrazolo[1,5-a]pyrimidine-3-carboxamide;

(R)—N-(2-(1H-imidazol-1-yl)ethyl)-5-(2-(2,5-difluorophenyl)pyrrolidin-1-yl)pyrazolo[1,5-a]pyrimidine-3-carboxamide;

5-((R)-2-(2,5-difluorophenyl)pyrrolidin-1-yl)-N—((S)-2,3-dihydroxypropyl)pyrazolo[1,5-a]pyrimidine-3-carboxamide;

(R)-5-(2-(2,5-difluorophenyl)pyrrolidin-1-yl)pyrazolo[1,5-a]pyrimidine-3-carboxamide;

(R)-(5-(2-(2,5-difluorophenyl)pyrrolidin-1-yl)pyrazolo[1,5-a]pyrimidin-3-yl)(3-hydroxyazetidin-1-yl)methanone;

(R)-(5-(2-(2,5-difluorophenyl)pyrrolidin-1-yl)pyrazolo[1,5-a]pyrimidin-3-yl)(3-hydroxy-3-methylazetidin-1-yl)methanone;

Trans-4-(5-((R)-2-(2,5-difluorophenyl)pyrrolidin-1-yl)pyrazolo[1,5-a]pyrimidine-3-carboxamido)cyclohexanecarboxylic acid;

5-((R)-2-(5-fluoro-2-methoxyphenyl)pyrrolidin-1-yl)-N-((trans)-4-hydroxycyclohexyl)pyrazolo[1,5-a]pyrimidine-3-carboxamide;

5-((R)-2-(3-fluorophenyl)pyrrolidin-1-yl)-N-((trans)-4-hydroxycyclohexyl)pyrazolo[1,5-a]pyrimidine-3-carboxamide;

(R)—N-tert-butyl-5-(2-(3-fluorophenyl)pyrrolidin-1-yl)pyrazolo[1,5-a]pyrimidine-3-carboxamide;

(R)—N-cyclopropyl-5-(2-(3-fluorophenyl)pyrrolidin-1-yl)pyrazolo[1,5-a]pyrimidine-3-carboxamide;

(R)—N-(2-cyanopropan-2-yl)-5-(2-(2,5-difluorophenyl)pyrrolidin-1-yl)pyrazolo[1,5-a]pyrimidine-3-carboxamide;

(R)—N-(cyanomethyl)-5-(2-(2,5-difluorophenyl)pyrrolidin-1-yl)pyrazolo[1,5-a]pyrimidine-3-carboxamide;

(R)-5-(2-(2,5-difluorophenyl)pyrrolidin-1-yl)-N-(1-fluoro-2-methylpropan-2-yl)pyrazolo[1,5-a]pyrimidine-3-carboxamide;

N-cyclopropyl-5-((2R,4R)-2-(3-fluorophenyl)-4-hydroxypyrrolidin-1-yl)pyrazolo[1,5-a]pyrimidine-3-carboxamide;

N-tert-butyl-5-((2R,4R)-2-(3-fluorophenyl)-4-hydroxypyrrolidin-1-yl)pyrazolo[1,5-a]pyrimidine-3-carboxamide;

5-((2R,4R)-2-(3-fluorophenyl)-4-hydroxypyrrolidin-1-yl)-N-methylpyrazolo[1,5-a]pyrimidine-3-carboxamide;

(R)-5-(2-(2,5-difluorophenyl)pyrrolidin-1-yl)-N-(1-(methyl sulfonyl)piperidin-4-yl)pyrazolo[1,5-a]pyrimidine-3-carboxamide;

(R)-5-(2-(2,5-difluorophenyl)pyrrolidin-1-yl)-N-(1-sulfamoylpiperidin-4-yl)pyrazolo[1,5-a]pyrimidine-3-carboxamide;

(R)-5-(2-(2,5-difluorophenyl)pyrrolidin-1-yl)-N-(2-(methylsulfonamido)ethyl)pyrazolo[1,5-a]pyrimidine-3-carboxamide;

(R)-5-(2-(2,5-difluorophenyl)pyrrolidin-1-yl)-N-(2-sulfamoylethyl)pyrazolo[1,5-a]pyrimidine-3-carboxamide;

(R)—N-cyclopropyl-5-(2-(5-fluoro-2-methoxyphenyl)pyrrolidin-1-yl)pyrazolo[1,5-a]pyrimidine-3-carboxamide;

(R)-5-(2-(5-fluoro-2-methoxyphenyl)pyrrolidin-1-yl)-N-(2-hydroxy-2-methylpropyl)pyrazolo[1,5-a]pyrimidine-3-carboxamide;

5-((R)-2-(2,5-difluorophenyl)pyrrolidin-1-yl)-N-(4-hydroxy-4-methyl cyclohexyl)pyrazolo[1,5-a]pyrimidine-3-carboxamide (Diastereomer 1);

5-((R)-2-(2,5-difluorophenyl)pyrrolidin-1-yl)-N-(4-hydroxy-4-methylcyclohexyl)pyrazolo[1,5-a]pyrimidine-3-carboxamide (Diasteromer 2);

(R)—N-cyclopropyl-5-(2-(5-fluoropyridin-3-yl)pyrrolidin-1-yl)pyrazolo[1,5-a]pyrimidine-3-carboxamide;

(R)—N-tert-butyl-5-(2-(5-fluoropyridin-3-yl)pyrrolidin-1-yl)pyrazolo[1,5-a]pyrimidine-3-carboxamide;

(R)-5-(2-(5-fluoro-2-methoxyphenyl)pyrrolidin-1-yl)-N-(2-morpholinoethyl)pyrazolo[1,5-a]pyrimidine-3-carboxamide;

N—((S)-2,3-dihydroxypropyl)-5-((R)-2-(5-fluoro-2-methoxyphenyl)pyrrolidin-1-yl)pyrazolo[1,5-a]pyrimidine-3-carboxamide;

N—((R)-2,3-dihydroxypropyl)-5-((R)-2-(5-fluoro-2-methoxyphenyl)pyrrolidin-1-yl)pyrazolo[1,5-a]pyrimidine-3-carboxamide;

(R)-5-(2-(2,5-difluorophenyl)pyrrolidin-1-yl)-N-(2-methyl-1-(methylsulfonamido)propan-2-yl)pyrazolo[1,5-a]pyrimidine-3-carboxamide;

(R)—N-(2-amino-2-methylpropyl)-5-(2-(2,5-difluorophenyl)pyrrolidin-1-yl)pyrazolo[1,5-a]pyrimidine-3-carboxamide;

(R)—N-tert-butyl-5-(4,4-difluoro-2-(3-fluorophenyl)pyrrolidin-1-yl)pyrazolo[1,5-a]pyrimidine-3-carboxamide;

(R)-5-(2-(2,5-difluorophenyl)pyrrolidin-1-yl)-N-(1,3-dihydroxy-2-methylpropan-2-yl)pyrazolo[1,5-a]pyrimidine-3-carboxamide;

5-((R)-2-(2,5-difluorophenyl)pyrrolidin-1-yl)-N-((3 S,4R)-3-fluoropiperidin-4-yl)pyrazolo[1,5-a]pyrimidine-3-carboxamide;

N—((S)-2,3-dihydroxypropyl)-5-((R)-2-(5-fluoro-2-(trifluoromethyl)phenyl) pyrrolidin-1-yl)pyrazolo[1,5-a]pyrimidine-3-carboxamide;

N—((R)-2,3-dihydroxypropyl)-5-((R)-2-(5-fluoro-2-(trifluoromethyl)phenyl) pyrrolidin-1-yl)pyrazolo[1,5-a]pyrimidine-3-carboxamide;

(R)-5-(2-(5-fluoro-2-(trifluoromethyl)phenyl)pyrrolidin-1-yl)pyrazolo[1,5-a]pyrimidine-3-carboxamide;

(R)-5-(2-(2,5-difluorophenyl)pyrrolidin-1-yl)-N-methoxypyrazolo[1,5-a]pyrimidine-3-carboxamide;

(R)-5-(5-(2,5-difluorophenyl)-2,2-dimethylpyrrolidin-1-yl) pyrazolo[1,5-a]pyrimidine-3-carboxamide;

(R)—N-cyclopropyl-5-(5-(2,5-difluorophenyl)-2,2-dimethylpyrrolidin-1-yl)pyrazolo[1,5-a]pyrimidine-3-carboxamide;

(R)—N-(2-cyanopropan-2-yl)-5-(2-(5-fluoropyridin-3-yl) pyrrolidin-1-yl)pyrazolo[1,5-a]pyrimidine-3-carboxamide;

(R)-5-(2-(5-fluoropyridin-3-yl)pyrrolidin-1-yl)-N-(1-(methylsulfonyl)piperidin-4-yl)pyrazolo[1,5-a]pyrimidine-3-carboxamide;

(R)—N-(1-fluoro-2-methylpropan-2-yl)-5-(2-(5-fluoropyridin-3-yl)pyrrolidin-1-yl)pyrazolo[1,5-a]pyrimidine-3-carboxamide;

(R)-5-(2-(5-fluoropyridin-3-yl)pyrrolidin-1-yl)-N-(tetrahydro-2H-pyran-4-yl)pyrazolo[1,5-a]pyrimidine-3-carboxamide;

(R)-5-(2-(5-fluoropyridin-3-yl)pyrrolidin-1-yl)-N-methoxypyrazolo[1,5-a]pyrimidine-3-carboxamide;

(R)-5-(2-(3-fluorophenyl)pyrrolidin-1-yl)pyrazolo[1,5-a] pyrimidine-3-carboxamide;

((R)-5-(2-(3-fluorophenyl)pyrrolidin-1-yl)-N-methoxypyrazolo[1,5-a]pyrimidine-3-carboxamide;

(R)-5-(2-(3-fluoro-5-(2-morpholinoethoxy)phenyl)pyrrolidin-1-yl)pyrazolo[1,5-a]pyrimidine-3-carboxamide;

(R)—N-cyclopropyl-5-(2-(3-fluoro-5-(2-methoxyethoxy) phenyl)pyrrolidin-1-yl)pyrazole [1,5-a]pyrimidine-3-carboxamide;

(R)-5-(2-(3-fluoro-5-(2-methoxyethoxy)phenyl)pyrrolidin-1-yl)pyrazolo[1,5-a]pyrimidine-3-carboxamide;

(R)—N-cyclopropyl-5-(2-(5-fluoro-2-methoxypyridin-3-yl) pyrrolidin-1-yl)pyrazolo[1,5-a]pyrimidine-3-carboxamide;

(R)—N-tert-butyl-5-(2-(5-fluoro-2-methoxypyridin-3-yl) pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-(1-fluoro-2-methylpropan-2-yl)pyrazolo[1,5-a]pyrimidine-3-carboxamide;

(R)-5-(2-(5-fluoro-2-methoxypyridin-3-yl)pyrrolidin-1-yl) pyrazolo[1,5-a]pyrimidine-3-carboxamide;

(R)-5-(2-(5-fluoro-2-methoxypyridin-3-yl)pyrrolidin-1-yl)-N-methoxypyrazolo[1,5-a]pyrimidine-3-carboxamide;

(R)-1-(5-(2-(2,5-difluorophenyl)pyrrolidin-1-yl)pyrazolo[1,5-a]pyrimidine-3-carboxamido)cyclopropanecarboxylic acid;

(R)—N-cyclopropyl-5-(2-(3-fluoro-5-(2-morpholinoethoxy)phenyl)pyrrolidin-1-yl)pyrazolo[1,5-a]pyrimidine-3-carboxamide;

(R)-5-(2-(5-fluoro-2-(2-morpholinoethoxy) phenyl) pyrrolidin-1-yl)pyrazolo[1,5-a]pyrimidine-3-carboxamide;

(R)—N-cyclopropyl-5-(2-(5-fluoro-2-(2-morpholinoethoxy)phenyl) pyrrolidin-1-yl)pyrazolo[1,5-a]pyrimidine-3-carboxamide;

5-((R)-2-(2,5-difluorophenyl)pyrrolidin-1-yl)-N—((S)-2,3-dihydroxypropoxy)pyrazolo[1,5-a]pyrimidine-3-carboxamide;

(R)-5-(2-(5-fluoro-2-(2-methoxyethoxy)phenyl)pyrrolidin-1-yl)pyrazolo[1,5-a]pyrimidine-3-carboxamide;

(R)—N-cyclopropyl-5-(2-(5-fluoro-2-(2-methoxyethoxy) phenyl) pyrrolidin-1-yl)pyrazolo[1,5-a]pyrimidine-3-carboxamide;

(R)-5-(2-(5-fluoropyridin-3-yl)pyrrolidin-1-yl)-N-(1-methylcyclopropyl)pyrazolo[1,5-a]pyrimidine-3-carboxamide;

(R)-(5-(2-(5-fluoropyridin-3-yl)pyrrolidin-1-yl)pyrazolo[1,5-a]pyrimidin-3-yl)(3-hydroxy-3-methylazetidin-1-yl) methanone;

(R)-5-(2-(5-fluoropyridin-3-yl)pyrrolidin-1-yl)-N-isopropylpyrazolo[1,5-a]pyrimidine-3-carboxamide;

(R)-(5-(2-(5-fluoropyridin-3-yl)pyrrolidin-1-yl)pyrazolo[1,5-a]pyrimidin-3-yl)(pyrrolidin-1-yl)methanone;

(R)—N-(5-fluoropyridin-2-yl)-5-(2-(5-fluoropyridin-3-yl) pyrrolidin-1-yl)pyrazolo[1,5-a]pyrimidine-3-carboxamide;

(R)-(5-(2-(5-fluoropyridin-3-yl)pyrrolidin-1-yl)pyrazolo[1,5-a]pyrimidin-3-yl)(3-methoxyazetidin-1-yl)methanone;

N-(3-chloro-2-fluoropropyl)-5-((R)-2-(5-fluoropyridin-3-yl)pyrrolidin-1-yl)pyrazolo[1,5-a]pyrimidine-3-carboxamide;

(R)-5-(2-(5-fluoropyridin-3-yl)pyrrolidin-1-yl)-N-(1-(trifluoromethyl)cyclopropyl)pyrazolo[1,5-a]pyrimidine-3-carboxamide;

5-((R)-2-(5-fluoropyridin-3-yl)pyrrolidin-1-yl)-N-((trans)-4-hydroxycyclohexyl)pyrazolo[1,5-a]pyrimidine-3-carboxamide;

5-((R)-2-(5-fluoropyridin-3-yl)pyrrolidin-1-yl)-N-((cis)-4-hydroxycyclohexyl)pyrazolo[1,5-a]pyrimidine-3-carboxamide;

(R)—N-cyclobutyl-5-(2-(5-fluoropyridin-3-yl)pyrrolidin-1-yl)pyrazolo[1,5-a]pyrimidine-3-carboxamide;

(R)-5-(2-(5-fluoropyridin-3-yl)pyrrolidin-1-yl)-N-(1-methylcyclobutyl)pyrazolo[1,5-a]pyrimidine-3-carboxamide;

5-((R)-2-(5-fluoropyridin-3-yl)pyrrolidin-1-yl)-N-((1S,2S)-2-hydroxycyclopentyl)pyrazolo[1,5-a]pyrimidine-3-carboxamide;

5-((R)-2-(5-fluoropyridin-3-yl)pyrrolidin-1-yl)-N-((1S,2R)-2-hydroxycyclopentyl)pyrazolo[1,5-a]pyrimidine-3-carboxamide;

5-((R)-2-(5-fluoropyridin-3-yl)pyrrolidin-1-yl)-N-((1 S,3 S)-3-hydroxycyclopentyl)pyrazolo[1,5-a]pyrimidine-3-carboxamide;

(R)—N-(cyclopropylmethyl)-5-(2-(5-fluoropyridin-3-yl) pyrrolidin-1-yl)pyrazolo[1,5-a]pyrimidine-3-carboxamide;

(R)-5-(2-(5-fluoropyridin-3-yl)pyrrolidin-1-yl)-N-(1-(hydroxymethyl)cyclopropyl)pyrazolo[1,5-a]pyrimidine-3-carboxamide;

(R)-(5-(2-(5-fluoropyridin-3-yl)pyrrolidin-1-yl)pyrazolo[1,5-a]pyrimidin-3-yl)(3-hydroxyazetidin-1-yl)methanone;

5-((R)-2-(5-fluoropyridin-3-yl)pyrrolidin-1-yl)-N—((S)-2-hydroxypropyl)pyrazolo[1,5-a]pyrimidine-3-carboxamide;

5-((R)-2-(5-fluoropyridin-3-yl)pyrrolidin-1-yl)-N—((R)-2-hydroxypropyl)pyrazolo[1,5-a]pyrimidine-3-carboxamide;

(R)-5-(2-(5-fluoropyridin-3-yl)pyrrolidin-1-yl)-N-(2-hydroxy-2-methylpropyl)pyrazolo[1,5-a]pyrimidine-3-carboxamide;

(R)-5-(2-(5-fluoropyridin-3-yl)pyrrolidin-1-yl)-N-(2-hydroxyethyl)pyrazolo[1,5-a]pyrimidine-3-carboxamide;

N-(1-cyclopropylethyl)-5-((R)-2-(5-fluoropyridin-3-yl)pyrrolidin-1-yl)pyrazolo[1,5-a]pyrimidine-3-carboxamide;

(R)-5-(2-(5-fluoropyridin-3-yl)pyrrolidin-1-yl)-N-methylpyrazolo[1,5-a]pyrimidine-3-carboxamide;

5-((R)-2-(5-fluoropyridin-3-yl)pyrrolidin-1-yl)-N—((R)-1-hydroxypropan-2-yl)pyrazolo[1,5-a]pyrimidine-3-carboxamide;

5-((R)-2-(5-fluoropyridin-3-yl)pyrrolidin-1-yl)-N—((S)-1-hydroxypropan-2-yl)pyrazolo[1,5-a]pyrimidine-3-carboxamide;

(R)-5-(2-(5-fluoropyridin-3-yl)pyrrolidin-1-yl)pyrazolo[1,5-a]pyrimidine-3-carboxamide;

5-((R)-2-(5-fluoropyridin-3-yl)pyrrolidin-1-yl)-N-(1-methoxypropan-2-yl)pyrazolo[1,5-a]pyrimidine-3-carboxamide;

5-((R)-2-(5-fluoropyridin-3-yl)pyrrolidin-1-yl)-N-(2-hydroxy-3-methoxypropyl)pyrazolo[1,5-a]pyrimidine-3-carboxamide;

5-((R)-2-(5-fluoropyridin-3-yl)pyrrolidin-1-yl)-N-((trans)-2-hydroxycyclopentyl)pyrazolo[1,5-a]pyrimidine-3-carboxamide;

5-((R)-2-(5-fluoropyridin-3-yl)pyrrolidin-1-yl)-N—((S)-1-hydroxy-3-methylbutan-2-yl)pyrazolo[1,5-a]pyrimidine-3-carboxamide;

5-((R)-2-(5-fluoropyridin-3-yl)pyrrolidin-1-yl)-N—((R)-1-hydroxy-3-methylbutan-2-yl)pyrazolo[1,5-a]pyrimidine-3-carboxamide;

N—((R)-1-cyclopropylethyl)-5-((R)-2-(5-fluoropyridin-3-yl)pyrrolidin-1-yl)pyrazolo[1,5-a]pyrimidine-3-carboxamide;

N—((S)-1-cyclopropylethyl)-5-((R)-2-(5-fluoropyridin-3-yl)pyrrolidin-1-yl)pyrazolo[1,5-a]pyrimidine-3-carboxamide;

(R)-5-(2-(5-fluoropyridin-3-yl)pyrrolidin-1-yl)-N-(3-hydroxy-2,2-dimethylpropyl)pyrazolo[1,5-a]pyrimidine-3-carboxamide;

(R)-azetidin-1-yl(5-(2-(5-fluoropyridin-3-yl)pyrrolidin-1-yl)pyrazolo[1,5-a]pyrimidin-3-yl)methanone;

(R)-(5-(2-(5-fluoropyridin-3-yl)pyrrolidin-1-yl)pyrazolo[1,5-a]pyrimidin-3-yl)(3-(hydroxymethyl)azetidin-1-yl)methanone;

(5-((R)-2-(5-fluoropyridin-3-yl)pyrrolidin-1-yl)pyrazolo[1,5-a]pyrimidin-3-yl)((S)-3-hydroxypyrrolidin-1-yl)methanone;

5-((R)-2-(5-fluoropyridin-3-yl)pyrrolidin-1-yl)-N—((R)-1,1,1-trifluoropropan-2-yl)pyrazolo[1,5-a]pyrimidine-3-carboxamide;

5-((R)-2-(5-fluoropyridin-3-yl)pyrrolidin-1-yl)-N—((S)-1,1,1-trifluoropropan-2-yl)pyrazolo[1,5-a]pyrimidine-3-carboxamide;

(R)-5-(2-(5-fluoropyridin-3-yl)pyrrolidin-1-yl)-N-(2,2,2-trifluoroethyl)pyrazolo[1,5-a]pyrimidine-3-carboxamide;

(R)-5-(2-(5-fluoropyridin-3-yl)pyrrolidin-1-yl)-N-(1-hydroxy-2-methylpropan-2-yl)pyrazolo[1,5-a]pyrimidine-3-carboxamide;

5-((R)-2-(5-fluoropyridin-3-yl)pyrrolidin-1-yl)-N-((1R,2R)-2-hydroxycyclopentyl)pyrazolo[1,5-a]pyrimidine-3-carboxamide;

(R)—N-(2,2-difluoroethyl)-5-(2-(5-fluoropyridin-3-yl)pyrrolidin-1-yl)pyrazolo[1,5-a]pyrimidine-3-carboxamide;

5-((R)-2-(5-fluoropyridin-3-yl)pyrrolidin-1-yl)-N-((1R,2S)-2-hydroxycyclopentyl)pyrazolo[1,5-a]pyrimidine-3-carboxamide;

5-((R)-2-(5-fluoropyridin-3-yl)pyrrolidin-1-yl)-N-((1R,2R)-2-hydroxycyclohexyl)pyrazolo[1,5-a]pyrimidine-3-carboxamide;

(R)-(5-(2-(5-fluoropyridin-3-yl)pyrrolidin-1-yl)pyrazolo[1,5-a]pyrimidin-3-yl)(piperidin-1-yl)methanone;

5-((R)-2-(5-fluoropyridin-3-yl)pyrrolidin-1-yl)-N-((2R,3S,4S)-3-(hydroxymethyl)bicyclo[2.2.1]heptan-2-yl)pyrazolo[1,5-a]pyrimidine-3-carboxamide;

(R)-(5-(2-(5-fluoro-2-methoxypyridin-3-yl)pyrrolidin-1-yl)pyrazolo[1,5-a]pyrimidin-3-yl)(3-hydroxyazetidin-1-yl)methanone;

5-((R)-2-(5-fluoro-2-methoxypyridin-3-yl)pyrrolidin-1-yl)-N-((trans)-4-hydroxycyclohexyl)pyrazolo[1,5-a]pyrimidine-3-carboxamide;

(R)-tert-butyl 3-(5-(2-(5-fluoro-2-methoxypyridin-3-yl)pyrrolidin-1-yl)pyrazolo[1,5-a]pyrimidine-3-carboxamido)propylcarbamate;

(R)—N-(3-aminopropyl)-5-(2-(5-fluoro-2-oxo-1,2-dihydropyridin-3-yl)pyrrolidin-1-yl)pyrazolo[1,5-a]pyrimidine-3-carboxamide;

N—((S)-2,3-dihydroxypropyl)-5-((R)-2-(5-fluoro-2-methoxypyridin-3-yl)pyrrolidin-1-yl)pyrazolo[1,5-a]pyrimidine-3-carboxamide;

N—((S)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide;

N—((R)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide;

(R)—N-(2-chloroethoxy)-5-(2-(5-fluoro-2-methoxypyridin-3-yl)pyrrolidin-1-yl)pyrazolo[1,5-a]pyrimidine-3-carboxamide;

(R)-(5-(2-(5-fluoro-2-methoxypyridin-3-yl)pyrrolidin-1-yl)pyrazolo[1,5-a]pyrimidin-3-yl)(3-hydroxy-3-methylazetidin-1-yl)methanone;

(R)-5-(2-(5-fluoro-2-methoxypyridin-3-yl)pyrrolidin-1-yl)-N-(3-hydroxypropyl)pyrazolo[1,5-a]pyrimidine-3-carboxamide;

N-(2,3-dihydroxypropyl)-5-((R)-2-(5-fluoro-2-methoxypyridin-3-yl)pyrrolidin-1-yl)pyrazolo[1,5-a]pyrimidine-3-carboxamide;

N—((R)-2,3-dihydroxypropyl)-5-((R)-2-(5-fluoro-2-methoxypyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-(4-hydroxybutyl)pyrazolo[1,5-a]pyrimidine-3-carboxamide;

(R)—N-(2-tert-butoxyethoxy)-5-(2-(5-fluoro-2-methoxypyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-methylpyrazolo[1,5-a]pyrimidine-3-carboxamide;

5-((R)-2-(5-fluoro-2-methoxypyridin-3-yl)pyrrolidin-1-yl)-N-((1 S,3 S)-3-hydroxycyclopentyl)pyrazolo[1,5-a]pyrimidine-3-carboxamide;

(R)-5-(2-(5-fluoro-2-methoxypyridin-3-yl)pyrrolidin-1-yl)-N-(2-hydroxyethyl)pyrazolo[1,5-a]pyrimidine-3-carboxamide;

5-((R)-2-(5-fluoro-2-methoxypyridin-3-yl)pyrrolidin-1-yl)-N—((S)-2-hydroxypropyl)pyrazolo[1,5-a]pyrimidine-3-carboxamide;

5-((R)-2-(5-fluoro-2-methoxypyridin-3-yl)pyrrolidin-1-yl)-N—((R)-2-hydroxypropyl)pyrazolo[1,5-a]pyrimidine-3-carboxamide;

(R)-5-(2-(5-fluoro-2-methoxypyridin-3-yl)pyrrolidin-1-yl)-N-(2-hydroxy-2-methylpropyl)pyrazolo[1,5-a]pyrimidine-3-carboxamide;

(R)—N-(1,3-dihydroxypropan-2-yl)-5-(2-(5-fluoro-2-methoxypyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-(6-oxo-1,6-dihydropyridin-3-yl)pyrazolo[1,5-a]pyrimidine-3-carboxamide;

R)-5-(2-(5-fluoro-2-methoxypyridin-3-yl)pyrrolidin-1-yl)-N-(1-(methylsulfonyl)piperidin-4-yl)pyrazolo[1,5-a]pyrimidine-3-carboxamide;

(R)—N-(2-chloroethyl)-5-(2-(5-fluoro-2-methoxypyridin-3-yl)pyrrolidin-1-yl)pyrazolo[1,5-a]pyrimidine-3-carboxamide;

(R)—N-(2-bromoethoxy)-5-(2-(5-fluoro-2-methoxypyridin-3-yl)pyrrolidin-1-yl)pyrazolo[1,5-a]pyrimidine-3-carboxamide;

5-(2-(2,5-difluorophenyl)pyrrolidin-1-yl)-N-(2-hydroxyethyl)pyrazolo[1,5-a]pyrimidine-3-carboxamide;

5-((R)-2-(2,5-difluorophenyl)pyrrolidin-1-yl)-N-(2-hydroxypropyl)pyrazolo[1,5-a]pyrimidine-3-carboxamide;

5-((R)-2-(2,5-difluorophenyl)pyrrolidin-1-yl)-N-(2-hydroxypropyl)pyrazolo[1,5-a]pyrimidine-3-carboxamide;

5-((R)-2-(2,5-difluorophenyl)pyrrolidin-1-yl)-N-(3-hydroxy-2,2-dimethylpropyl)pyrazolo[1,5-a]pyrimidine-3-carboxamide;

5-((R)-2-(2,5-difluorophenyl)pyrrolidin-1-yl)-N-((1 S,3 S)-3-hydroxycyclopentyl)pyrazolo[1,5-a]pyrimidine-3-carboxamide;

5-((R)-2-(2,5-difluorophenyl)pyrrolidin-1-yl)-N-(2-(4-hydroxypiperidin-1-yl)ethyl)pyrazolo[1,5-a]pyrimidine-3-carboxamide;

5-((R)-2-(2,5-difluorophenyl)pyrrolidin-1-yl)-N-(2-(4-methylpiperazin-1-yl)ethyl)pyrazolo[1,5-a]pyrimidine-3-carboxamide;

5-((R)-2-(2,5-difluorophenyl)pyrrolidin-1-yl)-N-(2-methoxyethyl)pyrazolo[1,5-a]pyrimidine-3-carboxamide;

5-((R)-2-(2,5-difluorophenyl)pyrrolidin-1-yl)-N-(1,3-dihydroxypropan-2-yl)pyrazolo[1,5-a]pyrimidine-3-carboxamide;

5-((R)-2-(2,5-difluorophenyl)pyrrolidin-1-yl)-N-((2S,3R)-1,3-dihydroxybutan-2-yl)pyrazolo[1,5-a]pyrimidine-3-carboxamide;

5-((R)-2-(2,5-difluorophenyl)pyrrolidin-1-yl)-N-((2S,3 S)-1,3-dihydroxybutan-2-yl)pyrazolo[1,5-a]pyrimidine-3-carboxamide;

5-((R)-2-(2,5-difluorophenyl)pyrrolidin-1-yl)-N-((2R,3 S)-1,3-dihydroxybutan-2-yl)pyrazolo[1,5-a]pyrimidine-3-carboxamide;

5-((R)-2-(2,5-difluorophenyl)pyrrolidin-1-yl)-N—((S)-1-hydroxypropan-2-yl)pyrazolo[1,5-a]pyrimidine-3-carboxamide;

5-((R)-2-(2,5-difluorophenyl)pyrrolidin-1-yl)-N—((S)-1-hydroxybutan-2-yl)pyrazolo[1,5-a]pyrimidine-3-carboxamide;

5-((R)-2-(2,5-difluorophenyl)pyrrolidin-1-yl)-N—((S)-1-hydroxy-3-methylbutan-2-yl)pyrazolo[1,5-a]pyrimidine-3-carboxamide;

5-((R)-2-(2,5-difluorophenyl)pyrrolidin-1-yl)-N—((S)-1-hydroxy-3,3-dimethylbutan-2-yl)pyrazolo[1,5-a]pyrimidine-3-carboxamide;

N-cyclopropyl-5-(2-(5-fluoro-2-methylpyridin-3-yl)pyrrolidin-1-yl)pyrazolo[1,5-a]pyrimidine-3-carboxamide;

N-cyclopropyl-5-(2-(2-ethyl-5-fluoropyridin-3-yl)pyrrolidin-1-yl)pyrazolo[1,5-a]pyrimidine-3-carboxamide;

(R)—N-tert-butyl-5-(2-(5-fluoro-2-methylpyridin-3-yl)pyrrolidin-1-yl)pyrazolo[1,5-a]pyrimidine-3-carboxamide;

(R)-5-(2-(5-fluoro-2-methylpyridin-3-yl)pyrrolidin-1-yl)-N-isopropylpyrazolo[1,5-a]pyrimidine-3-carboxamide;

(R)—N-cyclobutyl-5-(2-(5-fluoro-2-methylpyridin-3-yl)pyrrolidin-1-yl)pyrazolo[1,5-a]pyrimidine-3-carboxamide;

(R)-5-(2-(5-fluoro-2-methylpyridin-3-yl)pyrrolidin-1-yl)-N-methylpyrazolo[1,5-a]pyrimidine-3-carboxamide;

(R)-5-(2-(5-fluoro-2-methylpyridin-3-yl)pyrrolidin-1-yl)pyrazolo[1,5-a]pyrimidine-3-carboxamide;

(R)-5-(2-(5-fluoro-2-methylpyridin-3-yl)pyrrolidin-1-yl)-N-(2-hydroxyethyl)pyrazolo[1,5-a]pyrimidine-3-carboxamide;

(R)-5-(2-(5-fluoro-2-methylpyridin-3-yl)pyrrolidin-1-yl)-N—((R)-2-hydroxypropyl)pyrazolo[1,5-a]pyrimidine-3-carboxamide;

(R)-5-(2-(5-fluoro-2-methylpyridin-3-yl)pyrrolidin-1-yl)-N-(1-methylcyclopropyl)pyrazolo[1,5-a]pyrimidine-3-carboxamide;

(R)-5-(2-(5-fluoro-2-methylpyridin-3-yl)pyrrolidin-1-yl)-N-(2-methoxyethyl)pyrazolo[1,5-a]pyrimidine-3-carboxamide;

(R)-(5-(2-(5-fluoro-2-methylpyridin-3-yl)pyrrolidin-1-yl)pyrazolo[1,5-a]pyrimidin-3-yl)(3-hydroxyazetidin-1-yl)methanone;

(R)-5-(2-(5-fluoro-2-methylpyridin-3-yl)pyrrolidin-1-yl)-N-(1-(hydroxymethyl)cyclopropyl)pyrazolo[1,5-a]pyrimidine-3-carboxamide;

5-((R)-2-(5-fluoro-2-methylpyridin-3-yl)pyrrolidin-1-yl)-N-((trans)-4-hydroxycyclohexyl)pyrazolo[1,5-a]pyrimidine-3-carboxamide;

5-((R)-2-(5-fluoro-2-methylpyridin-3-yl)pyrrolidin-1-yl)-N-((cis)-4-hydroxycyclohexyl)pyrazolo[1,5-a]pyrimidine-3-carboxamide;

5-((R)-2-(5-fluoro-2-methylpyridin-3-yl)pyrrolidin-1-yl)-N-((1 S,3S)-3-hydroxycyclopentyl)pyrazolo[1,5-a]pyrimidine-3-carboxamide;

5-((R)-2-(5-fluoro-2-methylpyridin-3-yl)pyrrolidin-1-yl)-N-((1R,2R)-2-hydroxycyclopentyl)pyrazolo[1,5-a]pyrimidine-3-carboxamide;

5-((R)-2-(5-fluoro-2-methylpyridin-3-yl)pyrrolidin-1-yl)-N—((R)-quinuclidin-3-yl)pyrazolo[1,5-a]pyrimidine-3-carboxamide;

5-((R)-2-(2-ethyl-5-fluoropyridin-3-yl)pyrrolidin-1-yl)-N-((trans)-4-hydroxycyclohexyl)pyrazolo[1,5-a]pyrimidine-3-carboxamide;

5-((R)-2-(2-ethyl-5-fluoropyridin-3-yl)pyrrolidin-1-yl)-N-((1 S,3 S)-3-hydroxycyclopentyl)pyrazolo[1,5-a]pyrimidine-3-carboxamide;

(R)-5-(2-(2-ethyl-5-fluoropyridin-3-yl)pyrrolidin-1-yl)-N-(2-hydroxy-2-methylpropyl)pyrazolo[1,5-a]pyrimidine-3-carboxamide;

(R)—N-tert-butyl-5-(2-(5-fluoro-2-oxo-1,2-dihydropyridin-3-yl)pyrrolidin-1-yl)pyrazolo[1,5-a]pyrimidine-3-carboxamide;

(R)—N-(2-chloroethyl)-5-(2-(5-fluoro-2-oxo-1,2-dihydropyridin-3-yl)pyrrolidin-1-yl)pyrazolo[1,5-a]pyrimidine-3-carboxamide;

N-cyclopropyl-5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide;

5-((2R)-2-(2-((2,2-dimethyl-1,3-dioxolan-4-yl)methoxy)-5-fluorophenyl)pyrrolidin-1-yl)pyrazolo[1,5-a]pyrimidine-3-carboxamide;

N-cyclopropyl-5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide;

5-((2R)-2-(3-((2,2-dimethyl-1,3-dioxolan-4-yl)methoxy)-5-fluorophenyl)pyrrolidin-1-yl)pyrazolo[1,5-a]pyrimidine-3-carboxamide;

N-cyclopropyl-5-((2R)-2-(3-(2,3-dihydroxypropoxy)-5-fluorophenyl)pyrrolidin-1-yl)pyrazolo[1,5-a]pyrimidine-3-carboxamide;

5-((2R)-2-(3-(2,3-dihydroxypropoxy)-5-fluorophenyl)pyrrolidin-1-yl)pyrazolo[1,5-a]pyrimidine-3-carboxamide;

N-cyclopropyl-5-((2R)-2-(2-(2,3-dihydroxypropoxy)-5-fluorophenyl)pyrrolidin-1-yl)pyrazolo[1,5-a]pyrimidine-3-carboxamide;

5-((2R)-2-(2-(2,3-dihydroxypropoxy)-5-fluorophenyl)pyrrolidin-1-yl)pyrazolo[1,5-a]pyrimidine-3-carboxamide;

5-((2R,5S)-2-(5-fluoropyridin-3-yl)-5-(hydroxymethyl)pyrrolidin-1-yl)-N—((R)-1,1,1-trifluoropropan-2-yl)pyrazolo[1,5-a]pyrimidine-3-carboxamide;

5-((2R,5 S)-2-(5-fluoropyridin-3-yl)-5-(hydroxymethyl)pyrrolidin-1-yl)-N—((S)-1,1,1-trifluoropropan-2-yl)pyrazolo[1,5-a]pyrimidine-3-carboxamide;

5-((2R,5 S)-2-(5-fluoropyridin-3-yl)-5-(hydroxymethyl)pyrrolidin-1-yl)-N-(1-methylcyclopropyl)pyrazolo[1,5-a]pyrimidine-3-carboxamide;

5-((2R,5 S)-2-(5-fluoropyridin-3-yl)-5-(hydroxymethyl)pyrrolidin-1-yl)-N-isopropylpyrazolo[1,5-a]pyrimidine-3-carboxamide;

5-((2R,4S)-2-(3-fluorophenyl)-4-hydroxypyrrolidin-1-yl)-N—((S)-1,1,1-trifluoropropan-2-yl)pyrazolo[1,5-a]pyrimidine-3-carboxamide;

5-((2R,4S)-2-(3-fluorophenyl)-4-hydroxypyrrolidin-1-yl)-N-isopropylpyrazolo[1,5-a]pyrimidine-3-carboxamide;

5-((2R,4S)-2-(3-fluorophenyl)-4-hydroxypyrrolidin-1-yl)-N-methylpyrazolo[1,5-a]pyrimidine-3-carboxamide;

5-((2S,5R)-5-(5-fluoropyridin-3-yl)-2-(hydroxymethyl)-2-methylpyrrolidin-1-yl)-N-isopropylpyrazolo[1,5-a]pyrimidine-3-carboxamide;

5-((2S,5R)-5-(5-fluoropyridin-3-yl)-2-(hydroxymethyl)-2-methylpyrrolidin-1-yl)-N—((S)-1,1,1-trifluoropropan-2-yl)pyrazolo[1,5-a]pyrimidine-3-carboxamide;

(R)-(5-(2-(2-amino-5-fluoropyridin-3-yl)pyrrolidin-1-yl)pyrazolo[1,5-a]pyrimidin-3-yl)(azetidin-1-yl)methanone;

(R)-tert-butyl 3-(5-(2-(2-chloro-5-fluoropyridin-3-yl)pyrrolidin-1-yl)pyrazolo[1,5-a]pyrimidine-3-carboxamido)propylcarbamate;

(R)—N-(3-aminopropyl)-5-(2-(2-chloro-5-fluoropyridin-3-yl)pyrrolidin-1-yl)pyrazolo[1,5-a]pyrimidine-3-carboxamide;

(R)—N-(2-tert-butoxyethoxy)-5-(2-(2-chloro-5-fluoropyridin-3-yl)pyrrolidin-1-yl)pyrazolo[1,5-a]pyrimidine-3-carboxamide;

(R)-5-(2-(2-chloro-5-fluoropyridin-3-yl)pyrrolidin-1-yl)-N-(2-hydroxyethoxy)pyrazolo[1,5-a]pyrimidine-3-carboxamide;

(R)—N-tert-butyl-5-(2-(5-fluoro-1-methyl-2-oxo-1,2-dihydropyridin-3-yl)pyrrolidin-1-yl)pyrazolo[1,5-a]pyrimidine-3-carboxamide;

(R)-5-(2-(5-fluoro-1-methyl-2-oxo-1,2-dihydropyridin-3-yl)pyrrolidin-1-yl)-N-isopropylpyrazolo[1,5-a]pyrimidine-3-carboxamide;

(R)—N-cyclopropyl-5-(2-(5-fluoro-1-methyl-2-oxo-1,2-dihydropyridin-3-yl)pyrrolidin-1-yl)pyrazolo[1,5-a]pyrimidine-3-carboxamide;

(R)-5-(2-(5-fluoro-1-methyl-2-oxo-1,2-dihydropyridin-3-yl)pyrrolidin-1-yl)-N-(6-methylpyridin-3-yl)pyrazolo[1,5-a]pyrimidine-3-carboxamide;

(R)—N-cyclobutyl-5-(2-(5-fluoro-1-methyl-2-oxo-1,2-dihydropyridin-3-yl)pyrrolidin-1-yl)pyrazolo[1,5-a]pyrimidine-3-carboxamide;

(R)-5-(2-(5-fluoro-1-methyl-2-oxo-1,2-dihydropyridin-3-yl)pyrrolidin-1-yl)-N-(pyridin-3-yl)pyrazolo[1,5-a]pyrimidine-3-carboxamide;

(R)—N-(cyclopropylmethyl)-5-(2-(5-fluoro-1-methyl-2-oxo-1,2-dihydropyridin-3-yl)pyrrolidin-1-yl)pyrazolo[1,5-a]pyrimidine-3-carboxamide;

5-((R)-2-(5-fluoro-1-methyl-2-oxo-1,2-dihydropyridin-3-yl)pyrrolidin-1-yl)-N—((S)-1-hydroxy-3,3-dimethylbutan-2-yl)pyrazolo[1,5-a]pyrimidine-3-carboxamide;

5-((R)-2-(5-fluoro-1-methyl-2-oxo-1,2-dihydropyridin-3-yl)pyrrolidin-1-yl)-N-((1R,2R)-2-hydroxycyclohexyl)pyrazolo[1,5-a]pyrimidine-3-carboxamide;

N—((R)-1-cyclopropylethyl)-5-((R)-2-(5-fluoro-1-methyl-2-oxo-1,2-dihydropyridin-3-yl)pyrrolidin-1-yl)pyrazolo[1,5-a]pyrimidine-3-carboxamide;

N—((S)-1-cyclopropylethyl)-5-((R)-2-(5-fluoro-1-methyl-2-oxo-1,2-dihydropyridin-3-yl)pyrrolidin-1-yl)pyrazolo[1,5-a]pyrimidine-3-carboxamide;

(R)-5-(2-(5-fluoro-1-methyl-2-oxo-1,2-dihydropyridin-3-yl)pyrrolidin-1-yl)-N-(1-methylcyclopropyl)pyrazolo[1,5-a]pyrimidine-3-carboxamide;

5-((R)-2-(5-fluoro-1-methyl-2-oxo-1,2-dihydropyridin-3-yl)pyrrolidin-1-yl)-N-((trans)-4-hydroxycyclohexyl)pyrazolo[1,5-a]pyrimidine-3-carboxamide;

(R)-5-(2-(5-fluoro-1-methyl-2-oxo-1,2-dihydropyridin-3-yl)pyrrolidin-1-yl)-N-(5-fluoropyridin-2-yl)pyrazolo[1,5-a]pyrimidine-3-carboxamide;

(R)-5-(2-(5-fluoro-2-methoxypyridin-3-yl)pyrrolidin-1-yl)-N-(3-methyl-1H-pyrazol-5-yl)pyrazolo[1,5-a]pyrimidine-3-carboxamide;

(R)-5-(2-(5-fluoro-2-methoxypyridin-3-yl)pyrrolidin-1-yl)-N-(1-methyl-1H-pyrazol-3-yl)pyrazolo[1,5-a]pyrimidine-3-carboxamide;

(R)—N-(3-cyclopropyl-1H-pyrazol-5-yl)-5-(2-(5-fluoro-2-methoxypyridin-3-yl)pyrrolidin-1-yl)pyrazolo[1,5-a]pyrimidine-3-carboxamide;

(R)—N-(3-ethyl-1H-pyrazol-5-yl)-5-(2-(5-fluoro-2-methoxypyridin-3-yl)pyrrolidin-1-yl)pyrazolo[1,5-a]pyrimidine-3-carboxamide; and (R)-5-(2-(5-fluoro-2-methoxypyridin-3-yl)pyrrolidin-1-yl)-N-(1-isopropyl-1H-pyrazol-3-yl)pyrazolo[1,5-a]pyrimidine-3-carboxamide, or a pharmaceutically acceptable salt thereof.

In some embodiments, a Trk inhibitor is selected from the group consisting of:

5-fluoro-2-[[(1 S)-1-(5-fluoro-2-pyridyl)ethyl]amino]-6-[(5-isopropoxy-1H-pyrazol-3-yl)amino]pyridine-3-carbonitrile; ((2E)-3-[3,5-Bis(1,1-dimethylethyl)-4-hydroxyphenyl]-2-cyano-2-propenethioamide);

2,2-dichloro-N-[3-[(7-chloroquinolin-4-yl)amino]propyl]-N-methylacetamide;

N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea;

(S)-5-chloro-N2-(1-(5-fluoropyridin-2-yl)ethyl)-N4-(5-isopropoxy-1H-pyrazol-3-yl)pyrimidine-(S)—N-(1-(5-fluoropyrimidin-2-yl)ethyl)-3-(5-isopropoxy-1H-pyrazol-3-yl)-3H-imidazo[4,5-b]pyridin-5-amine,4-diamine;

5,6,7,13-tetrahydro-13-methyl-5-oxo-12H-indolo[2,3-a]pyrrolo[3,4-c]carbazole-12-propanenitrile;

1,3-dihydro-3-[(1-methyl-1H-indol-3-yl)methylene]-2H-pyrrolo[3,2-b]pyridin-2-one;

or a pharmaceutically acceptable salt thereof.

In some embodiments, a Trk inhibitor is selected from the group consisting of:

(2R)-2-({4-[(5-cyclopropyl-1H-pyrazol-3-yl)amino]-5-fluoropyrimidin-2-yl}amino)-2-(4-fluorophenyl)ethanol;

5-bromo-$N^4$-(3-cyclopropyl-1H-pyrazol-5-yl)-$N^2$-[(1 S)-1-(4-fluorophenyl)ethyl]pyrimidine-2,4-diamine;

(2R)-2-({5-chloro-4-[(3-cyclopropyl-1H-pyrazol-5-yl)amino]pyrimidin-2-yl}amino)-2-(4-fluorophenyl)ethanol;

(2R)-2-({5-chloro-4-[(3-isopropoxy-1H-pyrazol-5-yl)amino]pyrimidin-2-yl}amino)-2-(4-fluorophenyl)ethanol;

(3 S)-3-({5-chloro-4-[(5-cyclopropyl-1H-pyrazol-3-yl)amino]pyrimidin-2-yl}amino)-3-(4-fluorophenyl)-N-methylpropanamide;

2-({5-chloro-2-{[(1 S)-1-(4-fluorophenyl)ethyl]amino}-6-[(5-isopropoxy-1H-pyrazol-3-yl)amino]pyrimidin-4-yl}amino)propane-1,3-diol;

2-[(5-chloro-6-[(3-cyclopropyl-1H-pyrazol-5-yl)amino]-2-{[(1S)-1-(4-fluorophenyl)ethyl]amino]pyrimidin-4-yl)amino}propane-1,3-diol;

5-chloro-$N^4$-(5-cyclopropyl-1H-pyrazol-3-yl)-$N^2$-[(1 S)-(4-fluoro-phenyl)-ethyl]-6-(4-methyl-piperazin-1-yl)-pyrimidine-2,4-diamine;

(2R)-2-({4-[(5-cyclopropyl-1H-pyrazol-3-yl)amino]-7-fluoroquinazolin-2-yl}amino)-2-(4-fluorophenyl)ethanol; and 2-[(5-chloro-6-[(5-cyclopropyl-1H-pyrazol-3-yl)amino]-2-{[(1R)-1-(4-fluorophenyl)-2-hydroxyethyl]amino}pyrimidin-4-yl)amino]propane-1,3-diol;

or a pharmaceutically acceptable salt thereof.

In some embodiments, a Trk inhibitor is selected from the group consisting of 1-(3-tert-butyl-1-phenyl-1H-pyrazol-5-yl)-3-(trans-1-(2-methoxyethyl)-4-phenylpyrrolidin-3-yl)urea;

1-(3-tert-butyl-1-p-tolyl-1H-pyrazol-5-yl)-3-(trans-1-(2-methoxyethyl)-4-phenylpyrrolidin-3-yl)urea hydrochloride;

trans-1-(4-(3,4-difluorophenyl)-1-(2-methoxyethyl)pyrrolidin-3-yl)-3-(2-phenyl-2,4,5,6-tetrahydrocyclopenta[c]pyrazol-3-yl)urea;

trans-1-(4-(3,4-difluorophenyl)-1-(2-methoxyethyl)pyrrolidin-3-yl)-3-(3-isopropyl-1-phenyl-1H-pyrazol-5-yl)urea;

1-(3-tert-butyl-1-methyl-1H-pyrazol-5-yl)-3-(trans-1-(2-methoxyethyl)-4-phenylpyrrolidin-3-yl)urea;

1-(1,3-dimethyl-1H-pyrazol-5-yl)-3-(trans-1-(2-methoxyethyl)-4-phenylpyrrolidin-3-yl)urea;

1-(3-tert-butyl-1-(pyridin-3-yl)-1H-pyrazol-5-yl)-3-(trans-1-(2-methoxyethyl)-4-phenylpyrrolidin-3-yl)urea;

1-(3-tert-butyl-1-(4-fluorophenyl)-1H-pyrazol-5-yl)-3-(trans-1-(2-methoxyethyl)-4-phenylpyrrolidin-3-yl)urea;

1-(3-cyclopropyl-1-phenyl-1H-pyrazol-5-yl)-3-(trans-1-(2-methoxyethyl)-4-phenylpyrrolidin-3-yl)urea;

1-(1,3-diphenyl-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(3-methyl-1-phenyl-1H-pyrazol-5-yl)urea;

1-(3-isopropyl-1-phenyl-H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(1-methyl-3-phenyl-1H-pyrazol-5-yl)urea;

1-(trans-1-(2-methoxyethyl)-4-phenylpyrrolidin-3-yl)-3-(2-phenyl-2,4,5,6-tetrahydrocyclopenta[c]pyrazol-3-yl)urea;

1-(trans-1-(2-methoxyethyl)-4-phenylpyrrolidin-3-yl)-3-(1-phenyl-1H-pyrazol-5-yl)urea;

1-(3-tert-butyl-1-(2-fluorophenyl)-1H-pyrazol-5-yl)-3-(trans-1-(2-methoxyethyl)-4-phenylpyrrolidin-3-yl)urea;

1-(3-tert-butyl-1-(3-fluorophenyl)-1H-pyrazol-5-yl)-3-(trans-1-(2-methoxyethyl)-4-phenylpyrrolidin-3-yl)urea;

1-(3,4-dimethyl-1-phenyl-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(2-(pyridin-3-yl)-2,4,5,6-tetrahydrocyclopenta[c]pyrazol-3-yl)urea;

1-(trans-1-(2-methoxyethyl)-4-phenylpyrrolidin-3-yl)-3-(1-methyl-1H-pyrazol-5-yl)urea;

1-(trans-1-(2-methoxyethyl)-4-phenylpyrrolidin-3-yl)-3-(2-phenyl-2,4,5,6-tetrahydrocyclopenta[c]pyrazol-3-yl)thiourea;

1-(2-(3-fluorophenyl)-2,4,5,6-tetrahydrocyclopenta[c]pyrazol-3-yl)-3-(trans-1-(2-methoxyethyl)-4-phenylpyrrolidin-3-yl)urea;

1-(2-(4-fluorophenyl)-2,4,5,6-tetrahydrocyclopenta[c]pyrazol-3-yl)-3-(trans-1-(2-methoxyethyl)-4-phenylpyrrolidin-3-yl)urea;

1-(3-cyclopentyl-1-phenyl-1H-pyrazol-5-yl)-3-(trans-1-(2-methoxyethyl)-4-phenylpyrrolidin-3-yl)urea;

1-(1-ethyl-3-phenyl-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(2-phenyl-4,5,6,7-tetrahydro-2H-indazol-3-yl)urea;

1-(trans-1-(2-methoxyethyl)-4-phenylpyrrolidin-3-yl)-3-(2-methyl-2,4,5,6-tetrahydrocyclopenta[c]pyrazol-3-yl)urea;

1-(1,3-dimethyl-4-phenyl-1H-pyrazol-5-yl)-3-(trans-1-(2-methoxyethyl)-4-phenylpyrrolidin-3-yl)urea;

1-(3-tert-butyl-1-o-tolyl-1H-pyrazol-5-yl)-3-(trans-1-(2-methoxyethyl)-4-phenylpyrrolidin-3-yl)urea;

1-(3-tert-butyl-1-m-tolyl-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(1-methyl-4-phenyl-1H-pyrazol-5-yl)urea;

1-(4-cyano-3-methyl-1-phenyl-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(2-(1-methyl-1H-pyrazol-4-yl)-2,4,5,6-tetrahydrocyclopenta[c]pyrazol-3-yl)urea;

1-(3-tert-butyl-1-(tetrahyro-2H-pyran-4-yl)-1H-pyrazol-5-yl)-3-(trans-1-(2-methoxyethyl)-4-phenylpyrrolidin-3-yl)urea;

1-(trans-1-(2-methoxyethyl)-4-phenylpyrrolidin-3-yl)-3-(2-(pyridin-2-yl)-2,4,5,6-tetrahydrocyclopenta[c]pyrazol-3-yl)urea;

1-(6,6-dimethyl-2-phenyl-2,4,5,6-tetrahydro-yclopenta[c]pyrazol-3-yl)-3-(trans-1-(2-methoxyethyl)-4-phenylpyrrolidin-3-yl)urea;

1-(7,7-dimethyl-2-phenyl-4,5,6,7-tetrahydro-2H-indazol-3-yl)-3-(trans-1-(2-methoxyethyl)-4-phenylpyrrolidin-3-yl)urea;

1-(trans-1-(2-methoxyethyl)-4-(pyridin-4-yl)pyrrolidin-3-yl)-3-(2-phenyl-2,4,5,6-tetrahydrocyclopenta[c]pyrazol-3-yl)urea;

trans-1-(4-(3-fluorophenyl)-1-(2-methoxyethyl)pyrrolidin-3-yl)-3-(2-phenyl-2,4,5,6-tetrahydrocyclopenta[c]pyrazol-3-yl)urea;

trans-1-(-4-(3-fluorophenyl)-1-(2-methoxyethyl)pyrrolidin-3-yl)-3-(3-isopropyl-1-phenyl-1H-pyrazol-5-yl)urea;

trans-1-(4-(4-fluorophenyl)-1-(2-methoxyethyl)pyrrolidin-3-yl)-3-(3-isopropyl-1-phenyl-1H-pyrazol-5-yl)urea;
trans-1-(4-(3-chlorophenyl)-1-(2-methoxyethyl)pyrrolidin-3-yl)-3-(3-isopropyl-1-phenyl-1H-pyrazol-5-yl)urea;
trans-1-(4-(2-fluorophenyl)-1-(2-methoxyethyl)pyrrolidin-3-yl)-3-(3-isopropyl-1-phenyl-1H-pyrazol-5-yl)urea;
trans-1-(3-isopropyl-1-phenyl-1H-pyrazol-5-yl)-3-(1-(2-methoxyethyl)-4-(thiophen-2-yl)pyrrolidin-3-yl)urea;
1-((3,4-trans)-4-(2,4-dimethylthiazol-5-yl)-1-(2-methoxyethyl)pyrrolidin-3-yl)-3-(2-phenyl-2,4,5,6-tetrahydrocyclopenta[c]pyrazol-3-yl)urea;
1-(trans-1-(2-methoxyethyl)-4-(oxazol-5-yl)pyrrolidin-3-yl)-3-(2-phenyl-2,4,5,6-tetrahydrocyclopenta[c]pyrazol-3-yl)urea;
1-(trans-4-(isoxazol-5-yl)-1-(2-methoxyethyl)pyrrolidin-3-yl)-3-(2-phenyl-2,4,5,6-tetrahydrocyclopenta[c]pyrazol-3-yl)urea;
1-((3,4-trans)-1-(2-methoxyethyl)-4-(3-methoxyphenyl)pyrrolidin-3-yl)-3-(2-phenyl-2,4,5,6-tetrahydrocyclopenta[c]pyrazol-3-yl)urea;
1-(1-(2-methoxyethyl)-4-(thiazol-2-yl)pyrrolidin-3-yl)-3-(2-phenyl-2,4,5,6-tetrahydrocyclopenta[c]pyrazol-3-yl)urea;
1-((3 S,4R)-1-(2-methoxyethyl)-4-phenylpyrrolidin-3-yl)-3-(2-phenyl-2,4,5,6-tetrahydrocyclopenta[c]pyrazol-3-yl)urea;
1-(1,3-diphenyl-1H-pyrazol-5-yl)-3-((3 S,4R)-1-(2-methoxyethyl)-4-phenylpyrrolidin-3-yl)urea;
1-((3 S,4R)-1-(2-methoxyethyl)-4-phenylpyrrolidin-3-yl)-3-(1-methyl-3-phenyl-1H-pyrazol-5-yl)urea;
1-((3S,4R)-1-(2-methoxyethyl)-4-phenylpyrrolidin-3-yl)-3-(1-phenyl-3-(trifluoromethyl)-1H-pyrazol-5-yl)urea;
1-(1,4-dimethyl-3-phenyl-1H-pyrazol-5-yl)-3-((3S,4R)-1-(2-methoxyethyl)-4-phenylpyrrolidin-3-yl)urea;
1-(3-cyclopropyl-1-methyl-1H-pyrazol-5-yl)-3-((3 S,4R)-4-(3,5-difluorophenyl)-1-(2-methoxyethyl)pyrrolidin-3-yl)urea;
1-((3S,4R)-4-(3,5-difluorophenyl)-1-(2-methoxyethyl)pyrrolidin-3-yl)-3-(1-methyl-3-(pyridin-2-yl)-1H-pyrazol-5-yl)urea;
1-((3 S,4R)-4-(3,5-difluorophenyl)-1-(2-methoxyethyl)pyrrolidin-3-yl)-3-(1-methyl-3-(pyridin-3-yl)-1H-pyrazol-5-yl)urea;
1-((3 S,4R)-4-(3,4-difluorophenyl)-1-(2-methoxyethyl)pyrrolidin-3-yl)-3-(1,1'-dimethyl-1H, 1'H-3,4'-bipyrazol-5-yl)urea;
1-(3-(3-cyanophenyl)-1-methyl-1H-pyrazol-5-yl)-3-((3 S,4R)-4-(3,4-difluorophenyl)-1-(2-methoxyethyl)pyrrolidin-3-yl)urea;
1-(3-(4-cyanophenyl)-1-methyl-1H-pyrazol-5-yl)-3-((3 S,4R)-4-(3,4-difluorophenyl)-1-(2-methoxyethyl)pyrrolidin-3-yl)urea;
1-((3 S,4R)-4-(3,4-difluorophenyl)-1-(2-methoxyethyl)pyrrolidin-3-yl)-3-(3-(imidazo[1,2-a]pyridin-5-yl)-1-methyl-1H-pyrazol-5-yl)urea;
1-(4-chloro-1,3-diphenyl-1H-pyrazol-5-yl)-3-((3 S,4R)-4-(3,4-difluorophenyl)-1-(2-methoxyethyl)pyrrolidin-3-yl)urea;
1-(4-bromo-1,3-diphenyl-1H-pyrazol-5-yl)-3-((3 S,4R)-4-(3,4-difluorophenyl)-1-(2-methoxyethyl)pyrrolidin-3-yl)urea;
1-(4-chloro-3-methyl-1-phenyl-1H-pyrazol-5-yl)-3-((3 S,4R)-4-(3,4-difluorophenyl)-1-(2-methoxyethyl)pyrrolidin-3-yl)urea;
1-((3 S,4R)-4-(3,4-difluorophenyl)-1-(2-methoxyethyl)pyrrolidin-3-yl)-3-(1,3-dimethyl-4-phenyl-1H-pyrazol-5-yl)urea;
1-(4-cyano-3-methyl-1-phenyl-1H-pyrazol-5-yl)-3-((3 S,4R)-4-(3,4-difluorophenyl)-1-(2-methoxyethyl)pyrrolidin-3-yl)urea;
1-(4-chloro-1-methyl-3-phenyl-1H-pyrazol-5-yl)-3-((3 S,4R)-4-(3,4-difluorophenyl)-1-(2-methoxyethyl)pyrrolidin-3-yl)urea;
1-(4-bromo-1-methyl-3-phenyl-1H-pyrazol-5-yl)-3-((3 S,4R)-4-(3,4-difluorophenyl)-1-(2-methoxyethyl)pyrrolidin-3-yl)urea;
1-(4-cyano-3-(cyanomethyl)-1-phenyl-1H-pyrazol-5-yl)-3-((3 S,4R)-4-(3,4-difluorophenyl)-1-(2-methoxyethyl)pyrrolidin-3-yl)urea;
1-(3-(2-cyanopropan-2-yl)-1-phenyl-1H-pyrazol-5-yl)-3-((3 S,4R)-4-(3,4-difluorophenyl)-1-(2-methoxyethyl)pyrrolidin-3-yl)urea;
1-((3 S,4R)-4-(3,4-difluorophenyl)-1-(2-methoxyethyl)pyrrolidin-3-yl)-3-(3-ethyl-4-methyl-1-phenyl-1H-pyrazol-5-yl)urea;
1-((3 S,4R)-4-(3,4-difluorophenyl)-1-(2-methoxyethyl)pyrrolidin-3-yl)-3-(1'-methyl-1-phenyl-1H, 1'H-3,4'-bipyrazol-5-yl)urea;
1-((3S,4R)-4-(3,4-difluorophenyl)-1-(2-methoxyethyl)pyrrolidin-3-yl)-3-(4-methyl-3-(oxetan-3-ylmethoxy)-1-phenyl-1H-pyrazol-5-yl)urea;
1-((3 S,4R)-4-(3,4-difluorophenyl)-1-(2-methoxyethyl)pyrrolidin-3-yl)-3-(4-methyl-3-((3-methyloxetan-3-yl)methoxy)-1-phenyl-1H-pyrazol-5-yl)urea;
1-((3 S,4R)-4-(3,4-difluorophenyl)-1-(2-methoxyethyl)pyrrolidin-3-yl)-3-(3-(((S)-2,2-dimethyl-1,3-dioxolan-4-yl)methoxy)-4-methyl-1-phenyl-1H-pyrazol-5-yl)urea;
1-((3 S,4R)-4-(3,4-difluorophenyl)-1-(2-methoxyethyl)pyrrolidin-3-yl)-3-(3-(((R)-2,2-dimethyl-1,3-dioxolan-4-yl)methoxy)-4-methyl-1-phenyl-1H-pyrazol-5-yl)urea;
1-(3,4-dimethyl-1-phenyl-1H-pyrazol-5-yl)-3-((3 S,4R)-1-(2-methoxyethyl)-4-phenylpyrrolidin-3-yl)urea;
tert-butyl 3-(3-((3 S,4R)-1-(2-methoxyethyl)-4-phenylpyrrolidin-3-yl)ureido)-2-phenyl-4,6-dihydropyrrolo[3,4-c]pyrazole-5(2H)-carboxylate;
1-(3-isopropyl-4-methyl-1-phenyl-1H-pyrazol-5-yl)-3-((3S,4R)-1-(2-methoxyethyl)-4-phenylpyrrolidin-3-yl)urea;
1-((3 S,4R)-1-(2-methoxyethyl)-4-phenylpyrrolidin-3-yl)-3-(2-phenyl-4,6-dihydro-2H-furo[3,4-c]pyrazol-3-yl)urea;
1-((3 S,4R)-1-(2-methoxyethyl)-4-phenylpyrrolidin-3-yl)-3-(2-phenyl-4,6-dihydro-2H-thieno[3,4-c]pyrazol-3-yl)urea;
1-((3 S,4R)-4-(3,5-difluorophenyl)-1-(2-methoxyethyl)pyrrolidin-3-yl)-3-(3,4-dimethyl-1-phenyl-1H-pyrazol-5-yl)urea;
1-((3 S,4R)-4-(3,5-difluorophenyl)-1-(2-methoxyethyl)pyrrolidin-3-yl)-3-(2-phenyl-2,4,5,6-tetrahydrocyclopenta[c]pyrazol-3-yl)urea;
1-((3 S,4R)-4-(3,5-difluorophenyl)-1-(2-methoxyethyl)pyrrolidin-3-yl)-3-(3-isopropyl-1-phenyl-1H-pyrazol-5-yl)urea;
1-((3 S,4R)-4-(3,5-difluorophenyl)-1-(2-methoxyethyl)pyrrolidin-3-yl)-3-(3-methyl-1-phenyl-1H-pyrazol-5-yl)urea;
1-((3 S,4R)-4-(3,4-difluorophenyl)-1-(2-methoxyethyl)pyrrolidin-3-yl)-3-(2-phenyl-2,4,5,6-tetrahydrocyclopenta[c]pyrazol-3-yl)urea;
1-((3 S,4R)-4-(3,5-difluorophenyl)-1-(2-methoxyethyl)pyrrolidin-3-yl)-3-(2-phenyl-4,6-dihydro-2H-furo[3,4-c]pyrazol-3-yl)urea;
1-((3 S,4R)-4-(3,5-difluorophenyl)-1-(2-methoxyethyl)pyrrolidin-3-yl)-3-(2-phenyl-4,6-dihydro-2H-thieno[3,4-c]pyrazol-3-yl)urea;

1-((3 S,4R)-4-(3,4-difluorophenyl)-1-(2-methoxyethyl)pyrrolidin-3-yl)-3-(2-phenyl-4,6-dihydro-2H-furo[3,4-c]pyrazol-3-yl)urea;

1-((3 S,4R)-4-(3,4-difluorophenyl)-1-(2-methoxyethyl)pyrrolidin-3-yl)-3-(2-phenyl-4,6-dihydro-2H-thieno[3,4-c]pyrazol-3-yl)urea;

1-((3 S,4R)-4-(3,4-difluorophenyl)-1-(2-methoxyethyl)pyrrolidin-3-yl)-3-(3,4-dimethyl-1-phenyl-1H-pyrazol-5-yl)urea;

1-((3 S,4R)-4-(3,4-difluorophenyl)-1-(2-methoxyethyl)pyrrolidin-3-yl)-3-(1-methyl-3-phenyl-1H-pyrazol-5-yl)urea;

1-(3-(1-hydroxy-2-methylpropan-2-yl)-1-phenyl-1H-pyrazol-5-yl)-3-((3 S,4R)-1-(2-methoxyethyl)-4-phenylpyrrolidin-3-yl)urea;

1-((3 S,4R)-1-(2-methoxyethyl)-4-phenylpyrrolidin-3-yl)-3-(5-oxido-2-phenyl-4,6-dihydro-2H-thieno[3,4-c]pyrazol-3-yl)urea;

1-((3 S,4R)-1-(2-methoxyethyl)-4-phenylpyrrolidin-3-yl)-3-(1-methyl-3-(pyridin-4-yl)-1H-pyrazol-5-yl)urea;

1-((3 S,4R)-4-(3,4-difluorophenyl)-1-(2-methoxyethyl)pyrrolidin-3-yl)-3-(1-methyl-3-(pyridin-4-yl)-1H-pyrazol-5-yl)urea;

1-((3 S,4R)-4-(3,5-difluorophenyl)-1-(2-methoxyethyl)pyrrolidin-3-yl)-3-(1-methyl-3-phenyl-1H-pyrazol-5-yl)urea;

1-((3 S,4R)-4-(3,5-difluorophenyl)-1-(2-methoxyethyl)pyrrolidin-3-yl)-3-(1-methyl-3-(thiophen-2-yl)-1H-pyrazol-5-yl)urea;

1-((3 S,4R)-1-(2-methoxyethyl)-4-phenylpyrrolidin-3-yl)-3-(3-(methoxymethyl)-1-phenyl-1H-pyrazol-5-yl)urea;

1-((3S,4R)-1-(2-methoxyethyl)-4-phenylpyrrolidin-3-yl)-3-(3-(methoxymethyl)-4-methyl-1-phenyl-1H-pyrazol-5-yl)urea;

1-((3S,4R)-4-(3,4-difluorophenyl)-1-(2-methoxyethyl)pyrrolidin-3-yl)-3-(1-methyl-3-p-tolyl-1H-pyrazol-5-yl)urea;

1-((3 S,4R)-4-(3,4-difluorophenyl)-1-(2-methoxyethyl)pyrrolidin-3-yl)-3-(1-methyl-3-m-tolyl-1H-pyrazol-5-yl)urea;

1-((3 S,4R)-4-(3,4-difluorophenyl)-1-(2-methoxyethyl)pyrrolidin-3-yl)-3-(1-methyl-3-o-tolyl-1H-pyrazol-5-yl)urea;

1-((3S,4R)-4-(3,4-difluorophenyl)-1-(2-methoxyethyl)pyrrolidin-3-yl)-3-(3-(3-methoxyphenyl)-1-methyl-1H-pyrazol-5-yl)urea;

1-((3S,4R)-4-(3,4-difluorophenyl)-1-(2-methoxyethyl)pyrrolidin-3-yl)-3-(3-(2-methoxyphenyl)-1-methyl-1H-pyrazol-5-yl)urea;

1-(3-(4-fluorophenyl)-1-methyl-1H-pyrazol-5-yl)-3-((3 S,4R)-1-(2-methoxyethyl)-4-phenylpyrrolidin-3-yl)urea;

1-((3 S,4R)-1-(2-methoxyethyl)-4-phenylpyrrolidin-3-yl)-3-(3-(4-methoxyphenyl)-1-methyl-1H-pyrazol-5-yl)urea;

1-((3S,4R)-1-(2-methoxyethyl)-4-(3-(trifluoromethyl)phenyl)pyrrolidin-3-yl)-3-(1-methyl-3-phenyl-1H-pyrazol-5-yl)urea;

1-((3 S,4R)-4-(3-fluorophenyl)-1-(2-methoxyethyl)pyrrolidin-3-yl)-3-(1-methyl-3-phenyl-1H-pyrazol-5-yl)urea;

1-((3 S,4R)-4-(2,4-difluorophenyl)-1-(2-methoxyethyl)pyrrolidin-3-yl)-3-(1-methyl-3-phenyl-1H-pyrazol-5-yl)urea;

1-((3 S,4R)-4-(3-fluorophenyl)-1-(2-methoxyethyl)pyrrolidin-3-yl)-3-(3-(4-fluorophenyl)-1-methyl-1H-pyrazol-5-yl)urea;

1-((3 S,4R)-4-(3,4-difluorophenyl)-1-(2-methoxyethyl)pyrrolidin-3-yl)-3-(3-(4-fluorophenyl)-1-methyl-1H-pyrazol-5-yl)urea;

1-((3S,4R)-4-(3,4-difluorophenyl)-1-(2-methoxyethyl)pyrrolidin-3-yl)-3-(3-(3-fluorophenyl)-1-methyl-1H-pyrazol-5-yl)urea;

1-((3 S,4R)-4-(3,4-difluorophenyl)-1-(2-methoxyethyl)pyrrolidin-3-yl)-3-(3-(2-fluorophenyl)-1-methyl-1H-pyrazol-5-yl)urea;

1-((3 S,4R)-4-(3-fluorophenyl)-1-(2-methoxyethyl)pyrrolidin-3-yl)-3-(2-phenyl-2,4,5,6-tetrahydrocyclopenta[c]pyrazol-3-yl)urea;

1-(3-(1-hydroxy-2-methylpropan-2-yl)-4-methyl-1-phenyl-1H-pyrazol-5-yl)-3-((3 S,4R)-1-(2-methoxyethyl)-4-phenylpyrrolidin-3-yl)urea;

1-((3 S,4R)-4-(3,4-difluorophenyl)-1-(2-methoxyethyl)pyrrolidin-3-yl)-3-(3-(1-hydroxy-2-methylpropan-2-yl)-4-methyl-1-phenyl-1H-pyrazol-5-yl)urea;

1-(3-(4-chlorophenyl)-1-methyl-1H-pyrazol-5-yl)-3-((3 S,4R)-4-(3,4-difluorophenyl)-1-(2-methoxyethyl)pyrrolidin-3-yl)urea;

1-((3 S,4R)-4-(2,5-difluorophenyl)-1-(2-methoxyethyl)pyrrolidin-3-yl)-3-(3-(4-fluorophenyl)-1-methyl-1H-pyrazol-5-yl)urea;

methyl 4-(5-(3-((3 S,4R)-4-(3,4-difluorophenyl)-1-(2-methoxyethyl)pyrrolidin-3-yl)ureido)-1-methyl-1H-pyrazol-3-yl)benzoate;

1-((3 S,4R)-4-(3,4-difluorophenyl)-1-(2-methoxyethyl)pyrrolidin-3-yl)-3-(1-(2-hydroxyethyl)-3-phenyl-1H-pyrazol-5-yl)urea;

1-((3 S,4R)-4-(3,4-difluorophenyl)-1-(2-methoxyethyl)pyrrolidin-3-yl)-3-(3-(methoxymethyl)-4-methyl-1-phenyl-1H-pyrazol-5-yl)urea;

1-((3S,4R)-4-(3,5-difluorophenyl)-1-(2-methoxyethyl)pyrrolidin-3-yl)-3-(3-(methoxymethyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(1-methyl-3-(4-(methylthio)phenyl)-1H-pyrazol-5-yl)urea;

1-((3 S,4R)-4-(3,4-difluorophenyl)-1-(2-methoxyethyl)pyrrolidin-3-yl)-3-(1,3-diphenyl-1H-pyrazol-5-yl)urea;

1-((3 S,4R)-4-(3,4-difluorophenyl)-1-(2-methoxyethyl)pyrrolidin-3-yl)-3-(3-(3-methoxypropyl)-4-methyl-1-phenyl-1H-pyrazol-5-yl)urea;

1-((3 S,4R)-4-(4-fluorophenyl)-1-(2-methoxyethyl)pyrrolidin-3-yl)-3-(2-phenyl-2,4,5,6-tetrahydrocyclopenta[c]pyrazol-3-yl)urea;

1-(3,4-dimethyl-1-phenyl-1H-pyrazol-5-yl)-3-((3 S,4R)-4-(4-fluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(4-(2-methoxyethoxy)phenyl)-1-methyl-1H-pyrazol-5-yl)urea;

1-((3 S,4R)-4-(3,4-difluorophenyl)-1-(2-methoxyethyl)pyrrolidin-3-yl)-3-(4-methoxy-3-methyl-1-phenyl-1H-pyrazol-5-yl)urea;

1-((3S,4R)-4-(3,4-difluorophenyl)-1-(2-methoxyethyl)pyrrolidin-3-yl)-3-(3-(hydroxymethyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-hydroxyethyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-methoxyethyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-ethoxy-4-methyl-1-phenyl-1H-pyrazol-5-yl)urea;

1-(3-(benzyloxy)-1-methyl-1H-pyrazol-5-yl)-3-((3S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(2-methoxyethoxy)-4-methyl-1-phenyl-1H-pyrazol-5-yl)urea;

1-((3S,4R)-4-(3,5-difluorophenyl)-1-(2-methoxyethyl)pyrrolidin-3-yl)-3-(3-ethoxy-4-methyl-1-phenyl-1H-pyrazol-5-yl)urea;

trans-1-(3-ethoxy-4-methyl-1-phenyl-1H-pyrazol-5-yl)-3-1-(2-methoxyethyl)-4-phenylpyrrolidin-3-yl)urea;

1-((3 S,4R)-4-(3,4-difluorophenyl)-1-(2-methoxyethyl)pyrrolidin-3-yl)-3-(3-methoxy-4-methyl-1-phenyl-1H-pyrazol-5-yl)urea;

1-(3-(cyanomethoxy)-4-methyl-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluoro-phenyl)-1-(2-methoxyethyl)pyrrolidin-3-yl)-3-(3-(4-methoxybenzyloxy)-4-methyl-1-phenyl-1H-pyrazol-5-yl)urea;

1-((3S,4R)-4-(4-fluorophenyl)-1-(2-methoxyethyl)pyrrolidin-3-yl)-3-(3-methoxy-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-fluoroethoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-hydroxy-2-methylpropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-ethoxy-1-phenyl-1H-pyrazol-5-yl)urea;

1-(3-ethoxy-4-methyl-1-phenyl-1H-pyrazol-5-yl)-3-((3 S,4R)-4-(4-fluorophenyl)-1-(2-methoxyethyl)pyrrolidin-3-yl)urea;

1-(3-ethoxy-4-methyl-1-phenyl-1H-pyrazol-5-yl)-3-((3S,4R)-4-(3-fluorophenyl)-1-(2-methoxyethyl)pyrrolidin-3-yl)urea;

1-((3 S,4R)-4-(3,5-difluorophenyl)-1-(2-methoxyethyl)pyrrolidin-3-yl)-3-(3-(2-hydroxyethoxy)-4-methyl-1-phenyl-1H-pyrazol-5-yl)urea;

1-(2-cyclohexyl-2,4,5,6-tetrahydrocyclopenta[c]pyrazol-3-yl)-3-((3 S,4R)-4-(3,4-difluorophenyl)-1-(2-methoxyethyl)pyrrolidin-3-yl)urea;

1-((3 S,4R)-1-(2-methoxyethyl)-4-phenylpyrrolidin-3-yl)-3-(2-(pyridin-4-yl)-2,4,5,6-tetrahydrocyclopenta[c]pyrazol-3-yl)urea;

1-((3 S,4R)-4-(3,4-difluorophenyl)-1-(2-methoxyethyl)pyrrolidin-3-yl)-3-(1-methyl-3-(5-methylpyrazin-2-yl)-1H-pyrazol-5-yl)urea;

1-((3S,4R)-4-(3,4-difluorophenyl)-1-(2-methoxyethyl)pyrrolidin-3-yl)-3-(1,4-dimethyl-3-(5-methylpyrazin-2-yl)-1H-pyrazol-5-yl)urea;

ethyl 5-(3-((3S,4R)-4-(3,4-difluorophenyl)-1-(2-methoxyethyl)pyrrolidin-3-yl)ureido)-1-phenyl-1H-pyrazole-4-carboxylate;

1-((3 S,4R)-4-(3,4-difluorophenyl)-1-(2-methoxyethyl)pyrrolidin-3-yl)-3-(1-methyl-3-(pyrazin-2-yl)-1H-pyrazol-5-yl)urea;

1-((3 S,4R)-4-(3,4-difluorophenyl)-1-(2-methoxyethyl)pyrrolidin-3-yl)-3-(3-methoxy-1-methyl-4-phenyl-1H-pyrazol-5-yl)urea;

1-((3 S,4R)-4-(3,4-difluorophenyl)-1-(2-methoxyethyl)pyrrolidin-3-yl)-3-(3-ethoxy-1-methyl-4-phenyl-1H-pyrazol-5-yl)urea;

1-((3 S,4R)-1-(2-methoxyethyl)-4-phenylpyrrolidin-3-yl)-3-(2-phenyl-2,4,5,6-tetrahydropyrrolo[3,4-c]pyrazol-3-yl)urea dihydrochloride;

1-(5-acetyl-2-phenyl-2,4,5,6-tetrahydropyrrolo[3,4-c]pyrazol-3-yl)-3-((3 S,4R)-1-(2-methoxyethyl)-4-phenylpyrrolidin-3-yl)urea;

1-((3 S,4R)-4-(3,4-difluorophenyl)-1-(2-methoxyethyl)pyrrolidin-3-yl)-3-(4-(hydroxymethyl)-3-(methoxymethyl)-1-phenyl-1H-pyrazol-5-yl)urea;

4-(5-(3-((3 S,4R)-4-(3,4-difluorophenyl)-1-(2-methoxyethyl)pyrrolidin-3-yl)ureido)-1-methyl-1H-pyrazol-3-yl)benzoic acid;

4-(5-(3-((3 S,4R)-4-(3,4-difluorophenyl)-1-(2-methoxyethyl)pyrrolidin-3-yl)ureido)-1-methyl-1H-pyrazol-3-yl)benzamide;

4-(5-(3-((3 S,4R)-4-(3,4-difluorophenyl)-1-(2-methoxyethyl)pyrrolidin-3-yl)ureido)-1-methyl-1H-pyrazol-3-yl)-N-methylbenzamide;

4-(5-(3-((3 S,4R)-4-(3,4-difluorophenyl)-1-(2-methoxyethyl)pyrrolidin-3-yl)ureido)-1-methyl-1H-pyrazol-3-yl)-N,N-dimethylbenzamide;

1-((3 S,4R)-4-(3,4-difluorophenyl)-1-(2-methoxyethyl)pyrrolidin-3-yl)-3-(3-(4-(hydroxymethyl)phenyl)-1-methyl-1H-pyrazol-5-yl)urea;

1-((3 S,4R)-4-(3,4-difluorophenyl)-1-(2-methoxyethyl)pyrrolidin-3-yl)-3-(1-methyl-3-(4-(methylsulfonyl)phenyl)-1H-pyrazol-5-yl)urea;

1-((3 S,4R)-4-(3,4-difluorophenyl)-1-(2-methoxyethyl)pyrrolidin-3-yl)-3-(4-fluoro-3-methyl-1-phenyl-1H-pyrazol-5-yl)urea;

1-((3 S,4R)-4-(3,4-difluorophenyl)-1-(2-methoxyethyl)pyrrolidin-3-yl)-3-(4-fluoro-1-methyl-3-phenyl-1H-pyrazol-5-yl)urea;

1-((3 S,4R)-4-(3,4-difluorophenyl)-1-(2-methoxyethyl)pyrrolidin-3-yl)-3-(4-fluoro-1,3-diphenyl-1H-pyrazol-5-yl)urea;

2-methoxyethyl 4-(5-(3-((3 S,4R)-4-(3,4-difluorophenyl)-1-(2-methoxyethyl)pyrrolidin-3-yl)ureido)-1-methyl-1H-pyrazol-3-yl)benzoate;

1-((3 S,4R)-4-(3,4-difluorophenyl)-1-(2-methoxyethyl)pyrrolidin-3-yl)-3-(5,5-dioxido-2-phenyl-4,6-dihydro-2H-thieno[3,4-c]pyrazol-3-yl)urea;

1-(5,5-dioxido-2-phenyl-4,6-dihydro-2H-thieno[3,4-c]pyrazol-3-yl)-3-((3S,4R)-1-(2-methoxyethyl)-4-phenylpyrrolidin-3-yl)urea;

1-((3 S,4R)-4-(3,5-difluorophenyl)-1-(2-methoxyethyl)pyrrolidin-3-yl)-3-(5,5-dioxido-2-phenyl-4,6-dihydro-2H-thieno[3,4-c]pyrazol-3-yl)urea;

1-((3 S,4R)-4-(3,4-difluorophenyl)-1-(2-methoxyethyl)pyrrolidin-3-yl)-3-(4-methyl-3-(2-(methylsulfonyl)ethoxy)-1-phenyl-1H-pyrazol-5-yl)urea;

1-((3 S,4R)-4-(3,4-difluorophenyl)-1-(2-methoxyethyl)pyrrolidin-3-yl)-3-(4-(hydroxymethyl)-1-phenyl-1H-pyrazol-5-yl)urea;

1-((3 S,4R)-4-(3,4-difluorophenyl)-1-(2-methoxyethyl)pyrrolidin-3-yl)-3-(3-((R)-2,3-dihydroxypropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-((S)-2,3-dihydroxypropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-hydroxyethoxy)-4-methyl-1-phenyl-1H-pyrazol-5-yl)urea hydrochloride;

1-((3 S,4R)-4-(3,4-difluorophenyl)-1-(2-methoxyethyl)pyrrolidin-3-yl)-3-(3-((S)-2-hydroxypropoxy)-4-methyl-1-phenyl-1H-pyrazol-5-yl)urea hydrochloride;

1-((3R,4S)-4-hydroxy-1-(2-methoxyethyl)-4-phenylpyrrolidin-3-yl)-3-(2-phenyl-2,4,5,6-tetrahydrocyclopenta[c]pyrazol-3-yl)urea;

1-((3R,4S)-4-fluoro-1-(2-methoxyethyl)-4-phenylpyrrolidin-3-yl)-3-(2-phenyl-2,4,5,6-tetrahydrocyclopenta[c]pyrazol-3-yl)urea;

1-(trans-4-phenyl-1-(2-(trifluoromethoxy)ethyl)pyrrolidin-3-yl)-3-(2-phenyl-2,4,5,6-tetrahydrocyclopenta[c]pyrazol-3-yl)urea;

1-(trans-1-(2-(methylthio)ethyl)-4-phenylpyrrolidin-3-yl)-3-(2-phenyl-2,4,5,6-tetrahydrocyclopenta[c]pyrazol-3-yl)urea;

1-((3 S,4R)-1-((S)-2-methoxypropyl)-4-phenylpyrrolidin-3-yl)-3-(2-phenyl-2,4,5,6-tetrahydrocyclopenta[c]pyrazol-3-yl)urea;

1-((3,4-trans)-4-phenyl-1-(4,4,4-trifluorobutyl)pyrrolidin-3-yl)-3-(2-phenyl-2,4,5,6-tetrahydrocyclopenta[c]pyrazol-3-yl)urea;

1-((3 S,4R)-1-(cyanomethyl)-4-(3,4-difluorophenyl)pyrrolidin-3-yl)-3-(2-phenyl-2,4,5,6-tetrahydrocyclopenta[c]pyrazol-3-yl)urea;

1-((3 S,4R)-1-(cyanomethyl)-4-(3,4-difluorophenyl)pyrrolidin-3-yl)-3-(3-(2-methoxyethoxy)-4-methyl-1-phenyl-1H-pyrazol-5-yl)urea;

1-((3,4-trans)-1-(cyanomethyl)-4-phenylpyrrolidin-3-yl)-3-(2-phenyl-2,4,5,6-tetrahydrocyclopenta[c]pyrazol-3-yl)urea;

1-((3 S,4R)-1-(cyanomethyl)-4-phenylpyrrolidin-3-yl)-3-(2-phenyl-2,4,5,6-tetrahydrocyclopenta[c]pyrazol-3-yl)urea;

2-((3R,4S)-3-phenyl-4-(3-(2-phenyl-2,4,5,6-tetrahydrocyclopenta[c]pyrazol-3-yl)ureido)pyrrolidin-1-yl)acetamide;

1-((3 S,4R)-4-(3,4-difluorophenyl)-1-(2-hydroxyethyl)pyrrolidin-3-yl)-3-(3,4-dimethyl-1-phenyl-1H-pyrazol-5-yl)urea;

1-((trans)-1-(3,3,4,4,4-pentafluorobutyl)-4-phenylpyrrolidin-3-yl)-3-(2-phenyl-2,4,5,6-tetrahydrocyclopenta[c]pyrazol-3-yl)urea;

1-((trans)-1-ethyl-4-phenylpyrrolidin-3-yl)-3-(2-phenyl-2,4,5,6-tetrahydrocyclopenta[c]pyrazol-3-yl)urea;

1-((trans)-4-phenyl-1-(2,2,2-trifluoroethyl)pyrrolidin-3-yl)-3-(2-phenyl-2,4,5,6-tetrahydrocyclopenta[c]pyrazol-3-yl)urea;

1-(3,4-dimethyl-1-phenyl-1H-pyrazol-5-yl)-3-((trans)-4-phenyl-1-(2,2,2-trifluoroethyl)pyrrolidin-3-yl)urea;

1-(3-(2-methoxyethoxy)-4-methyl-1-phenyl-1H-pyrazol-5-yl)-3-((trans)-4-phenyl-1-(2,2,2-trifluoroethyl)pyrrolidin-3-yl)urea;

1-((trans)-4-phenyl-1-(2,2,2-trifluoroethyl)pyrrolidin-3-yl)-3-(2-phenyl-2,4,5,6-tetrahydrocyclopenta[c]pyrazol-3-yl)urea;

1-(3,4-dimethyl-1-phenyl-1H-pyrazol-5-yl)-3-((3 S,4R)-4-phenyl-1-(2,2,2-trifluoroethyl)pyrrolidin-3-yl)urea;

1-(3-(2-methoxyethoxy)-4-methyl-1-phenyl-1H-pyrazol-5-yl)-3-((3 S,4R)-4-phenyl-1-(2,2,2-trifluoroethyl)pyrrolidin-3-yl)urea;

1-((3 S,4R)-4-(3-fluorophenyl)-1-(2,2,2-trifluoroethyl)pyrrolidin-3-yl)-3-(2-phenyl-2,4,5,6-tetrahydrocyclopenta[c]pyrazol-3-yl)urea;

1-(3,4-dimethyl-1-phenyl-1H-pyrazol-5-yl)-3-((3 S,4R)-4-(3-fluorophenyl)-1-(2,2,2-trifluoroethyl)pyrrolidin-3-yl)urea;

1-((3 S,4R)-4-(3-fluorophenyl)-1-(2,2,2-trifluoroethyl)pyrrolidin-3-yl)-3-(3-(2-methoxyethoxy)-4-methyl-1-phenyl-1H-pyrazol-5-yl)urea;

1-((3 S,4R)-4-(3-fluorophenyl)-1-(2,2,2-trifluoroethyl)pyrrolidin-3-yl)-3-(1-methyl-3-phenyl-1H-pyrazol-5-yl)urea;

1-((3R,4S)-4-(3-fluorophenyl)-1-(2,2,2-trifluoroethyl)pyrrolidin-3-yl)-3-(2-phenyl-2,4,5,6-tetrahydrocyclopenta[c]pyrazol-3-yl)urea;

1-(3-ethoxy-4-methyl-1-phenyl-1H-pyrazol-5-yl)-3-((3R,3 S)-4-(3-fluorophenyl)-1-(2,2,2-trifluoroethyl)pyrrolidin-3-yl)urea;

1-((trans)-1-(1,3-difluoropropan-2-yl)-4-phenylpyrrolidin-3-yl)-3-(2-phenyl-2,4,5,6-tetrahydrocyclopenta[c]pyrazol-3-yl)urea;

(trans)-tert-butyl 3-(3-methoxyphenyl)-4-(3-(2-phenyl-2,4,5,6-tetrahydrocyclopenta[c]pyrazol-3-yl)ureido)pyrrolidine-1-carboxylate;

1-((trans)-4-(3-chlorophenyl)-1-(2,2,2-trifluoroethyl)pyrrolidin-3-yl)-3-(2-phenyl-2,4,5,6-tetrahydrocyclopenta[c]pyrazol-3-yl)urea;

1-(2-phenyl-2,4,5,6-tetrahydrocyclopenta[c]pyrazol-3-yl)-3-((trans)-4-(pyridin-2-yl)-1-(2,2,2-trifluoroethyl)pyrrolidin-3-yl)urea;

1-((trans)-4-(4-fluorophenyl)-1-(2,2,2-trifluoroethyl)pyrrolidin-3-yl)-3-(2-phenyl-2,4,5,6-tetrahydrocyclopenta[c]pyrazol-3-yl)urea;

1-((trans)-4-(4-chlorophenyl)-1-(2,2,2-trifluoroethyl)pyrrolidin-3-yl)-3-(2-phenyl-2,4,5,6-tetrahydrocyclopenta[c]pyrazol-3-yl)urea;

1-((trans)-4-(2-chlorophenyl)-1-(2,2,2-trifluoroethyl)pyrrolidin-3-yl)-3-(2-phenyl-2,4,5,6-tetrahydrocyclopenta[c]pyrazol-3-yl)urea;

1-(2-phenyl-2,4,5,6-tetrahydrocyclopenta[c]pyrazol-3-yl)-3-((trans)-4-(pyridin-3-yl)-1-(2,2,2-trifluoroethyl)pyrrolidin-3-yl)urea;

1-((trans)-4-(2-fluorophenyl)-1-(2,2,2-trifluoroethyl)pyrrolidin-3-yl)-3-(2-phenyl-2,4,5,6-tetrahydrocyclopenta[c]pyrazol-3-yl)urea;

1-((trans)-4-(4-fluorophenyl)-1-(2,2-difluoroethyl)pyrrolidin-3-yl)-3-(2-phenyl-2,4,5,6-tetrahydrocyclopenta[c]pyrazol-3-yl)urea;

1-((3 S,4R)-4-(3,4-difluorophenyl)-1-(1H-pyrazol-4-yl)pyrrolidin-3-yl)-3-(3-ethoxy-4-methyl-1-phenyl-1H-pyrazol-5-yl)urea;

1-((3 S,4R)-4-(3,5-difluorophenyl)-1-(1H-pyrazol-4-yl)pyrrolidin-3-yl)-3-(3-ethoxy-4-methyl-1-phenyl-1H-pyrazol-5-yl)urea;

1-((3 S,4R)-4-(3,5-difluorophenyl)-1-(1H-pyrazol-3-yl)pyrrolidin-3-yl)-3-(3-ethoxy-4-methyl-1-phenyl-1H-pyrazol-5-yl)urea;

1-((3 S,4R)-4-(3,4-difluorophenyl)-1-(3-methyl-1H-pyrazol-4-yl)pyrrolidin-3-yl)-3-(3-ethoxy-4-methyl-1-phenyl-1H-pyrazol-5-yl)urea;

1-((3 S,4R)-4-(3,4-difluorophenyl)-1-(3-(trifluoromethyl)-1H-pyrazol-4-yl)pyrrolidin-3-yl)-3-(3-ethoxy-4-methyl-1-phenyl-1H-pyrazol-5-yl)urea;

1-((3 S,4R)-4-(3,4-difluorophenyl)-1-(1H-pyrazol-4-yl)pyrrolidin-3-yl)-3-(3-((S)-2-hydroxypropoxy)-4-methyl-1-phenyl-1H-pyrazol-5-yl)urea;

1-((3 S,4R)-4-(3,4-difluorophenyl)-1-(1H-pyrazol-4-yl)pyrrolidin-3-yl)-3-(3-((R)-2,3-dihydroxypropoxy)-4-methyl-1-phenyl-1H-pyrazol-5-yl)urea;

1-((3 S,4R)-4-(3,5-difluoro-phenyl)-1-(1H-pyrazol-4-yl)pyrrolidin-3-yl)-3-(3,4-dimethyl-1-phenyl-1H-pyrazol-5-yl)urea;

1-((3S,4R)-4-(3,4-difluorophenyl)-1-(1H-pyrazol-4-yl)pyrrolidin-3-yl)-3-(3,4-dimethyl-1-phenyl-1H-pyrazol-5-yl)urea;

1-((3S,4R)-4-(3,4-difluorophenyl)-1-(1H-pyrazol-4-yl)pyrrolidin-3-yl)-3-(3-(3-methoxypropyl)-4-methyl-1-phenyl-1H-pyrazol-5-yl)urea;

1-((3S,4R)-4-(3,4-difluorophenyl)-1-(1H-pyrazol-4-yl)pyrrolidin-3-yl)-3-(3-(2-methoxyethoxy)-4-methyl-1-phenyl-1H-pyrazol-5-yl)urea;

1-((3 S,4R)-4-(3,4-difluorophenyl)-1-(1H-pyrazol-4-yl)pyrrolidin-3-yl)-3-(3-(2-hydroxy-2-methylpropoxy)-4-methyl-1-phenyl-1H-pyrazol-5-yl)urea;

1-(3-ethoxy-4-methyl-1-phenyl-1H-pyrazol-5-yl)-3-((3 S,4R)-1-(1-methyl-1H-pyrazol-5-yl)-4-phenylpyrrolidin-3-yl)urea;

1-(3-ethoxy-4-methyl-1-phenyl-1H-pyrazol-5-yl)-3-((3R,4S)-1-(1-methyl-1H-pyrazol-5-yl)-4-phenylpyrrolidin-3-yl)urea;

1-((3 S,4R)-4-(3,5-difluorophenyl)-1-(1-methyl-1H-pyrazol-5-yl)pyrrolidin-3-yl)-3-(3-ethoxy-4-methyl-1-phenyl-1H-pyrazol-5-yl)urea;

1-((3R,4S)-4-(3,5-difluorophenyl)-1-(1-methyl-1H-pyrazol-5-yl)pyrrolidin-3-yl)-3-(3-ethoxy-4-methyl-1-phenyl-1H-pyrazol-5-yl)urea;

1-((3 S,4R)-4-(3,4-difluorophenyl)-1-phenylpyrrolidin-3-yl)-3-(3-ethoxy-4-methyl-1-phenyl-1H-pyrazol-5-yl) urea;

1-((3 S,4R)-4-(3,4-difluorophenyl)-1-(2-methoxyphenyl) pyrrolidin-3-yl)-3-(3-ethoxy-4-methyl-1-phenyl-1H-pyrazol-5-yl)urea;

1-(3-ethoxy-4-methyl-1-phenyl-1H-pyrazol-5-yl)-3-((3 S,4R)-1-(2-fluorophenyl)-4-phenylpyrrolidin-3-yl)urea;

1-(3-ethoxy-4-methyl-1-phenyl-1H-pyrazol-5-yl)-3-((3 S,4R)-1-(4-fluorophenyl)-4-phenylpyrrolidin-3-yl)urea;

1-(3-ethoxy-4-methyl-1-phenyl-1H-pyrazol-5-yl)-3-((3S,4R)-1-(2-methylphenyl)-4-phenylpyrrolidin-3-yl)urea;

1-(3-ethoxy-4-methyl-1-phenyl-1H-pyrazol-5-yl)-3-((3 S,4R)-1-(2-methoxyphenyl)-4-phenylpyrrolidin-3-yl) urea;

1-(3-ethoxy-4-methyl-1-phenyl-1H-pyrazol-5-yl)-3-((3 S,4R)-1-(2-chlorophenyl)-4-phenylpyrrolidin-3-yl)urea;

1-(3-ethoxy-4-methyl-1-phenyl-1H-pyrazol-5-yl)-3-((3 S,4R)-4-phenyl-1-(2-(trifluoromethoxy)phenyl)pyrrolidin-3-yl)urea;

1-((3 S,4R)-1-(2,6-difluorophenyl)-4-phenylpyrrolidin-3-yl)-3-(3-ethoxy-4-methyl-1-phenyl-1H-pyrazol-5-yl) urea;

1-(3-ethoxy-4-methyl-1-phenyl-1H-pyrazol-5-yl)-3-((3 S,4R)-1-(2-methoxypyridin-4-yl)-4-phenylpyrrolidin-3-yl)urea;

1-(3-ethoxy-4-methyl-1-phenyl-1H-pyrazol-5-yl)-3-((3 S,4R)-1-(2-methoxypyridin-3-yl)-4-phenylpyrrolidin-3-yl)urea;

1-(3-ethoxy-4-methyl-1-phenyl-1H-pyrazol-5-yl)-3-((3S,4R)-1-(2-ethoxypyridin-3-yl)-4-phenylpyrrolidin-3-yl) urea;

1-(1',4-dimethyl-1-phenyl-1H,1'H-[3,4'-bipyrazol]-5-yl)-3-((3 S,4R)-1-(2-methoxypyridin-3-yl)-4-phenylpyrrolidin-3-yl)urea;

1-((3S,4R)-1-(2-methoxypyridin-3-yl)-4-phenylpyrrolidin-3-yl)-3-(4-methyl-1,3-diphenyl-1H-pyrazol-5-yl)urea;

1-(4-bromo-1'-methyl-1-phenyl-1H,1'H-[3,4'-bipyrazol]-5-yl)-3-((3 S,4R)-1-(2-methoxypyridin-3-yl)-4-phenylpyrrolidin-3-yl)urea;

1-(4-bromo-1,3-diphenyl-1H-pyrazol-5-yl)-3-((3 S,4R)-1-(2-methoxypyridin-3-yl)-4-phenylpyrrolidin-3-yl)urea;

1-((3 S,4R)-1-((1,2,3-thiadiazol-4-yl)methyl)-4-(3,4-difluorophenyl)pyrrolidin-3-yl)-3-(2-phenyl-2,4,5,6-tetrahydrocyclopenta[c]pyrazol-3-yl)urea;

1-((3 S,4R)-1-((1,2,3-thiadiazol-4-yl)methyl)-4-(3,4-difluorophenyl)pyrrolidin-3-yl)-3-(3-ethoxy-4-methyl-1-phenyl-1H-pyrazol-5-yl)urea;

1-((3 S,4R)-1-((1,2,3-thiadiazol-4-yl)methyl)-4-(3,4-difluorophenyl)pyrrolidin-3-yl)-3-(3-(cyanomethoxy)-4-methyl-1-phenyl-1H-pyrazol-5-yl)urea;

1-((3 S,4R)-1-((1,2,3-thiadiazol-4-yl)methyl)-4-(3,4-difluorophenyl)pyrrolidin-3-yl)-3-(1',4-dimethyl-1-phenyl-1H, 11'H-3,4'-bipyrazol-5-yl)urea;

1-((3S,4R)-1-((1,2,3-thiadiazol-4-yl)methyl)-4-(3,4-difluorophenyl)pyrrolidin-3-yl)-3-(4-methyl-3-(1-methyl-1H-imidazol-4-yl)-1-phenyl-1H-pyrazol-5-yl)urea;

1-((3 S,4R)-4-(3,4-difluorophenyl)-1-((1-methyl-1H-1,2,3-triazol-4-yl)methyl)pyrrolidin-3-yl)-3-(2-phenyl-2,4,5,6-tetrahydrocyclopenta[c]pyrazol-3-yl)urea;

1-((3 S,4R)-4-(3,4-difluorophenyl)-1-(1,3-dimethoxypropan-2-yl)pyrrolidin-3-yl)-3-(3-ethoxy-4-methyl-1-phenyl-1H-pyrazol-5-yl)urea;

1-((3 S,4R)-4-(3,4-difluorophenyl)-1-(1-methoxypropan-2-yl)pyrrolidin-3-yl)-3-(3-ethoxy-4-methyl-1-phenyl-1H-pyrazol-5-yl)urea;

1-((trans)-4-(4-fluorophenyl)-1-(2-(methylamino)ethyl)pyrrolidin-3-yl)-3-(2-phenyl-2,4,5,6-tetrahydrocyclopenta[c] pyrazol-3-yl)urea;

1-((trans)-1-((1H-imidazol-2-yl)methyl)-4-phenylpyrrolidin-3-yl)-3-(2-phenyl-2,4,5,6-tetrahydrocyclopenta[c] pyrazol-3-yl)urea;

methyl 3-methoxy-2-((trans)-3-phenyl-4-(3-(2-phenyl-2,4,5,6-tetrahydrocyclopenta[c]pyrazol-3-yl)ureido)pyrrolidin-1-yl)propanoate;

1-((3 S,4R)-4-(3,4-difluorophenyl)-1-(1-methoxypropan-2-yl)pyrrolidin-3-yl)-3-(3-ethoxy-4-methyl-1-phenyl-1H-pyrazol-5-yl)urea;

1-((3 S,4R)-4-(3,4-difluorophenyl)-1-(1-hydroxy-3-methoxypropan-2-yl)pyrrolidin-3-yl)-3-(2-phenyl-2,4,5,6-tetrahydrocyclopenta[c]pyrazol-3-yl)urea;

1-((3 S,4R)-4-(3,4-difluorophenyl)-1-(3-hydroxy-1-methoxy-3-methylbutan-2-yl)pyrrolidin-3-yl)-3-(2-phenyl-2,4,5,6-tetrahydrocyclopenta[c]pyrazol-3-yl)urea;

2-((3R,4S)-3-(3,4-difluorophenyl)-4-(3-(2-phenyl-2,4,5,6-tetrahydrocyclopenta[c]pyrazol-3-yl)ureido)pyrrolidin-1-yl)-3-methoxypropanoic acid hydrochloride;

1-((3 S,4R)-4-(3,4-difluorophenyl)-1-(1-hydroxy-3-methoxypropan-2-yl)pyrrolidin-3-yl)-3-(3-ethoxy-4-methyl-1-phenyl-1H-pyrazol-5-yl)urea;

1-(4-chloro-1'-methyl-1-phenyl-1H, 1'H-3,4'-bipyrazol-5-yl)-3-((3 S,4R)-4-(3,4-difluorophenyl)-1-(1-hydroxy-3-methoxypropan-2-yl)pyrrolidin-3-yl)urea;

1-((3 S,4R)-4-(3,4-difluorophenyl)-1-(2-methoxyethyl)pyrrolidin-3-yl)-3-(3-methoxy-1-phenyl-4-(trifluoromethyl)-1H-pyrazol-5-yl)urea;

1-(3-(2-fluoroethoxy)-4-methyl-1-phenyl-1H-pyrazol-5-yl)-3-((3R,4S)-4-phenyl-1-(2,2,2-trifluoroethyl)pyrrolidin-3-yl)urea;

1-(3-ethoxy-4-methyl-1-phenyl-1H-pyrazol-5-yl)-3-((3R,4S)-4-phenyl-1-(2,2,2-trifluoroethyl)pyrrolidin-3-yl)urea;

1-(3-(cyanomethoxy)-4-methyl-1-phenyl-1H-pyrazol-5-yl)-3-((3R,4S)-4-phenyl-1-(2,2,2-trifluoroethyl)pyrrolidin-3-yl)urea;

1-(1',4-dimethyl-1-phenyl-1H, 1'H-3,4'-bipyrazol-5-yl)-3-((3R,4S)-4-phenyl-1-(2,2,2-trifluoroethyl)pyrrolidin-3-yl)urea;

1-(4-chloro-1'-methyl-1-phenyl-1H,1'H-3,4'-bipyrazol-5-yl)-3-((3R,4S)-4-phenyl-1-(2,2,2-trifluoroethyl)pyrrolidin-3-yl)urea;

1-(3-(((S)-2,2-dimethyl-1,3-dioxolan-4-yl)methoxy)-4-methyl-1-phenyl-1H-pyrazol-5-yl)-3-((3R,4S)-4-phenyl-1-(2,2,2-trifluoroethyl)pyrrolidin-3-yl)urea;

1-(3-((R)-2,3-dihydroxypropoxy)-4-methyl-1-phenyl-1H-pyrazol-5-yl)-3-((3R,4S)-4-phenyl-1-(2,2,2-trifluoroethyl)pyrrolidin-3-yl)urea;

(R,S) 1-((2α,3β,4α)-2-methyl-4-phenyl-1-(2,2,2-trifluoroethyl)pyrrolidin-3-yl)-3-(2-phenyl-2,4,5,6-tetrahydrocyclopenta[c]pyrazol-3-yl)urea;

(R,S)-1-((3 (3,4α,5α)-5-methyl-4-phenyl-1-(2,2,2-trifluoroethyl)pyrrolidin-3-yl)-3-(2-phenyl-2,4,5,6-tetrahydrocyclopenta[c]pyrazol-3-yl)urea;

1-((3 S,4R)-4-(3,4-difluorophenyl)-1-((S)-1,1,1-trifluoro-3-hydroxypropan-2-yl)pyrrolidin-3-yl)-3-(3-ethoxy-4-methyl-1-phenyl-1H-pyrazol-5-yl)urea;

1-((3 S,4R)-4-(3,4-difluorophenyl)-1-((S)-1,1,1-trifluoro-3-methoxypropan-2-yl)pyrrolidin-3-yl)-3-(3-ethoxy-4-methyl-1-phenyl-1H-pyrazol-5-yl)urea;

1-((3 S,4R)-4-(3,4-difluorophenyl)-1-((S)-1,1,1-trifluoro-3-methoxypropan-2-yl)pyrrolidin-3-yl)-3-(3-((S)-2-hydroxypropoxy)-4-methyl-1-phenyl-1H-pyrazol-5-yl)urea;

1-(4-chloro-1'-methyl-1-phenyl-1H, 1'H-3,4'-bipyrazol-5-yl)-3-((3 S,4R)-4-(3,4-difluorophenyl)-1-((R)-1,1,1-trifluoro-3-methoxypropan-2-yl)pyrrolidin-3-yl)urea;

1-((3 S,4R)-4-(3,4-difluorophenyl)-1-((R)-1,1,1-trifluoro-3-methoxypropan-2-yl)pyrrolidin-3-yl)-3-(3-((S)-2-hydroxypropoxy)-4-methyl-1-phenyl-1H-pyrazol-5-yl)urea;

1-((3 S,4R)-4-(3,4-difluorophenyl)-1-(2-methoxyethyl) pyrrolidin-3-yl)-3-(3-methyl-4-(methylthio)-1-phenyl-1H-pyrazol-5-yl)urea;

1-((3 S,4R)-4-(3,5-difluorophenyl)-1-(2-methoxyethyl)pyrrolidin-3-yl)-3-(3-(3-methoxypropyl)-4-methyl-1-phenyl-1H-pyrazol-5-yl)urea;

1-(3-(1,1-difluoro-2-hydroxyethyl)-4-methyl-1-phenyl-1H-pyrazol-5-yl)-3-((3 S,4R)-4-(3,4-difluorophenyl)-1-(2-methoxyethyl)pyrrolidin-3-yl)urea;

1-(3-(1,1-difluoro-2-hydroxyethyl)-4-methyl-1-phenyl-1H-pyrazol-5-yl)-3-((3 S,4R)-4-(3,5-difluorophenyl)-1-(2-methoxyethyl)pyrrolidin-3-yl)urea;

1-(3-(1,1-difluoro-2-hydroxyethyl)-4-methyl-1-phenyl-1H-pyrazol-5-yl)-3-((3 S,4R)-4-(4-fluorophenyl)-1-(2-methoxyethyl)pyrrolidin-3-yl)urea;

1-(3-(1,1-difluoro-2-hydroxyethyl)-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,5-difluorophenyl)-1-(2-methoxyethyl)pyrrolidin-3-yl)-3-(3-(2-hydroxyethyl)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-(2-hydroxyethyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-hydroxy-2-methylpropyl)-4-methyl-1-phenyl-1H-pyrazol-5-yl)urea;

1-((3S,4R)-4-(3,4-difluorophenyl)-1-(2-methoxyethyl)pyrrolidin-3-yl)-3-(3-((S)-2-hydroxypropyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-((R)-2-hydroxypropyl)-4-methyl-1-phenyl-1H-pyrazol-5-yl)urea;

ethyl 5-(3-((3S,4R)-4-(3,4-difluorophenyl)-1-(2-methoxyethyl)pyrrolidin-3-yl)ureido)-4-methyl-1-phenyl-1H-pyrazole-3-carboxylate;

5-(3-((3 S,4R)-4-(4-fluorophenyl)-1-(2-methoxyethyl)pyrrolidin-3-yl)ureido)-N,4-dimethyl-1-phenyl-1H-pyrazole-3-carboxamide;

1-(trans-4-(3-chloro-4-fluorophenyl)-1-(2-methoxyethyl) pyrrolidin-3-yl)-3-(1',4-dimethyl-1-phenyl-1H, 1'H-[3,4'-bipyrazol]-5-yl)urea;

1-(trans-4-(4-chloro-3-fluorophenyl)-1-(2-methoxyethyl) pyrrolidin-3-yl)-3-(1',4-dimethyl-1-phenyl-1H, 1'H-[3,4'-bipyrazol]-5-yl)urea;

1-(trans-4-(3-chloro-5-fluorophenyl)-1-(2-methoxyethyl) pyrrolidin-3-yl)-3-(1',4-dimethyl-1-phenyl-1H, 1'H-[3,4'-bipyrazol]-5-yl)urea;

1-(trans-4-(3-chlorophenyl)-1-(2-methoxyethyl)pyrrolidin-3-yl)-3-(1',4-dimethyl-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(4-methyl-3-(5-methyl-1,3,4-oxadiazol-2-yl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(3-methyl-1,2,4-oxadiazol-5-yl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-1-phenyl-3-(3-(trifluoromethyl)-1,2,4-oxadiazol-5-yl)-1H-pyrazol-5-yl)urea;

1-((3 S,4R)-4-(4-fluorophenyl)-1-(2-methoxyethyl)pyrrolidin-3-yl)-3-(4-methyl-1-phenyl-3-(3-(trifluoromethyl)-1,2,4-oxadiazol-5-yl)-1H-pyrazol-5-yl)urea;

5-(3-(trans-4-(3-chloro-4-fluorophenyl)-1-(2-methoxyethyl) pyrrolidin-3-yl)ureido)-N,4-dimethyl-1-phenyl-1H-pyrazole-3-carboxamide;

5-(3-(trans-4-(4-chloro-3-fluorophenyl)-1-(2-methoxyethyl) pyrrolidin-3-yl)ureido)-N,4-dimethyl-1-phenyl-1H-pyrazole-3-carboxamide;

1-(trans-4-(4-chloro-3-fluorophenyl)-1-(2-methoxyethyl) pyrrolidin-3-yl)-3-(4-methyl-3-(1-methyl-2-oxo-1,2-dihydropyridin-4-yl)-1-phenyl-1H-pyrazol-5-yl)urea;

1-(trans-4-(3-chloro-4-fluorophenyl)-1-(2-methoxyethyl) pyrrolidin-3-yl)-3-(4-methyl-3-(1-methyl-2-oxo-1,2-dihydropyridin-4-yl)-1-phenyl-1H-pyrazol-5-yl)urea;

1-((3 S,4R)-4-(3,4-difluorophenyl)-1-(2-methoxyethyl)pyrrolidin-3-yl)-3-(1',4,5'-trimethyl-1-phenyl-1H, 1'H-[3,3'-bipyrazol]-5-yl)urea;

1-((3 S,4R)-4-(3,5-difluorophenyl)-1-(2-methoxyethyl)pyrrolidin-3-yl)-3-(1',4,5'-trimethyl-1-phenyl-1H, 1'H-[3,3'-bipyrazol]-5-yl)urea;

1-((3 S,4R)-4-(4-fluorophenyl)-1-(2-methoxyethyl)pyrrolidin-3-yl)-3-(1',4,5'-trimethyl-1-phenyl-1H, 1'H-[3,3'-bipyrazol]-5-yl)urea;

1-((3 S,4R)-4-(3,4-difluorophenyl)-1-(2-methoxyethyl)pyrrolidin-3-yl)-3-(2',4,5'-trimethyl-1-phenyl-1H,2'H-[3,3'-bipyrazol]-5-yl)urea;

1-(4-cyclopropyl-1'-methyl-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-isopropyl-1'-methyl-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(4-ethyl-1'-methyl-1-phenyl-1H, 1'H-[3,4'-bipyrazol]-5-yl)urea;

1-((3S,4R)-4-(3,4-difluorophenyl)-1-(2-methoxyethyl)pyrrolidin-3-yl)-3-(1-(4-fluorophenyl)-1',4-dimethyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(1-(3-fluorophenyl)-1',4-dimethyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(1-(2-fluorophenyl)-1',4-dimethyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(1-(3-chlorophenyl)-1',4-dimethyl-1H, 1'H-[3,4'-bipyrazol]-5-yl)urea;

1-(1-(3-chloro-4-fluorophenyl)-1',4-dimethyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(1-(3-chloro-2-fluorophenyl)-1',4-dimethyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(4-fluorophenyl)-1-(2-methoxyethyl)pyrrolidin-3-yl)-3-(1-(4-fluorophenyl)-1',4-dimethyl-1H, 1'H-[3,4'-bipyrazol]-5-yl)urea;

1-((3 S,4R)-4-(4-fluorophenyl)-1-(2-methoxyethyl)pyrrolidin-3-yl)-3-(1-(3-fluorophenyl)-1',4-dimethyl-1H, 1'H-[3,4'-bipyrazol]-5-yl)urea;

1-((3 S,4R)-4-(4-fluorophenyl)-1-(2-methoxyethyl)pyrrolidin-3-yl)-3-(1-(2-fluorophenyl)-1',4-dimethyl-1H, 1'H-[3,4'-bipyrazol]-5-yl)urea;

1-((3 S,4R)-4-(3,4-fluorophenyl)-1-(2-methoxyethyl)pyrrolidin-3-yl)-3-(1-(3-chlorophenyl)-1',4-dimethyl-1H,1'H-[3,4'-bipyrazol]-5-yl)urea;

1-(1-(3-chloro-4-fluorophenyl)-1',4-dimethyl-1H, 1'H-[3,4'-bipyrazol]-5-yl)-3-((3S,4R)-4-(4-difluorophenyl)-1-(2-methoxyethyl)pyrrolidin-3-yl)urea;

1-(1-(3-chloro-2-fluorophenyl)-1',4-dimethyl-1H, 1'H-[3,4'-bipyrazol]-5-yl)-3-((3 S,4R)-4-(4-difluorophenyl)-1-(2-methoxyethyl)pyrrolidin-3-yl)urea;

1-((3S,4R)-4-(2,4-difluorophenyl)-1-(2-methoxyethyl)pyrrolidin-3-yl)-3-(1',4-dimethyl-1-phenyl-1H, 1'H-[3,4'-bipyrazol]-5-yl)urea;

1-((3 S,4R)-4-(3-cyanophenyl)-1-(2-methoxyethyl)pyrrolidin-3-yl)-3-(1',4-dimethyl-1-phenyl-1H,1'H-[3,4'-bipyrazol]-5-yl)urea;

1-((3 S,4R)-4-(4-cyanophenyl)-1-(2-methoxyethyl)pyrrolidin-3-yl)-3-(1',4-dimethyl-1-phenyl-1H, 1'H-[3,4'-bipyrazol]-5-yl)urea;

1-(1',4-dimethyl-1-phenyl-1H, 1'H-[3,4'-bipyrazol]-5-yl)-3-((3 S,4R)-1-(2-methoxyethyl)-4-(p-tolyl)pyrrolidin-3-yl)urea;

1-((3S,4R)-4-(3,4-difluorophenyl)-1-(2-methoxyethyl)pyrrolidin-3-yl)-3-(4-methyl-1,3-diphenyl-1H-pyrazol-5-yl)urea;

1-((3 S,4R)-4-(3,5-difluorophenyl)-1-(2-methoxyethyl)pyrrolidin-3-yl)-3-(4-methyl-1,3-diphenyl-1H-pyrazol-5-yl)urea;

1-((3 S,4R)-4-(3,4,5-trifluorophenyl)-1-(2-methoxyethyl)pyrrolidin-3-yl)-3-(4-methyl-1,3-diphenyl-1H-pyrazol-5-yl)urea;

1-((3 S,4R)-4-(4-fluorophenyl)-1-(2-methoxyethyl)pyrrolidin-3-yl)-3-(4-methyl-1,3-diphenyl-1H-pyrazol-5-yl)urea;

1-(4-bromo-3-methyl-1-phenyl-1H-pyrazol-5-yl)-3-trans-1-(2-methoxyethyl)-4-(1-methyl-1H-pyrazol-4-yl)pyrrolidin-3-yl)urea;

1-(1',4-dimethyl-1-phenyl-1H, 1'H-[3,4'-bipyrazol]-5-yl)-3-(trans-1-(2-methoxyethyl)-4-(1-methyl-1H-pyrazol-4-yl)pyrrolidin-3-yl)urea;

1-(1',4-dimethyl-1-phenyl-1H, 1'H-[3,4'-bipyrazol]-5-yl)-3-((trans-1-(2-methoxyethyl)-4-(1,2,3-thiadiazol-4-yl)pyrrolidin-3-yl)urea;

1-(3-ethoxy-4-methyl-1-phenyl-1H-pyrazol-5-yl)-3-(trans-1-(2-methoxyethyl)-4-(3-(trifluoromethyl)phenyl)pyrroli-din-3-yl)urea;

1-(3,4-dimethyl-1-phenyl-1H-pyrazol-5-yl)-3-((3 S,4R)-1-(2-methoxyethyl)-4-(3-(trifluoromethyl)phenyl)pyrrolidin-3-yl)urea;

1-((3 S,4R)-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea;

1-((3R,4S)-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea;

1-(3-(2-fluoroethoxy)-4-methyl-1-phenyl-1H-pyrazol-5-yl)-3-((3S,4R)-4-(5-fluoropyridin-3-yl)-1-(2-methoxyethyl)pyrrolidin-3-yl)urea;

1-(3-(2-fluoroethoxy)-4-methyl-1-phenyl-1H-pyrazol-5-yl)-3-((3R,4S)-4-(5-fluoropyridin-3-yl)-1-(2-methoxyethyl)pyrrolidin-3-yl)urea;

1-(trans-4-(5-fluoropyridin-3-yl)-1-(2-methoxyethyl)pyrrolidin-3-yl)-3-(2-phenyl-2,4,5,6-tetrahydrocyclopenta[c]pyrazol-3-yl)urea;

1-(trans-4-(5-chloropyridin-3-yl)-1-(2-methoxyethyl) pyrrolidin-3-yl)-3-(3-ethoxy-4-methyl-1-phenyl-1H-pyrazol-5-yl)urea;

1-(trans-4-(5-chloropyridin-3-yl)-1-(2-methoxyethyl)pyrrolidin-3-yl)-3-(3,4-dimethyl-1-phenyl-1H-pyrazol-5-yl)urea;

1-(trans-4-(5-fluoropyridin-3-yl)-1-(2-methoxyethyl)pyrrolidin-3-yl)-3-(4-methyl-1,3-diphenyl-1H-pyrazol-5-yl)urea;

1-(1',4-dimethyl-1-phenyl-1H, 1'H-[3,4'-bipyrazol]-5-yl)-3-(trans-4-(5-fluoropyridin-2-yl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(3-fluoropyridin-4-yl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-3-(1-methyl-1H-1,2,4-triazol-3-yl)-1-phenyl-1H-pyrazol-5-yl)urea;

1-((3 S,4R)-4-(3,4-difluorophenyl)-1-(2-methoxyethyl)pyrrolidin-3-yl)-3-(1'-(2-methoxyethyl)-4-methyl-1-phenyl-1H, 1'H-[3,4'-bipyrazol]-5-yl)urea;

1-(3-cyano-4-methyl-1-phenyl-1H-pyrazol-5-yl)-3-((3S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(1'-(2-hydroxyethyl)-4-methyl-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea;

1-(3-bromo-4-methyl-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(5-methyl-6-oxo-2-phenyl-2,4,5,6-tetrahydropyrrolo[3,4-c]pyrazol-3-yl)urea;

1-((3 S,4R)-4-(3,5-difluorophenyl)-1-(2-methoxyethyl)pyrrolidin-3-yl)-3-(5-methyl-6-oxo-2-phenyl-2,4,5,6-tetrahydropyrrolo[3,4-c]pyrazol-3-yl)urea;

1-((3 S,4R)-4-(3,4-difluorophenyl)-1-(2-methoxyethyl)pyrrolidin-3-yl)-3-(4-methyl-3-((5-methyl-1,3,4-oxadiazol-2-yl)methoxy)-1-phenyl-1H-pyrazol-5-yl)urea;

1-(4-chloro-3-ethoxy-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-ethoxy-4-fluoro-1-phenyl-1H-pyrazol-5-yl)urea;

1-(4-bromo-3-(2-hydroxy-2-methylpropoxy)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-(2-hydroxy-2-methylpropoxy)-1-phenyl-1H-pyrazol-5-yl)-3-((3S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-((S)-2-hydroxybutoxy)-4-methyl-1-phenyl-1H-pyrazol-5-yl)urea;

ethyl 2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)acetate;

1-((3 S,4R)-4-(4-fluorophenyl)-1-(2-methoxyethyl)pyrrolidin-3-yl)-3-(3-(2-hydroxy-2-methylpropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-hydroxy-2-methylpropoxy)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-((R)-2-hydroxypropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-((R)-2-hydroxypropoxy)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-((R)-2-hydroxypropoxy)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(4-methyl-1-phenyl-3-((R)-3,3,3-trifluoro-2-hydroxypropoxy)-1H-pyrazol-5-yl)urea;

1-((3 S,4R)-4-(4-fluorophenyl)-1-(2-methoxyethyl)pyrrolidin-3-yl)-3-(3-((S)-2-hydroxypropoxy)-4-methyl-1-phenyl-1H-pyrazol-5-yl)urea;

1-((3S,4R)-4-(3,5-difluorophenyl)-1-(2-methoxyethyl)pyrrolidin-3-yl)-3-(4-methyl-1-phenyl-3-((S)-3,3,3-trifluoro-2-hydroxypropoxy)-1H-pyrazol-5-yl)urea;

1-(4-chloro-3-(2-hydroxy-2-methylpropoxy)-1-phenyl-1H-pyrazol-5-yl)-3-((3 S,4R)-4-(3,5-difluorophenyl)-1-(2-methoxyethyl)pyrrolidin-3-yl)urea;

1-(4-chloro-3-(2-hydroxy-2-methylpropoxy)-1-phenyl-1H-pyrazol-5-yl)-3-((3 S,4R)-4-(4-fluorophenyl)-1-(2-methoxyethyl)pyrrolidin-3-yl)urea;

1-(4-chloro-3-((R)-2-hydroxypropoxy)-1-phenyl-1H-pyrazol-5-yl)-3-((3S,4R)-4-(3,4-difluorophenyl)-1-(2-methoxyethyl)pyrrolidin-3-yl)urea;

1-(4-chloro-3-((R)-2-hydroxypropoxy)-1-phenyl-1H-pyrazol-5-yl)-3-((3S,4R)-4-(3,5-difluorophenyl)-1-(2-methoxyethyl)pyrrolidin-3-yl)urea;

1-(4-chloro-3-((R)-2-hydroxypropoxy)-1-phenyl-1H-pyrazol-5-yl)-3-((3S,4R)-4-(4-fluorophenyl)-1-(2-methoxyethyl)pyrrolidin-3-yl)urea;

1-(4-bromo-3-((R)-2-hydroxypropoxy)-1-phenyl-1H-pyrazol-5-yl)-3-((3S,4R)-4-(3,4-difluorophenyl)-1-(2-methoxyethyl)pyrrolidin-3-yl)urea;

1-(4-bromo-3-((R)-2-hydroxypropoxy)-1-phenyl-1H-pyrazol-5-yl)-3-((3 S,4R)-4-(3,5-difluorophenyl)-1-(2-methoxyethyl)pyrrolidin-3-yl)urea;

1-(4-bromo-3-((R)-2-hydroxypropoxy)-1-phenyl-1H-pyrazol-5-yl)-3-((3 S,4R)-4-(4-fluorophenyl)-1-(2-methoxyethyl)pyrrolidin-3-yl)urea;

1-((3S,4R)-4-(3,5-difluorophenyl)-1-(2-methoxyethyl)pyrrolidin-3-yl)-3-(3-((R)-2-hydroxybutoxy)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-((R)-2-hydroxybutoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-((R)-2-hydroxybutoxy)-4-methyl-1-phenyl-1H-pyrazol-5-yl)urea;

ethyl 4-bromo-5-(3-((3S,4R)-4-(3,4-difluorophenyl)-1-(2-methoxyethyl)pyrrolidin-3-yl)ureido)-1-phenyl-1H-pyrazole-3-carboxylate;

1-((3 S,4R)-4-(4-fluorophenyl)-1-(2-methoxyethyl)pyrrolidin-3-yl)-3-(1'-(2-methoxyethyl)-4-methyl-1-phenyl-1H,1'H-[3,4'-bipyrazol]-5-yl)urea;

1-((3 S,4R)-4-(3-fluorophenyl)-1-(2-methoxyethyl)pyrrolidin-3-yl)-3-(1'-(2-methoxyethyl)-4-methyl-1-phenyl-1H,1'H-[3,4'-bipyrazol]-5-yl)urea;

1-((3 S,4R)-4-(3-fluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea;

1-((3 S,4R)-4-(4-fluorophenyl)-1-(2-methoxyethyl)pyrrolidin-3-yl)-3-(4-methyl-3-(2-methyl-2H-1,2,3-triazol-4-yl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(2-morpholinoethoxy)-1-phenyl-1H-pyrazol-5-yl)urea;

1-((3 S,4R)-4-(3,4-difluorophenyl)-1-(2-methoxyethyl)pyrrolidin-3-yl)-3-(3-(2-(1,3-dioxoisoindolin-2-yl)ethoxy)-4-methyl-1-phenyl-1H-pyrazol-5-yl)urea;

tert-butyl 4-(2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)ethyl)piperazine-1-carboxylate;

Trans-1-(2-methoxyethyl)-4-phenylpyrrolidin-3-yl)-3-(2-phenyl-2H-indazol-3-yl)urea;

1-((3 S,4R)-4-(3,4-difluorophenyl)-1-(2-methoxyethyl)pyrrolidin-3-yl)-3-(2-phenyl-2H-indazol-3-yl)urea;

1-((3 S,4R)-4-(3,4-difluorophenyl)-1-(2-methoxyethyl)pyrrolidin-3-yl)-3-(4-methyl-3-((1-methyl-1H-1,2,4-triazol-3-yl)methoxy)-1-phenyl-1H-pyrazol-5-yl)urea;

1-((3 S,4R)-4-(3,5-difluorophenyl)-1-(2-methoxyethyl)pyrrolidin-3-yl)-3-(3-((R)-2,2-dimethyl-1,3-dioxolan-4-yl)methoxy)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-(((S)-2,2-dimethyl-1,3-dioxolan-4-yl)methoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-ethoxy-4-methyl-1-(pyrazin-2-yl)-1H-pyrazol-5-yl)urea;

1-((3S,4R)-4-(3,4-difluorophenyl)-1-(2-methoxyethyl)pyrrolidin-3-yl)-3-(2-(pyridazin-4-yl)-2,4,5,6-tetrahydrocyclopenta[c]pyrazol-3-yl)urea;

5-(3-((3 S,4R)-4-(3,4-difluorophenyl)-1-(2-methoxyethyl)pyrrolidin-3-yl)ureido)-4-methyl-1-phenyl-1H-pyrazol-3-yl dimethylcarbamate;

5-(3-((3 S,4R)-4-(3,4-difluorophenyl)-1-(2-methoxyethyl)pyrrolidin-3-yl)ureido)-4-methyl-1-phenyl-1H-pyrazol-3-yl morpholine-4-carboxylate;

1-(3-(((S)-2,2-dimethyl-1,3-dioxolan-4-yl)methoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-(((R)-2,2-dimethyl-1,3-dioxolan-4-yl)methoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-((S)-2-(tert-butyldimethylsilyloxy)propoxy)-4-methyl-1-phenyl-1-pyrazol-5-yl)-3-((3 S,4R)-1-(2-methoxyethyl)-4-(3,4,5-trifluorophenyl)pyrrolidin-3-yl)urea;

1-(3-(2-hydroxy-2-methylpropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-((S)-2-(tert-butyldimethylsilyloxy)-3-methoxypropoxy)-4-methyl-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-(methoxy-methyl)-1-phenyl-1H-pyrazol-5-yl)-3-((3 S,4R)-4-(3,4-difluorophenyl)-1-(2-methoxyethyl)pyrrolidin-3-yl)urea;

1-(4-bromo-3-(methoxy-methyl)-1-phenyl-1H-pyrazol-5-yl)-3-((3S,4R)-4-(3,4-difluorophenyl)-1-(2-methoxyethyl)pyrrolidin-3-yl)urea;

1-(4-chloro-3-(methoxy-methyl)-1-phenyl-1H-pyrazol-5-yl)-3-((3 S,4R)-4-(3,5-difluorophenyl)-1-(2-methoxyethyl)pyrrolidin-3-yl)urea;

1-(4-bromo-3-(methoxy-methyl)-1-phenyl-1H-pyrazol-5-yl)-3-((3S,4R)-4-(3,5-difluorophenyl)-1-(2-methoxyethyl)pyrrolidin-3-yl)urea;

1-(4-chloro-3-(methoxy-methyl)-1-phenyl-1H-pyrazol-5-yl)-3-((3S,4R)-4-(4-fluorophenyl)-1-(2-methoxyethyl)pyrrolidin-3-yl)urea;

1-(4-bromo-3-(methoxy-methyl)-1-phenyl-1H-pyrazol-5-yl)-3-((3 S,4R)-4-(4-fluorophenyl)-1-(2-methoxyethyl)pyrrolidin-3-yl)urea;

1-(4-chloro-3-(1,1-difluoro-2-hydroxyethyl)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-(1,1-difluoro-2-hydroxyethyl)-1-phenyl-1H-pyrazol-5-yl)-3-((3 S,4R)-4-(3,5-difluorophenyl)-1-(2-methoxyethyl)pyrrolidin-3-yl)urea;

1-(4-chloro-3-(1,1-difluoro-2-hydroxyethyl)-1-phenyl-1H-pyrazol-5-yl)-3-((3 S,4R)-4-(4-fluorophenyl)-1-(2-methoxyethyl)pyrrolidin-3-yl)urea;

1-(4-chloro-3-((S)-2-hydroxypropyl)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-((R)-2-hydroxypropyl)-1-phenyl-1H-pyrazol-5-yl)-3-((3 S,4R)-4-(3,4-difluorophenyl)-1-(2-methoxyethyl)pyrrolidin-3-yl)urea;

1-(4-bromo-3-((R)-2-hydroxypropyl)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-(2-hydroxy-2-methylpropyl)-1-phenyl-1H-pyrazol-5-yl)-3-((3S,4R)-4-(3,4-difluorophenyl)-1-(2-methoxyethyl)pyrrolidin-3-yl)urea;

1-(4-chloro-3-(3-methyl-1,2,4-oxadiazol-5-yl)-1-phenyl-1H-pyrazol-5-yl)-3-((3S,4R)-4-(3,4-difluorophenyl)-1-(2-methoxyethyl)pyrrolidin-3-yl)urea;

1-(4-bromo-3-(2-cyanopropan-2-yl)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-(2-cyanopropan-2-yl)-1-phenyl-1H-pyrazol-5-yl)-3-((3 S,4R)-4-(3,4-difluorophenyl)-1-(2-methoxyethyl)pyrrolidin-3-yl)urea;

1-(4-bromo-1'-methyl-1-phenyl-1H, 1'H-[3,4'-bipyrazol]-5-yl)-3-((3 S,4R)-4-(3,5-difluorophenyl)-1-(2-methoxyethyl)pyrrolidin-3-yl)urea;

1-(4-bromo-1'-methyl-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(4-bromo-1'-methyl-1-phenyl-1H, 1'H-[3,4'-bipyrazol]-5-yl)-3-((3-4-(4-difluorophenyl)-1-(2-methoxyethyl)pyrrolidin-3-yl)urea;

1-(4-chloro-1'-methyl-1-phenyl-1H, 1'H-[3,4'-bipyrazol]-5-yl)-3-((3 S,4R)-4-(3,5-difluorophenyl)-1-(2-methoxyethyl)pyrrolidin-3-yl)urea;

1-(4-chloro-1'-methyl-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(4-chloro-1'-methyl-1-phenyl-1H, 1'H-[3,4'-bipyrazol]-5-yl)-3-((3 S,4R)-4-(4-fluorophenyl)-1-(2-methoxyethyl)pyrrolidin-3-yl)urea;

1-(4-chloro-1'-methyl-1-phenyl-1H, 1'H-[3,4'-bipyrazol]-5-yl)-3-((3 S,4R)-4-phenyl-1-(2-methoxyethyl)pyrrolidin-3-yl)urea;

1-(4-chloro-1,3-diphenyl-1H-pyrazol-5-yl)-3-((3 S,4R)-4-(3,5-difluorophenyl)-1-(2-methoxyethyl)pyrrolidin-3-yl)urea;

1-(4-bromo-1,3-diphenyl-1H-pyrazol-5-yl)-3-((3 S,4R)-4-(3,5-difluorophenyl)-1-(2-methoxyethyl)pyrrolidin-3-yl)urea;

1-(4-bromo-1,3-diphenyl-1H-pyrazol-5-yl)-3-((3 S,4R)-4-(4-fluorophenyl)-1-(2-methoxyethyl)pyrrolidin-3-yl)urea;

1-(4-chloro-3-methyl-1-phenyl-1H-pyrazol-5-yl)-3-((3 S,4R)-4-(3,5-difluorophenyl)-1-(2-methoxyethyl)pyrrolidin-3-yl)urea;

1-(4-bromo-3-methyl-1-phenyl-1H-pyrazol-5-yl)-3-((3S, 4R)-4-(3,5-difluorophenyl)-1-(2-methoxyethyl)pyrrolidin-3-yl)urea;

1-(4-chloro-1'-methyl-1-phenyl-1H, 1'H-[3,4'-bipyrazol]-5-yl)-3-((3 S,4R)-4-(5-fluoropyridin-3-yl)-1-(2-methoxyethyl)pyrrolidin-3-yl)urea;

1-(4-fluoro-1'-methyl-1-phenyl-1H, 1'H-[3,4'-bipyrazol]-5-yl)-3-((3 S,4R)-4-(5-fluoropyridin-3-yl)-1-(2-methoxyethyl)pyrrolidin-3-yl)urea;

1-(4-bromo-3-methyl-1-phenyl-1H-pyrazol-5-yl)-3-trans-4-(5-fluoropyridin-3-yl)-1-(2-methoxyethyl)pyrrolidin-3-yl)urea;

1-(4-bromo-3-methyl-1-phenyl-1H-pyrazol-5-yl)-3-trans-4-(5-fluoropyridin-3-yl)-1-(2-methoxyethyl)pyrrolidin-3-yl)urea;

1-(4-bromo-1,3-diphenyl-1H-pyrazol-5-yl)-3-(trans-4-(5-fluoropyridin-3-yl)-1-(2-methoxyethyl)pyrrolidin-3-yl)urea;

1-(4-chloro-1,3-diphenyl-1H-pyrazol-5-yl)-3-(trans-4-(5-fluoropyridin-3-yl)-1-(2-methoxyethyl)pyrrolidin-3-yl)urea;

1-(4-bromo-3-methyl-1-phenyl-1H-pyrazol-5-yl)-3-(trans-4-(5-fluoropyridin-2-yl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-fluoro-1'-methyl-1-phenyl-1H, 1'H-[3,4'-bipyrazol]-5-yl)urea;

1-((3S,4R)-4-(3,5-difluorophenyl)-1-(2-methoxyethyl)pyrrolidin-3-yl)-3-(4-fluoro-1'-methyl-1-phenyl-1H, 1'H-[3,4'-bipyrazol]-5-yl)urea;

1-(4-bromo-1'-methyl-1-phenyl-1H, 1'H-[3,4'-bipyrazol]-5-yl)-3-((3 S,4R)-4-(5-fluoropyridin-3-yl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(4-fluorophenyl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(3,5-difluorophenyl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(3,4,5-trifluorophenyl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(1',4-dimethyl-1-phenyl-1H, 1'H-[3,4'-bipyrazol]-5-yl)-3-((3 S,4R)-4-(fluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(1'-(4-methoxybenzyl)-4-methyl-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(1'-(4-methoxybenzyl)-4-methyl-1-phenyl-1H, 1'H-[3,4'-bipyrazol]-5-yl)urea trifluoroacetate;

2-(4-chloro-5-(3-((3 S,4R)-4-(3,4-difluorophenyl)-1-(2-methoxyethyl)pyrrolidin-3-yl)ureido)-1-phenyl-1H-pyrazol-3-yl)ethyl acetate;

1-(4-chloro-3-(2-hydroxyethyl)-1-phenyl-1H-pyrazol-5-yl)-3-((3S,4R)-4-(3,4-difluorophenyl)-1-(2-methoxyethyl) pyrrolidin-3-yl)urea;

1-((3 S,4R)-4-(3,4-difluorophenyl)-1-(2-methoxyethyl)pyrrolidin-3-yl)-3-(3-(cis-3-hydroxycyclobutyl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(trans-3-hydroxycyclobutyl)-4-methyl-1-phenyl-1H-pyrazol-5-yl)urea;

1-(4-chloro-3-(cis-3-hydroxycyclobutyl)-1-phenyl-1H-pyrazol-5-yl)-3-((3 S,4R)-4-(3,4-difluorophenyl)-1-(2-methoxyethyl)pyrrolidin-3-yl)urea;

1-(4-chloro-3-((1r,3 S)-3-hydroxycyclobutyl)-1-phenyl-1H-pyrazol-5-yl)-3-(trans-4-(3,4-difluorophenyl)-1-(2-methoxyethyl)pyrrolidin-3-yl)urea;

1-((3 S,4R)-4-(4-fluorophenyl)-1-(2-methoxyethyl)pyrrolidin-3-yl)-3-(3-(cis-3-hydroxycyclobutyl)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-(trans-3-hydroxycyclobutyl)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-(cis-3-hydroxycyclobutyl)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-(trans-3-hydroxycyclobutyl)-4-methyl-1-phenyl-1H-pyrazol-5-yl)urea;

5-(3-((3 S,4R)-4-(3,4-difluorophenyl)-1-(2-methoxyethyl) pyrrolidin-3-yl)ureido)-4-methyl-1-phenyl-1H-pyrazole-3-carboxylic acid;

5-(3-((3 S,4R)-4-(3,4-difluorophenyl)-1-(2-methoxyethyl) pyrrolidin-3-yl)ureido)-N,4-dimethyl-1-phenyl-1H-pyrazole-3-carboxamide;

5-(3-((3 S,4R)-4-(3,4-difluorophenyl)-1-(2-methoxyethyl) pyrrolidin-3-yl)ureido)-N,N,4-trimethyl-1-phenyl-1H-pyrazole-3-carboxamide;

5-(3-((3 S,4R)-4-(3,4-difluorophenyl)-1-(2-methoxyethyl) pyrrolidin-3-yl)ureido)-N-ethyl-4-methyl-1-phenyl-1H-pyrazole-3-carboxamide;

5-(3-((3 S,4R)-4-(3,4-difluorophenyl)-1-(2-methoxyethyl) pyrrolidin-3-yl)ureido)-N-isopropyl-4-methyl-1-phenyl-1H-pyrazole-3-carboxamide;

5-(3-((3 S,4R)-4-(3,4-difluorophenyl)-1-(2-methoxyethyl) pyrrolidin-3-yl)ureido)-4-methyl-1-phenyl-1H-pyrazole-3-carboxamide;

1-((3 S,4R)-4-(3,5-difluorophenyl)-1-(2-methoxyethyl)pyrrolidin-3-yl)-3-(3-ethoxy-4-(hydroxymethyl)-1-phenyl-1H-pyrazol-5-yl)urea;

1-((3 S,4R)-4-(3-chloro-4-fluorophenyl)-1-(2-methoxyethyl)pyrrolidin-3-yl)-3-(1',4-dimethyl-1-phenyl-1H, 1'H-3,4'-bipyrazol-5-yl)urea;

1-((3 S,4R)-4-(4-chloro-3-fluorophenyl)-1-(2-methoxyethyl)pyrrolidin-3-yl)-3-(1',4-dimethyl-1-phenyl-1H,1'H-3,4'-bipyrazol-5-yl)urea;

1-((3 S,4R)-4-(3-chloro-5-fluorophenyl)-1-(2-methoxyethyl)pyrrolidin-3-yl)-3-(1',4-dimethyl-1-phenyl-1H,1'H-3,4'-bipyrazol-5-yl)urea;

2-((3R,4S)-3-(3,4-difluorophenyl)-4-(3-(3-ethoxy-4-methyl-1-phenyl-1H-pyrazol-5-yl)ureido)pyrrolidin-1-yl) acetate;

1-((3 S,4R)-4-(3,4-difluorophenyl)-1-(3,3,3-trifluoro-2-hydroxypropyl)pyrrolidin-3-yl)-3-(3-ethoxy-4-methyl-1-phenyl-1H-pyrazol-5-yl)urea;

1-((3 S,4R)-4-(3,4-difluorophenyl)-1-(2-hydroxypropyl) pyrrolidin-3-yl)-3-(3-ethoxy-4-methyl-1-phenyl-1H-pyrazol-5-yl)urea;

1-((3 S,4R)-1-(2-cyanoethyl)-4-(3,4-difluorophenyl)pyrrolidin-3-yl)-3-(3-ethoxy-4-methyl-1-phenyl-1H-pyrazol-5-yl)urea;

2-((3R,4S)-3-(3,4-difluorophenyl)-4-(3-(3-ethoxy-4-methyl-1-phenyl-1H-pyrazol-5-yl)ureido)pyrrolidin-1-yl)-N-methylacetamide;

1-(1-cyclohexyl-3,4-dimethyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(3-hydroxy-2-(hydroxymethyl) propoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(4-methyl-1-phenyl-3-(2,2,2-trifluoroethoxy)-1H-pyrazol-5-yl)urea;

1-((3 S,4R)-4-(4-fluorophenyl)-1-(2-methoxyethyl)pyrrolidin-3-yl)-3-(4-methyl-1-phenyl-3-(2,2,2-trifluoroethoxy)-1H-pyrazol-5-yl)urea;

1-((3 S,4R)-4-(3,5-difluorophenyl)-1-(2-methoxyethyl)pyrrolidin-3-yl)-3-(4-methyl-1-phenyl-3-(2,2,2-trifluoroethoxy)-1H-pyrazol-5-yl)urea;

1-(3-(2,2-difluoroethoxy)-4-methyl-1-phenyl-1H-pyrazol-5-yl)-3-((3 S,4R)-4-(3,4-difluorophenyl)-1-(2-methoxyethyl)pyrrolidin-3-yl)urea;

1-(4-chloro-1-phenyl-3-(2,2,2-trifluoroethoxy)-1H-pyrazol-5-yl)-3-((3 S,4R)-4-(3,4-difluorophenyl)-1-(2-methoxyethyl)pyrrolidin-3-yl)urea;

1-(4-chloro-1-phenyl-3-(pyridin-2-yl)-1H-pyrazol-5-yl)-3-((3 S,4R)-4-(3,4-difluorophenyl)-1-(2-methoxyethyl)pyrrolidin-3-yl)urea;

1-(4-chloro-1-phenyl-3-(pyridin-4-yl)-1H-pyrazol-5-yl)-3-((3 S,4R)-4-(3,4-difluorophenyl)-1-(2-methoxyethyl)pyrrolidin-3-yl)urea;

1-(4-chloro-1-phenyl-3-(pyridin-3-yl)-1H-pyrazol-5-yl)-3-((3 S,4R)-4-(3,4-difluorophenyl)-1-(2-methoxyethyl)pyrrolidin-3-yl)urea;

1-(4-bromo-1-phenyl-3-(pyridin-3-yl)-1H-pyrazol-5-yl)-3-((3 S,4R)-4-(3,4-difluorophenyl)-1-(2-methoxyethyl)pyrrolidin-3-yl)urea;

1-(4-bromo-1-phenyl-3-(pyridin-2-yl)-1H-pyrazol-5-yl)-3-((3 S,4R)-4-(3,4-difluorophenyl)-1-(2-methoxyethyl)pyrrolidin-3-yl)urea;

1-(4-chloro-3-phenyl-1-(pyridin-3-yl)-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-1-phenyl-3-(pyridin-3-yl)-1H-pyrazol-5-yl)urea;

1-((3 S,4R)-4-(3,4-difluorophenyl)-1-(2-methoxyethyl)pyrrolidin-3-yl)-3-(4-methyl-1-phenyl-3-(pyridin-4-yl)-1H-pyrazol-5-yl)urea;

1-((3 S,4R)-4-(3,4-difluorophenyl)-1-(2-methoxyethyl)pyrrolidin-3-yl)-3-(4-methyl-1-phenyl-3-(pyridin-2-yl)-1H-pyrazol-5-yl)urea;

1-((3 S,4R)-4-(3,4-difluorophenyl)-1-(2-methoxyethyl)pyrrolidin-3-yl)-3-(3-(5-fluoropyridin-3-yl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(5-fluoropyridin-3-yl)-4-methyl-1-(pyridin-3-yl)-1H-pyrazol-5-yl)urea;

1-((3 S,4R)-4-(3,4-difluorophenyl)-1-(2-methoxyethyl)pyrrolidin-3-yl)-3-(1',4-dimethyl-1-phenyl-1H, 1'H-[3,3'-bipyrazol]-5-yl)urea;

1-(1',4-dimethyl-1-phenyl-1H, 1'H-[3,3'-bipyrazol]-5-yl)-3-((3 S,4R)-4-(4-fluorophenyl)-1-(2-methoxyethyl)pyrrolidin-3-yl)urea;

1-((3 S,4R)-4-(3,5-difluorophenyl)-1-(2-methoxyethyl)pyrrolidin-3-yl)-3-(1',4-dimethyl-1-phenyl-1H, 1'H-[3,3'-bipyrazol]-5-yl)urea;

1-((3 S,4R)-4-(3,4-difluorophenyl)-1-(2-methoxyethyl)pyrrolidin-3-yl)-3-(2',4-dimethyl-1-phenyl-1H,2'H-[3,3'-bipyrazol]-5-yl)urea;

1-((3 S,4R)-4-(3,4-difluorophenyl)-1-(2-methoxyethyl)pyrrolidin-3-yl)-3-(1-(5-fluoropyridin-3-yl)-1',4-dimethyl-1H,1'H-[3,4'-bipyrazol]-5-yl)urea;

1-((3 S,4R)-4-(3,4-difluorophenyl)-1-(2-methoxyethyl)pyrrolidin-3-yl)-3-(1',4-dimethyl-1-(5-methylpyridin-3-yl)-1H, 1'H-[3,4'-bipyrazol]-5-yl)urea;

1-(1-(5-chloropyridin-3-yl)-1',4-dimethyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-1-phenyl-1'-(2,2,2-trifluoro-1-(2,2,2-trifluoroethoxy)ethyl)-1H,1'H-[3,4'-bipyrazol]-5-yl)urea;

1-((3 S,4R)-4-(3,4-difluorophenyl)-1-(2-methoxyethyl)pyrrolidin-3-yl)-3-(4-methyl-1-phenyl-1'-(2,2,2-trifluoroethyl)-1H,1'H-[3,4'-bipyrazol]-5-yl)urea;

1-(1'-(cyclopropylmethyl)-4-methyl-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(1'-(cyclopropanecarbonyl)-4-methyl-1-phenyl-1H,1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-1'-(methylsulfonyl)-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(1'-isopropyl-4-methyl-1-phenyl-1H, 1'H-[3,4'-bipyrazol]-5-yl)urea;

1-((3 S,4R)-4-(3,4-difluorophenyl)-1-(2-methoxyethyl)pyrrolidin-3-yl)-3-(4-methyl-1-phenyl-3-(pyrimidin-5-yl)-1H-pyrazol-5-yl)urea;

1-((3 S,4R)-4-(3,4-difluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)urea;

1-((3 S,4R)-4-(3,4-difluorophenyl)-1-(2-methoxyethyl)pyrrolidin-3-yl)-3-(1',4,5'-trimethyl-1-phenyl-1H,1'H-[3,4'-bipyrazol]-5-yl)urea;

1-((3 S,4R)-4-(3,4-difluorophenyl)-1-(2-methoxyethyl)pyrrolidin-3-yl)-3-(1',3',4-trimethyl-1-phenyl-1H, 1'H-[3,4'-bipyrazol]-5-yl)urea;

1-(1'-cyclopropyl-4-methyl-1-phenyl-1H,1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-3-(2-methylthiazol-5-yl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(2-methylpyrimidin-5-yl)-1-phenyl-1H-pyrazol-5-yl)urea;

1-(3-(2-aminopyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(2,4-dimethylthiazol-5-yl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2,6-dimethylpyridin-4-yl)-4-methyl-1-phenyl-1H-pyrazol-5-yl)urea;

1-(3-(6-aminopyridin-3-yl)-4-methyl-1-phenyl-1H-pyrazol-5-yl)-3-((3 S,4R)-4-(3,4-difluorophenyl)-1-(2-methoxyethyl)pyrrolidin-3-yl)urea;

1-(3-bromo-4-methyl-1-phenyl-1H-pyrazol-5-yl)-3-((3 S,4R)-4-(4-fluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-3-(6-oxo-1-(2,2,2-trifluoroethyl)-1,6-dihydropyridin-3-yl)-1-phenyl-1H-pyrazol-5-yl)urea;

1-((3 S,4R)-4-(4-fluorophenyl)-1-(2-methoxyethyl)pyrrolidin-3-yl)-3-(1'-isopropyl-4-methyl-1-phenyl-1H, 1'H-[3,4'-bipyrazol]-5-yl)urea;

1-((3 S,4R)-4-(4-fluorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)urea;

1-(3-bromo-4-methyl-1-phenyl-1H-pyrazol-5-yl)-3-((3R,4S)-4-phenyl-1-(2,2,2-trifluoroethyl)pyrrolidin-3-yl)urea;

1-(4-methyl-3-(1-methyl-6-oxo-1,6-dihydropyridin-3-yl)-1-phenyl-1H-pyrazol-5-yl)-3-((3R,4S)-4-phenyl-1-(2,2,2-trifluoroethyl)pyrrolidin-3-yl)urea;

1-(3-(2-aminopyrimidin-5-yl)-4-methyl-1-phenyl-1H-pyrazol-5-yl)-3-((3R,4S)-4-phenyl-1-(2,2,2-trifluoroethyl)pyrrolidin-3-yl)urea bis(2,2,2-trifluoroacetate;

1-((3 S,4R)-4-(3,4-difluorophenyl)-1-(2-methoxyethyl)pyrrolidin-3-yl)-3-(1'-ethyl-4-methyl-1-phenyl-1H, 1'H-[3,4'-bipyrazol]-5-yl)urea;

1-(1'-ethyl-4-methyl-1-phenyl-1H, 1'H-[3,4'-bipyrazol]-5-yl)-3-((3 S,4R)-4-(4-fluorophenyl)-1-(2-methoxyethyl)pyrrolidin-3-yl)urea;

5-(3-((3 S,4R)-4-(3,4-difluorophenyl)-1-(2-methoxyethyl)pyrrolidin-3-yl)ureido)-4-methyl-1-phenyl-1H-pyrazol-3-yl trifluoromethanesulfonate;

1-((3 S,4R)-4-(3,4-difluorophenyl)-1-(2-methoxyethyl)pyrrolidin-3-yl)-3-(3-(2-methoxypyrimidin-5-yl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-(2-(dimethylamino)pyrimidin-5-yl)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-(2-methoxypyrimidin-5-yl)-4-methyl-1-phenyl-1H-pyrazol-5-yl)urea;

1-(3-(2-(dimethylamino)pyrimidin-5-yl)-4-methyl-1-phenyl-1H-pyrazol-5-yl)-3-((3 S,4R)-4-(4-fluorophenyl)-1-(2-methoxyethyl)pyrrolidin-3-yl)urea;

1-(1'-ethyl-4-methyl-1-phenyl-1H, 1'H-[3,4'-bipyrazol]-5-yl)-3-((3 S,4R)-4-(3-fluorophenyl)-1-(2-methoxyethyl)pyrrolidin-3-yl)urea;

1-((3 S,4R)-4-(3-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea;

1-((3 S,4R)-4-(4-fluorophenyl)-1-(2-methoxyethyl)pyrrolidin-3-yl)-3-(4-methyl-3-(1-methyl-2-oxo-1,2-dihydropyridin-4-yl)-1-phenyl-1H-pyrazol-5-yl)urea;

1-(3-cyclopropyl-4-methyl-1-phenyl-1H-pyrazol-5-yl)-3-((3 S,4R)-4-(3,4-difluorophenyl)-1-(2-methoxyethyl)pyrrolidin-3-yl)urea;

1-(3-cyclopropyl-4-methyl-1-phenyl-1H-pyrazol-5-yl)-3-((3 S,4R)-4-(4-fluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(1-isopropyl-6-oxo-1,6-dihydropyridin-3-yl)-4-methyl-1-phenyl-1H-pyrazol-5-yl)urea;

1-((3 S,4R)-4-(4-fluorophenyl)-1-(2-methoxyethyl)pyrrolidin-3-yl)-3-(3-(1-isopropyl-6-oxo-1,6-dihydropyridin-3-yl)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-((S)-2-hydroxypropoxy)-4-methyl-1-phenyl-1H-pyrazol-5-yl)urea dihydrochloride;

1-((3 S,4R)-4-(3,5-difluorophenyl)-1-(2-methoxyethyl)pyrrolidin-3-yl)-3-(4-methyl-1-phenyl-3-(2-(piperazin-1-yl)ethoxy)-1H-pyrazol-5-yl)urea trihydrochloride;

1-(3-(benzyl oxy)-4-chloro-1-methyl-1H-pyrazol-5-yl)-3-((3 S,4R)-4-(3,4-difluorophenyl)-1-(2-methoxyethyl)pyrrolidin-3-yl)urea;

2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)acetic acid;

2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)-N-ethylacetamide;

1-((3 S,4R)-4-(3,4-difluorophenyl)-1-(2-methoxyethyl)pyrrolidin-3-yl)-3-(4-ethyl-3-(2-hydroxy-2-methylpropoxy)-1-phenyl-1H-pyrazol-5-yl)urea;

1-(3-(2-aminoethoxy)-4-methyl-1-phenyl-1H-pyrazol-5-yl)-3-((3 S,4R)-4-(3,4-difluorophenyl)-1-(2-methoxyethyl)pyrrolidin-3-yl)urea;

N-(2-((5-(3-((3 S,4R)-4-(3,4-difluorophenyl)-1-(2-methoxyethyl)pyrrolidin-3-yl)ureido)-4-methyl-1-phenyl-H-pyrazol-3-yl)oxy)ethyl)methanesulfonamide;

N-(2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)ethyl)acetamide;

1-(3-(2-(4-acetylpiperazin-1-yl)ethoxy)-4-methyl-1-phenyl-1H-pyrazol-5-yl)-3-((3 S,4R)-4-(3,4-difluorophenyl)-1-(2-methoxyethyl)pyrrolidin-3-yl)urea;

2-((5-(3-((3 S,4R)-4-(3,4-difluorophenyl)-1-(2-methoxyethyl)pyrrolidin-3-yl)ureido)-4-methyl-1-phenyl-1H-pyrazol-3-yl)oxy)acetamide;

N-(5-(3-((3 S,4R)-4-(3,4-difluorophenyl)-1-(2-methoxyethyl)pyrrolidin-3-yl)ureido)-3-ethoxy-1-phenyl-1H-pyrazol-4-yl)-2,2,2-trifluoroacetamide;

1-(4-amino-3-ethoxy-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-ethoxy-4-(2-hydroxyethyl)-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(2-(4-methylpiperazin-1-yl)ethoxy)-1-phenyl-1H-pyrazol-5-yl)urea trihydrochl oride;

1-((3 S,4R)-4-(3,4-difluorophenyl)-1-(2-methoxyethyl)pyrrolidin-3-yl)-3-(4-methyl-3-(2-morpholino-2-oxoethoxy)-1-phenyl-1H-pyrazol-5-yl)urea;

4-bromo-5-(3-((3 S,4R)-4-(3,4-difluorophenyl)-1-(2-methoxyethyl)pyrrolidin-3-yl)ureido)-1-phenyl-1H-pyrazole-3-carboxylic acid;

4-bromo-5-(3-((3 S,4R)-4-(3,4-difluorophenyl)-1-(2-methoxyethyl)pyrrolidin-3-yl)ureido)-N-methyl-1-phenyl-1H-pyrazole-3-carboxamide;

4-bromo-5-(3-((3 S,4R)-4-(3,4-difluorophenyl)-1-(2-methoxyethyl)pyrrolidin-3-yl)ureido)-N-methoxy-1-phenyl-1H-pyrazole-3-carboxamide;

1-(4-chloro-1'-(2-methoxyethyl)-1-phenyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-((3 S,4R)-4-(3,5-difluorophenyl)-1-(2-methoxyethyl)pyrrolidin-3-yl)-3-(3-((S)-2,3-dihydroxypropoxy)-4-methyl-1-phenyl-1H-pyrazol-5-yl)urea;

1-((3 S,4R)-4-(3,5-difluorophenyl)-1-(2-methoxyethyl)pyrrolidin-3-yl)-3-(3-((R)-2,3-dihydroxypropoxy)-4-methyl-1-phenyl-1H-pyrazol-5-yl)urea;

1-(3-((R)-2,3-dihydroxypropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-((S)-2,3-dihydroxypropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-((S)-2-hydroxypropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-((3 S,4R)-4-(3,4-difluorophenyl)-1-(2-methoxyethyl)pyrrolidin-3-yl)-3-(3-((S)-2-hydroxy-3-methoxypropoxy)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(3-((R)-2-hydroxy-3-methoxypropoxy)-4-methyl-1-phenyl-1H-pyrazol-5-yl)urea;

1-(3-((S)-2-hydroxy-3-methoxypropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(3-((R)-2-hydroxy-3-methoxypropoxy)-4-methyl-1-phenyl-1H-pyrazol-5-yl)-3-((3 S,4R)-1-(2-methoxyethyl)-4-(3,4,5-trifluorophenyl)pyrrolidin-3-yl)urea;

1-(4-bromo-1,1'-dimethyl-1H, 1'H-[3,4'-bipyrazol]-5-yl)-3-((3 S,4R)-4-(3,4-difluorophenyl)-1-(2-methoxyethyl)pyrrolidin-3-yl)urea;

1-(4-chloro-1,1'-dimethyl-1H,1'H-[3,4'-bipyrazol]-5-yl)-3-((3 S,4R)-4-(3,4-difluorophenyl)-1-(2-methoxyethyl)pyrrolidin-3-yl)urea;

1-(4-chloro-1-phenyl-3-(tetrahydro-2H-pyran-4-yl)-1H-pyrazol-5-yl)-3-((3 S,4R)-4-(3,4-difluorophenyl)-1-(2-methoxyethyl)pyrrolidin-3-yl)urea;

Tert-butyl 4-(4-chloro-5-(3-((3 S,4R)-4-(3,4-difluorophenyl)-1-(2-methoxyethyl)pyrrolidin-3-yl)ureido)-1-phenyl-1H-pyrazol-3-yl)piperidine-1-carboxylate;

1-(4-chloro-1-phenyl-3-(tetrahydro-2H-pyran-4-yl)-1H-pyrazol-5-yl)-3-((3 S,4R)-4-(4-fluorophenyl)-1-(2-methoxyethyl)pyrrolidin-3-yl)urea;

1-(4-chloro-3-(3,5-dimethylisoxazol-4-yl)-1-phenyl-1H-pyrazol-5-yl)-3-((3 S,4R)-4-(3,4-difluorophenyl)-1-(2-methoxyethyl)pyrrolidin-3-yl)urea;

(R)-tert-butyl 2-(4-chloro-5-(3-((3 S,4R)-4-(3,4-difluorophenyl)-1-(2-methoxyethyl)pyrrolidin-3-yl)ureido)-1-phenyl-1H-pyrazol-3-yl)pyrrolidine-1-carboxylate;

(S)-tert-butyl 2-(4-chloro-5-(3-((3 S,4R)-4-(3,4-difluorophenyl)-1-(2-methoxyethyl)pyrrolidin-3-yl)ureido)-1-phenyl-1H-pyrazol-3-yl)pyrrolidine-1-carboxylate;

1-(4-bromo-1-phenyl-3-(tetrahydro-2H-pyran-4-yl)-1H-pyrazol-5-yl)-3-((3 S,4R)-4-(3,4-difluorophenyl)-1-(2-methoxyethyl)pyrrolidin-3-yl)urea;

Tert-butyl 4-(4-bromo-5-(3-((3 S,4R)-4-(3,4-difluorophenyl)-1-(2-methoxyethyl)pyrrolidin-3-yl)ureido)-1-phenyl-1H-pyrazol-3-yl)piperidine-1-carboxylate;

1-(4-bromo-1-phenyl-3-(tetrahydro-2H-pyran-4-yl)-1H-pyrazol-5-yl)-3-((3 S,4R)-4-(4-fluorophenyl)-1-(2-methoxyethyl)pyrrolidin-3-yl)urea;

1-(4-bromo-3-(3,5-dimethylisoxazol-4-yl)-1-phenyl-1H-pyrazol-5-yl)-3-difluorophenyl)-1-(2-methoxyethyl)pyrrolidin-3-yl)urea;

(R)-tert-butyl 2-(4-bromo-5-(3-((3 S,4R)-4-(3,4-difluorophenyl)-1-(2-methoxyethyl)pyrrolidin-3-yl)ureido)-1-phenyl-1H-pyrazol-3-yl)pyrrolidine-1-carboxylate;

tert-butyl 4-((4-bromo-5-(3-((3 S,4R)-4-(3,4-difluorophenyl)-1-(2-methoxyethyl)pyrrolidin-3-yl)ureido)-1-phenyl-1H-pyrazol-3-yl)methoxy)piperidine-1-carboxylate;

1-((3 S,4R)-4-(3,4-difluorophenyl)-1-(2-methoxyethyl)pyrrolidin-3-yl)-3-(1-phenyl-3-(piperidin-4-yl)-1H-pyrazol-5-yl)urea dihydrochloride;

1-(4-chloro-1-phenyl-3-(piperidin-4-yl)-1H-pyrazol-5-yl)-3-((3S,4R)-4-(3,4-difluorophenyl)-1-(2-methoxyethyl)pyrrolidin-3-yl)urea dihydrochloride;

1-(4-bromo-1-phenyl-3-(piperidin-4-yl)-1H-pyrazol-5-yl)-3-((3 S,4R)-4-(3,4-difluorophenyl)-1-(2-methoxyethyl)pyrrolidin-3-yl)urea dihydrochloride;

1-((3 S,4R)-4-(3,4-difluorophenyl)-1-(2-methoxyethyl)pyrrolidin-3-yl)-3-(4-methyl-1-phenyl-3-((R)-pyrrolidin-2-yl)-1H-pyrazol-5-yl)urea dihydrochloride;

1-((3 S,4R)-4-(3,4-difluorophenyl)-1-(2-methoxyethyl)pyrrolidin-3-yl)-3-(4-methyl-1-phenyl-3-((S)-pyrrolidin-2-yl)-1H-pyrazol-5-yl)urea dihydrochloride;

1-((3 S,4R)-4-(3,4-difluorophenyl)-1-(2-methoxyethyl)pyrrolidin-3-yl)-3-(4-chloro-1-phenyl-3-((R)-pyrrolidin-2-yl)-1H-pyrazol-5-yl)urea dihydrochloride;

1-((3S,4R)-4-(3,5-difluorophenyl)-1-(2-methoxyethyl)pyrrolidin-3-yl)-3-(4-methyl-1-phenyl-3-((S)-pyrrolidin-2-yl)-1H-pyrazol-5-yl)urea dihydrochloride;

1-((3S,4R)-4-(3,4-difluorophenyl)-1-(2-methoxyethyl)pyrrolidin-3-yl)-3-(4-chloro-1-phenyl-3-((S)-pyrrolidin-2-yl)-1H-pyrazol-5-yl)urea dihydrochloride;

1-(4-bromo-1-phenyl-3-((R)-pyrrolidin-2-yl)-1H-pyrazol-5-yl)-3-((3 S,4R)-4-(3,4-difluorophenyl)-1-(2-methoxyethyl)pyrrolidin-3-yl)urea dihydrochloride;

1-((3 S,4R)-4-(3,4-difluorophenyl)-1-(2-methoxyethyl)pyrrolidin-3-yl)-3-(1-phenyl-3-((piperidin-4-yloxy)methyl)-1H-pyrazol-5-yl)urea dihydrochloride;

1-(4-chloro-1-phenyl-3-((piperidin-4-yloxy)methyl)-1H-pyrazol-5-yl)-3-((3 S,4R)-4-(3,4-difluorophenyl)-1-(2-methoxyethyl)pyrrolidin-3-yl)urea dihydrochloride;

1-(4-bromo-1-phenyl-3-((piperidin-4-yloxy)methyl)-1H-pyrazol-5-yl)-3-((3 S,4R)-4-(3,4-difluorophenyl)-1-(2-methoxyethyl)pyrrolidin-3-yl)urea dihydrochloride;

1-(4-bromo-3-(1-(methylsulfonyl)piperidin-4-yl)-1-phenyl-1H-pyrazol-5-yl)-3-((3 S,4R)-4-(3,4-difluorophenyl)-1-(2-methoxyethyl)pyrrolidin-3-yl)urea;

1-(3-(1-acetylpiperidin-4-yl)-4-bromo-1-phenyl-1H-pyrazol-5-yl)-3-((3 S,4R)-4-(3,4-difluorophenyl)-1-(2-methoxyethyl)pyrrolidin-3-yl)urea;

1-(4-chloro-1-phenyl-3-(1-(trifluoromethylsulfonyl)piperidin-4-yl)-1H-pyrazol-5-yl)-3-((3 S,4R)-4-(3,4-difluorophenyl)-1-(2-methoxyethyl)pyrrolidin-3-yl)urea hydrochloride;

1-((3 S,4R)-4-(3,4-difluorophenyl)-1-(2-methoxyethyl)pyrrolidin-3-yl)-3-(4-methyl-3-((R)-1-(methylsulfonyl)pyrrolidin-2-yl)-1-phenyl-1H-pyrazol-5-yl)urea;

1-(3-((R)-1-acetylpyrrolidin-2-yl)-4-methyl-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(4-methyl-3-((R)-1-methylpyrrolidin-2-yl)-1-phenyl-1H-pyrazol-5-yl)urea dihydrochloride;

1-((3 S,4R)-4-(3,5-difluorophenyl)-1-(2-methoxyethyl)pyrrolidin-3-yl)-3-(4-methyl-3-((S)-1-methylpyrrolidin-2-yl)-1-phenyl-1H-pyrazol-5-yl)urea dihydrochloride;

1-(4-bromo-3-((1-(methylsulfonyl)piperidin-4-yloxy)methyl)-1-phenyl-1H-pyrazol-5-yl)-3-((3 S,4R)-4-(3,4-difluorophenyl)-1-(2-methoxyethyl)pyrrolidin-3-yl)urea;

1-(3-((1-acetylpiperidin-4-yloxy)methyl)-4-bromo-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3,4-difluorophenyl)-1-(2-methoxyethyl)pyrrolidin-3-yl)-3-(3-(4-isopropyl-5-oxo-4,5-dihydro-1,3,4-oxadiazol-2-yl)-4-methyl-1-phenyl-1H-pyrazol-5-yl)urea;

1-((3 S,4R)-4-(3,4-difluorophenyl)-1-(2-methoxyethyl)pyrrolidin-3-yl)-3-(4-methyl-3-(4-methyl-5-oxo-4,5-dihydro-1,3,4-oxadiazol-2-yl)-1-phenyl-1H-pyrazol-5-yl)urea;

1-((3 S,4R)-4-(4-fluorophenyl)-1-(2-methoxyethyl)pyrrolidin-3-yl)-3-(4-methyl-1-phenyl-3-(pyrazin-2-yloxy)-1H-pyrazol-5-yl)urea;

1-((3 S,4R)-1-(2-methoxyethyl)-4-(3,4,5-trifluorophenyl)pyrrolidin-3-yl)-3-(4-methyl-3-(1-methyl-6-oxo-1,6-dihydropyridin-3-yl)-1-phenyl-1H-pyrazol-5-yl)urea;

1-((3 S,4R)-4-(3,4-difluorophenyl)-1-(2-methoxyethyl)pyrrolidin-3-yl)-3-(3-methoxy-1-phenyl-4-(trifluoromethyl)-1H-pyrazol-5-yl)urea;

1-((3 S,4R)-4-(3,5-difluorophenyl)-1-(2-methoxyethyl)pyrrolidin-3-yl)-3-(3-methoxy-1-phenyl-4-(trifluoromethyl)-1H-pyrazol-5-yl)urea;

1-((3 S,4R)-4-(4-fluorophenyl)-1-(2-methoxyethyl)pyrrolidin-3-yl)-3-(3-methoxy-1-phenyl-4-(trifluoromethyl)-1H-pyrazol-5-yl)urea;

1-((3 S,4R)-4-(3,4-difluorophenyl)-1-(2-methoxyethyl)pyrrolidin-3-yl)-3-(3-methoxy-1-phenyl-4-(trifluoromethyl)-1H-pyrazol-5-yl)urea;

1-((trans)-4-(4-chloro-3-fluorophenyl)-1-(2-methoxyethyl)pyrrolidin-3-yl)-3-(4-methyl-5-oxo-2-phenyl-2,5-dihydro-1H-pyrazol-3-yl)urea;

1-((trans)-4-(3-chloro-4-fluorophenyl)-1-(2-methoxyethyl)pyrrolidin-3-yl)-3-(4-methyl-5-oxo-2-phenyl-2,5-dihydro-1H-pyrazol-3-yl)urea;

1-((3 S,4R)-4-(3,5-difluorophenyl)-1-(2-methoxyethyl)pyrrolidin-3-yl)-3-(4-methyl-5-oxo-2-phenyl-2,5-dihydro-1H-pyrazol-3-yl)urea;

1-((3 S,4R)-1-(2-methoxyethyl)-4-(3,4,5-trifluorophenyl)pyrrolidin-3-yl)-3-(4-methyl-5-oxo-2-phenyl-2,5-dihydro-1H-pyrazol-3-yl)urea;

1-((3S,4R)-4-(3-fluorophenyl)-1-(2-methoxyethyl)pyrrolidin-3-yl)-3-(4-methyl-5-oxo-2-phenyl-2,5-dihydro-1H-pyrazol-3-yl)urea;

1-((trans)-4-(3-chloro-5-fluorophenyl)-1-(2-methoxyethyl)pyrrolidin-3-yl)-3-(4-methyl-5-oxo-2-phenyl-2,5-dihydro-1H-pyrazol-3-yl)urea;

1-(4-cyano-3-methoxy-1-phenyl-1H-pyrazol-5-yl)-3-((3 S,4R)-4-(3,4-difluorophenyl)-1-(2-methoxyethyl)pyrrolidin-3-yl)urea;

1-((3 S,4R)-4-(3-chl oro-5-fluorophenyl)-1-(2-methoxyethyl)pyrrolidin-3-yl)-3-(4-methyl-5-oxo-2-phenyl-2,5-dihydro-1H-pyrazol-3-yl)urea;

1-(4-cyano-1-phenyl-3-(trifluoromethyl)-1H-pyrazol-5-yl)-3-((3 S,4R)-4-(3,4-difluorophenyl)-1-(2-methoxyethyl) pyrrolidin-3-yl)urea;

1-(4-cyano-5-oxo-2-phenyl-2,5-dihydro-1H-pyrazol-3-yl)-3-((3 S,4R)-4-(3,4-difluorophenyl)-1-(2-methoxyethyl) pyrrolidin-3-yl)urea;

5-(3-((3 S,4R)-4-(3,4-difluorophenyl)-1-(2-methoxyethyl) pyrrolidin-3-yl)ureido)-3-methoxy-1-phenyl-1H-pyrazole-4-carboxamide;

5-(3-((3 S,4R)-4-(3,4-difluoro-phenyl)-1-(2-methoxyethyl) pyrrolidin-3-yl)ureido)-3-methyl-1-phenyl-1H-pyrazole-4-carboxamide;

5-(3-((3 S,4R)-4-(3,4-difluorophenyl)-1-(2-methoxyethyl) pyrrolidin-3-yl)ureido)-3-ethyl-1-phenyl-1H-pyrazole-4-carboxamide;

5-(3-((3 S,4R)-4-(3,4-difluorophenyl)-1-(2-methoxyethyl) pyrrolidin-3-yl)ureido)-1-phenyl-3-(trifluoromethyl)-1H-pyrazole-4-carboxamide;

5-(3-((trans)-4-(3-chloro-4-fluorophenyl)-1-(2-methoxyethyl)pyrrolidin-3-yl)ureido)-3-methyl-1-phenyl-1H-pyrazole-4-carboxamide;

5-(3-((trans)-4-(4-chloro-3-fluorophenyl)-1-(2-methoxyethyl)pyrrolidin-3-yl)ureido)-3-methyl-1-phenyl-1H-pyrazole-4-carboxamide;

5-(3-((trans)-4-(3-chloro-5-fluorophenyl)-1-(2-methoxyethyl)pyrrolidin-3-yl)ureido)-3-methyl-1-phenyl-1H-pyrazole-4-carboxamide;

5-(3-((3 S,4R)-4-(3,5-difluorophenyl)-1-(2-methoxyethyl) pyrrolidin-3-yl)ureido)-3-methyl-1-phenyl-1H-pyrazole-4-carboxamide;

5-(3-((3 S,4R)-4-(3,4-difluorophenyl)-1-(2-methoxyethyl) pyrrolidin-3-yl)ureido)-1-phenyl-1H-pyrazole-4-carboxamide;

5-(3-((3 S,4R)-4-(3,4-difluorophenyl)-1-(2-methoxyethyl) pyrrolidin-3-yl)ureido)-1-phenyl-1H-pyrazole-4-carboxamide;

1-(4-bromo-3-methyl-1-phenyl-1H-pyrazol-5-yl)-3-((3 S,4R)-4-(3,4-difluorophenyl)-1-(2-methoxyethyl)pyrrolidin-3-yl)guanidine dihydrochloride;

1-(4-bromo-3-methyl-1-phenyl-1H-pyrazol-5-yl)-3-((3 S,4R)-4-(3,4-difluorophenyl)-1-(2-methoxyethyl)pyrrolidin-3-yl)thiourea;

1-((3 S,4R)-4-(3,4-difluorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)thiourea;

1-((3 S,4R)-4-(3,4-difluorophenyl)-1-(2-methoxyethyl)pyrrolidin-3-yl)-3-(1',4-dimethyl-1-phenyl-1H, 1'H-3,4'-bipyrazol-5-yl)thiourea;

1-((3 S,4R)-4-(4-fluorophenyl)-1-(2-methoxyethyl)pyrrolidin-3-yl)-3-(1',4-dimethyl-1-phenyl-1H,1'H-3,4'-bipyrazol-5-yl)thiourea;

Trans-1-(2-methoxyethyl)-4-phenylpyrrolidin-3-yl)-3-(2-phenylpyrazolo[1,5-a]pyridin-3-yl)urea;

1-((3 S,4R)-4-(3,4-difluorophenyl)-1-(2-methoxyethyl)pyrrolidin-3-yl)-3-(2-phenylpyrazolo[1,5-a]pyridin-3-yl) urea;

Trans-1-(2-methoxyethyl)-4-phenylpyrrolidin-3-yl)-3-(pyrazolo[1,5-a]pyridin-3-yl)urea;

1-((3 S,4R)-4-(3,4-difluorophenyl)-1-(2-methoxyethyl)pyrrolidin-3-yl)-3-(pyrazolo[1,5-a]pyridin-3-yl)urea;

1-((3 S,4R)-4-(3,4-difluorophenyl)-1-(2-methoxyethyl)pyrrolidin-3-yl)-3-(5-methyl-3-phenyl-1-(pyrazin-2-yl)-1H-pyrazol-4-yl)urea;

1-((3 S,4R)-4-(3,4-difluorophenyl)-1-(2-methoxyethyl)pyrrolidin-3-yl)-3-(1,5-dimethyl-3-phenyl-1H-pyrazol-4-yl) urea;

1-((3S,4R)-4-(3,5-difluorophenyl)-1-(2-methoxyethyl)pyrrolidin-3-yl)-3-(1,5-dimethyl-3-phenyl-1H-pyrazol-4-yl) urea;

1-((3 S,4R)-4-(3,4-difluorophenyl)-1-(2-methoxyethyl)pyrrolidin-3-yl)-3-(1-isopropyl-5-methyl-3-phenyl-1H-pyrazol-4-yl)urea;

1-((3S,4R)-4-(3,5-difluorophenyl)-1-(2-methoxyethyl)pyrrolidin-3-yl)-3-(1-isopropyl-5-methyl-3-phenyl-1H-pyrazol-4-yl)urea;

1-((3 S,4R)-4-(3,4-difluorophenyl)-1-(2-methoxyethyl)pyrrolidin-3-yl)-3-(5-methyl-3-phenyl-1-(2,2,2-trifluoroethyl)-1H-pyrazol-4-yl)urea;

1-((3 S,4R)-4-(3,4-difluorophenyl)-1-(2-methoxyethyl)pyrrolidin-3-yl)-3-(1-ethyl-5-methyl-3-phenyl-1H-pyrazol-4-yl)urea;

1-((3S,4R)-4-(3,4-difluorophenyl)-1-(2-methoxyethyl)pyrrolidin-3-yl)-3-(1-ethyl-3-methyl-5-phenyl-1H-pyrazol-4-yl)urea;

1-((3 S,4R)-4-(3,4-difluorophenyl)-1-(2-methoxyethyl)pyrrolidin-3-yl)-3-(1-methyl-5-phenyl-3-(trifluoromethyl)-1H-pyrazol-4-yl)urea;

1-((3S,4R)-4-(3,4-difluorophenyl)-1-(2-methoxyethyl)pyrrolidin-3-yl)-3-(1-methyl-3-phenyl-5-(trifluoromethyl)-1H-pyrazol-4-yl)urea;

1-((3 S,4R)-4-(3,4-difluorophenyl)-1-(2-methoxyethyl)pyrrolidin-3-yl)-3-(3-methyl-1-phenyl-1H-pyrazol-4-yl) urea;

1-((3 S,4R)-4-(3,4-difluorophenyl)-1-(2-methoxyethyl)pyrrolidin-3-yl)-3-(1-phenyl-3-(trifluoromethyl)-1H-pyrazol-4-yl)urea;

or a pharmaceutically acceptable salt thereof.

In some embodiments, a Trk inhibitor is selected from the group consisting of:

5-Chloro-N-(5-cyclopropyl-1H-pyrazol-3-yl)-$N^2$-(1-phenylethyl)pyrimidine-2,4-diamine;

5-Bromo-N-(3-ethyl-1H-pyrazol-5-yl)-$N^2$-(1-phenylethyl) pyrimidine-2,4-diamine;

$N^4$-(3-tert-Butyl-1H-pyrazol-5-yl)-5-chloro-$N^2$-(1-phenylethyl)pyrimidine-2,4-diamine;

$N^4$-(3-Cyclopropyl-1H-pyrazol-5-yl)-$N^2$-(1-phenylethyl)-5-(trifluoromethyl)pyrimidine-2,4-diamine:

5-Bromo-$N^4$-(3-cyclopropyl-1H-pyrazol-5-yl)-$N^2$-[(1 S)-1-(4-fluorophenyl)ethyl]pyrimidine-2,4-diamine:

5-Bromo-$N^4$-(3-cyclopropyl-1 I-pyrazol-5-yl)-$N^2$-[(1S)-1-phenylpropyl]pyrimidine-2,4-diamine;

5-Bromo-$N^4$-(3-cyclopropyl-1H-pyrazol-5-yl)-$N^2$-[(1 S)-1-(4-nitrophenyl)ethyl]pyrimidine-2,4-diamine;

(2R)-2-({5-Bromo-4-[(3-cyclopropyl-1H-pyrazol-5-yl) amino]pyrimidin-2yl}amino)-2-phenylethanol;

5-Bromo-N-(5-cyclopropyl-1H-pyrazol-3-yl)-$N^2$-(1-phenylethyl)pyrimidine-2,4-diamine;

5-Chloro-N-(5-cyclopropyl-1H-pyrazol-3-yl)-N-(1-phenylpropyl)pyrimidine-2,4-diamine, or a pharmaceutically acceptable salt thereof.

In some embodiments, a Trk inhibitor is one or more compounds of Table 5, or a pharmaceutically acceptable salt thereof.

TABLE 5

| Exemplary Trk inhibitors | | |
|---|---|---|
| Compound No. | Compound Structure | Compound Name |
| 1 | 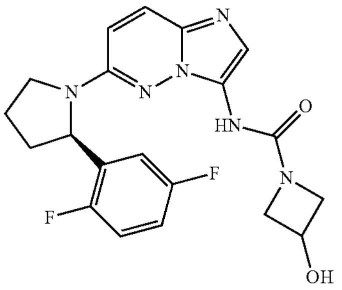 [SMILES: O=C(Nc1cnc2ccc(N3CCC[C@@H]3c3cc(F)ccc3F)nn12)N1CC(O)C1] | (R)-N-(6-(2-(2,5-difluorophenyl)pyrrolidin-1-yl)imidazo[1,2-b]pyridazin-3-yl)-3-hydroxyazetidine-1-carboxamide |
| 2 | 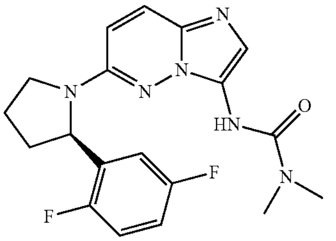 [SMILES: CN(C)C(=O)Nc1cnc2ccc(N3CCC[C@@H]3c3cc(F)ccc3F)nn12] | (R)-3-(6-(2-(2,5-difluorophenyl)pyrrolidin-1-yl)imidazo[1,2-b]pyridazin-3-yl)-1,1-dimethylurea |
| 3 | 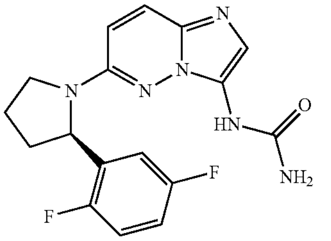 [SMILES: NC(=O)Nc1cnc2ccc(N3CCC[C@@H]3c3cc(F)ccc3F)nn12] | (R)-1-(6-(2-(2,5-difluorophenyl)pyrrolidin-1-yl)imidazo[1,2-b]pyridazin-3-yl)urea |
| 4 | 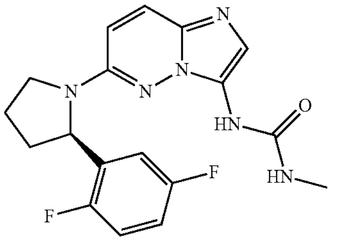 [SMILES: CNC(=O)Nc1cnc2ccc(N3CCC[C@@H]3c3cc(F)ccc3F)nn12] | (R)-1-(6-(2-(2,5-difluorophenyl)pyrrolidin-1-yl)imidazo[1,2-b]pyridazin-3-yl)-3-methylurea |
| 5 | 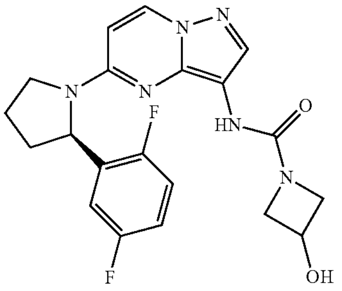 [SMILES: O=C(Nc1cnn2ccc(N3CCC[C@@H]3c3cc(F)ccc3F)nc12)N1CC(O)C1] | (R)-N-(5-(2-(2,5-difluorophenyl)pyrrolidin-1-yl)pyrazolo[1,5-a]pyrimidin-3-yl)-3-hydroxyazetidine-1-carboxamide |

TABLE 5-continued

| Compound No. | Compound Structure | Compound Name |
|---|---|---|
| | Exemplary Trk inhibitors | |
| 6 | 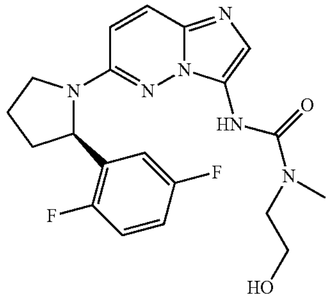 [SMILES: CN(CCO)C(=O)Nc1cnc2ccc(N3CCC[C@@H]3c3cc(F)ccc3F)nn12] | (R)-3-(6-(2-(2,5-difluorophenyl)pyrrolidin-1-yl)imidazo[1,2-b]pyridazin-3-yl)-1-(2-hydroxyethyl)-1-methylurea |
| 7 | 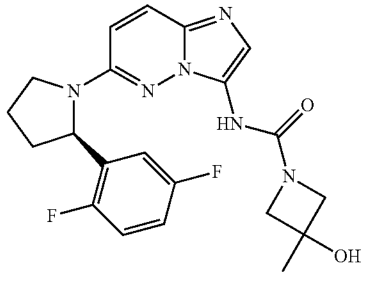 [SMILES: CC1(O)CN(C(=O)Nc2cnc3ccc(N4CCC[C@@H]4c4cc(F)ccc4F)nn23)C1] | (R)-N-(6-(2-(2,5-difluorophenyl)pyrrolidin-1-yl)imidazo[1,2-b]pyridazin-3-yl)-3-hydroxy-3-methylazetidine-1-carboxamide |
| 8 | 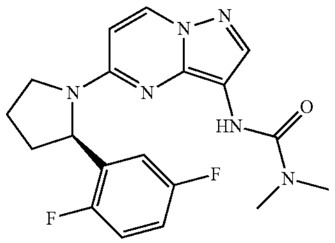 [SMILES: CN(C)C(=O)Nc1cnn2ccc(N3CCC[C@@H]3c3cc(F)ccc3F)nc12] | (R)-3-(5-(2-(2,5-difluorophenyl)pyrrolidin-1-yl)pyrazolo[1,5-a]pyrimidin-3-yl)-1,1-dimethylurea |
| 9 | 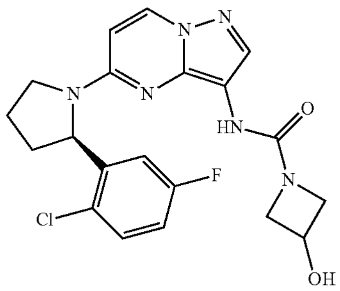 [SMILES: O=C(Nc1cnn2ccc(N3CCC[C@@H]3c3cc(F)ccc3Cl)nc12)N1CC(O)C1] | (R)-N-(5-(2-(2-chloro-5-fluorophenyl) pyrrolidin-1-yl)pyrazolo[1,5-a]pyrimidin-3-yl)-3-hydroxyazetidine-1-carboxamide |
| 10 | 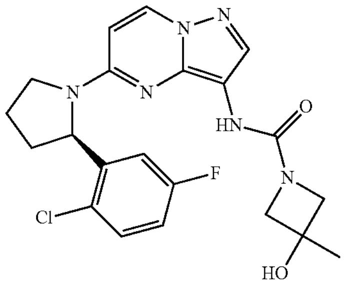 [SMILES: CC1(O)CN(C(=O)Nc2cnn3ccc(N4CCC[C@@H]4c4cc(F)ccc4Cl)nc23)C1] | (R)-N-(5-(2-(2-chloro-5-fluorophenyl) pyrrolidin-1-yl)pyrazolo[1,5-a]pyrimidin-3-yl)-3-hydroxy-3-methylazetidine-1-carboxamide |

TABLE 5-continued

| Exemplary Trk inhibitors | | |
|---|---|---|
| Compound No. | Compound Structure | Compound Name |
| 11 | 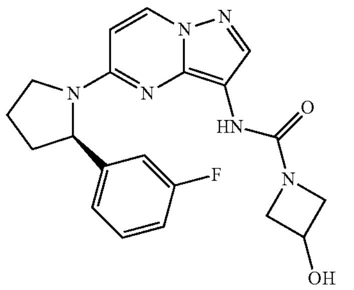 [SMILES: O=C(Nc1cnn2ccc(N3CCC[C@@H]3c3cccc(F)c3)nc12)N1CC(O)C1] | (R)-N-(5-(2-(3-fluorophenyl)pyrrolidin-1-yl)pyrazolo[1,5-a]pyrimidin-3-yl)-3-hydroxyazetidine-1-carboxamide |
| 12 | 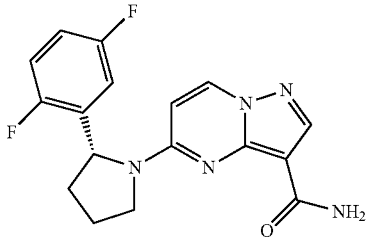 [SMILES: NC(=O)c1cnn2ccc(N3CCC[C@@H]3c3cc(F)ccc3F)nc12] | (R)-5-(2-(2,5-difluorophenyl)pyrrolidin-1-yl)pyrazolo[1,5-a]pyrimidine-3-carboxamide |
| 13 | 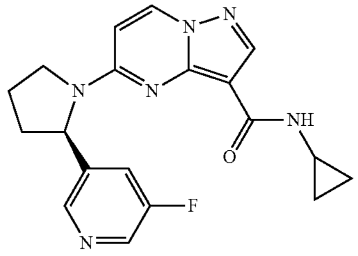 [SMILES: O=C(NC1CC1)c1cnn2ccc(N3CCC[C@@H]3c3cncc(F)c3)nc12] | (R)-N-cyclopropyl-5-(2-(5-fluoro-pyridin-3-yl)pyrrolidin-1-yl)pyrazolo[1,5-a]pyrimidine-3-carboxamide |
| 14 | 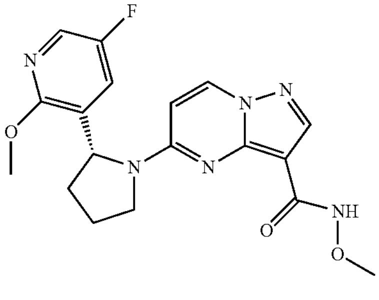 [SMILES: CONC(=O)c1cnn2ccc(N3CCC[C@@H]3c3cc(F)cnc3OC)nc12] | (R)-5-(2-(5-fluoro-2-methoxypyridin-3-yl)pyrrolidin-1-yl)-N-methoxy-pyrazolo[1,5-a]pyrimidine-3-carboxamide |
| 15 | 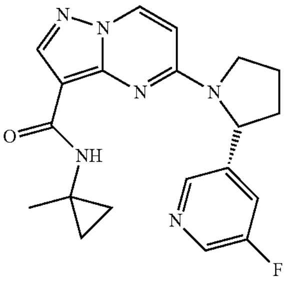 | (R)-5-(2-(5-fluoropyridin-3-yl)pyrrolidin-1-yl)-N-(1-methylcyclopropyl)pyrazolo[1,5-a]pyrimidine-3-carboxamide |

TABLE 5-continued

| Exemplary Trk inhibitors | | |
|---|---|---|
| Compound No. | Compound Structure | Compound Name |
| 16 | 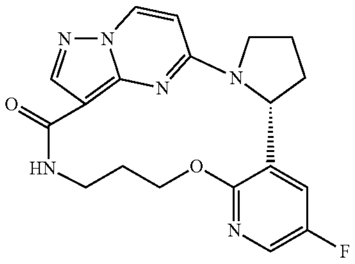 [SMILES: O=C1NCCCOc2ncc(F)cc2[C@H]2CCCN2c2ccn3ncc1c3n2] | (6R)-9-fluoro-13-oxa-2,11,17,21,22,25-hexaazapentacyclo[17.5.2.$0^{2,6}$.$0^{7,12}$.$0^{22,26}$]-hexacosa-1(25),7,9,11,19(26),20,23-heptaen-18-one |
| 17 | 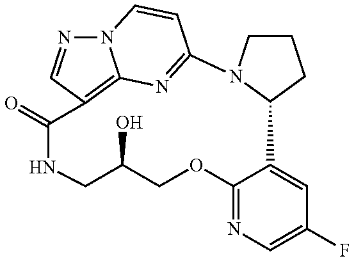 [SMILES: O=C1NC[C@@H](O)COc2ncc(F)cc2[C@H]2CCCN2c2ccn3ncc1c3n2] | (6R,15R)-9-fluoro-15-hydroxy-13-oxa-2,11,17,21,22,25-hexaazapentacyclo-[17.5.2.$0^{2,6}$.$0^{7,12}$.$0^{22,26}$]-hexacosa-1(25), 7,9,11,19(26),20,23-heptaen-18-one |
| 18 | 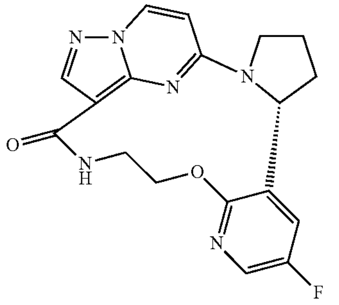 [SMILES: O=C1NCCOc2ncc(F)cc2[C@H]2CCCN2c2ccn3ncc1c3n2] | (6R)-9-fluoro-13-oxa-2,11,18,22,23,26-hexaazapentacyclo[18.5.2.$0^{2,6}$.$0^{7,12}$.$0^{23,27}$]-heptacosa-1(26),7,9,11,20(27),21,24-heptaen-19-one |
| 19 | 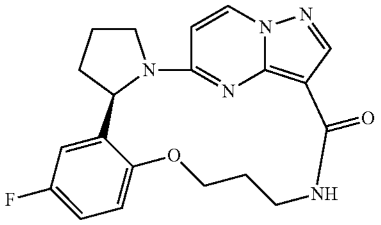 [SMILES: O=C1NCCCOc2ccc(F)cc2[C@H]2CCCN2c2ccn3ncc1c3n2] | (6R)-9-fluoro-13-oxa-2,17,21,22,25-pentaazapentacyclo[17.5.2.$0^{2,6}$.$0^{7,12}$.$0^{22,26}$] hexacosa-1(25),7,9,11,19(26),20,23-heptaen-18-one |
| 20 | 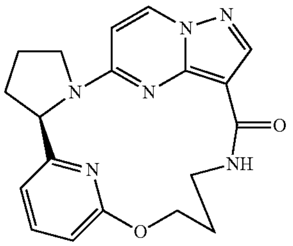 [SMILES: O=C1NCCCOc2cccc(n2)[C@H]2CCCN2c2ccn3ncc1c3n2] | (6R)-12-oxa-2,16,20,21,24,26-hexaazapentacyclo[16.5.2.$1^{7,11}$.$0^{2,6}$.$0^{21,25}$]-hexacosa-1(24),7(26),8,10,18(25),19,22-heptaen-17-one |

TABLE 5-continued

Exemplary Trk inhibitors

| Compound No. | Compound Structure | Compound Name |
|---|---|---|
| 21 | 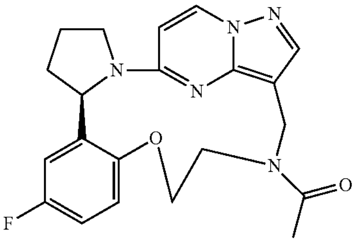 [SMILES: CC(=O)N1CCOc2ccc(F)cc2[C@H]2CCCN2c2ccn3ncc(c3n2)C1] | 1-[(6R)-9-fluoro-13-oxa-2,16,20,21,24-pentaazapentacyclo[16.5.2.$0^{2,6}$.$0^{7,12}$.$0^{21,25}$]pentacosa-1(24),7,9,11,18(25),19,22-heptaen-16-yl]ethan-1-one |
| 22 | 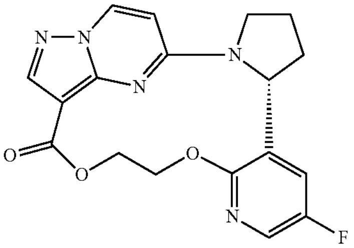 [SMILES: O=C1OCCOc2ncc(F)cc2[C@H]2CCCN2c2ccn3ncc1c3n2] | (6R)-9-fluoro-13,16-dioxa-2,11,20,21,24-pentaazapentacyclo[16.5.2.$0^{2,6}$.$0^{7,12}$.$0^{21,25}$]-pentacosa-1(24),7,9,11,18(25),19,22-heptaen-17-one |
| 23 | 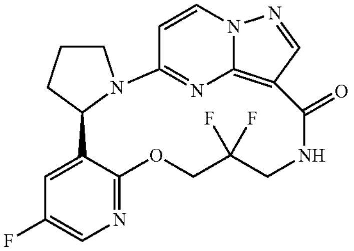 [SMILES: O=C1NCC(F)(F)COc2ncc(F)cc2[C@H]2CCCN2c2ccn3ncc1c3n2] | (6R)-9,15,15-trifluoro-13-oxa-2,11,17,21,22,25-hexaazapentacyclo[17.5.2.$0^{2,6}$.$0^{7,12}$.$0^{22,26}$]hexacosa-1(25),7,9,11,19(26),20,23-heptaen-18-one |
| 24 | 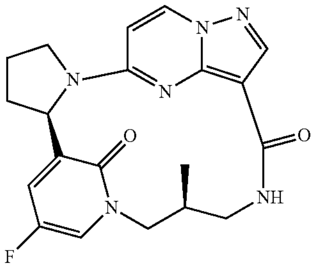 [SMILES: C[C@H]1CNC(=O)c2cnn3ccc(nc23)N2CCC[C@@H]2c2cc(F)cn(c2=O)C1] | (6R,13S)-9-fluoro-13-methyl-2,11,15,19,20,23-hexaazapentacyclo[15.5.2.$^{17,11}$.$0^{2,6}$.$0^{20,24}$]pentacosa-1(23),7,9,17(24),18,21-hexaene-16,25-dione |
| 25 | 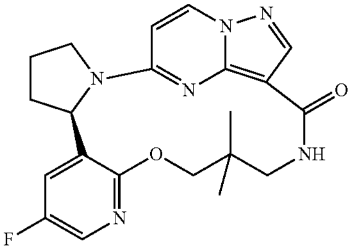 [SMILES: CC1(C)CNC(=O)c2cnn3ccc(nc23)N2CCC[C@@H]2c2cc(F)cnc2OC1] | (6R)-9-fluoro-15,15-dimethyl-13-oxa-2,11,17,21,22,25-hexaazapentacyclo[17,5.2.$0^{2,6}$.$0^{7,12}$.$0^{22,26}$]hexacosa-1(25),7,9,11,19(26),20,23-heptaen-18-one |
| 26 | 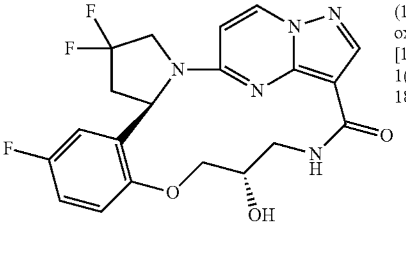 | (15S)-4,4,9-trifluoro-15-hydroxy-13-oxa-2,17,21,22.25-pentaazapentacyclo[17.5.2.$0^{2,6}$.$0^{7,12}$.$0^{22,26}$]hexacosa-1(25),7(12),8,10,19(26),20,23-heptaen-18-one |

TABLE 5-continued

| Compound No. | Compound Structure | Compound Name |
|---|---|---|
| Exemplary Trk inhibitors | | |
| 27 | 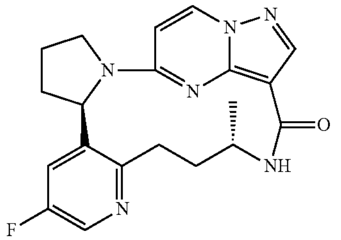 [SMILES: C[C@H]1CCc2ncc(F)cc2[C@H]2CCCN2c2ccn3ncc(c3n2)C(=O)N1] | (6R,15S)-9-fluoro-15-methyl-2,11,16,20,21,24-hexaazapentacyclo[16.5.2.$0^{2,6}$.$0^{7,12}$.$0^{21,25}$]pentacosa-1(24),7,9,11,18(25),19,22-heptaen-17-one |
| 28 | 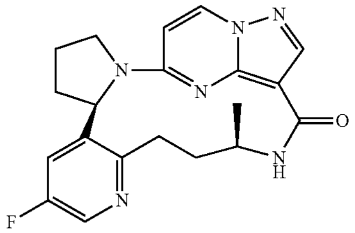 [SMILES: C[C@@H]1CCc2ncc(F)cc2[C@H]2CCCN2c2ccn3ncc(c3n2)C(=O)N1] | (6R,15R)-9-fluoro-15-methyl-2,11,16,20,21,24-hexaazapentacyclo[16.5.2.$0^{2,6}$.$0^{7,12}$.$0^{21,25}$]pentacosa-1(24),7,9,11,18(25),19,22-heptaen-17-one |

Additional examples of Trk inhibitors are described in U.S. Patent Application Ser. No. 62/080,374, International Application Publication Nos. WO 11/006074, WO 11/146336, WO 10/033941, and WO 10/048314, and U.S. Pat. Nos. 8,933,084, 8,791,123, 8,637,516, 8,513,263, 8,450,322, 7,615,383, 7,384,632, 6,153,189, 6,027,927, 6,025,166, 5,910,574, 5,877,016, and 5,844,092, each of which is herein incorporated by reference in its entirety. Additional Trk inhibitors are known in the art.

In some embodiments, a first Trk inhibitor is selected from the group consisting of: entrectinib (N-[5-(3,5-difluoro-benzyl)-1H-indazol-3-yl]-4-(4-methylpiperazin-1-yl)-2-(tetrahydro-pyran-4-ylamino)-benzamide); (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; cabozantinib ((N-(4-((6,7-Dimethoxyquinolin-4-yl)oxy)phenyl)-N'-(4-fluorophenyl)cyclpropane-1,1-dicarboxamide)); dovatinib (4-amino-5-fluoro-3-[6-(4-methylpiperazin-1-yl)-1H-benzimidazol-2-yl]quinolin-2(1H)-one mono 2-hydroxypropanoate hydrate); belizatinib (4-fluoro-N-(6-((4-(2-hydroxypropan-2-yl)piperidin-1-yl)methyl)-1-((1 s,4s)-4-(isopropylcarbamoyl)cyclohexyl)-1H-benzo[d]imidazol-2-yl)benzamide); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); PLX7486; altiratinib (N-(4-((2-(cyclopropanecarboxamido)pyridin-4-yl)oxy)-2,5-difluorophenyl)-N-(4-fluorophenyl)cyclopropane-1,1-dicarboxamide); and AZD7451 ((S)—N-(1-(5-fluoropyrimidin-2-yl)ethyl)-3-(5-isopropoxy-1H-pyrazol-3-yl)-3H-imidazo[4,5-b]pyridin-5-amine)). For example, a first Trk inhibitor can be entrectinib or S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (or a polymorph thereof).

In some embodiments, a second Trk inhibitor is a compound of Table 5, or a pharmaceutically acceptable salt thereof.

In some embodiments, a second Trk inhibitor does not include a compound selected from the group consisting of: entrectinib (N-[5-(3,5-difluoro-benzyl)-1H-indazol-3-yl]-4-(4-methylpiperazin-1-yl)-2-(tetrahydro-pyran-4-ylamino)-benzamide); (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; cabozantinib ((N-(4-((6,7-Dimethoxyquinolin-4-yl)oxy)phenyl)-N'-(4-fluorophenyl)cyclopropane-1,1-dicarboxamide)); dovatinib (4-amino-5-fluoro-3-[6-(4-methylpiperazin-1-yl)-1H-benzimidazol-2-yl]quinolin-2(1H)-one mono 2-hydroxypropanoate hydrate); belizatinib (4-fluoro-N-(6-((4-(2-hydroxypropan-2-yl)piperidin-1-yl)methyl)-1-((1 s,4s)-4-(isopropylcarbamoyl)cyclohexyl)-1H-benzo[d]imidazol-2-yl)benzamide); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); PLX7486; altiratinib (N-(4-((2-(cyclopropanecarboxamido)pyridin-4-yl)oxy)-2,5-difluorophenyl)-N-(4-fluorophenyl)cyclopropane-1,1-dicarboxamide); and AZD7451 ((S)—N-(1-(5-fluoropyrimidin-2-yl)ethyl)-3-(5-isopropoxy-1H-pyrazol-3-yl)-3H-imidazo[4,5-b]pyridin-5-amine)).

Further provided herein are pharmaceutical compositions containing one or more Trk inhibitors as provided herein with a pharmaceutically acceptable carrier. Pharmaceutical compositions containing one or more Trk inhibitors as the active ingredient can be prepared by mixing the Trk inhibitor with a pharmaceutical carrier according to conventional pharmaceutical techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared.

In some embodiments, a Trk inhibitor as provided herein can be administered as a tablet or capsule.

In some embodiments, a Trk inhibitor provided herein can be administered as a liquid formulation. For example, provided herein is a liquid formulation including:

(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the Formula I:

(I)

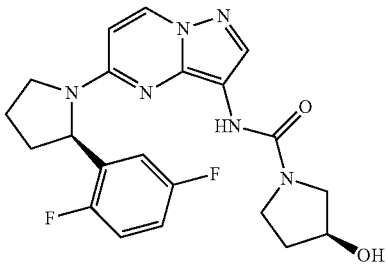

a pharmaceutically acceptable salt thereof, or a combination thereof;

(b) a solubilizing agent (e.g., a cyclodextrin such as a hydroxypropyl-β-cyclodextrin) present in an amount of about 5 wt. % to about 35 wt. %; and (c) a buffer (e.g., a citrate buffer such as sodium citrate) present in an amount of about 0.1 wt. % to about 5 wt. %;

(d) a sweetener (e.g., a sweetener comprising sucrose or an intense sweetener) present in an amount of about 30 wt. % to about 70 wt. %;

(e) a bitterness masking agent present in an amount of about 0.2 wt. % to about 0.5 wt. %; and (f) a flavoring agent present in an amount of about 0.01 wt. % to about 2 wt. %. In some embodiments, the formulation has a pH of about 3 to about 4. In some embodiments, the compound of Formula I has a concentration of about 20 mg/mL to about 30 mg/mL in the liquid formulation. Further examples of a liquid formulation can be found in U.S. Provisional Ser. Nos. 62/380,773 and 62/329,561, both of which are incorporated by reference in their entireties herein.

In some embodiments, the liquid formulation is prepared from a pharmaceutically acceptable salt of the compound of Formula I. For example, the pharmaceutically acceptable salt is a hydrogen sulfate salt. In some embodiments, the liquid formulation is prepared from a crystalline form of the compound of Formula I. For example, the crystalline form of the compound of Formula I can have the Formula I-HS:

I-HS

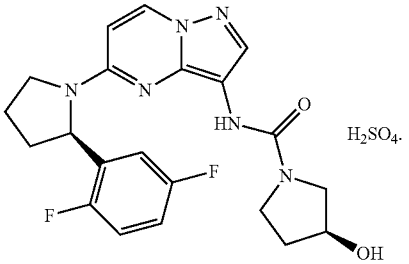

In the methods provided herein, a Trk inhibitor can be orally, subcutaneously, intraperitoneally, intravenously, or intramuscularly administered. In some examples, a Trk inhibitor can be administered in one or more doses including between about 1 mg and about 250 mg, between about 1 mg and about 200 mg, between about 1 mg and about 180 mg, between about 1 mg and about 160 mg, between about 1 mg and about 140 mg, between about 1 mg and about 120 mg, between about 1 mg and about 100 mg, between about 1 mg and about 80 mg, between about 1 mg and about 60 mg, between about 1 mg and about 40 mg, between about 1 mg and about 40 mg, between about 10 mg and about 200 mg, between about 10 mg and about 180 mg, between about 10 mg and about 160 mg, between about 10 mg and about 140 mg, between about 10 mg and about 120 mg, between about 10 mg and about 100 mg, between about 10 mg and about 80 mg, between about 10 mg and about 60 mg, between about 10 mg and about 40 mg, between about 10 mg and about 20 mg, between about 20 mg and about 200 mg, between about 20 mg and about 180 mg, between about 20 mg and about 160 mg, between about 20 mg and about 140 mg, between about 20 mg and about 120 mg, between about 20 mg and about 100 mg, between about 20 mg and about 80 mg, between about 20 mg and about 60 mg, between about 20 mg and about 40 mg, between about 40 mg and about 200 mg, between about 40 mg and about 180 mg, between about 40 mg and about 160 mg, between about 40 mg and about 140 mg, between about 40 mg and about 120 mg, between about 40 mg and about 100 mg, between about 40 mg and about 80 mg, between about 40 mg and about 60 mg, between about 60 mg and about 200 mg, between about 60 mg and about 180 mg, between about 60 mg and about 140 mg, between about 60 mg and about 120 mg, between about 60 mg and about 100 mg, between about 60 mg and about 80 mg, between about 80 mg and about 200 mg, between about 80 mg and about 180 mg, between about 80 mg and about 160 mg, between about 80 mg and about 140 mg, between about 80 mg and about 120 mg, between about 80 mg and about 100 mg, between about 90 mg and about 110 mg, between about 95 mg and about 105 mg, between about 100 mg and about 200 mg, between about 100 mg and about 180 mg, between about 100 mg and about 160 mg, between about 100 mg and about 140 mg, between about 100 mg and about 120 mg, between about 120 mg and about 200 mg, between about 120 mg and about 180 mg, between about 120 mg and about 160 mg, between about 120 mg and about 140 mg, between about 140 mg and about 200 mg, between about 140 mg and about 180 mg, between about 140 mg and about 160 mg, between about 160 mg and about 200 mg, between about 160 mg and about 200 mg, between about 160 mg and about 180 mg, or between about 180 mg and about 200 mg of the Trk inhibitor. The appropriate dose of a Trk inhibitor to be administered to a subject can be determined by a medical professional, e.g., based upon one or more of the subject's mass, the subject's condition, subject's gender, and the other diseases that the subject may have.

Multiple doses of the Trk inhibitor (e.g., any of the doses described herein) can be administered once every six months, once every five months, once every four months, once every three months, once every two months, once every six weeks, once a month, once every three weeks, once every two weeks, once a week, twice a week, three times a week, four times a week, three times a week, every other day, once a day, twice a day, or three times a day as part of a treatment. The Trk inhibitor can be self-administered (e.g., by the subject having a cancer) or can be administered by a health care professional (e.g., a physician, a nurse, a physician's assistance, or a pharmacist) as part of a treatment as described herein.

Treatments that do not Include a Trk Inhibitor as a Monotherapy and Additional Anticancer Agents and Therapies In any of the methods described herein, a treatment that does not include a Trk inhibitor (e.g., a first Trk inhibitor as described herein) (e.g., entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy can be, e.g., a treatment that includes another anticancer agent or anticancer therapy. In some embodiments, a treatment that does not include a Trk inhibitor as a monotherapy can be, for example, a treatment that includes one or more of: surgery, radiation therapy, chemotherapy, immunotherapy, hormone therapy, small molecule drugs targeting other kinases in a Trk-signaling pathway, recombinant antibodies, and stem cell transplant. In some embodiments, an additional anticancer agent is selected from the group consisting of: chemotherapy, immunotherapy, hormone therapy, small molecule drugs targeting other kinases in a Trk-signaling pathway, and recombinant antibodies. In some embodiments, an anticancer therapy is selected from the group consisting of: surgery, radiation therapy, and stem cell transplant.

In some embodiments, a treatment that does not include a Trk inhibitor (e.g., a first Trk inhibitor) as a monotherapy can be, e.g., a combination treatment that includes (i) one or more of surgery, radiation therapy, chemotherapy, immunotherapy, hormone therapy, small molecule drugs targeting other kinases in a Trk-signaling pathway, recombinant antibodies, and stem cell transplant, and (ii) one or more Trk inhibitors (e.g., any of the Trk inhibitors described herein). In some embodiments, a treatment that does not include a Trk inhibitor as a monotherapy can be, e.g., a treatment that includes two or more Trk inhibitors (e.g., any of the Trk inhibitors described herein).

In some embodiments, a treatment that does not include a first Trk inhibitor as a monotherapy can be, e.g., a treatment that includes a second Trk inhibitor as a monotherapy. In some embodiments, a treatment that does not include a first Trk inhibitor as a monotherapy can be, e.g., a treatment that includes one or more compounds of Table 5, or a pharmaceutically acceptable salt thereof.

Non-limiting examples of surgery include, e.g., open surgery or minimally invasive surgery. Surgery can include, e.g., removing an entire tumor, debulking of a tumor, or removing a tumor that is causing pain or pressure in the subject. Methods for performing open surgery and minimally invasive surgery on a subject having a cancer are known in the art.

Non-limiting examples of radiation therapy include external radiation beam therapy (e.g., external beam therapy using kilovoltage X-rays or megavoltage X-rays) or internal radiation therapy. Internal radiation therapy (also called brachytherapy) can include the use of, e.g., low-dose internal radiation therapy or high-dose internal radiation therapy. Low-dose internal radiation therapy includes, e.g., inserting small radioactive pellets (also called seeds) into or proximal to a cancer tissue in the subject. High-dose internal radiation therapy includes, e.g., inserting a thin tube (e.g., a catheter) or an implant into or proximal to a cancer tissue in the subject, and delivering a high dose of radiation to the thin tube or implant using a radiation machine. Methods for performing radiation therapy on a subject having a cancer are known in the art.

In some embodiments provided herein, an additional anticancer agent is administered. Non-limiting examples of such additional anticancer agents are as follows.

Non-liming examples of chemotherapy include, e.g., an alkylating agent, an antimetabolite, an anti-microtubule agent, a topoisomerase inhibitor, and a cytotoxic antibiotic. Examples of alkylating agents include, e.g., nitrogen mustards (e.g., cyclophosphamide, mechlorethamine or mustine, uramustine or uracil mustard, melphalan, chlorambucil, ifosfamide, and bendamustine), nitrosoureas (e.g., carmustine, lomustine, and streptozocin), and alkyl suflonates (e.g., busulfan). Additional examples of alkylating agents include, e.g., cisplatin, carboplatin, nedaplatin, oxaliplatin, satraplatin, triplatin tetranitrate, procarbazine, altretamine, dacarbazine, mitozolomide, and temozolomide. Non-limiting examples of anti-metabolites include fluorouracil, cladribine, capecitabine, mercaptopurine, pemetrexed, fludarabine, gemcitabine, hydroxyurea, methotrexate, nelarabine, clofarabine, cytarabine, decitabine, pralatrexate, floxuridine, and thioguanine. Non-limiting examples of anti-microtubule agents include colchicine, dolastatin 15, nocodazole, paclitaxel, podophyllotoxin, rhizoxin, vinblastine, vincristine, vindesine, and vinorelbine. Non-limiting examples of topoisomerase inhibitors include camptosar, hycamtin, irinotecan, topotecan, voreloxin, camptothecin, SN-38, gimatecan, belotecan, lurtotecan, exatecan, diflometecan, S 39625, NSC 314622, NSC 706744, NSC 725776, NSC 724998, topovale (ARC-111), endotecarin (ED-709), BMS-250749, and indenoisoquinoline. Non-limiting examples of cytotoxic antibiotics include bleomycin, dactinomycin, daunorubicin, plicamycin, mitomycin, mitoxantrone, daunorubicin, doxorubicin, epirubicin, idarubicin, and mitoxantrone. Additional examples of chemotherapy are known in the art.

Non-limiting examples of immunotherapy include adoptive cell transfer, a cytokine, a cancer vaccine, bispecific T cell engagers (e.g., Huehls et al., *Immunol. Cell Biol.* 93:290-296, 2015), and *Bacillus* Calmette-Guérom. Non-limiting examples of adoptive cell transfer include tumor infiltrating lymphocytes (Demaria et al., *Clin. Cancer Res.* 7:3025-3030, 2001), sensitized B cells (Li et al., *J. Immunol.* 183:3195-3203, 2009), sensitized T cells (Wang et al., *Breast Cancer Res. Treatment* 134:61-70, 2012), antigen-loaded dendritic cells (Ponsaerts et al., *Clin. Exp. Immunol.* 134:378-384, 2003), chimeric antigen receptor-T cells (CAR-T cells) (Hinrichs et al., *Immunol. Rev.* 257:56-71, 2014), artificial antigen presenting cells (aAPCs) (e.g., Turtle et al., *Cancer J.* 16:374-381, 2010), immunomodulated NK cells (e.g., Flannery et al., *Eur. J. Cancer Clin. Oncol.* 20:791-798, 1984), and T cells genetically engineered with T cell receptors (e.g., Essand et al., *J. Intern Med.* 273:166-181, 2013). Additional examples of immunotherapy are known in the art.

Non-limiting examples of hormone therapy include drugs that block estrogen, drugs that lower estrogen levels, progesterone-like drugs, and anti-androgen drugs. Examples of drugs that block estrogen include, e.g., vorozole, testolactone, formestane, tamoxifen, clomifene, arzooxifene, clomiphene, anastrozole, lentrozole, exemestane, raloxifene, toremifene, and fulvestrant. Examples of anti-progestrone agent of mifepristone and aglepristone. Examples of drugs that are anti-androgen drugs include, e.g., bicalutamide, flutamide, nilutamide, and enzalutamide. Additional examples of hormone therapy are known in the art.

Non-limiting examples of small molecule drugs targeting other kinases in a Trk-signaling pathway including inhibitors of PI3K, Akt, Ras, Raf, MEK, and ERK. Examples of a PI3K include A-769662, acalisib (GS-9820 or CAL-120), afuresertib (GSK-2110183), AMG-319, ARQ-092, AS-252424, AS-604850, AS-605240, AZD6482, BAY 80-6940, BEZ235 (NVP-BEZ235), BGT-226, buparlisib (BKM120), BYL719, CAL-101, CAY10505, CC-115, CC-223, CH5132799, copanlisib (BAY 80-6946), CUDC-907, CZC24832, D-106669, D-116883, D-87503, deguelin, DS-3078a, duvelisib (IPI-145), everolimus (RAD001), GDC-0032, GDC-0349 (RG7603), GDC-0980 (RG7422), GSK1059615, GSK2126458, GSK-2141795, HS-173, IC-87114, idelalisib (CAL-101 or GS-1101), INCB040093, INK1117, LY2780301, LY294002 (SF1101), MK-2206, MLN0128, NU7441, OSI-027, panulisib, PF-04691502, PF376304, phenformin hydrochloride, PI-103, pictilisib (GDC-0941 or RG7321), PIK-124, PIK-294, PIK-39, PIK-90, PIK-93, PIK-402, PKI-587, PP121, PWT33597, PX-866, quercetin (sophoretin), ridaforolimus, rigosertib (ON 01910.Na), RP-6539, SAR245408 (XL147), SAR260301, SF1126, SF1326, sirolimus, staurosporine, TASP0415914, temsirolimus, TG100-115, TGR-1202, TGX221, theophylline, triciribine, VS-5584, wortmannin, XL-765 (SAR245409), and ZSTK474.

Non-limiting examples of Akt inhibitors include A-443654, A-674563, afuresertib (GSK-2110183), API-1, ARQ-094, AT7867, AZ7328, AZD-5363, CCT128930, DC120, deguelin, GDC-0068, GSK-2141795, GSK-690693, ISC-4, KP372-1, LY2780301, LY294002, Y294005, MK-2206, oleandrin (PBI-05204), palomid 529, perifosine, PF-AKT400, PHT-427, PX-316, SC66, semaxanib, SH-5, SR13668, temsirolimus, trametinib, and triciribine.

Non-limiting examples of Ras inhibitors include Kobe2602, manumycin A, L-744,832 dihydrochloride, farnesyl thiosalicylic acid, FTI-276 trifluoroacetate salt, SCH 51344, tipifarnib, and K-ras(G12C) inhibitor 12, and K-ras(G12C) inhibitor 6. Non-limiting examples of Raf inhibitors include sorafenib (Nexavar or BAY 43-9006), GDC0879, RAF265, dabrafenib (GSK2118436), vemurafenib (PLX-4032), SB590885, PLX-4720, encorafenib (LGX818), LY3009120, AZ 628, CEP-32496, TAK-632, ZM 336372, NVP-BHG712, and GW5074.

Non-limiting examples of MEK inhibitors include CI-1040, trametinib (GSK1120212), selumetinib (AZD6244), binimetinib (MEK162, ARRY-162, or ARRY-438162), PD-325901, cobimetinib (XL518), CI-1040, PD035901, U0126, PD184352 (CI-1040), PD98059, BIX 02189, pimasertib (AS-703026), BIX 02188, TAK-733, AZD8330, PD318088, honokiol, SL-327, refametinib (RDEAI19 or Bay 86-9766), GDC-0623, and BI-847325.

Non-limiting examples of ERK inhibitors include SCH772984, XMD8-92, FR 180204, GDC-0994, ERK5-IN-1, ulixertinib (BVD-523 or VRT752271), FR180204, BIX 02189, pluripotin, TCS ERK lie, TMCB, XMD 8-92, U0126, trametinib, and selumetinib.

Non-limiting examples of recombinant antibodies include monoclonal antibodies, bispecific antibodies (e.g., BiTE® antibodies), Fab, Fab2, Fab3, scFv, Bis-scFv, minibody, triabody, diabody, tetrabody, VhH domain, V-NAR domain, IgNAR, and camel Ig. Additional examples of a recombinant antibody (e.g., a recombinant human antibody) are IgG (e.g., IgG1, IgG2, IgG3, or IgG4), IgM, IgE, IgD, and IgA. Non-limiting examples of recombinant antibodies include human antibodies, humanized antibodies, or chimeric antibodies. Non-limiting examples of recombinant antibodies include antibodies that specifically bind to NGF.

Non-limiting examples of recombinant antibodies that bind specifically to NGF include tanezumab, futuximab, MNAC13, fasinumab (REGN475), mAb NGF30 (e.g., Saragovi et al., *J. Biol. Chem.* 273:34933-34940, 1998), ME20.4, and ME82.11. Additional antibodies that bind specifically to NGF are described, e.g., in U.S. Pat. Nos. 8,106,167; 8,148,107; and 8,911,734; U.S. Patent Application Publication Nos. 2009/0041717, 2011/0268725, and 2014/0227287; International Patent Application Publication Nos. WO 06/131051 and WO 12/024650; and European Patent No. 18646451.

Additional examples of recombinant antibodies include, e.g., 3F8, 8H9, abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, atezolizumab, bavituximab, bectumomab, belimumab, besilesomab, bevacizumab, bivatuzumab mertansine, blinatumomab, brentuximab, brontictuzumab, cantuzumab mertansine, cantuzumab ravansine, capromab pendetide, carlumab, catumaxomab, cBR96-doxorubicin immunoconjugate, CC49, cetuximab, Ch. 14.18, citatuzumab bogatox, cixutumumab, clivatuzumab tetraxetan, codrituzumab, coltuximab ravtansine, conatumumab, dacetuzumab, dalotuzumab, daratumumab, demcizumab, denintuzumab mafodotin, denosumab, derlotuximab biotin, detumomab, dinutuximab, drozitumab, durvalumab, dusigitumab, ecromeximab, edrecolomab, elgemtumab, elotuzumab, emactuzumab, emibetuzumab, enavatuzumab, enfortunmab vedotin, enoblituzumab, ensituximab, epratuzumab, ertumaxomab, etaracizumab, farletuzumab, FBTA05, ficlatuzumab, figitumumab, flanvotumab, galiximab, ganitumab, gemtuzumab ozogamicin, girentuximab, glembatumumab vedotin, ibritumomab, icrucumab, igovomab, IMAB362, imalumab, imgatuzumab, indatuzimab ravtansine, indusatumab vedotin, intetumumab, inotuzumab ozogamicin, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, milatuzumab, mirvetuximab soravtansine, mitumomab, mogamulizumab, moxetumomab pasudotox, nacolomab tafenatox, naptumomab estafenatox, narnatumab, necitumumab, nesvacumab, nimotuzumab, nivolumab, nofetumomab merpentan, obinutuzumab, ocaratuzumab, ofatumumab, olaratumab, onartuzumab, ontuxizumab, oportuzumab monatox, oregovomab, otlertuzumab, panitumumab, pankomab, parsatuzumab, pasotuxizumab, patritumab, pembrolizumab, pemtumomab, pertuzumab, pidilizumab, pinatuzumab vedotin, pintumomab, polatuzumab vedotin, pritumumab, racotumomab, radretumab, ramucirumab, rilotumumab, rituximab, robatumumab, sacituzumab govitecan, samalizumab, satumomab pendetide, seribantumab, sibrotuzumab, SGN-CD19A, SGN-CD33A, siltuximab, sofituzumab vedotin, tabalumab, tacatuzumab tetraxetan, taplitumomab paptox, tarextumab, tenatumomab, teprotumumab, TGN1412, ticilimumab (tremelimumab), tigatuzumab, TNX-650, tositumomab, tovetumab, trastuzumab, TRBS07, tremelimumab, tucotuzumab celmoleukin, ublituximab, ulocuplumab, urelumab, vandortuzumab vedotin, vantictumab, vanucizumab, veltuzumab, volociximab, vorsetuzumab mafodotin, votumumab, zalutumamab, zanolimumab, and zatuximab.

Non-limiting examples of stem cell transplant include autologous stem cell transplant, allogeneic stem cell transplant, and syngeneic stem cell transplant. Methods for performing autologous stem cell transplant are described in, e.g., Perales et al., *Biol. Blood Marrow Transplant.*, e-published ahead of print, 2015; and Isdori et al., *World J. Stem Cells* 7:1039-1046, 2015. Methods for performing allogeneic stem cell transplant is described in, e.g., Imamura et al.,

*Exp. Hematol. Oncol.* 4:20, 2015; Hobbs et al., *J. Clin. Med.* 19:488-503, 2015; and Bensinger et al., *Stem Cells* 14:90-105, 1996. Methods for performing syngeneic stem cell transplant are described in, e.g., Engman et al., *Clin. Adv. Heamtol. Oncol.* 7:321-323, 2009; and Richard et al., *Br. J. Haematol.* 117:245-246, 2002. Additional methods for isolating stem cells and administering stem cells to a subject are known in the art.

In some examples, the subject is hospitalized or receives a treatment not including a Trk inhibitor as a monotherapy on in inpatient basis. In other examples, the subject is treated or receives a treatment not including a Trk inhibitor as a monotherapy on an outpatient basis.

In some examples, the subject is hospitalized or receives a treatment including one or more compounds of Table 5, or a pharmaceutically acceptable salt thereof, and an additional anticancer agent or anticancer therapy including one or more compounds of Table 5, or a pharmaceutically acceptable salt thereof, on an inpatient basis. In other examples, the subject is treated or receives a treatment including one or more compounds of Table 5, or a pharmaceutically acceptable salt thereof, and an additional anticancer agent or a treatment including one or more compounds of Table 5, or a pharmaceutically acceptable salt thereof, on an outpatient basis.

Methods of Treating a Subject Having a Cancer

Provided herein are methods of treating a subject having a cancer (e.g., any of the cancers described herein) that include identifying a subject having a cancer cell that has at least one point mutation in a NTRK gene that results in the expression of a Trk protein including a mutation at one or more of the amino acid positions shown in Tables 1, 2, or 3, and administering to the identified subject a treatment that does not include a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy (e.g., any of treatments that do not include a Trk inhibitor as a monotherapy described herein).

Also provided herein are methods of treating a subject having a cancer (e.g., any of the cancers described herein) and identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3) that include administering to the identified subject a treatment that does not include a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy (e.g., any of treatments that do not include a Trk inhibitor as a monotherapy described herein).

Also provided herein are methods of treating a subject that include administering a therapeutically effective amount of a treatment that does not include a Trk inhibitor (e.g., a first Trk inhibitor) as a monotherapy, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and administering to the identified subject a treatment that includes one or more compounds of Table 5, or a pharmaceutically acceptable salt thereof.

Also provided herein are methods of treating a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); and administering to the identified subject a treatment that includes one or more compounds of Table 5, or a pharmaceutically acceptable salt thereof, and another anticancer agent (e.g., any one or more of the anticancer agents described herein) or anticancer therapy (e.g., any one or more of the anticancer therapies provided herein.

Also provided herein are methods of treating a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3), that include administering to the subject a treatment that includes one or more compounds of Table 5, or a pharmaceutically acceptable salt thereof.

Also provided herein are methods of treating a subject identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3), that include administering to the subject a treatment that includes one or more compounds of Table 5, or a pharmaceutically acceptable salt thereof, and another anticancer agent (e.g., any one or more of the another anticancer agents described herein) or anticancer therapies (e.g., any one or more of the anticancer therapies described herein).

Also provided herein are methods of treating a subject that include administering a therapeutically effective amount of a treatment that includes one or more compounds of Table 5, or a pharmaceutically acceptable salt thereof, to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject that include administering a therapeutically effective amount of a treatment that includes one or more compounds of Table 5, or a pharmaceutically acceptable salt thereof, and another anticancer agent (e.g., any one or more of the anticancer agents described herein) or anticancer therapies (e.g., any one or more of the anticancer therapies described herein), to a subject having a clinical record that indicates that the subject has a cancer cell that has at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include (a) administering one or more doses Trk inhibitor (e.g., a first Trk inhibitor, such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3), and (c) administering a different Trk inhibitor or a treatment that does not include the Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) determining whether a cancer cell in a sample obtained from a subject having a cancer and previously administered one or more doses of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate), has at least one point mutation in a NTRK gene that results in the expression of a Trk protein including a mutation at one or more amino acid positions (e.g., a mutation at one or more of the amino acid positions shown in Tables 1, 2, or 3); (b) administering a different Trk inhibitor than that administered in step (a) or a treatment that does not include the Trk inhibitor of step (a) as a monotherapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the Trk inhibitor of step (a) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3). In some embodiments, the different Trk inhibitor is a second Trk inhibitor (e.g., a compound of Table 5 or a pharmaceutically acceptable salt thereof).

Also provided herein are methods of treating a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering a treatment including one or more doses of a second Trk inhibitor to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering a treatment including one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering a treatment including one or more compounds of Table 5, or a pharmaceutically acceptable salt thereof, and another anticancer agent or anticancer therapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more of the amino acid positions shown in Tables 1, 2, or 3); (b) administering a treatment that includes one or more doses of a second Trk inhibitor to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more of the amino acid positions shown in Tables 1, 2, or 3); (b) administering a treatment that includes one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

Also provided herein are methods of treating a subject having a cancer, that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more of the amino acid positions shown in Tables 1, 2, or 3); (b) administering a treatment that includes one or more compounds of Table 5, or a pharmaceutically acceptable salt thereof, and another anticancer agent or anticancer therapy to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering additional doses of the first Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

In some embodiments, the first Trk inhibitor of step (a) is selected from the group consisting of: entrectinib (N-[5-(3,5-difluoro-benzyl)-1H-indazol-3-yl]-4-(4-methylpiperazin-1-yl)-2-(tetrahydro-pyran-4-ylamino)-benzamide); (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; cabozantinib ((N-(4-((6,7-Dimethoxyquinolin-4-yl)oxy)phenyl)-N'-(4-fluorophenyl)cyclopropane 1,1-dicarboxamide)); dovatinib (4-amino-5-fluoro-3-[6-(4-methylpiperazin-1-yl)-1H-benzimidazol-2-yl]quinolin-2(1H)-one mono 2-hydroxypropanoate hydrate); belizatinib (4-fluoro-N-(6-((4-(2-hydroxypropan-2-yl)piperidin-1-yl)methyl)-1-((1 s,4s)-4-(isopropylcarbamoyl)cyclohexyl)-1H-benzo[d]imidazol-2-yl)benzamide); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); PLX7486; altiratinib (N-(4-((2-(cyclopropanecarboxamido)pyridin-4-yl)oxy)-2,5-difluorophenyl)-N-(4-fluorophenyl)cyclopropane-1,1-dicarboxamide); AZD7451 ((S)—N-(1-(5-fluoropyrimidin-2-yl)ethyl)-3-(5-isopropoxy-1H-pyrazol-3-yl)-3H-imidazo[4,5-b]pyridin-5-amine). For example, the first Trk inhibitor can be entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (or a polymorph thereof).

In some embodiments, a second Trk inhibitor is a compound of Table 5, or a pharmaceutically acceptable salt thereof. For example, the second Trk inhibitor can be selected from the group consisting of:

(R)—N-(6-(2-(2,5-difluorophenyl)pyrrolidin-1-yl)imidazo[1,2-b]pyridazin-3-yl)-3-hydroxyazetidine-1-carboxamide;

(R)-3-(6-(2-(2,5-difluorophenyl)pyrrolidin-1-yl)imidazo[1,2-b]pyridazin-3-yl)-1,1-dimethylurea;

(R)-1-(6-(2-(2,5-difluorophenyl)pyrrolidin-1-yl)imidazo[1,2-b]pyridazin-3-yl)urea;

(R)-1-(6-(2-(2,5-difluorophenyl)pyrrolidin-1-yl)imidazo[1,2-b]pyridazin-3-yl)-3-methylurea;

(R)-3-(6-(2-(2,5-difluorophenyl)pyrrolidin-1-yl)imidazo[1,2-b]pyridazin-3-yl)-1-(2-hydroxyethyl)-1-methylurea;

(R)—N-(6-(2-(2,5-difluorophenyl)pyrrolidin-1-yl)imidazo[1,2-b]pyridazin-3-yl)-3-hydroxy-3-methylazetidine-1-carboxamide;

or a pharmaceutically acceptable salt thereof. In some embodiments, the second Trk inhibitor is selected from the group consisting of:

(R)—N-(5-(2-(2,5-difluorophenyl)pyrrolidin-1-yl)pyrazolo[1,5-a]pyrimidin-3-yl)-3-hydroxyazetidine-1-carboxamide;

(R)-3-(5-(2-(2,5-difluorophenyl)pyrrolidin-1-yl)pyrazolo[1,5-a]pyrimidin-3-yl)-1,1-dimethylurea;

(R)—N-(5-(2-(2-chloro-5-fluorophenyl)pyrrolidin-1-yl)pyrazol o[1,5-a]pyrimidin-3-yl)-3-hydroxyazetidine-1-carboxamide;

(R)—N-(5-(2-(2-chloro-5-fluorophenyl)pyrrolidin-1-yl)pyrazolo[1,5-a]pyrimidin-3-yl)-3-hydroxy-3-methylazetidine-1-carboxamide;

(R)—N-(5-(2-(3-fluorophenyl)pyrrolidin-1-yl)pyrazolo[1,5-a]pyrimidin-3-yl)-3-hydroxyazetidine-1-carboxamide;

or a pharmaceutically acceptable salt thereof. In some embodiments, the second Trk inhibitor is selected from the group consisting of:

(R)-5-(2-(2,5-difluorophenyl)pyrrolidin-1-yl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-methoxypyrazolo[1,5-a]pyrimidine-3-carboxamide;

(R)-5-(2-(5-fluoropyridin-3-yl)pyrrolidin-1-yl)-N-(1-methylcyclopropyl)pyrazolo[1,5-a]pyrimidine-3-carboxamide;

or a pharmaceutically acceptable salt thereof. In some embodiments, the second Trk inhibitor is selected from the group consisting of:

(6R)-9-fluoro-13-oxa-2,11,17,21,22,25-hexaazapentacyclo[$17.5.2.0^{2,6}.0^{7,12}.0^{22,26}$]-hexacosa-1(25),7,9,11,19(26),20,23-heptaen-18-one;

(6R,15R)-9-fluoro-15-hydroxy-13-oxa-2,11,17,21,22,25-hexaazapentacyclo-[$17.5.2.0^{2,6}.0^{7,12}.0^{22,26}$]-hexacosa-1(25),7,9,11,19(26),20,23-heptaen-18-one;

(6R)-9-fluoro-13-oxa-2,11,18,22,23,26-hexaazapentacyclo[$18.5.2.0^{2,6}.0^{7,12}.0^{23,27}$]-heptacosa-1(26),7,9,11,20(27),21,24-heptaen-19-one;

(6R)-9-fluoro-13-oxa-2,17,21,22,25-pentaazapentacyclo[$17.5.2.0^{2,6}.0^{7,12}.0^{22,26}$]hexacosa-1(25), 7,9,11,19(26),20,23-heptaen-18-one;

(6R)-12-oxa-2,16,20,21,24,26-hexaazapentacyclo[16.5.2.$^{17,11}$.0$^{2,6}$.0$^{21,25}$]-hexacosa-1(24), 7(26), 8,10,18(25), 19,22-heptaen-17-one;

1-[(6R)-9-fluoro-13-oxa-2,16,20,21,24-pentaazapentacyclo[16.5.2.0$^{2,6}$.0$^{7,12}$.0$^{21,25}$]pentacosa-1(24), 7,9,11,18(25), 19,22-heptaen-16-yl]ethan-1-one;

(6R)-9-fluoro-13,16-dioxa-2,11,20,21,24-pentaazapentacyclo[16.5.2.0$^{2,6}$.0$^{7,12}$.0$^{21,25}$]-pentacosa-1(24), 7,9,11,18(25), 19,22-heptaen-17-one;

(6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(6R,13 S)-9-fluoro-13-methyl-2,11,15,19,20,23-hexaazapentacyclo[15.5.2.$^{17,11}$.0$^{2,6}$.0$^{20,24}$]pentacosa-1(23),7,9,17(24), 18,21-hexaene-16,25-dione;

(6R)-9-fluoro-15,15-dimethyl-13-oxa-2,11,17,21,22,25-hexaazapentacyclo[17.5.2.0$^{2,6}$.0$^{7,12}$.0$^{22,26}$]hexacosa-1(25), 7,9,11,19(26),20,23-heptaen-18-one;

(15S)-4,4,9-trifluoro-15-hydroxy-13-oxa-2,17,21,22.25-pentaazapentacyclo[17.5.2.0$^{2,6}$.0$^{7,12}$.0$^{22,26}$]hexacosa-1(25),7(12),8,10,19(26),20,23-heptaen-18-one;

(6R,15S)-9-fluoro-15-methyl-2,11,16,20,21,24-hexaazapentacyclo[16.5.2.0$^{2,6}$.0$^{7,12}$.0$^{21,25}$]pentacosa-1 (24),7,9,11,18(25), 19,22-heptaen-17-one;

(6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25), 19,22-heptaen-17-one;

or a pharmaceutically acceptable salt thereof.

In some embodiments of the methods provided herein, the first Trk inhibitor is entrectinib (N-[5-(3,5-difluoro-benzyl)-1H-indazol-3-yl]-4-(4-methylpiperazin-1-yl)-2-(tetrahydro-pyran-4-ylamino)-benzamide); and the second Trk inhibitor is selected from the group consisting of:

(R)—N-(6-(2-(2,5-difluorophenyl)pyrrolidin-1-yl)imidazo[1,2-b]pyridazin-3-yl)-3-hydroxyazetidine-1-carboxamide;

(R)-3-(6-(2-(2,5-difluorophenyl)pyrrolidin-1-yl)imidazo[1,2-b]pyridazin-3-yl)-1,1-dimethylurea;

(R)-1-(6-(2-(2,5-difluorophenyl)pyrrolidin-1-yl)imidazo[1,2-b]pyridazin-3-yl)urea;

(R)-1-(6-(2-(2,5-difluorophenyl)pyrrolidin-1-yl)imidazo[1,2-b]pyridazin-3-yl)-3-methylurea;

(R)-3-(6-(2-(2,5-difluorophenyl)pyrrolidin-1-yl)imidazo[1,2-b]pyridazin-3-yl)-1-(2-hydroxyethyl)-1-methylurea;

(R)—N-(6-(2-(2,5-difluorophenyl)pyrrolidin-1-yl)imidazo[1,2-b]pyridazin-3-yl)-3-hydroxy-3-methylazetidine-1-carboxamide;

or a pharmaceutically acceptable salt thereof. In some embodiments of the methods provided herein, the first Trk inhibitor is entrectinib (N-[5-(3,5-difluoro-benzyl)-1H-indazol-3-yl]-4-(4-methylpiperazin-1-yl)-2-(tetrahydro-pyran-4-ylamino)-benzamide); and the second Trk inhibitor is selected from the group consisting of:

(R)—N-(5-(2-(2,5-difluorophenyl)pyrrolidin-1-yl)pyrazolo[1,5-a]pyrimidin-3-yl)-3-hydroxyazetidine-1-carboxamide;

(R)-3-(5-(2-(2,5-difluorophenyl)pyrrolidin-1-yl)pyrazolo[1,5-a]pyrimidin-3-yl)-1,1-dimethylurea;

(R)—N-(5-(2-(2-chloro-5-fluorophenyl)pyrrolidin-1-yl)pyrazolo[1,5-a]pyrimidin-3-yl)-3-hydroxyazetidine-1-carboxamide;

(R)—N-(5-(2-(2-chloro-5-fluorophenyl)pyrrolidin-1-yl)pyrazolo[1,5-a]pyrimidin-3-yl)-3-hydroxy-3-methyl azetidine-1-carboxamide;

(R)—N-(5-(2-(3-fluorophenyl)pyrrolidin-1-yl)pyrazolo[1,5-a]pyrimidin-3-yl)-3-hydroxyazetidine-1-carboxamide;

or a pharmaceutically acceptable salt thereof. In some embodiments of the methods provided herein, the first Trk inhibitor is entrectinib (N-[5-(3,5-difluoro-benzyl)-1H-indazol-3-yl]-4-(4-methylpiperazin-1-yl)-2-(tetrahydro-pyran-4-ylamino)-benzamide); and the second Trk inhibitor is selected from the group consisting of:

(R)-5-(2-(2,5-difluorophenyl)pyrrolidin-1-yl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-methoxypyrazolo[1,5-a]pyrimidine-3-carboxamide;

(R)-5-(2-(5-fluoropyridin-3-yl)pyrrolidin-1-yl)-N-(1-methylcyclopropyl)pyrazolo[1,5-a]pyrimidine-3-carboxamide;

or a pharmaceutically acceptable salt thereof. In some embodiments of the methods provided herein, the first Trk inhibitor is entrectinib (N-[5-(3,5-difluoro-benzyl)-1H-indazol-3-yl]-4-(4-methylpiperazin-1-yl)-2-(tetrahydro-pyran-4-ylamino)-benzamide); and the second Trk inhibitor is selected from the group consisting of:

(6R)-9-fluoro-13-oxa-2,11,17,21,22,25-hexaazapentacyclo[17.5.2.0$^{2,6}$.0$^{7,12}$0.0$^{22,26}$]-hexacosa-1(25),7,9,11,19(26), 20,23-heptaen-18-one;

(6R,15R)-9-fluoro-15-hydroxy-13-oxa-2,11,17,21,22,25-hexaazapentacyclo-[17.5.2.0$^{2,6}$.0$^{7,12}$.0$^{22,26}$]-hexacosa-1(25),7,9,11,19(26),20,23-heptaen-18-one;

(6R)-9-fluoro-13-oxa-2,11,18,22,23,26-hexaazapentacyclo[18.5.2.0$^{2,6}$.0$^{7,12}$.0$^{23,27}$]-heptacosa-1(26),7,9,11,20(27), 21,24-heptaen-19-one;

(6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20, 23-heptaen-18-one;

(6R)-12-oxa-2,16,20,21,24,26-hexaazapentacyclo[16.5.2.$^{17,}$$_{11}$.0$^{2,6}$.0$^{21,25}$]-hexacosa-1(24),7(26),8,10,18(25), 19,22-heptaen-17-one;

1-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25), 19,22-heptaen-16-yl]ethan-1-one;

(6R)-9-fluoro-13,16-dioxa-2,11,20,21,24-pentaazapentacyclo[16.5.2.0$^{2,6}$.0$^{7,12}$.0$^{21,25}$]-pentacosa-1(24), 7,9,11,18(25), 19,22-heptaen-17-one;

(6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9,11, 19(26),20,23-heptaen-18-one;

(6R,13 S)-9-fluoro-13-methyl-2,11,15,19,20,23-hexaazapentacyclo[15.5.2.$^{17,11}$.0$^{2,6}$.0$^{20,24}$]pentacosa-1 (23),7,9, 17(24),18,21-hexaene-16,25-dione;

(6R)-9-fluoro-15,15-dimethyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(15S)-4,4,9-trifluoro-15-hydroxy-13-oxa-2,17,21,22.25-pentaazapentacyclo[17.5.2.0$^{2,6}$.0$^{7,12}$.0$^{22,26}$]hexacosa-1(25),7(12),8,10,19(26),20,23-heptaen-18-one;

(6R,15S)-9-fluoro-15-methyl-2,11,16,20,21,24-hexaazapentacyclo[16.5.2.0$^{2,6}$.0$^{7,12}$.0$^{21,25}$]pentacosa-1(24), 7,9, 11,18(25), 19,22-heptaen-17-one;

(6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9, 11,18(25), 19,22-heptaen-17-one;

or a pharmaceutically acceptable salt thereof.

In some embodiments of the methods provided herein, the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and the second Trk inhibitor is selected from the group consisting of:

(R)—N-(6-(2-(2,5-difluorophenyl)pyrrolidin-1-yl)imidazo[1,2-b]pyridazin-3-yl)-3-hydroxyazetidine-1-carboxamide;

(R)-3-(6-(2-(2,5-difluorophenyl)pyrrolidin-1-yl)imidazo[1,2-b]pyridazin-3-yl)-1,1-di methylurea;

(R)-1-(6-(2-(2,5-difluorophenyl)pyrrolidin-1-yl)imidazo[1,2-b]pyridazin-3-yl)urea;

(R)-1-(6-(2-(2,5-difluorophenyl)pyrrolidin-1-yl)imidazo[1,2-b]pyridazin-3-yl)-3-methylurea;

(R)-3-(6-(2-(2,5-difluorophenyl)pyrrolidin-1-yl)imidazo[1,2-b]pyridazin-3-yl)-1-(2-hydroxyethyl)-1-methylurea;

(R)—N-(6-(2-(2,5-difluorophenyl)pyrrolidin-1-yl)imidazo[1,2-b]pyridazin-3-yl)-3-hydroxy-3-methylazetidine-1-carboxamide;

or a pharmaceutically acceptable salt thereof. In some embodiments of the methods provided herein, the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and the second Trk inhibitor is selected from the group consisting of:

(R)—N-(5-(2-(2,5-difluorophenyl)pyrrolidin-1-yl)pyrazolo[1,5-a]pyrimidin-3-yl)-3-hydroxyazetidine-1-carboxamide;

(R)-3-(5-(2-(2,5-difluorophenyl)pyrrolidin-1-yl)pyrazolo[1,5-a]pyrimidin-3-yl)-1,1-dimethylurea;

(R)—N-(5-(2-(2-chloro-5-fluorophenyl)pyrrolidin-1-yl)pyrazolo[1,5-a]pyrimidin-3-yl)-3-hydroxyazetidine-1-carboxamide;

(R)—N-(5-(2-(2-chloro-5-fluorophenyl)pyrrolidin-1-yl)pyrazolo[1,5-a]pyrimidin-3-yl)-3-hydroxy-3-methylazetidine-1-carboxamide;

(R)—N-(5-(2-(3-fluorophenyl)pyrrolidin-1-yl)pyrazolo[1,5-a]pyrimidin-3-yl)-3-hydroxyazetidine-1-carboxamide;

or a pharmaceutically acceptable salt thereof. In some embodiments of the methods provided herein, the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and the second Trk inhibitor is selected from the group consisting of:

(R)-5-(2-(2,5-difluorophenyl)pyrrolidin-1-yl)pyrazolo[1,5-a]pyrimidine-3-carboxamide;

(R)—N-cyclopropyl-5-(2-(5-fluoropyridin-3-yl)pyrrolidin-1-yl)pyrazolo[1,5-a]pyrimidine-3-carboxamide;

(R)-5-(2-(5-fluoro-2-methoxypyridin-3-yl)pyrrolidin-1-yl)-N-methoxypyrazolo[1,5-a]pyrimidine-3-carboxamide;

(R)-5-(2-(5-fluoropyridin-3-yl)pyrrolidin-1-yl)-N-(1-methylcyclopropyl)pyrazolo[1,5-a]pyrimidine-3-carboxamide;

or a pharmaceutically acceptable salt thereof. In some embodiments of the methods provided herein, the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and the second Trk inhibitor is selected from the group consisting of:

(6R)-9-fluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(6R,15R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1(25),7,9,11,19(26),20,23-heptaen-18-one;

(6R)-9-fluoro-13-oxa-2,11,18,22,23,26-hexaazapentacyclo[18.5.2.0$^{2,6}$.0$^{7,12}$.0$^{23,27}$]-heptacosa-1(26),7,9,11,20(27),21,24-heptaen-19-one;

(6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaen-18-one;

(6R)-12-oxa-2,16,20,21,24,26-hexaazapentacyclo[16.5.2.$^{17,11}$.0$^{2,6}$.0$^{21,25}$]-hexacosa-1(24),7(26),8,10,18(25),19,22-heptaen-17-one;

1-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-16-yl]ethan-1-one;

(6R)-9-fluoro-13,16-dioxa-2,11,20,21,24-pentaazapentacyclo[16.5.2.0$^{2,6}$.0$^{7,12}$.0$^{21,25}$]pentacosa-1(24),7,9,11,18(25), 19,22-heptaen-17-one;

(6R)-9,15,15-trifluoro-13-oxa-2,11,17,21,22,25-hexaazapentacyclo[17.5.2.0$^{2,6}$.0$^{7,12}$. 0$^{22,26}$]hexacosa-1 (25),7,9,11,19(26),20,23-heptaen-18-one;

(6R,13 S)-9-fluoro-13-methyl-2,11,15,19,20,23-hexaazapentacyclo[15.5.2.$^{17,11}$.0$^{2,6}$.0$^{20,24}$]pentacosa-1(23),7,9,17(24),18,21-hexaene-16,25-dione;

(6R)-9-fluoro-15,15-dimethyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(15S)-4,4,9-trifluoro-15-hydroxy-13-oxa-2,17,21,22.25-pentaazapentacyclo[17.5.2.0$^{2,6}$.0$^{7,12}$.0$^{22,26}$]hexacosa-1(25),7(12), 8,10,19(26),20,23-heptaen-18-one;

(6R,15S)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25), 19,22-heptaen-17-one;

(6R,15R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25), 19,22-heptaen-17-one;

or a pharmaceutically acceptable salt thereof.

Some examples of these methods further include recording in the subject's clinical record (e.g., a computer readable medium) that the subject should be administered a treatment that does not include the Trk inhibitor in step (a) as a monotherapy or a different Trk inhibitor in the future.

Provided herein are methods of treating a subject having a cancer (e.g., any of the cancers described herein) that include identifying a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3), and administering to the identified subject a treatment that includes an increased dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) (e.g., as compared to control dosage of a Trk inhibitor). As used anywhere herein, a control dosage of a Trk inhibitor is a dosage of the Trk inhibitor sufficient to treat a subject having a cancer that is not a Trk inhibitor-resistant cancer (e.g., a cancer that does not include at least one point mutation in a NTRK gene that results in the expression of a Trk protein including a mutation at one or more amino acid positions (e.g., a mutation at one or more of the amino acid positions shown in Tables 1, 2, or 3)).

Also provided herein are methods of treating a subject having a cancer (e.g., any of the cancers described herein) and identified as having a cancer cell that has at least one point mutation in a NTRK gene that results in the expression of a Trk protein including a mutation at one or more amino acid positions (e.g., a mutation at one or more of the amino acid positions shown in Tables 1, 2, or 3), that include administering to the identified subject a treatment that includes an increased dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) (e.g., as compared to control dosage of a Trk inhibitor).

In some examples, the step of identifying a subject having a cancer cell that has the at least one point mutation (e.g., any of the point mutations described herein) in a NTRK1 gene that results in the expression of a TrkA including a mutation at one or more amino acid position(s) and/or the at least one point mutation (e.g., any of the point mutations described herein) in a NTRK2 gene that results in the expression of a TrkB including a mutation at one or more amino acid position(s), and/or the at least one point mutation (e.g., any of the point mutations described herein) in a NTRK3 gene that results in the expression of a TrkC including a mutation at one or more amino acid position(s), comprises performing an assay to determine the presence of the at least one point mutation in a NTRK1 gene and/or the at least one point mutation in a NTRK2 gene and/or the at least one point mutation in a NTRK3 gene in a cancer cell in a sample (e.g., a biopsy sample) from the subject. Any of the assays described herein can be used to determine the presence of the at least one point mutation in a NTRK1 gene and/or the at least one point mutation in a NTRK2 gene and/or the at least one point mutation in a NTRK3 gene. In addition, any of the kits provided herein can be used in an assay to determine the presence of the at least one point mutation in a NTRK1 gene and/or the at least one point mutation in a NTRK2 gene and/or the at least one point mutation in a NTRK3 gene. In some examples, the assay includes sequencing a segment of a NTRK1 including the at least one point mutation and/or a segment of a NTRK2 gene including the at least one point mutation and/or a segment of a NTRK3 gene including the at least one point mutation.

Also provided herein are methods of treating a subject having a cancer that include (a) administering a control dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more of the amino acid positions shown in Tables 1, 2, or 3); and (c) administering an increased dosage of the Trk inhibitor to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (d) administering a control dosage of the Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3). As used anywhere herein, a control dosage of a Trk inhibitor is a dosage of the Trk inhibitor sufficient to treat a subject having a cancer that is not a Trk inhibitor-resistant cancer (e.g., a cancer that does not include at least one point mutation in a NTRK gene that results in the expression of a Trk protein including a mutation at one or more amino acid positions (e.g., a mutation at one or more of the amino acid positions shown in Tables 1, 2, or 3)).

Also provided herein are methods of treating a subject having a cancer that include: (a) determining whether a cancer cell in a sample obtained from a subject having a cancer and previously administered a control dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate), has at least one point mutation in a NTRK gene that results in the expression of a Trk protein including a mutation at one or more amino acid positions (e.g., a mutation at one or more of the amino acid positions shown in Tables 1, 2, or 3); and (b) administering an increased dosage of the Trk inhibitor to a subject having a cancer cell that has at least one point mutation in a NTRK gene that results in the expression of a Trk protein including a mutation at one or more amino acid positions (e.g., a mutation at one or more of the amino acid positions shown in Tables 1, 2, or 3); or (c) administering a control dosage of the Trk inhibitor to a subject having a cancer cell that does not have at least one point mutation in a NTRK gene that results in the expression of a Trk protein including a mutation at one or more amino acid positions (e.g., a mutation at one or more of the amino acid positions shown in Tables 1, 2, or 3).

The cancer can be any of the exemplary cancers described herein. In some embodiments, the subject has previously been identified or diagnosed as having a cancer. In some examples, the subject has previously been administered a treatment for cancer, and the treatment for cancer has been unsuccessful (e.g., high toxicity in the subject or no positive response to the previously administered treatment for cancer).

Some examples of these methods further include recording in the subject's clinical record (e.g., a computer readable medium) that the subject should be administered a treatment that includes an increased dosage of a Trk inhibitor in the future.

Some embodiments of these methods include administering an increased dosage of the Trk inhibitor in step (b). Some embodiments of these methods include administering a control dosage of a Trk inhibitor in step (c).

Some examples of these methods further include recording in the subject's clinical record (e.g., a computer readable medium) that the subject should be administered an elevated dosage of the Trk inhibitor in the future. Some examples of these methods further include recording in the subject's clinical record (e.g., a computer readable medium) that the subject should be administered a treatment that does not include a Trk inhibitor as a monotherapy in the future.

In some of the embodiments provided herein, the at least one point mutation in a NTRK gene that results in the expression of a Trk protein including a mutation at one or more amino acid positions includes (i) at least one (e.g., one, two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A). In some embodiments, the at least one point mutation in a NTRK gene that results in the expression of a Trk protein including a mutation at one or more amino acid positions is selected from a mutation at one or more of the amino acid positions shown in Tables 1, 2, or 3.

Methods of Selecting a Treatment for a Subject Having a Cancer

Also provided herein are methods of selecting a treatment that does not include a Trk inhibitor (e.g., a first Trk inhibitor such as entrectinib or (S)—N-(5-((R)-2-(2,5-difluorophenyl)pyrrolidin-1-yl)pyrazol o[1,5-a]pyrimidin-3-yl)-3-hydroxypyrrolidine-1-carboxamide sulfate) as a monotherapy for a subject having a cancer (e.g., any of the cancers described herein) that include identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3), and selecting a treatment that does not include a Trk inhibitor as a monotherapy (e.g., any of the treatments that do not include a Trk inhibitor as a monotherapy described herein) for the identified subject.

Also provided herein are methods of selecting a treatment that does not include a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy for a subject having a cancer (e.g., any of the treatments that do not include a Trk inhibitor as a monotherapy described herein) that include selecting a treatment that does not include a Trk inhibitor as a monotherapy (e.g., any of the treatments that do not include a Trk inhibitor as a monotherapy described herein) for a subject identified as having a cancer cell that has at least one point mutation in a NTRK gene that results in the expression of a Trk protein including a mutation at one or more amino acid positions (e.g., a mutation at one or more amino acid positions shown in Table 1, 2, or 3).

Some of these methods include selecting a different Trk inhibitor (e.g., a second Trk inhibitor) or a treatment that does not include the Trk inhibitor of step (a) as a monotherapy to a subject having a cancer cell that has at least one point mutation in a NTRK gene that results in the expression of a Trk protein including a mutation at one or more amino acid positions (e.g., a mutation at one or more amino acid positions shown in Table 1, 2, or 3). In some embodiments, the different Trk inhibitor is a compound of Table 5, or a Also provided herein are methods of selecting a treatment for a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting a treatment that includes one or more compounds of Table 5, or a pharmaceutically acceptable salt thereof, for the identified subject.

Also provided herein are methods of selecting a treatment for a subject having a cancer (e.g., any of the cancers described herein or known in the art) that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting a treatment that includes one or more compounds of Table 5, or a pharmaceutically acceptable salt thereof, and another anticancer agent (e.g., any one or more of the anticancer agents described herein or known in the art) or anticancer therapy (e.g., any one or more of the anticancer therapies described herein or known in the art) for the identified subject.

Also provided herein are methods of selecting a treatment for a subject having a cancer that include: selecting a treatment that includes one or more compounds of Table 5, or a pharmaceutically acceptable salt thereof, for a subject identified as having a cancer cell that has at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer that include: selecting a treatment that includes one or more compounds of Table 5, or a pharmaceutically acceptable salt thereof, and another anticancer agent (e.g., any one or more of the anticancer agents described herein or known in the art) or anticancer therapy (e.g., any one or more of the anticancer therapies described herein or known in the art) for a subject identified as having a cancer cell that has at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer that include: (a) administering one or more doses Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and (c) selecting a different Trk inhibitor or a treatment that does not include the Trk inhibitor of step (a) (e.g., (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (d) selecting additional doses of the Trk inhibitor of step (a) (e.g., (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer that include: (a) determining whether a cancer cell in a sample obtained from a subject having a cancer and previously administered one or more doses of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate), has at least one point mutation in a NTRK gene that results in the expression of a Trk protein including a mutation at one or more amino acid positions (e.g., a mutation at one or more amino acid positions shown in Table 1, 2, or 3); (b) selecting a different Trk inhibitor or a treatment that does not include the Trk inhibitor of step (a) as a monotherapy for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (c) selecting additional doses of the Trk inhibitor of step (a) for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and (c) selecting a treatment including one or more doses of a second Trk inhibitor for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (d) selecting additional doses of the first Trk inhibitor for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and (c) selecting a treatment including one or more compounds of Table 5, or a pharmaceutically acceptable salt thereof, for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (d) selecting additional doses of the first Trk inhibitor for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer, that include: (a) administering one or more doses of a first Trk inhibitor to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and (c) selecting a treatment including one or more compounds of Table 5, or a pharmaceutically acceptable salt thereof, and another anticancer agent or anticancer therapy for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (d) selecting additional doses of the first Trk inhibitor for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer, that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more amino acid positions shown in Table 1, 2, or 3); (b) selecting a treatment that includes one or more doses of a second Trk inhibitor to a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (c) selecting additional doses of the first Trk inhibitor to a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment for a subject having a cancer, that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more amino acid positions shown in Table 1, 2, or 3); (b) selecting a treatment that includes one or more compounds of Table 5, or a pharmaceutically acceptable salt thereof, to a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (c) selecting additional doses of the first Trk inhibitor to a subject having a cancer cell that does not have at least one point mutation in a NTRK gene that results in the expression of a Trk protein including a mutation at one or more more amino acid positions (e.g., a mutation at one or more amino acid positions shown in Table 1, 2, or 3).

Also provided herein are methods of selecting a treatment for a subject having a cancer, that include: (a) determining whether a cancer cell in a sample obtained from a subject having a cancer and previously administered one or more doses of a first Trk inhibitor has at least one point mutation in a NTRK gene that results in the expression of a Trk protein including a mutation at one or more amino acid positions (e.g., a mutation at one or more amino acid positions shown in Table 1, 2, or 3); (b) selecting a treatment that includes one or more compounds of Table 5, or a pharmaceutically acceptable salt thereof, and an another anticancer agent or anticancer therapy to a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (c) selecting additional doses of the first Trk inhibitor to a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Also provided herein are methods of selecting a treatment that includes an increased dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) (e.g., as compared to control dosage of a Trk inhibitor) for a subject having a cancer (e.g., any of the cancers described herein) that include identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3), and selecting an increased dosage of a Trk inhibitor (e.g., as compared to control dosage of a Trk inhibitor) for the identified subject. As used anywhere herein, a control dosage of a Trk inhibitor is a dosage of the Trk inhibitor sufficient to treat a subject having a cancer that is not a Trk inhibitor-resistant cancer (e.g., a cancer that does not include at least one point mutation in a NTRK gene that results in the expression of a Trk protein including a mutation at one or more amino acid positions (e.g., a mutation at one or more amino acid positions shown in Table 1, 2, or 3)).

Also provided herein are methods of selecting a treatment that includes an increased dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) (e.g., as compared to control dosage of a Trk inhibitor) for a subject having a cancer (e.g., any of the cancers described herein) that include selecting a treatment that includes an increased dosage of a Trk inhibitor (e.g., as compared to control dosage of a Trk inhibitor) for a subject identified as having a cancer cell that has at least one point mutation in a NTRK gene that results in the expression of a Trk protein including a mutation at one or more amino acid positions (e.g., a mutation at one or more amino acid positions shown in Table 1, 2, or 3)).

Also provided herein are methods of selecting a treatment for a subject having a cancer that include: (a) administering a control dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) to the subject for a period of time; (b) after (a), determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and (c) selecting an increased dosage of the Trk inhibitor for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (d) selecting a control dosage of the Trk inhibitor for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3). As used anywhere herein, a control dosage of a Trk inhibitor is a dosage of the Trk inhibitor sufficient to treat a subject having a cancer that is not a Trk inhibitor-resistant cancer (e.g., a cancer that does not include at least one point mutation in a NTRK gene that results in the expression of a Trk protein including a mutation at one or more amino acid positions (e.g., a mutation at one or more amino acid positions shown in Table 1, 2, or 3)).

Also provided herein are methods of selecting a treatment for a subject having a cancer that include: (a) determining whether a cancer cell in a sample obtained from a subject having a cancer and previously administered a control dosage of a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate), has at least one point mutation in a NTRK gene that results in the expression of a Trk protein including a mutation at one or more amino acid positions (e.g., a mutation at one or more amino acid positions shown in Table 1, 2, or 3); (b) selecting an increased dosage of the Trk inhibitor for a subject having a cancer cell that has at least one point mutation in a NTRK gene that results in the expression of a Trk protein including a mutation at one or more amino acid positions (e.g., a mutation at one or more amino acid positions shown in Table 1, 2, or 3); or (c) selecting a control dosage of the Trk inhibitor for a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3).

Some examples of these methods further include administering the selected treatment to the identified subject. In some examples, the selected treatment is self-administered. In other examples, the selected treatment is administered by a medical professional (e.g., any of the medical professionals described herein). Some examples of these methods further include recording the selected treatment in the identified subject's clinical record (e.g., a computer readable medium).

In some of the embodiments provided herein, the at least one point mutation in a NTRK gene that results in the expression of a Trk protein including a mutation at one or more amino acid positions includes (i) at least one (e.g., one, two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A). In some embodiments, the at least one point mutation in a NTRK gene that results in the expression of a Trk protein including a mutation at one or more amino acid positions is selected from a mutation at one or more of the amino acid positions shown in Tables 1, 2, or 3.

Methods of Selecting a Subject Having a Cancer for Treatment

Also provided herein are methods of selecting a subject having a cancer for a treatment that does not include a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy that include identifying a subject as having a cancer cell that has at least one point mutation in a NTRK gene that results in the expression of a Trk protein including a mutation at one or more amino acid positions (e.g., a mutation at one or more amino acid positions shown in Table 1, 2, or 3), and selecting the identified subject for a treatment that does not include a Trk inhibitor as a monotherapy (e.g., any of the treatments that do not include a Trk inhibitor as a monotherapy described herein).

Also provided herein are methods of selecting a subject having a cancer for a treatment that does not include a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy that include selecting a subject having a cancer (e.g., any of the cancers described herein) and identified as having a cancer cell that has at least one point mutation in a NTRK gene that results in the expression of a Trk protein including a mutation at one or more amino acid positions (e.g., a mutation at one or more amino acid positions shown in Table 1, 2, or 3), for a treatment that does not include a Trk inhibitor as a monotherapy (e.g., any of the treatments that do not include a Trk inhibitor as a monotherapy described herein).

In some examples, the treatment that does not include a Trk inhibitor as a monotherapy includes one or more of: surgery (e.g., open surgery or minimally invasive surgery), radiation therapy (e.g., external beam radiation therapy or internal radiation therapy), chemotherapy (e.g., an alkylating agent, antimetabolites, anti-microtubule agents, topoisomerase inhibitors, and cytotoxic antibiotics), immunotherapy (e.g., adoptive cell transfer, a cytokine, a cancer vaccine, and *Bacillus* Calmette-Guérom), hormone therapy (e.g., a drug that blocks estrogen, a drug that lowers estrogen levels, a progesterone-like drug, or an anti-androgen drug), small molecule drugs targeting other kinases in a Trk-signaling pathway, recombinant antibodies (e.g., any of exemplary recombinant antibodies described herein, e.g., anti-NGF antibodies), and stem cell transplant. In some examples, the treatment that does not include a Trk inhibitor as a monotherapy can be, e.g., a treatment that includes (i) one or more of surgery, radiation therapy, chemotherapy, immunotherapy, hormone therapy, small molecule drugs targeting other kinases in a Trk-signaling pathway, recombinant antibodies, and stem cell transplant, and (ii) one or more Trk inhibitors (e.g., any of the Trk inhibitors described herein). In some embodiments, the treatment that does not include a Trk inhibitor as a monotherapy can be, e.g., a treatment that includes two or more Trk inhibitors (e.g., any of the Trk inhibitors described herein). Additional examples of treatments that do not include a Trk inhibitor as a monotherapy, and doses and routes of administration of the same, are described herein or known in the art.

Some examples of these methods further include administering a treatment that does not include a Trk inhibitor as a monotherapy (e.g., using any of the treatments that do not include a Trk inhibitor as a monotherapy, any of the routes of administration, any of the doses, and/or any of the frequencies of administration described herein) to the selected subject. In some examples, the treatment that does not include a Trk inhibitor as a monotherapy is self-administered. In other examples, the treatment that does not include a Trk inhibitor as a monotherapy is administered to the selected subject by a medical professional. In some examples, the selected subject is hospitalized. In other examples, the subject is administered the treatment that does not include a Trk inhibitor as a monotherapy, on an outpatient basis. Some methods further include recording in the subject's clinical record (e.g., a computer readable medium) that the subject is selected for a treatment that does not include a Trk inhibitor as a monotherapy.

Also provided herein are methods of selecting a subject having a cancer for a treatment that includes one or more compounds of Table 5, or a pharmaceutically acceptable salt thereof, that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting the identified subject for a treatment that includes one or more compounds of Table 5, or a pharmaceutically acceptable salt thereof.

Also provided herein are methods of selecting a subject having a cancer for a treatment that includes one or more compounds of Table 5, or a pharmaceutically acceptable salt thereof, and another anticancer agent (e.g., any one or more of the another anticancer agents described herein or known in the art) or another anticancer therapy that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting the identified subject for a treatment that includes one or more compounds of Table 5, or a pharmaceutically acceptable salt thereof, and another anticancer agent or anticancer therapy.

Also provided herein are methods of selecting a subject having a cancer for a treatment that includes one or more compounds of Table 5, or a pharmaceutically acceptable salt thereof, that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting the identified subject for a treatment that includes one or more compounds of Table 5, or a pharmaceutically acceptable salt thereof.

Also provided herein are methods of selecting a subject having a cancer for a treatment that includes one or more compounds of Table 5, or a pharmaceutically acceptable salt thereof, and another anticancer agent or anticancer therapy that include: identifying a subject having a cancer cell that has at least one point mutation in a NTRK gene that results in the expression of a Trk protein including a mutation at one or more amino acid positions (e.g., a mutation at one or more amino acid positions shown in Table 1, 2, or 3); and selecting the identified subject for a treatment that includes one or more compounds of Table 5, or a pharmaceutically acceptable salt thereof, and another anticancer agent or anticancer therapy.

Some examples of these methods further include administering a treatment that includes one or more compounds of Table 5, or a pharmaceutically acceptable salt thereof, or a treatment that includes one or more compounds of Table 5, or a pharmaceutically acceptable salt thereof, and another anticancer agent or anticancer therapy to the selected subject.

In some of the embodiments provided herein, the at least one point mutation in a NTRK gene that results in the expression of a Trk protein including a mutation at one or more amino acid positions includes (i) at least one (e.g., one, two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A). In some embodiments, the at least one point mutation in a NTRK gene that results in the expression of a Trk protein including a mutation at one or more amino acid positions is selected from a mutation at one or more of the amino acid positions shown in Tables 1, 2, or 3.

Methods of Determining the Likelihood that a Subject Having a Cancer Will have a Positive Response to a Treatment with a Trk Inhibitor as a Monotherapy Also provided herein are methods of determining the likelihood that a subject having a cancer (e.g., any of the cancers described herein) will have a positive response to a treatment with a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy that include determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3), has a decreased likelihood of having a positive response to a treatment with a Trk inhibitor as a monotherapy (e.g., as compared to a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3)).

Also provided herein are methods of determining the likelihood that a subject having cancer (e.g., any of the cancers described herein) will have a positive response to a treatment with a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy that include determining that a subject having a cancer cell that has at least one point mutation in a NTRK gene that results in the expression of a Trk protein including a mutation at one or more amino acid positions (e.g., a mutation at one or more amino acid positions shown in Table 1, 2, or 3), has a decreased likelihood of having a positive response to treatment with a Trk inhibitor as a monotherapy (e.g., as compared to a subject having a cancer cell that does not have at least one point mutation in a NTRK gene that results in the expression of a Trk protein including a mutation at one or more amino acid positions (e.g., a mutation at one or more amino acid positions shown in Table 1, 2, or 3)).

Some examples of these methods include administering a treatment that does not include a Trk inhibitor as a monotherapy (e.g., any of the treatments that do not include a Trk inhibitor as a monotherapy described herein) to a subject determined to have a decreased likelihood of having a positive response to treatment with a Trk inhibitor as a monotherapy.

In some examples, the treatment that does not include a Trk inhibitor as a monotherapy includes one or more of: surgery (e.g., open surgery or minimally invasive surgery), radiation therapy (e.g., external beam radiation therapy or internal radiation therapy), chemotherapy (e.g., an alkylating agent, antimetabolites, anti-microtubule agents, topoisomerase inhibitors, and cytotoxic antibiotics), immunotherapy (e.g., adoptive cell transfer, a cytokine, a cancer vaccine, and *Bacillus* Calmette-Guérom), hormone therapy (e.g., a drug that blocks estrogen, a drug that lowers estrogen levels, a progesterone-like drug, or an anti-androgen drug), small molecule drugs targeting other kinases in a Trk-signaling pathway, recombinant antibodies (e.g., any of exemplary recombinant antibodies described herein, e.g., anti-NGF antibodies), and stem cell transplant. In some examples, the treatment that does not include a Trk inhibitor as a monotherapy can be, e.g., a treatment that includes (i) one or more of surgery, radiation therapy, chemotherapy, immunotherapy, hormone therapy, small molecule drugs targeting other kinases in a Trk-signaling pathway, recombinant antibodies, and stem cell transplant, and (ii) one or more Trk inhibitors (e.g., any of the Trk inhibitors described herein). In some embodiments, the treatment that does not include a Trk inhibitor as a monotherapy can be, e.g., a treatment that includes two or more Trk inhibitors (e.g., any of the Trk inhibitors described herein). Additional examples of treatments that do not include a Trk inhibitor as a monotherapy, and doses and routes of administration of the same, are described herein or known in the art.

In some examples, the treatment that does not include a Trk inhibitor as a monotherapy is self-administered. In other examples, the treatment that does not include a Trk inhibitor as a monotherapy is administered to the subject by a medical professional. In some examples, the subject is hospitalized. In other examples, the subject is administered the treatment that does not include a Trk inhibitor as a monotherapy, on an outpatient basis. Some methods further include recording in the subject's clinical record (e.g., a computer readable medium) that the subject has a decreased likelihood of having a positive response to treatment with a Trk inhibitor as a monotherapy.

Also provided herein are methods of determining the likelihood that a subject having a cancer will have a positive response to treatment that includes one or more compounds of Table 5, or a pharmaceutically acceptable salt thereof, that include: determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3), has an increased likelihood of having a positive response to treatment that includes one or more compounds of Table 5, or a pharmaceutically acceptable salt thereof.

Also provided herein are methods of determining the likelihood that a subject having cancer will have a positive response to treatment that includes one or more compounds of Table 5, or a pharmaceutically acceptable salt thereof, that include: determining that a subject having a cancer cell that has at least one point mutation in a NTRK gene that results in the expression of a Trk protein including a mutation at one or more amino acid positions (e.g., a mutation at one or more amino acid positions shown in Table 1, 2, or 3), has an increased likelihood of having a positive response to treatment including one or more compounds of Table 5, or a pharmaceutically acceptable salt thereof.

In some of the embodiments provided herein, the at least one point mutation in a NTRK gene that results in the expression of a Trk protein including a mutation at one or more amino acid positions includes (i) at least one (e.g., one, two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A). In some embodiments, the at least one point mutation in a NTRK gene that results in the expression of a Trk protein including a mutation at one or more amino acid positions is selected from a mutation at one or more of the amino acid positions shown in Tables 1, 2, or 3.

Methods of Predicting the Efficacy of Treatment with a Trk Inhibitor as a Monotherapy in a Subject Having Cancer Also provided herein are methods of predicting the efficacy of treatment with a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy in a subject having cancer (e.g., any of the cancers described herein) that include determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3), and determining that a treatment with a Trk inhibitor as a monotherapy is less likely to be effective in a subject having a cancer cell in a sample obtained from the subject that has at least one point mutation in a NTRK gene that results in the expression of a Trk protein including a mutation at one or more amino acid positions (e.g., a mutation at one or more amino acid positions shown in Table 1, 2, or 3) (e.g., as compared to a subject having a cancer cell in a sample obtained from the subject that does not have at least one point mutation in a NTRK gene that results in the expression of a Trk protein including a mutation at one or more amino acid positions (e.g., a mutation at one or more amino acid positions shown in Table 1, 2, or 3)).

Also provided herein are methods of predicting the efficacy of a treatment with a Trk inhibitor (e.g., a first Trk inhibitor such as entrectinib or (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate) as a monotherapy in a subject having a cancer (e.g., any of the cancers described herein) that include determining that treatment with a Trk inhibitor as a monotherapy is less likely to be effective in a subject having a cancer cell in a sample obtained from the subject that has at least one point mutation in a NTRK gene that results in the expression of a Trk protein including a mutation at one or more amino acid positions (e.g., a mutation at one or more amino acid positions shown in Table 1, 2, or 3) (e.g., as compared to a subject having a cancer cell in a sample obtained from the subject that does not have at least one point mutation in a NTRK gene that results in the expression of a Trk protein including a mutation at one or more amino acid positions (e.g., a mutation at one or more amino acid positions shown in Table 1, 2, or 3)).

Some methods further include recording in the subject's clinical record (e.g., a computer readable medium) the predicted efficacy of a treatment with a Trk inhibitor as a monotherapy, in the subject having a cancer. Some examples of these methods further include selecting a treatment that does not include a Trk inhibitor as a monotherapy for the subject. Some examples further include administering the selected treatment to the subject (e.g., using any of the treatments that do not include a Trk inhibitor as a monotherapy, any of the routes of administration, any of the doses, and/or any of the frequencies of administration described herein).

In some examples, the treatment that does not include a Trk inhibitor as a monotherapy includes one or more of: surgery (e.g., open surgery or minimally invasive surgery), radiation therapy (e.g., external beam radiation therapy or internal radiation therapy), chemotherapy (e.g., an alkylating agent, antimetabolites, anti-microtubule agents, topoisomerase inhibitors, and cytotoxic antibiotics), immunotherapy (e.g., adoptive cell transfer, a cytokine, a cancer vaccine, and *Bacillus* Calmette-Guérom), hormone therapy (e.g., a drug that blocks estrogen, a drug that lowers estrogen levels, a progesterone-like drug, or an anti-androgen drug), small molecule drugs targeting other kinases in a Trk-signaling pathway, recombinant antibodies (e.g., any of exemplary recombinant antibodies described herein, e.g., anti-NGF antibodies), and stem cell transplant. In some examples, the treatment that does not include a Trk inhibitor as a monotherapy can be, e.g., a treatment that includes (i) one or more of surgery, radiation therapy, chemotherapy, immunotherapy, hormone therapy, small molecule drugs targeting other kinases in a Trk-signaling pathway, recombinant antibodies, and stem cell transplant, and (ii) one or more Trk inhibitors (e.g., any of the Trk inhibitors described herein). In some embodiments, the treatment that does not include a Trk inhibitor as a monotherapy can be, e.g., a treatment that includes two or more Trk inhibitors (e.g., any of the Trk inhibitors described herein). Additional examples of treatments that do not include a Trk inhibitor as a monotherapy, and doses and routes of administration of the same, are described herein or known in the art.

In some examples, the treatment that does not include a Trk inhibitor as a monotherapy is self-administered. In other examples, the treatment that does not include a Trk inhibitor as a monotherapy is administered to the subject by a medical professional. In some examples, the subject is hospitalized. In other examples, the subject is administered the treatment that does not include a Trk inhibitor as a monotherapy, on an outpatient basis.

Also provided herein are methods of predicting the efficacy of treatment with a treatment including one or more compounds of Table 5, or a pharmaceutically acceptable salt thereof, in a subject having cancer, that include: determining whether a cancer cell in a sample obtained from the subject has at least one point mutation in a NTRK gene that results in the expression of a Trk protein including a mutation at one or more amino acid positions (e.g., a mutation at one or more amino acid positions shown in Table 1, 2, or 3); and determining that treatment including one or more compounds of Table 5, or a pharmaceutically acceptable salt thereof, is more likely to be effective in a subject having a cancer cell in a sample obtained from the subject that has at least one point mutation in a NTRK gene that results in the expression of a Trk protein including a mutation at one or more amino acid positions (e.g., a mutation at one or more amino acid positions shown in Table 1, 2, or 3).

Also provided herein are methods of predicting the efficacy of treatment including one or more compounds of Table 5, or a pharmaceutically acceptable salt thereof, in a subject having cancer, that include: determining that treatment including one or more compounds of Table 5, or a pharmaceutically acceptable salt thereof, is more likely to be effective in a subject having a cancer cell in a sample obtained from the subject that has at least one point mutation in a NTRK gene that results in the expression of a Trk protein including a mutation at one or more amino acid positions (e.g., a mutation at one or more amino acid positions shown in Table 1, 2, or 3).

In some of the embodiments provided herein, the at least one point mutation in a NTRK gene that results in the expression of a Trk protein including a mutation at one or more amino acid positions includes (i) at least one (e.g., one, two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G; F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A). In some embodiments, the at least one point mutation in a NTRK gene that results in the expression of a Trk protein including a mutation at one or more amino acid positions is selected from a mutation at one or more of the amino acid positions shown in Tables 1, 2, or 3.

Methods of Predicting a Subject's Risk for Developing a Trk Inhibitor-Resistant Cancer Also provided herein are methods of identifying a determining a subject's risk for developing a Trk inhibitor-resistant cancer (e.g., any of the cancers described herein) that include determining whether a cell in a sample obtained from the subject has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S) and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), and identifying a subject having a cell that has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), as having an increased likelihood of developing a Trk inhibitor-resistant cancer (e.g., as compared to a subject not having (i) a point mutation in a NTRK1 gene that results in the expression of a TrkA protein including a mutation at one or more amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), or (ii) a point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), or (iii) a point mutation in a NTRK3 gene that results in the expression of a TrkC protein including a mutation at one or more amino acid position(s) selected from the group consisting of: 545, 570, 596, 601, 617, 623, 624, 628, 630, 675, 685, 686, 696, and 705 (e.g., one or more substitutions of G545R, A570V, F617L, G623R, D624V, C685Y, C685F, L686V, and G696A)).

Also provided herein are methods of determining a subject's risk for developing a Trk inhibitor-resistant cancer (e.g., any of the cancers described herein) that include identifying a subject having a cell that has (i) at least one (e.g., two, three, four, five, six, seven, eight, nine, ten, eleven, twelve, thirteen, fourteen, or fifteen) point mutation(s) in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), as having an increased likelihood of developing a Trk inhibitor-resistant cancer (e.g., as compared to a subject having a cell that does not have (i) a point mutation in a NTRK1 gene that results in the expression of a TrkA protein including a mutation at one or more amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), or (ii) a point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), or (iii) a point mutation in a NTRK3 gene that results in the expression of a TrkC protein including a mutation at one or more amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A)).

Some methods further include recording in the subject's clinical record (e.g., a computer readable medium) the subject's risk of developing a Trk inhibitor-resistant cancer. The Trk inhibitor-resistant cancer can be any of the exemplary cancers described herein. Some methods further include periodic testing for the presence of a Trk inhibitor-resistant cancer in the subject.

In some examples, the subject is identified as having been exposed to a significant level of carcinogen(s) (e.g., tobacco smoke, UVB radiation, and gamma irradiation). In some examples, the subject is suspected of having cancer, presents with one or more symptoms of cancer (e.g., any of the symptoms of cancer described herein), and/or has a family history of cancer.

In some examples, the step of determining whether a cancer cell in a sample obtained from the subject has (i) at least one (e.g., two, three, four, five, six, seven, eight, nine, ten, eleven, twelve, thirteen, fourteen, or fifteen) point mutation in a NTRK1 gene that results in the expression of a TrkA protein including one or more (e.g., two, three, four, five, six, seven, eight, nine, ten, eleven, twelve, thirteen, fourteen, or fifteen) mutations (e.g., any of the mutations in TrkA described herein), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including one or more (e.g., two, three, four, five, six, seven, eight, nine, ten, eleven, twelve, thirteen, fourteen, or fifteen) mutations (e.g., any of the mutations in TrkB described herein), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including one or more (e.g., two, three, four, five, six, seven, eight, nine, ten, eleven, twelve, thirteen, fourteen, or fifteen) mutations (e.g., any of the mutations in TrkC described herein), comprises performing an assay to determine the presence of the at least one point mutation in a NTRK1 gene and/or the at least one point mutation in a NTRK2 gene and/or the at least one point mutation in a NTRK3 gene in a cancer cell in the sample (e.g., a biopsy sample) from the subject. Any of the assays described herein can be used to determine the presence of the at least one point mutation in a NTRK1 gene and/or the at least one point mutation in a NTRK2 gene and/or the at least one point mutation in a NTRK3 gene. In addition, any of the kits provided herein can be used in an assay to determine the presence of the at least one point mutation in a NTRK1 gene and/or the at least one point mutation in a NTRK2 gene and/or the at least one point mutation in a NTRK3 gene. In some examples, the assay includes sequencing a segment of a NTRK1 gene including the at least one point mutation and/or a segment of a NTRK2 gene including the at least one point mutation and/or a segment of a NTRK3 gene including the at least one point mutation.

Methods of Determining the Presence of a Trk Inhibitor-Resistant Cancer in a Subject Also provided herein are methods of determining the presence of a Trk inhibitor-resistant cancer (e.g., any of the cancers described herein) in a subject that include determining whether a cell in a sample obtained from the subject has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), and determining that a subject having a cell that has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), has a Trk inhibitor-resistant cancer.

Also provided herein are methods of determining the presence of a Trk inhibitor-resistant cancer (e.g., any of the cancers described herein) in a subject that include determining that a subject having a cell that has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G; F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), has a Trk inhibitor-resistant cancer (e.g., as compared to a subject having a cell that does not have (i) a point mutation in a NTRK1 gene that results in the expression of a TrkA protein including a mutation at one or more amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), or (ii) a point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G; F617L, F617C, F617I, G623S, G623R, D624V, R630K, C682Y, C682F, L683V, G693S, and G713S), or (iii) a point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A)).

Some embodiments further include confirming a diagnosis of a Trk inhibitor-resistant cancer in the subject. Confirming the diagnosis of a Trk inhibitor-resistant cancer in a subject can include, e.g., performing additional laboratory tests (e.g., urine or blood tests, e.g., complete blood count), imaging tests (e.g., computerized tomography (CT), bone scan, magnetic resonance imaging (MRI), positron emission tomography (PET) scan, ultrasound, and X-ray), and/or physical examination, e.g., before and after administration of a treatment with a Trk inhibitor as a monotherapy.

Some methods further include recording in the subject's clinical record (e.g., a computer readable medium) that the subject has a Trk inhibitor-resistant cancer. The cancer can be any of the exemplary cancers described herein.

Some examples further includes administering a treatment that does not include a Trk inhibitor as a monotherapy (e.g., any of the treatments that do not include a Trk inhibitor as a monotherapy described herein). In some examples, the treatment that does not include a Trk inhibitor as a monotherapy includes one or more of: surgery (e.g., open surgery or minimally invasive surgery), radiation therapy (e.g., external beam radiation therapy or internal radiation therapy), chemotherapy (e.g., an alkylating agent, antimetabolites, anti-microtubule agents, topoisomerase inhibitors, and cytotoxic antibiotics), immunotherapy (e.g., adoptive cell transfer, a cytokine, a cancer vaccine, and *Bacillus* Calmette-Guérom), hormone therapy (e.g., a drug that blocks estrogen, a drug that lowers estrogen levels, a progesterone-like drug, or an anti-androgen drug), small molecule drugs targeting other kinases in a Trk-signaling pathway, recombinant antibodies (e.g., any of exemplary recombinant antibodies described herein, e.g., anti-NGF antibodies), and stem cell transplant. In some examples, the treatment that does not include a Trk inhibitor as a monotherapy can be, e.g., a treatment that includes (i) one or more of surgery, radiation therapy, chemotherapy, immunotherapy, hormone therapy, small molecule drugs targeting other kinases in a Trk-signaling pathway, recombinant antibodies, and stem cell transplant, and (ii) one or more Trk inhibitors (e.g., any of the Trk inhibitors described herein). In some embodiments, the treatment that does not include a Trk inhibitor as a monotherapy can be, e.g., a treatment that includes two or more Trk inhibitors (e.g., any of the Trk inhibitors described herein). Additional examples of treatments that do not include a Trk inhibitor as a monotherapy, and doses and routes of administration of the same, are described herein or known in the art.

In some examples, the treatment that does not include a Trk inhibitor as a monotherapy is self-administered. In other examples, the treatment that does not include a Trk inhibitor as a monotherapy is administered to the subject by a medical professional. In some examples, the subject is hospitalized. In other examples, the subject is administered the treatment that does not include a Trk inhibitor as a monotherapy, on an outpatient basis.

In some examples, the subject is identified as having been exposed to a significant level of carcinogen(s) (e.g., tobacco smoke, UVB radiation, and gamma irradiation). In some examples, the subject is suspected of having cancer, presents with one or more symptoms of cancer (e.g., any of the symptoms of cancer described herein), and/or has a family history of cancer.

In some examples, the step of determining whether a cancer cell in a sample obtained from the subject has (i) at least one (e.g., two, three, four, five, six, seven, eight, nine, ten, eleven, twelve, thirteen, fourteen, or fifteen) point mutation in a NTRK1 gene that results in the expression of a TrkA protein including one or more (e.g., two, three, four, five, six, seven, eight, nine, ten, eleven, twelve, thirteen, fourteen, or fifteen) mutations (e.g., any of the mutations in TrkA described herein) and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including one or more (e.g., two, three, four, five, six, seven, eight, nine, ten, eleven, twelve, thirteen, fourteen, or fifteen) mutations (e.g., any of the TrkB mutations described herein), and/or (iii) at least one (e.g., two, three, four, five, six, or seven, eight, nine, ten, eleven, twelve, thirteen, fourteen, or fifteen) point mutation in a NTRK3 gene that results in the expression of a TrkC protein including one or more (e.g., two, three, four, five, six, or seven, eight, nine, ten, eleven, twelve, thirteen, fourteen, or fifteen) mutations (e.g., any of the mutations in TrkC described herein), comprises performing an assay to determine the presence of the at least one point mutation in a NTRK1 gene and/or the at least one point mutation in a NTRK2 gene and/or the at least one point mutation in a NTRK3 gene in a cancer cell in the sample (e.g., a biopsy sample) from the subject. Any of the assays described herein can be used to determine the presence of the at least one point mutation in a NTRK1 gene and/or the at least one point mutation in a NTRK2 gene and/or the at least one point mutation in a NTRK3 gene. In addition, any of the kits provided herein can be used in an assay to determine the presence of the at least one point mutation in a NTRK1 gene and/or the at least one point mutation in a NTRK2 gene and/or the at least one point mutation in a NTRK3 gene. In some examples, the assay includes sequencing a segment of a NTRK1 gene including the at least one point mutation and/or a segment of a NTRK2 gene including the at least one point mutation and/or a segment of a NTRK3 gene including the at least one point mutation.

Methods of Selecting a Subject Having a Cancer for Participation in a Clinical Study Also provided herein are methods of selecting a subject having a cancer for participation in a clinical study that includes administration of treatment for a cancer that include (a) determining whether a cancer cell in a sample obtained from the subject has (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S) and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A); and (b) selecting a subject having a cancer cell having (i) at least one (e.g., two, three, four, five, six, seven, eight, nine, ten, eleven, twelve, thirteen, fourteen, or fifteen) point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), for participation in a clinical study that includes administration of a treatment for a cancer.

Also provided herein are methods of selecting a subject having a cancer for participation in a clinical study that includes administration of a Trk inhibitor that include (a) determining whether a cancer cell in a sample obtained from the subject has (i) at least one point (e.g., two, three, four, five, six, seven, eight, nine, ten, eleven, twelve, thirteen, fourteen, or fifteen) mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), and/or (ii) at least one (e.g., two, three, four, five, six, seven, eight, nine, ten, eleven, twelve, thirteen, fourteen, or fifteen) point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), and/or (iii) at least one (e.g., two, three, four, five, six, seven, eight, nine, ten, eleven, twelve, thirteen, fourteen, or fifteen) point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A); and (b) selecting a subject having a cancer cell that does not have (i) a point mutation in a NTRK1 gene that results in the expression of a TrkA protein including a mutation at one or more (e.g., two, three, four, five, six, seven, eight, nine, ten, eleven, twelve, thirteen, fourteen, or fifteen) amino acid position(s) selected from the group consisting of: 517, 542, 568, 573, 589, 595, 599, 600, 602, 646, 656, 657, 667, and 676 (e.g., one or more of the substitutions of G517R, A542V, V573M, F589L, F589C, G595S, G595R, D596V, F600L, F646V, C656Y, C656F, L657V, G667S, G667C, and Y676S), or (ii) a point mutation in a NTRK2 gene that results in the expression of a TrkB protein including a mutation at one or more (e.g., two, three, four, five, six, seven, eight, nine, ten, eleven, twelve, thirteen, fourteen, or fifteen) amino acid positions selected from the group consisting of: 545, 570, 596, 601, 617, 623, 624, 628, 630, 672, 682, 683, 693, and 702 (e.g., one or more of the substitutions of G545R, A570V, Q596E, Q596P, V601G, F617L, F617C, F617I, G623S, G623R, D624V, R630K, C682Y, C682F, L683V, G693S, and G713S), or (iii) a point mutation in a NTRK3 gene that results in the expression of a TrkC protein including a mutation at one or more (e.g., two, three, four, five, six, seven, eight, nine, ten, eleven, twelve, thirteen, fourteen, or fifteen) amino acid position(s) selected from the group consisting of: 545, 570, 596, 601, 617, 623, 624, 628, 630, 675, 685, 686, 696, and 705 (e.g., one or more of the substitutions of G545R, A570V, F617L, G623R, D624V, C685Y, C685F, L686V, and G696A), for participation in a clinical study that includes administration of a Trk inhibitor.

The cancer can be any of the exemplary cancers described herein. In some embodiments, the subject has previously been identified or diagnosed as having a cancer. In some examples, the subject has previously been administered a treatment for cancer, and the treatment for cancer has been unsuccessful (e.g., high toxicity in the subject or no positive response to the previously administered treatment for cancer).

In some examples, the step of determining whether a cancer cell in a sample obtained from the subject has the at least one point mutation (e.g., any of the point mutations described herein) in a NTRK1 gene that results in the expression of a TrkA including a mutation at one or more amino acid position(s) and/or the at least one point mutation (e.g., any of the point mutations described herein) in a NTRK2 gene that results in the expression of a TrkB including a mutation at one or more amino acid position(s) and/or the at least one point mutation (e.g., any of the point mutations described herein) in a NTRK3 gene that results in the expression of a TrkC including a mutation at one or more amino acid position(s), comprises performing an assay to determine the presence of the at least one point mutation in a NTRK1 gene and/or the at least one point mutation in a NTRK2 gene and/or the at least one point mutation in a NTRK3 gene in a cancer cell in a sample (e.g., a biopsy sample) from the subject. Any of the assays described herein can be used to determine the presence of the at least one point mutation in a NTRK1 gene and/or the at least one point mutation in a NTRK2 gene and/or the at least one point mutation in a NTRK3 gene. In addition, any of the kits provided herein can be used in an assay to determine the presence of the at least one point mutation in a NTRK1 gene and/or the at least one point mutation in a NTRK2 gene and/or the at least one point mutation in a NTRK3 gene. In some examples, the assay includes sequencing a segment of a NTRK1 including the at least one point mutation and/or a segment of a NTRK2 including the at least one point mutation and/or a segment of a NTRK3 including the at least one point mutation.

Kits

Also provided herein are kits that include one or more (e.g., two, three, four, five, six, or seven) probes that specifically hybridize to a segment of a NTRK1 gene that comprises one of the point mutations described herein (e.g., any point mutation that results in an amino acid substitution at amino acid position 517, 542, 568, 573, 589, 595, 599, 600, 602, 646, 656, 657, 667, and 676 in TrkA); and/or one or more (e.g., two, three, four, five, six, seven, eight, nine, ten, eleven, twelve, thirteen, fourteen, or fifteen) probes that specifically hybridize to a segment of a NTRK2 gene that comprises one of the point mutations described herein (e.g., any point mutation that results in an amino acid substitution at amino acid position 545, 570, 596, 601, 617, 623, 624, 628, 630, 672, 682, 683, 693, 702, or 713; and/or one or more (e.g., two, three, four, five, six, seven, eight, nine, ten, eleven, twelve, thirteen, fourteen, or fifteen) probes that specifically hybridizes to a segment of a NTRK3 gene that comprises one of the point mutations described herein (e.g., any point mutation that results in an amino acid substitution at amino acid position 545, 570, 596, 601, 617, 623, 624, 628, 630, 675, 685, 686, 696, 705, or 730 in TrkC). For example, the kits provided herein can include one or more probes that specifically hybridize to a segment of a NTRK1 gene that encodes a mutation selected from the group consisting of: G517R, A542V, V573M, F589L, F589C, G595S, G595R, D596V, F600L, F646V, C656Y, C656F, L657V, G667S, G667C, and Y676S in a TrkA protein); and/or one or more probes that specifically hybridize to a segment of a NTRK2 gene that encodes a mutation selected from the group consisting of: G545R, A570V, Q596E, Q596P, V601G, F617L, F617C, F617I, G623S, G623R, D624V, R630K, C682Y, C682F, L683V, G693S, and G713S; and/or one or more probes that specifically hybridizes to a segment of a NTRK3 gene that encodes a mutation selected from the group consisting of: G545R, A570V, F617L, G623R, D624V, C685Y, C685F, L686V, and G696A.

Each of the one or more probes can have a length of 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides. In some embodiments, the one or more probes include a detectable label (e.g., a fluorophore, a quencher, a radioisotope, or a metal). In some embodiments, the one or more probes can be covalently attached to a substrate (e.g., a film, a plate, or a bead).

The invention is further described in the following examples, which do not limit the scope of the invention described in the claims.

EXAMPLES

Example 1. Identification of Trk Inhibitor-Resistance Point Mutations

A genetic screen was performed to determine if resistance mutations arise in cancer subjects having NTRK+ tumors treated with Trk inhibitors. In the genetic screen cDNAs harboring the MPRIP-NTRK1 oncogene were introduced into Ba/F3 cells. The Ba/F3 cells were treated with the mutagen, 100 μg/mL N-ethyl-N-nitrosourea (ENU; Sigma Aldrich, St. Louis, Mo.), overnight. The ENU-treated Ba/F3 cells were plated into 96-well plates in media supplemented with different concentrations of (S)—N-(5-((R)-2-(2,5-difluorophenyl)pyrrolidin-1-yl)pyrazol o[1,5-a]pyrimidin-3-yl)-3-hydroxypyrrolidine-1-carboxamide sulfate (25 nM, 50 nM, 100 nM, 250 nM, 500 nM, or 1 μM). The wells were observed for media color change and cell growth. The contents of the outgrown wells were expanded in 12-well plates in media supplemented with (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate at the same concentration as in the initial 96-well plate. At confluence, the cells were collected and genomic DNA was extracted. The NTRK1 kinase region was amplified and the PCR products were purified and sequenced. A plasmids encoding MPRIP-NTRK1 mutations were generated with Quick-Change site-directed mutagenesis according to the manufacturer's instructions using a sequence encoding a wildtype MPRIP-NTRK1 fusion protein as a template. Each mutation was confirmed by DNA sequencing. The Ba/F3 cells and NIH353 cells expressing MPRIP-NTRK1 mutants were generated by infecting Ba/F3 and NIH353 parental cells with lentivirus encoding the mutation MPRIP-NTRK1 fusion proteins, followed by selection with puromycin. A flow chart showing the steps in the experimental methods is shown in FIG. 1.

Figure 2:
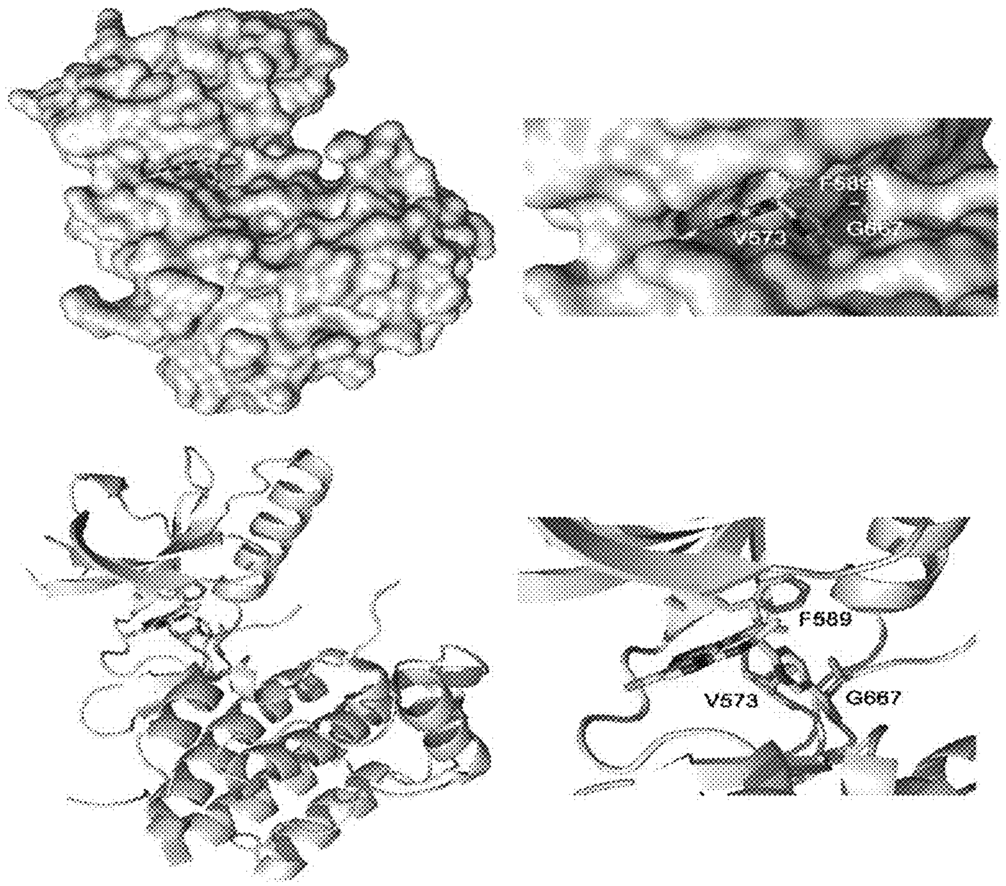
FIG. 2 is a crystal structure of TrkA showing the location of some of the Trk inhibitor-resistance amino acid substitutions.
Figure 3:
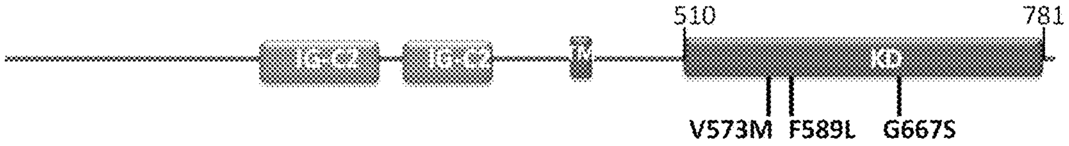
FIG. 3 is a diagram showing the position of some of the Trk inhibitor-resistance amino acid substitutions.
Figure 4:
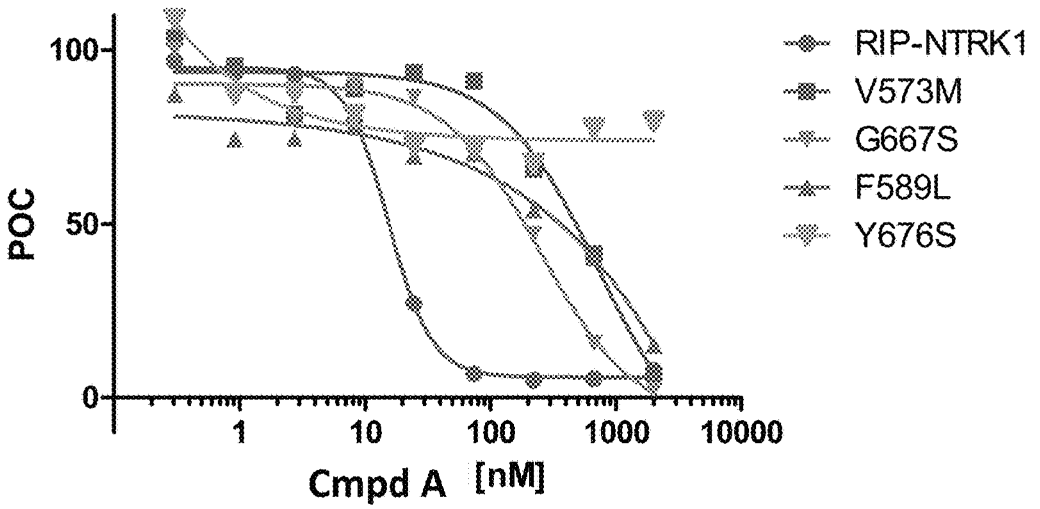
FIG. 4 is a graph of the POC of cells expressing a MPRIP-NTRK1 fusion protein including one of the Trk inhibitor resistance mutations at different concentrations of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A).

The identified (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations resulted in the following amino acid substitutions in TrkA: V573M, F589L, F600L, G667S, and Y676S. The location of three substitutions in TrkA resulting from (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations were mapped onto the crystal structure of TrkA: V573, F589, and G667 (FIG. 2) and a diagram of the domain structure of TrkA (FIG. 3). Cancer cells having a MPRIP-NTRK1 point mutation have increased resistance to (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (FIG. 4).

These experiments show that the presence of one or more of the V573M, F589L, F600L, G667S, and Y676S substitutions in TrkA (or one or more of the corresponding point mutations in a NTRK1 gene) in a cancer cell can be used to predict the resistance of the cancer cell to (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate and other Trk inhibitors, and indicate that the cancer cell will not be sensitive to treatment with (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate and other Trk inhibitors.

Example 2. Identification of Trk Inhibitor-Resistance Point Mutations

N-ethyl-N-nitrosourea (ENU)-exposed Ba/F3-MPRIP-NTRK1 and Ba/F3-TRIM24-NTRK2 cells were used to generate mutations permitting growth of Ba/F3 cells in the absence of IL-3 despite the presence of 100, 250, or 500 nM (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate. The Mutations identified by genomic DNA sequencing in the initial screen were validated by cloning the mutation-bearing cDNAs back into Ba/F3 cells to evaluate their sensitivity to (S)—N-(5-((R)-2-(2,5-DIFLUOROPHENYL)PYRROLIDIN-1-YL)PYRAZOLO[1,5-A]PYRIMIDIN-3-YL)-3-HYDROXYPYRROLIDINE-1-CARBOXAMIDE SULFATE using both proliferation assays and TRK phosphorylation by immunoblot analyses. Modeling of the mutations was performed by mapping of the amino acid substitutions onto a drug-bound TRK kinase domain crystal structure.

Mutations at 6 amino acid positions in the TRKA protein and 3 amino acid positions in the TRKB protein that induce resistance to (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate were identified. In the TRKA kinase domain, the (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance mutations of V573M, and F589L/C, G595S, F600L, F646V, and G667S were identified. In the TRKB kinase domain, the (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance mutations of Q596E/P, F617L/C/I, and G623S were identified. These TRK mutations reduce target inhibition by (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate as measured by TRK tyrosine phosphorylation and resultant downstream signaling through the MAPK or other critical pathways.

Figure 5:
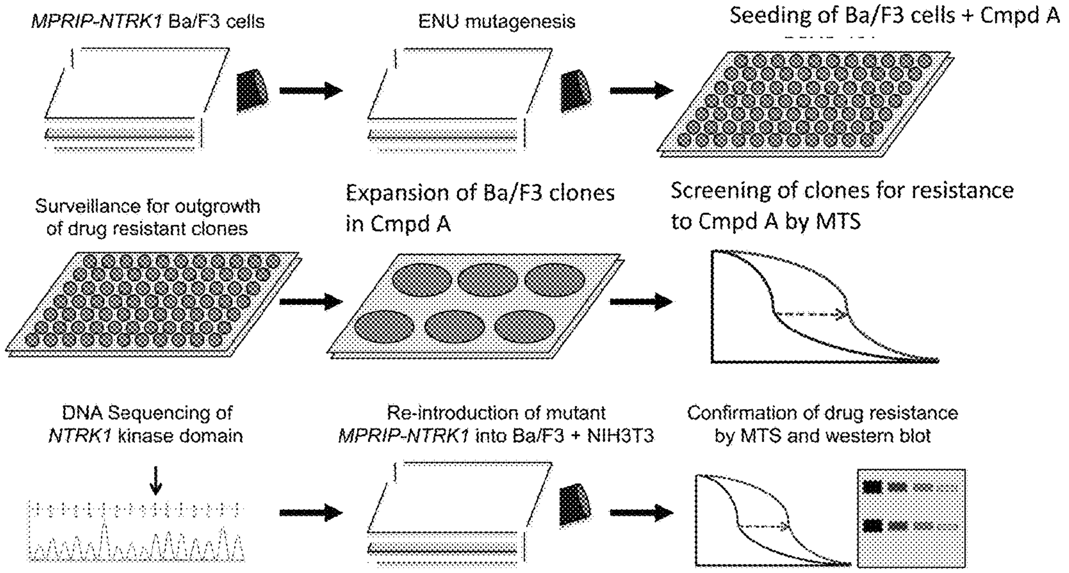
FIG. 5 is a flow chart of the experimental methods used in Example 3.

Example 3. Identification of TRKA and TRKB Kinase Domain Mutations that Induce Resistance to a Pan-TRK Inhibitor A mutagenesis and genetic screening approach to identify candidate mutations in TRKA and TRKB that mediate resistance to (S)—N-(5-((R)-2-(2,5-DIFLUOROPHENYL)PYRROLIDIN-1-YL)PYRAZOLO[1,5-A]PYRIMIDIN-3-YL)-3-HYDROXYPYRROLIDINE-1-CARBOXAMIDE SULFATE was performed. A flow chart showing the steps in the experimental methods is shown in FIG. 5.

Ba/F3 cells stably expressing MPRIP-NTRK1 or TRIM24-NTRK2 were treated overnight with 100 mg/ml N-Ethyl-N-nitrosourea (ENU), pelleted, resuspended in fresh media, and distributed in 96-well plates in 200 μL media supplemented with (S)—N-(5-((R)-2-(2,5-DIFLUOROPHENYL)PYRROLIDIN-1-YL)PYRAZOLO[1,5-A]PYRIMIDIN-3-YL)-3-HYDROXYPYRROLIDINE-1-CARBOXAMIDE SULFATE (100, 250, and 500 nM). The wells were observed for media color change and cell growth. The contents of outgrown wells were expanded in 12-well plates in media supplemented with (S)—N-(5-((R)-2-(2,5-DIFLUOROPHENYL)PYRROLIDIN-1-YL)PYRAZOLO[1,5-A]PYRIMIDIN-3-YL)-3-HYDROXYPYRROLIDINE-1-CARBOXAMIDE SULFATE at the same concentration as in the initial 96-well plate. At confluence, cells were collected and genomic DNA was extracted. The NTRK1 and NTRK2 kinase region was PCR-amplified and sequenced. Plasmids encoding MPRIP-NTRK1 and TRIM24-NTRK2 mutations were generated with Quick-Change site-directed mutagenesis and confirmed by DNA sequencing. Ba/F3 cells and NIH3T3 cells expressing MPRIP-NTRK1 mutants were generated by infecting Ba/F3 and NIH3T3 parental cells with lentivirus encoding MPRIP-NTRK1 mutation followed by selection with puromycin.

Figure 6A:
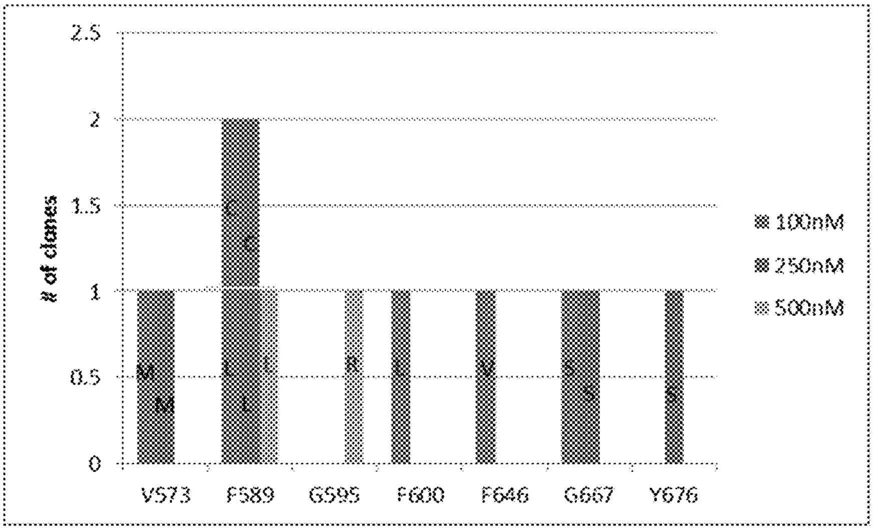
FIG. 6A is a graph representing the frequency of mutations and the dose of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A) from which they were isolated.
Figure 6B:
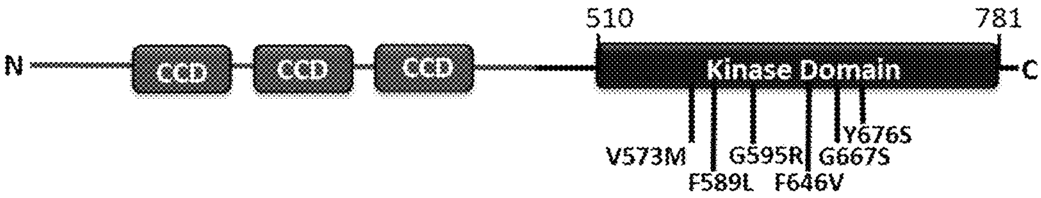
FIG. 6B is a schematic of RIP-TRKA (encoded by MPRIP-NTRK1) with selected protein domains and resistance mutations that were identified.
Figure 6C:
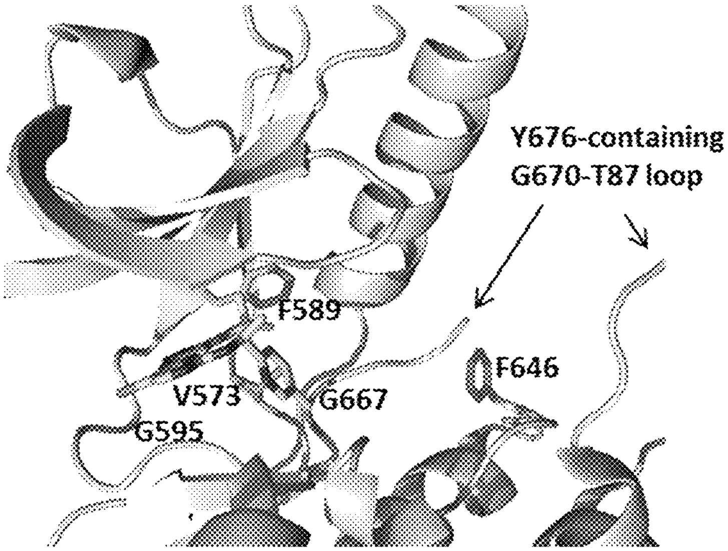
FIG. 6C is a ribbon representation of the crystallographic structure of the TRKA kinase domain in complex with the TRK inhibitor AZ-23 (PDB 4AOJ) showing localization of mutations that were identified.
Figure 7:
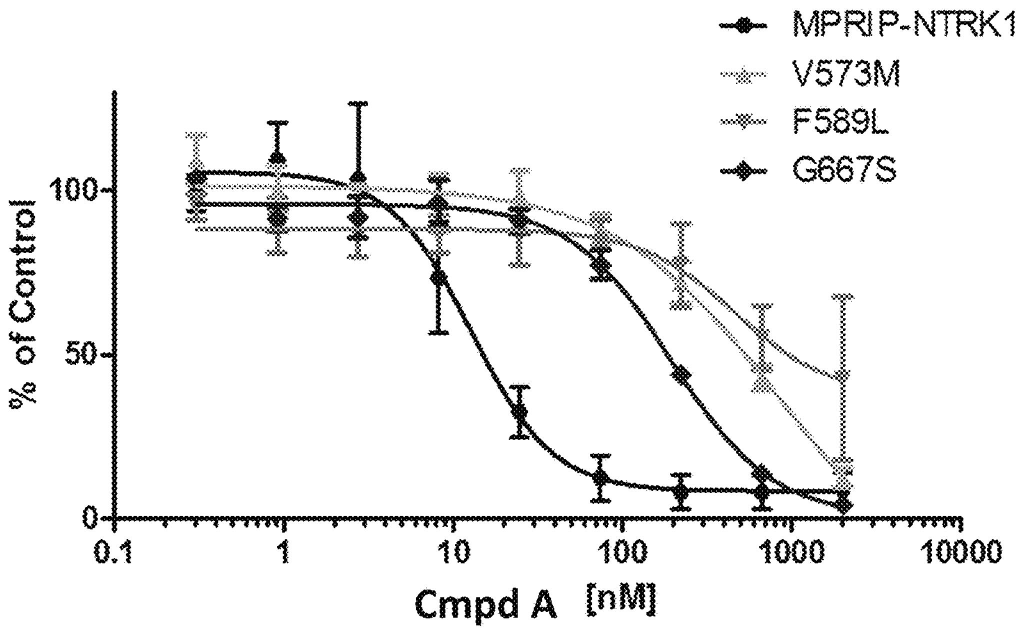
FIG. 7 is a graph of the percent of control of cells expressing a MPRIP-NTRK1 fusion protein including certain of the identified TrkA inhibitor resistance mutations at different concentrations of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A).
Figure 8:
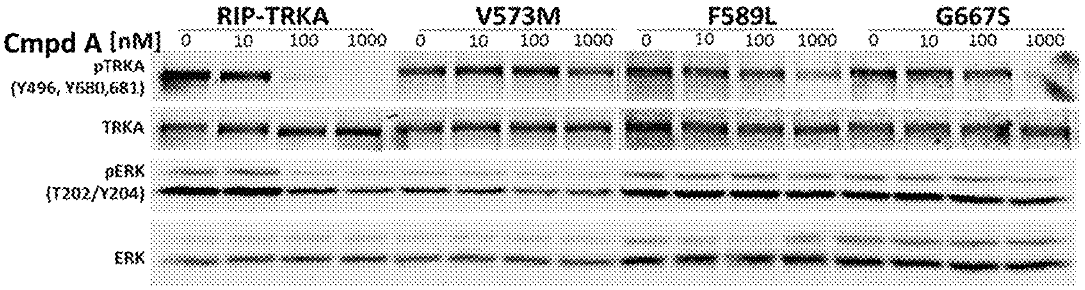
FIG. 8 is a photograph of a Western blot analysis of NIH3T3 cells treated with the indicated concentrations of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A) for 2 hours.

The identified (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations resulted in the following amino acid substitutions in RIP-TrkA: V573M, F589L, F589C, G595R, F600L, F646V, G667S, and Y676S (FIG. 6A). The location of selected substitutions in TrkA resulting from (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations were mapped onto a diagram of the domain structure of TrkA (FIG. 6B) and the crystal structure of TrkA (FIG. 6C). Cancer cells having a MPRIP-NTRK1 point mutation resulting in amino acid substitutions V573M, F589L, and G667S exhibit increased resistance to (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (FIG. 7). TRKA and downstream signaling is not inhibited in NIH3T3 cells expressing these TRKA kinase domain mutations: TRKA, and ERK1/2 activation are sensitive to (S)—N-(5-((R)-2-(2,5-DIFLUOROPHENYL) PYRROLIDIN-1-YL)PYRAZOLO[1,5-A]PYRIMIDIN-3-YL)-3-HYDROXYPYRROLIDINE-1-CARBOXAMIDE SULFATE inhibition in NIH3T3 cells expressing MPRIP-NTRK1 wr[1] fusion, whereas NIH3T3 cells expressing MPRIP-NTRK 1 [V$^{73M}$], MPRIP-NTRK1$^{[F589L]}$ or MPRIP-NTRK1$^{[G667S]}$ fusions are resistant (FIG. 8).

Figure 9A:
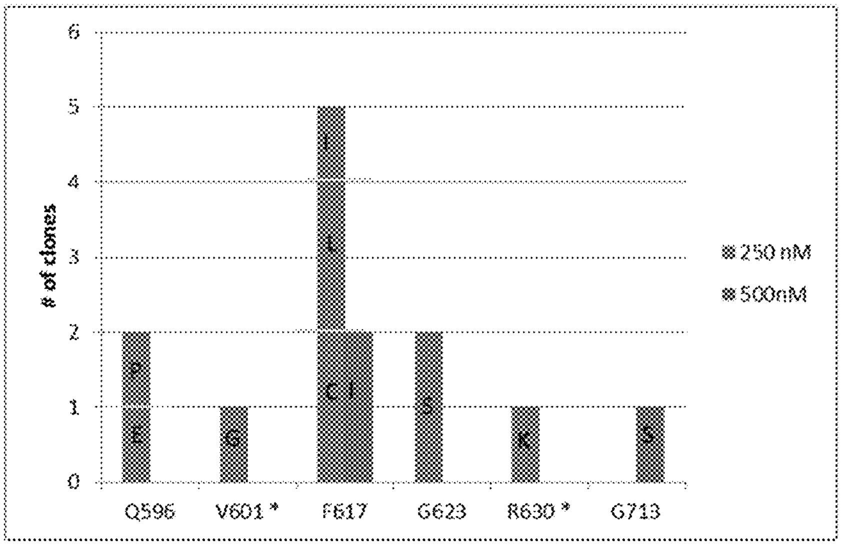
Figure 9B:
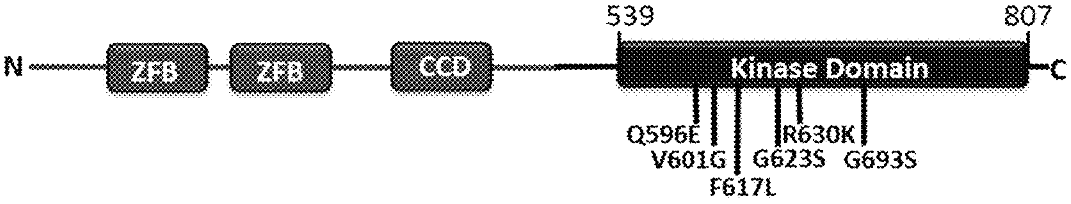
FIG. 9B is a schematic of TRIM24-TRKB (encoded by TRIIM24-NTRK1) with selected protein domains and resistance mutations that were identified.
Figure 9C:
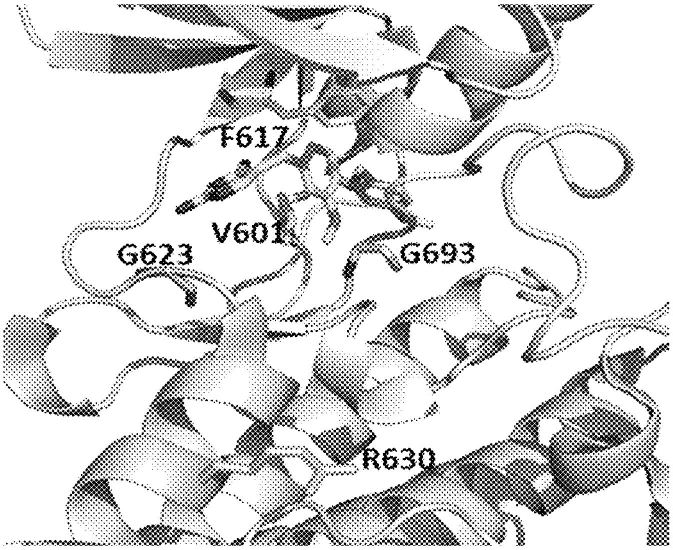
FIG. 9C is a ribbon representation of the crystallographic structure of the TRKB kinase domain in complex with the TRK inhibitor AZ-23 (PDB 4AOJ) showing localization of mutations that were identified.
Figure 10:
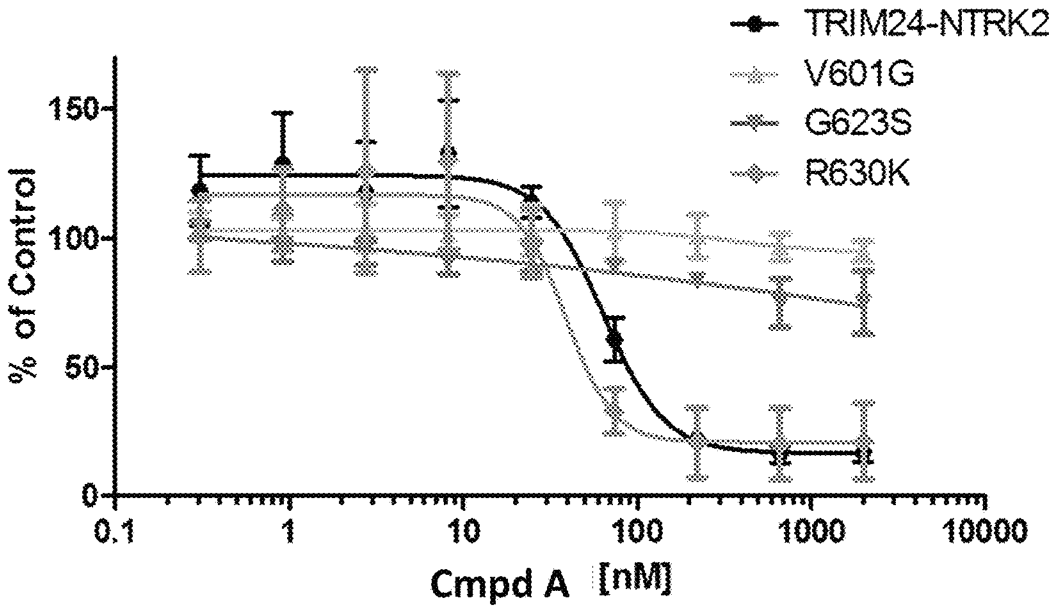
FIG. 10 is a graph of the percent of control of cells expressing a TRIM24-NTRK2 fusion protein including certain of the identified TrkB inhibitor resistance mutations at different concentrations of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A).
Figure 11:
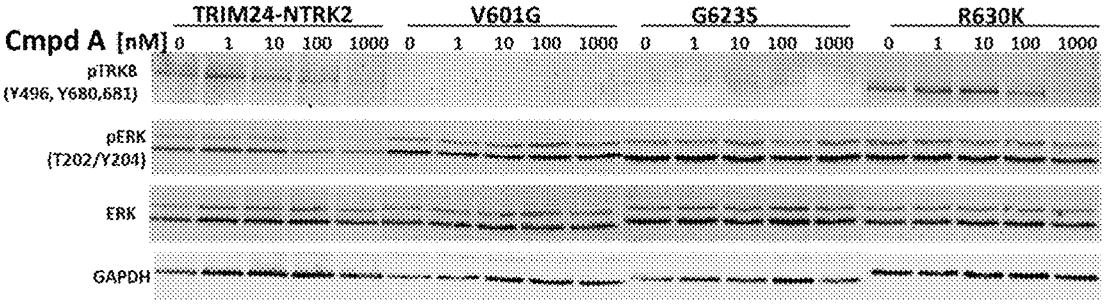
FIG. 11 is a photograph of a Western blot analysis of NIH3T3 cells treated with the indicated concentrations of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (Cmpd A) for 2 hours.

The identified (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations resulted in the following amino acid substitutions in TRIM24-TrkB: Q596E, Q596P, V601G, F617C, F617I, F617I, G623S, R630K, and G713S (FIG. 9A). The location of selected substitutions in TrkB resulting from (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate resistance point mutations were mapped onto a diagram of the domain structure of TrkB (FIG. 9B) and the crystal structure of TrkB (FIG. 9C). Cancer cells having a TRIM24-NTRK2 point mutation resulting in amino acid substitutions V601G, G623S, and R630K exhibit increased resistance to (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (FIG. 10). TRKB and downstream signaling is not inhibited in NIH3T3 cells expressing these TRKB kinase domain mutations: TRKB, and ERK1/2 activation are sensitive to (S)—N-(5-((R)-2-(2,5-DIFLUOROPHENYL) PYRROLIDIN-1-YL)PYRAZOLO [1,5-A]PYRIMIDIN-3-YL)-3-HYDROXYPYRROLIDINE-1-CARBOXAMIDE SULFATE inhibition in NIH3T3 cells expressing TRIM24-NTRK2$^{[WT]}$ fusion, whereas NIH3T3 cells expressing TRIM24-NTRK2$^{[V601G]}$, TRIM24-NTRK2$^{[G623S]}$ or TRIM24-NTRK2$^{[R630K]}$ fusions are resistant. (FIG. 11).

FIG. 12 shows the $IC_{50}$ of certain Ba/F3 (S)—N-(5-((R)-2-(2,5-DIFLUOROPHENYL)PYRROLIDIN-1-YL)PYRAZOLO [1,5-A]PYRIMIDIN-3-YL)-3-HYDROXYPYRROLIDINE-1-CARBOXAMIDE SULFATE-resistant clones that were identified. The $IC_{50}$ measurements for the mutations shown were determined by an average of 3 experiments. Clones are ordered by conserved amino acids residues between TRKA and TRKB.

An alignment of kinase domains from selected oncogenes with known resistance mutations is shown in FIG. 13.

Novel mutations in the TRKA kinase domain of the MPRIP-NTRK1 oncogene and in the TRKB kinase domain of TRIM24-NTRK2 were identified using a combined mutagenesis/genetic screen. All mutations identified confer resistance to the pan-TRK inhibitor (S)—N-(5-((R)-2-(2,5-DIFLUOROPHENYL)PYRROLIDIN-1-YL)PYRAZOLO [1,5-A]PYRIMIDIN-3-YL)-3-HYDROXYPYRROLIDINE-1-CARBOXAMIDE SULFATE as assessed by cellular proliferation assays and measurement of cell signaling. The majority of the mutations cluster to the back of the ATP/drug-binding pocket, possibly functioning by altering the topology of this pocket, thereby inhibiting (S)—N-(5-((R)-2-(2,5-DIFLUOROPHENYL)PYRROLIDIN-1-YL) PYRAZOLO[1,5-A]PYRIMIDIN-3-YL)-3-HYDROXY-PYRROLIDINE-1-CARBOXAMIDE SULFATE binding. Evaluation of tumors or circulating free DNA at disease progression for these and other resistance mutations permits the use of structurally distinct TRK inhibitors to overcome drug resistance.

Example 4. Trk Enzyme Assay

The activity of the various Trk compounds exemplified in Table 6 was determined by monitoring the incorporation of [$^{33}$P]$PO_4$ from [γ-$^{33}$P]ATP into poly-EAY (Sigma-Aldrich, P3899).

TABLE 6

Compounds tested in the Trk Enzyme Assay

| Compound No. | Compound Structure | Compound Name |
|---|---|---|
| 1 | 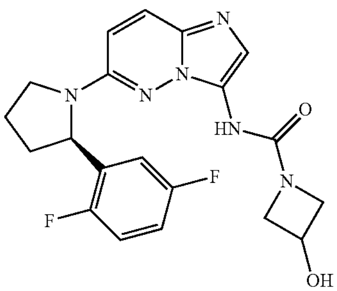 [SMILES: O=C(Nc1cnc2ccc(N3CCC[C@@H]3c3cc(F)ccc3F)nn12)N1CC(O)C1] | (R)-N-(6-(2-(2,5-difluorophenyl)pyrrolidin-1-yl)imidazo[1,2-b]pyridazin-3-yl)-3-hydroxyazetidine-1-carboxamide |

TABLE 6-continued

| Compounds tested in the Trk Enzyme Assay | | |
|---|---|---|
| Compound No. | Compound Structure | Compound Name |
| 2 | 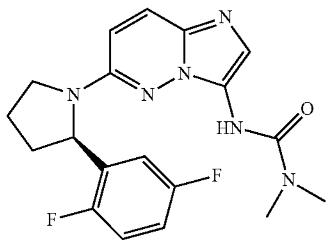 [SMILES: CN(C)C(=O)Nc1cnc2ccc(N3CCC[C@@H]3c3cc(F)ccc3F)nn12] | (R)-3-(6-(2-(2,5-difluorophenyl)pyrrolidin-1-yl)imidazo[1,2-b]pyridazin-3-yl)-1,1-dimethylurea |
| 3 | 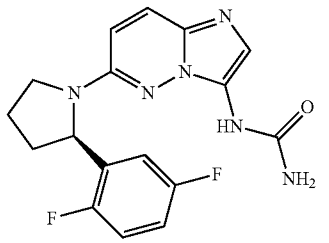 [SMILES: NC(=O)Nc1cnc2ccc(N3CCC[C@@H]3c3cc(F)ccc3F)nn12] | (R)-1-(6-(2-(2,5-difluorophenyl)pyrrolidin-1-yl)imidazo[1,2-b]pyridazin-3-yl)urea |
| 4 | 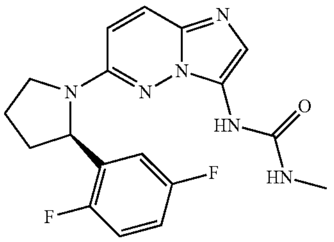 [SMILES: CNC(=O)Nc1cnc2ccc(N3CCC[C@@H]3c3cc(F)ccc3F)nn12] | (R)-1-(6-(2-(2,5-difluorophenyl)pyrrolidin-1-yl)imidazo[1,2-b]pyridazin-3-yl)-3-methylurea |
| 5 | 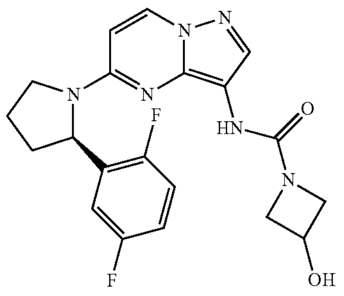 [SMILES: O=C(Nc1cnn2ccc(N3CCC[C@@H]3c3cc(F)ccc3F)nc12)N1CC(O)C1] | (R)-N-(5-(2-(2,5-difluorophenyl)pyrrolidin-1-yl)pyrazolo[1,5-a]pyrimidin-3-yl)-3-hydroxyazetidine-1-carboxamide |
| 6 | 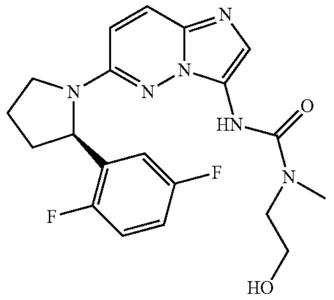 [SMILES: CN(CCO)C(=O)Nc1cnc2ccc(N3CCC[C@@H]3c3cc(F)ccc3F)nn12] | (R)-3-(6-(2-(2,5-difluorophenyl)pyrrolidin-1-yl)imidazo[1,2-b]pyridazin-3-yl)-1-(2-hydroxyethyl)-1-methylurea |

TABLE 6-continued

| Compound No. | Compound Structure | Compound Name |
| --- | --- | --- |
| Compounds tested in the Trk Enzyme Assay | | |
| 7 | 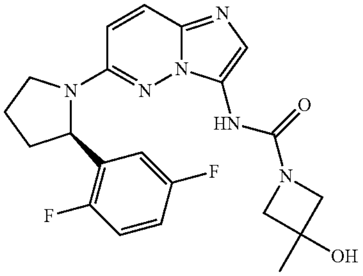 [SMILES: CC1(O)CN(C(=O)Nc2cnc3ccc(N4CCC[C@@H]4c4cc(F)ccc4F)nn23)C1] | (R)-N-(6-(2-(2,5-difluorophenyl)pyrrolidin-1-yl)imidazo[1,2-b]pyridazin-3-yl)-3-hydroxy-3-methylazetidine-1-carboxamide |
| 8 | 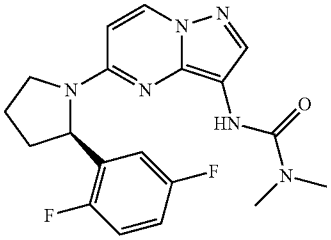 [SMILES: CN(C)C(=O)Nc1cnn2ccc(N3CCC[C@@H]3c3cc(F)ccc3F)nc12] | (R)-3-(5-(2-(2,5-difluorophenyl)pyrrolidin-1-yl)pyrazolo[1,5-a]pyrimidin-3-yl)-1,1-dimethylurea |
| 9 | 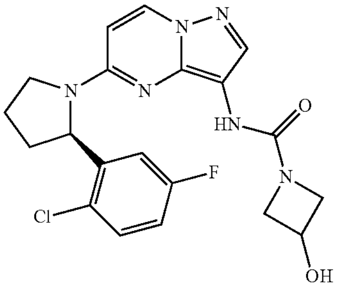 [SMILES: O=C(Nc1cnn2ccc(N3CCC[C@@H]3c3cc(F)ccc3Cl)nc12)N1CC(O)C1] | (R)-N-(5-(2-(2-chloro-5-fluorophenyl)pyrrolidin-1-yl)pyrazolo[1,5-a]pyrimidin-3-yl)-3-hydroxyazetidine-1-carboxamide |
| 10 | 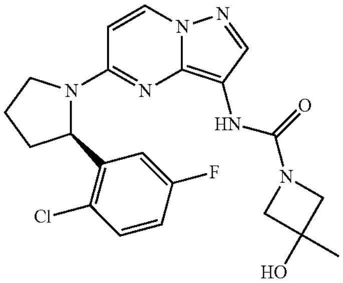 [SMILES: CC1(O)CN(C(=O)Nc2cnn3ccc(N4CCC[C@@H]4c4cc(F)ccc4Cl)nc23)C1] | (R)-N-(5-(2-(2-chloro-5-fluorophenyl)pyrrolidin-1-yl)pyrazolo[1,5-a]pyrimidin-3-yl)-3-hydroxy-3-methylazetidine-1-carboxamide |
| 11 | 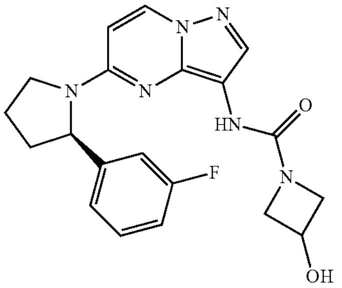 [SMILES: O=C(Nc1cnn2ccc(N3CCC[C@@H]3c3cccc(F)c3)nc12)N1CC(O)C1] | (R)-N-(5-(2-(3-fluorophenyl)pyrrolidin-1-yl)pyrazolo[1,5-a]pyrimidin-3-yl)-3-hydroxyazetidine-1-carboxamide |

TABLE 6-continued

| Compounds tested in the Trk Enzyme Assay | | |
|---|---|---|
| Compound No. | Compound Structure | Compound Name |
| 12 | 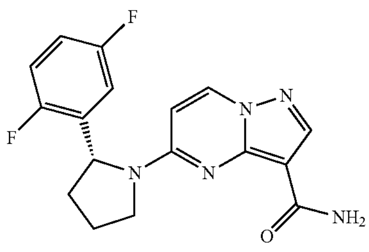 [SMILES: NC(=O)c1cnn2ccc(N3CCC[C@@H]3c3cc(F)ccc3F)nc12] | (R)-5-(2-(2,5-difluorophenyl)pyrrolidin-1-yl)pyrazolo[1,5-a]pyrimidine-3-carboxamide |
| 13 | 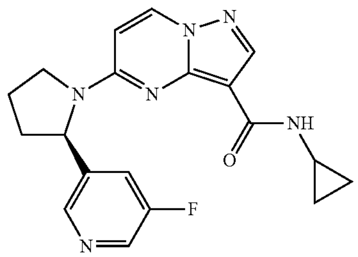 [SMILES: O=C(NC1CC1)c1cnn2ccc(N3CCC[C@@H]3c3cncc(F)c3)nc12] | (R)-N-cyclopropyl-5-(2-(5-fluoro-pyridin-3-yl)pyrrolidin-1-yl)pyrazolo[1,5-a]pyrimidine-3-carboxamide |
| 14 | 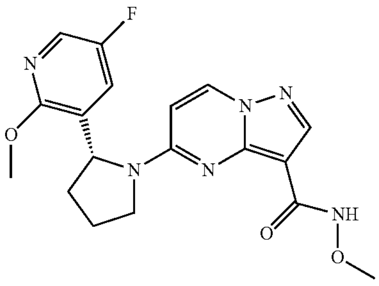 [SMILES: CONC(=O)c1cnn2ccc(N3CCC[C@@H]3c3cc(F)cnc3OC)nc12] | (R)-5-(2-(5-fluoro-2-methoxypyridin-3-yl)pyrrolidin-1-yl)-N-methoxy-pyrazolo[1,5-a]pyrimidine-3-carboxamide |
| 15 | 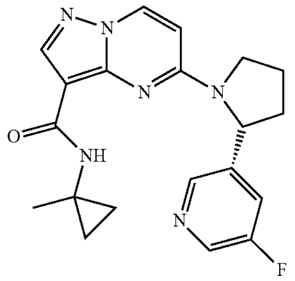 | (R)-5-(2-(5-fluoropyridin-3-yl)pyrrolidin-1-yl)-N-(1-methylcyclopropyl)pyrazolo[1,5-a]pyrimidine-3-carboxamide |
| 16 | 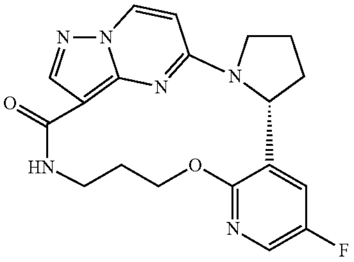 [SMILES: O=C1NCCCOc2ncc(F)cc2[C@H]2CCCN2c2ccn3ncc1c3n2] | (6R)-9-fluoro-13-oxa-2,11,17,21,22,25-hexaazapentacyclo[17.5.2.0$^{2,6}$.0$^{7,12}$.0$^{22,26}$]-hexacosa-1(25),7,9,11,19(26),20,23-heptaen-18-one |

TABLE 6-continued

Compounds tested in the Trk Enzyme Assay

| Compound No. | Compound Structure | Compound Name |
|---|---|---|
| 17 | 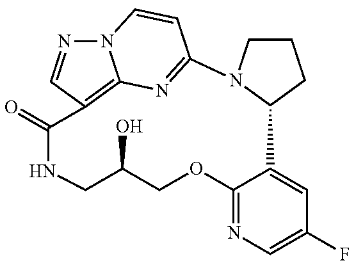 [SMILES: O=C1NC[C@@H](O)COc2ncc(F)cc2[C@H]2CCCN2c2ccn3ncc1c3n2] | (6R,15R)-9-fluoro-15-hydroxy-13-oxa-2,11,17,21,22,25-hexaazapentacyclo-[17.5.2.0$^{2,6}$.0$^{7,12}$.0$^{22,26}$]-hexacosa-1(25),7,9,11,19(26),20,23-heptaen-18-one |
| 18 | 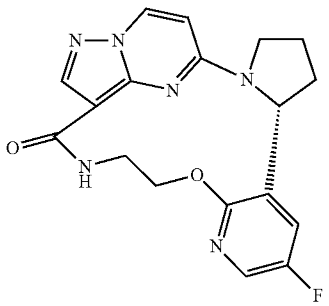 [SMILES: O=C1NCCOc2ncc(F)cc2[C@H]2CCCN2c2ccn3ncc1c3n2] | (6R)-9-fluoro-13-oxa-2,11,18,22,23,26-hexaazapentacyclo[18.5.2.0$^{2,6}$.0$^{7,12}$.0$^{23,27}$]-heptacosa-1(26),7,9,11,20(27),21,24-heptaen-19-one |
| 19 | 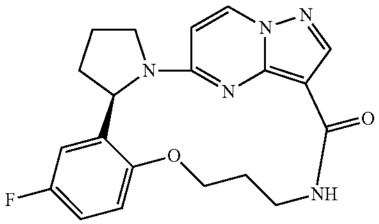 [SMILES: O=C1NCCCOc2ccc(F)cc2[C@H]2CCCN2c2ccn3ncc1c3n2] | (6R)-9-fluoro-13-oxa-2,17,21,22,25-pentaazapentacyclo[17.5.2.0$^{2,6}$.0$^{7,12}$.0$^{22,26}$] hexacosa-1(25),7,9,11,19(26),20,23-heptaen-18-one |
| 20 | 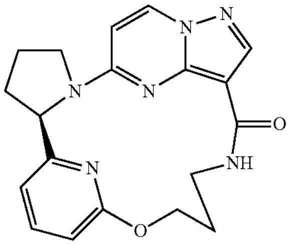 [SMILES: O=C1NCCCOc2cccc(n2)[C@H]2CCCN2c2ccn3ncc1c3n2] | (6R)-12-oxa-2,16,20,21,24,26-hexaazapentacyclo[16.5.2.$^{17,11}$.0$^{2,6}$.0$^{21,25}$]-hexacosa-1(24),7(26),8,10,18(25),19,22-heptaen-17-one |
| 21 | 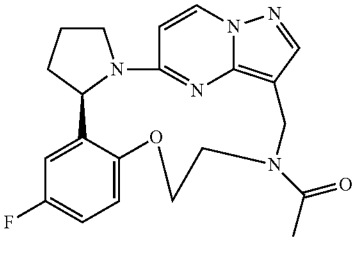 [SMILES: CC(=O)N1CCOc2ccc(F)cc2[C@H]2CCCN2c2ccn3ncc(c3n2)C1] | 1-[(6R)-9-fluoro-13-oxa-2,16,20,21,24-pentaazapentacyclo[16.5.2.0$^{2,6}$.0$^{7,12}$.0$^{21,25}$] pentacosa-1(24),7,9,11,18(25),19,22-heptaen-16-yl]ethan-1-one |

TABLE 6-continued

Compounds tested in the Trk Enzyme Assay

| Compound No. | Compound Structure | Compound Name |
| --- | --- | --- |
| 22 | 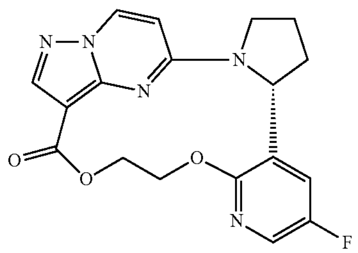 [SMILES: O=C1OCCOc2ncc(F)cc2[C@H]2CCCN2c2ccn3ncc1c3n2] | (6R)-9-fluoro-13,16-dioxa-2,11,20,21,24-pentaazapentacyclo[16.5.2.0$^{2,6}$.0$^{7,12}$.0$^{21,25}$]-pentacosa-1(24),7,9,11,18(25),19,22-heptaen-17-one |
| 23 | 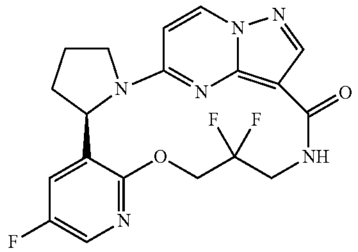 [SMILES: O=C1NCC(F)(F)COc2ncc(F)cc2[C@H]2CCCN2c2ccn3ncc1c3n2] | (6R)-9,15,15-trifluoro-13-oxa-2,11,17,21,22,25-hexaazapentacyclo [17.5.2.0$^{2,6}$.0$^{7,12}$.0$^{22,26}$]hexacosa-1(25),7,9,11,19(26),20,23-heptaen-18-one |
| 24 | 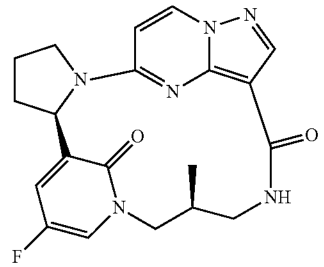 [SMILES: C[C@H]1CNC(=O)c2cnn3ccc(nc23)N2CCC[C@@H]2c2cc(F)cn(c2=O)C1] | (6R,13S)-9-fluoro-13-methyl-2,11,15,19,20,23-hexaazapentacyclo [15.5.2.$^{17,11}$.0$^{2,6}$.0$^{20,24}$]pentacosa-1(23),7,9,17(24),18,21-hexaene-16,25-dione |
| 25 | 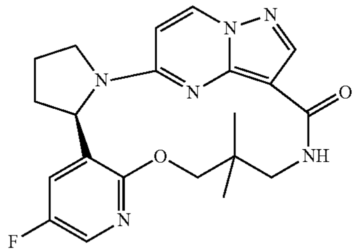 [SMILES: CC1(C)CNC(=O)c2cnn3ccc(nc23)N2CCC[C@@H]2c2cc(F)cnc2OC1] | (6R)-9-fluoro-15,15-dimethyl-13-oxa-2,11,17,21,22,25-hexaazapentacyclo [17,5.2.0$^{2,6}$.0$^{7,12}$.0$^{22,26}$]hexacosa-1(25),7,9,11,19(26),20,23-heptaen-18-one |
| 26 | 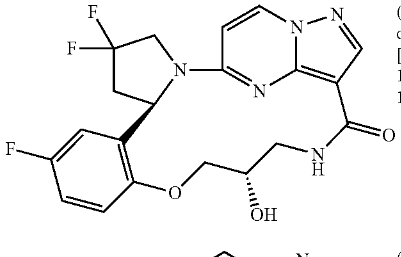 | (15S)-4,4,9-trifluoro-15-hydroxy-13-oxa-2,17,21,22.25-pentaazapentacyclo [17.5.2.0$^{2,6}$.0$^{7,12}$.0$^{22,26}$]hexacosa-1(25),7(12),8,10,19(26),20,23-heptaen-18-one |
| 27 | 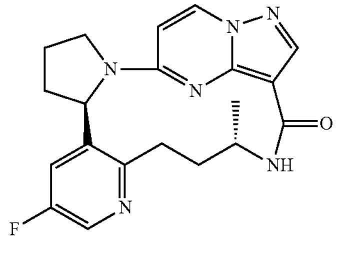 [SMILES: C[C@H]1CCc2ncc(F)cc2[C@H]2CCCN2c2ccn3ncc(c3n2)C(=O)N1] | (6R,15S)-9-fluoro-15-methyl-2,11,16,20,21,24-hexaazapentacyclo [16.5.2.0$^{2,6}$.0$^{7,12}$.0$^{21,25}$]pentacosa-1(24),7,9,11,18(25),19,22-heptaen-17-one |

TABLE 6-continued

| Compounds tested in the Trk Enzyme Assay | | |
|---|---|---|
| Compound No. | Compound Structure | Compound Name |
| 28 | 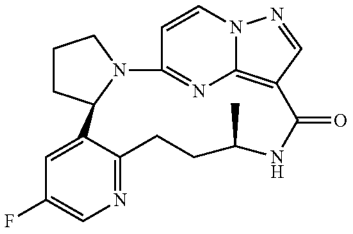 [SMILES: C[C@@H]1CCc2ncc(F)cc2[C@H]2CCCN2c2ccn3ncc(c3n2)C(=O)N1] | (6R,15R)-9-fluoro-15-methyl-2,11,16,20,21,24-hexaazapentacyclo[16.5.2.$0^{2,6}$.$0^{7,12}$.$0^{21,25}$]pentacosa-1(24),7,9,11,18(25),19,22-heptaen-17-one |

The assays were conducted in 96-well polypropylene v-bottom microtitre plates (Corning, Costar® 3363) in a total volume of 50 μL. Reaction mixtures typically contained 25 mM $Na^+$MOPS, pH 7.4, 5 mM $MgCl_2$, 0.005% Triton X-100, 2% DMSO, 1 mM DTT, 5 M [$^{33}$P]ATP (50 μCi/mL), 100 jag/mL poly-EAY, Trk enzyme (Trk A, B or C, wild-type or mutant at an appropriate concentration ranging from 0.1-10 nM, depending on the compound) and compound varying over a 10-point, three-fold dilution series ranging from 2000 to 0.1 nM. Incubations were conducted at 22° C. for 60 minutes and quenched by the addition of 100 μL aliquots of 25% trichloroacetic acid. The radiolabeled product was then captured on glass fiber filter plates (PerkinElmer, Unifilter®-96, GF/B®) and washed with 5% phosphoric acid to remove unbound radiolabel using a Tomtec MACH III Harvester 96®. After adding 35 μL/well of Bio-Safe II™ liquid scintillation cocktail (Research Products International), the plates were counted in a TopCount NXT (PerkinElmer) using a counting time of 30 s/well. The activity at each concentration of compound was expressed as percent of control (POC) and plotted versus compound concentration. An $IC_{50}$ was estimated using a 4-parameter logistic model fit to the dose-response plots, with $IC_{50}$ being defined as the concentration of compound where the best-fit curve crosses 50 POC. The $IC_{50}$ values for the compounds tested in this assay are provided in Table 7.

TABLE 7

| $IC_{50}$ values of compounds tested in the assay of Example 4. | | | | | | | | | | | |
|---|---|---|---|---|---|---|---|---|---|---|---|
| | $IC_{50}$ (nM) | | | | | | | | | | |
| Compound Number | TrkA WT | TrkA V573M | TrkA F589L | TrkA G595R | TrkA G667C | TrkA G667S | TrkB WT | TrkB G623R | TrkC WT | TrkC G623R | TrkC F617L |
| 1 | 1.0 | 94.9 | 124.0 | 24.8 | 91.3 | 30.1 | 5.7 | 59.7 | <2.5 | 29.3 | 58.0 |
| 2 | 0.8 | 76.4 | 61.5 | 19.4 | 46.3 | 21.3 | 4.5 | 34.1 | <2.5 | 23.1 | 37.6 |
| 3 | 2.8 | 627.6 | 577.5 | 61.0 | 295.7 | 91.1 | 11.9 | 90.0 | 4.5 | 55.7 | 273.0 |
| 3 | 2.5 | 547.4 | 384.8 | 57.0 | 298.1 | 108.5 | 10.6 | 132.3 | 3.1 | 70.8 | 177.0 |
| 5 | 1.1 | 151.6 | 231.6 | 84.6 | 141.2 | 38.5 | 5.9 | 131.9 | <2.5 | 95.0 | 153.7 |
| 6 | 0.8 | 74.9 | 78.5 | 25.3 | 55.1 | 23.3 | 5.0 | 27.5 | <2.5 | 24.1 | 49.7 |
| 7 | <0.5 | 67.1 | 83.1 | 30.5 | 52.5 | 26.4 | 7.0 | 47.9 | <2.5 | 22.7 | 42.5 |
| 8 | 0.9 | 129.3 | 153.5 | 49.6 | 84.2 | 19.7 | 5.0 | 64.6 | <2.5 | 54.9 | 67.1 |
| 9 | 0.8 | 106.4 | 90.7 | 91.9 | 76.5 | 21.6 | 4.6 | 104.3 | <2.5 | 92.6 | 66.5 |
| 10 | 0.9 | 104.8 | 102.6 | 107.3 | 89.2 | 27.0 | 6.5 | 149.8 | <2.5 | 100.5 | 80.1 |
| 11 | 6.9 | 1198.9 | 1084.1 | 560.6 | 830.4 | 274.6 | 19.0 | 671.4 | 4.4 | 445.7 | 476.2 |
| 12 | <0.5 | 14.9 | 21.0 | 1.0 | 15.6 | 3.6 | 3.3 | 1.3 | <2.5 | 1.6 | 9.9 |
| 13 | <0.5 | 20.9 | 37.2 | 3.3 | 32.4 | 4.1 | 3.5 | 2.7 | <2.5 | 3.1 | 8.7 |
| 14 | <0.5 | 12.1 | 14.8 | 1.5 | 9.0 | 2.8 | 4.4 | 1.5 | <2.5 | 2.7 | 12.4 |
| 15 | <0.5 | 6.3 | 7.3 | 1.6 | 8.1 | 1.4 | <2.5 | 1.6 | <2.5 | 1.7 | <5.0 |
| 16 | <0.5 | <5.0 | <1.0 | 0.9 | 1.1 | 0.4 | 2.9 | 0.9 | <2.5 | 1.3 | <5.0 |
| 17 | <0.5 | <5.0 | 2.1 | 1.5 | 2.6 | 0.7 | 3.6 | 1.1 | <2.5 | 1.8 | <5.0 |
| 18 | <0.5 | <5.0 | 3.9 | 1.3 | 2.6 | 0.6 | 4.1 | 1.0 | <2.5 | 1.4 | 5.5 |
| 19 | 0.5 | <5.0 | 1.1 | 1.2 | 0.9 | 0.3 | 4.4 | 1.0 | <2.5 | 1.8 | 5.1 |
| 20 | <0.5 | 36.5 | 48.3 | 2.7 | 13.3 | 3.2 | 3.1 | 3.1 | <2.5 | 3.1 | 18.3 |
| 21 | 0.6 | 29.1 | 66.3 | 7.3 | 22.2 | 8.4 | 5.6 | 12.4 | <2.5 | 7.8 | 48.5 |
| 22 | 0.5 | <5.0 | 8.4 | 1.5 | 5.7 | 0.9 | 2.9 | 1.3 | <2.5 | 1.5 | 5.4 |
| 23 | 0.7 | <5.0 | <1.0 | 1.6 | 0.8 | 0.3 | 6.1 | 1.1 | 2.7 | 2.1 | 5.8 |
| 24 | 0.5 | 38.3 | 86.8 | 3.3 | 22.3 | 4.7 | 4.7 | 4.2 | <2.5 | 4.5 | 61.9 |
| 25 | 1.0 | <5.0 | 1.1 | 3.0 | 1.0 | 0.5 | 8.7 | 2.3 | 4.0 | 4.7 | 8.1 |
| 26 | 0.6 | <5.0 | 3.9 | 2.1 | 1.0 | 0.5 | 3.3 | 1.8 | <2.5 | 2.6 | 9.6 |
| 27 | <0.5 | 9.3 | 21.0 | 1.5 | 5.6 | 2.1 | 3.4 | 1.7 | <2.5 | 2.2 | 9.5 |
| 28 | 0.5 | <5.0 | 3.3 | 2.0 | 9.8 | 2.3 | 3.2 | 1.9 | <2.5 | 2.8 | <5.0 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a Trk-associated cancer, the method comprising:

(a) administering one or more doses of a first Trk inhibitor to the subject for a period of time, wherein the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and (b) after (a), administering a treatment comprising one or more doses of the first Trk inhibitor and a second Trk inhibitor to the subject, wherein the second Trk inhibitor is (6R, 15R)-9-fluoro-15-methyl-2,11,16,20,21,24-hexaazapentacyclo[16.5.2.$0^{2,6}$.$0^{7,12}$.$0^{21,25}$]pentacosa-1(24),7,9,11,18(25),19,22-heptaen-17-one;

wherein the subject is identified as having at least one solvent front mutation, wherein the at least one solvent front mutation comprises (i) at least one point mutation in a NTRK1 gene that results in the expression of a TrkA kinase polypeptide comprising a mutation at amino acid position 595, and/or (ii) at least one point mutation in a NTRK3 gene that results in the expression of a TrkC kinase polypeptide comprising a mutation at amino acid position 623, wherein the at least one solvent front mutation is expressed in the Trk-associated cancer.

2. The method of claim 1, wherein the at least one solvent front mutation comprises TrkA G595R, TrkC G623R, or both.

3. The method of claim 1, wherein the subject, following administration of one or more doses of the first Trk inhibitor in step (a), is identified as having at least one solvent front mutation, wherein the at least one solvent front mutation comprises (i) at least one point mutation in a NTRK1 gene that results in the expression of a TrkA kinase polypeptide comprising a mutation at amino acid position 595, and/or (ii) at least one point mutation in a NTRK3 gene that results in the expression of a TrkC kinase polypeptide comprising a mutation at amino acid position 623, wherein the at least one solvent front mutation is expressed in the Trk-associated cancer.

4. The method of claim 3, wherein the at least one solvent front mutation comprises TrkA G595R, TrkC G623R, or both.

5. The method of claim 1, wherein the Trk-associated cancer is selected from the group consisting of: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

6. A method of treating a subject having a Trk-associated cancer, the method comprising administering to the subject one or more doses of (S)—N-(5-((R)-2-(2,5-difluorophenyl) pyrrolidin-1-yl)pyrazolo[1,5-a]pyrimidin-3-yl)-3-hydroxy-pyrrolidine-1-carboxamide sulfate and (6R, 15R)-9-fluoro-15-methyl-2,11,16,20,21,24-hexaazapentacyclo[16.5.2.$0^{2,6}.0^{7,12}.0^{21,25}$]pentacosa-1 (24),7,9,11,18(25), 19,22-heptaen-17-one;

wherein the subject is identified as having at least one solvent front mutation, wherein the at least one solvent front mutation comprises (i) at least one point mutation in a NTRK1 gene that results in the expression of a TrkA kinase polypeptide comprising a mutation at amino acid position 595, and/or (ii) at least one point mutation in a NTRK3 gene that results in the expression of a TrkC kinase polypeptide comprising a mutation at amino acid position 623, wherein the at least one solvent front mutation is expressed in the Trk-associated cancer.

7. The method of claim 6, wherein the at least one solvent front mutation comprises TrkA G595R, TrkC G623R, or both.

8. The method of claim 6, wherein the subject was previously administered one or more doses of (S)—N-(5-((R)-2-(2,5-difluorophenyl)pyrrolidin-1-yl)pyrazolo[1,5-a] pyrimidin-3-yl)-3-hydroxypyrrolidine-1-carboxamide sulfate prior to being identified as having at least one solvent front mutation, wherein the at least one solvent front mutation comprises (i) at least one point mutation in a NTRK1 gene that results in the expression of a TrkA kinase polypeptide comprising a mutation at amino acid position 595, and/or (ii) at least one point mutation in a NTRK3 gene that results in the expression of a TrkC kinase polypeptide comprising a mutation at amino acid position 623, wherein the at least one solvent front mutation is expressed in the Trk-associated cancer.

9. The method of claim 8, wherein the at least one solvent front mutation comprises TrkA G595R, TrkC G623R, or both.

10. The method of claim 6, wherein the Trk-associated cancer is selected from the group consisting of: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

11. A method of treating a subject having a Trk-associated cancer, the method comprising:

(a) administering one or more doses of a first Trk inhibitor to the subject for a period of time, wherein the first Trk inhibitor is (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate; and (b) after (a), administering a treatment comprising one or more doses of the first Trk inhibitor and a second Trk inhibitor to the subject, wherein the second Trk inhibitor is (6R, 15R)-9-fluoro-15-methyl-2,11,16,20,21,24-hexaazapentacyclo[16.5.2.$0^{2,6}$.$0^{7,12}$.$0^{21,25}$]pentacosa-1(24),7,9,11,18(25),19,22-heptaen-17-one;

wherein the subject is identified as having (i) at least one point mutation in a NTRK1 gene that results in the expression of a TrkA kinase polypeptide comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB kinase polypeptide comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC kinase polypeptide comprising a mutation at one or more amino acid position(s) selected from the group consisting of: 545, 570, 596, 601, 617, 623, 624, 628, 630, 675, 685, 686, 696, and 705.

12. The method of claim 11, wherein the at least one point mutation comprises (i) at least one point mutation in a NTRK1 gene that results in the expression of a TrkA kinase polypeptide comprising a mutation selected from the group consisting of: G517R, A542V, Q568x, V573M, F589L, F589C, G595S, G595R, F600L, R602x, F646V, C656Y, C656F, L657V, G667C, G667S, and Y676S, and/or (ii) at least one point mutation in a NTRK2 gene that results in the expression of a TrkB kinase polypeptide comprising a mutation selected from the group consisting of: G545R, A570V, Q596E, Q596P, V601G, F617L, F617C, F617I, G623S, G623R, D624V, F628x, R630K, F672x, C682Y, C682F, L683V, G693S, and Y702x, and/or (iii) at least one point mutation in a NTRK3 gene that results in the expression of a TrkC kinase polypeptide comprising a mutation at one or more amino acid position(s) selected from the group consisting of: G545R, A570V, Q596x, F617L, G623R, D624V, F628x, R630x, F675x, C685Y, C685F, L686V, G696A, and Y705x.

13. The method of claim 11, wherein the subject, following administration of one or more doses of the first Trk inhibitor in step (a), is identified as having (i) at least one point mutation in a NTRK1 gene that results in the expression of a TrkA kinase polypeptide comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB kinase polypeptide comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC kinase polypeptide comprising a mutation at one or more amino acid position(s) selected from the group consisting of: 545, 570, 596, 601, 617, 623, 624, 628, 630, 675, 685, 686, 696, and 705.

14. The method of claim 13, wherein the at least one point mutation comprises (i) at least one point mutation in a NTRK1 gene that results in the expression of a TrkA kinase polypeptide comprising a mutation selected from the group consisting of: G517R, A542V, Q568x, V573M, F589L, F589C, G595S, G595R, F600L, R602x, F646V, C656Y, C656F, L657V, G667C, G667S, and Y676S, and/or (ii) at least one point mutation in a NTRK2 gene that results in the expression of a TrkB kinase polypeptide comprising a mutation selected from the group consisting of: G545R, A570V, Q596E, Q596P, V601G, F617L, F617C, F617I, G623S, G623R, D624V, F628x, R630K, F672x, C682Y, C682F, L683V, G693S, and Y702x, and/or (iii) at least one point mutation in a NTRK3 gene that results in the expression of a TrkC kinase polypeptide comprising a mutation at one or more amino acid position(s) selected from the group consisting of: G545R, A570V, Q596x, F617L, G623R, D624V, F628x, R630x, F675x, C685Y, C685F, L686V, G696A, and Y705x.

15. The method of claim 11, wherein the Trk-associated cancer is selected from the group consisting of: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

16. A method of treating a subject having a Trk-associated cancer, the method comprising administering to the subject one or more doses of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate and (6R, 15R)-9-fluoro-15-methyl-2,11,16,20,21,24-hexaazapentacyclo [16.5.2.$0^{2,6}$.$0^{7,12}$.$0^{21,25}$]pentacosa-1 (24),7,9,11,18(25), 19,22-heptaen-17-one;

wherein the subject is identified as having (i) at least one point mutation in a NTRK1 gene that results in the expression of a TrkA kinase polypeptide comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB kinase polypeptide comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC kinase polypeptide comprising a mutation at one or more amino acid position(s) selected from the group consisting of: 545, 570, 596, 601, 617, 623, 624, 628, 630, 675, 685, 686, 696, and 705.

17. The method of claim 16, wherein the at least one point mutation comprises (i) at least one point mutation in a NTRK1 gene that results in the expression of a TrkA kinase polypeptide comprising a mutation selected from the group consisting of: G517R, A542V, Q568x, V573M, F589L, F589C, G595S, G595R, F600L, R602x, F646V, C656Y, C656F, L657V, G667C, G667S, and Y676S, and/or (ii) at least one point mutation in a NTRK2 gene that results in the expression of a TrkB kinase polypeptide comprising a mutation selected from the group consisting of: G545R, A570V, Q596E, Q596P, V601G, F617L, F617C, F617I, G623S, G623R, D624V, F628x, R630K, F672x, C682Y, C682F, L683V, G693S, and Y702x, and/or (iii) at least one point mutation in a NTRK3 gene that results in the expression of a TrkC kinase polypeptide comprising a mutation at one or more amino acid position(s) selected from the group consisting of: G545R, A570V, Q596x, F617L, G623R, D624V, F628x, R630x, F675x, C685Y, C685F, L686V, G696A, and Y705x.

18. The method of claim 16, wherein the subject was previously administered one or more doses of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate prior to being identified as having (i) at least one point mutation in a NTRK1 gene that results in the expression of a TrkA kinase polypeptide comprising a mutation at one or more amino acid position(s) selected from the group consisting of: 517, 542, 568, 573, 589, 595, 599, 600, 602, 646, 656, 657, 667, and 676, and/or (ii) at least one point mutation in a NTRK2 gene that results in the expression of a TrkB kinase polypeptide comprising a mutation at one or more amino acid position(s) selected from the group consisting of: 545, 570, 596, 601, 617, 623, 624, 628, 630, 672, 682, 683, 693, and 702, and/or (iii) at least one point mutation in a NTRK3 gene that results in the expression of a TrkC kinase polypeptide comprising a mutation at one or more amino acid position(s) selected from the group consisting of: 545, 570, 596, 601, 617, 623, 624, 628, 630, 675, 685, 686, 696, and 705.

19. The method of claim 18, wherein the at least one point mutation comprises (i) at least one point mutation in a NTRK1 gene that results in the expression of a TrkA kinase polypeptide comprising a mutation selected from the group consisting of: G517R, A542V, Q568x, V573M, F589L, F589C, G595S, G595R, F600L, R602x, F646V, C656Y, C656F, L657V, G667C, G667S, and Y676S, and/or (ii) at least one point mutation in a NTRK2 gene that results in the expression of a TrkB kinase polypeptide comprising a mutation selected from the group consisting of: G545R, A570V, Q596E, Q596P, V601G, F617L, F617C, F617I, G623S, G623R, D624V, F628x, R630K, F672x, C682Y, C682F, L683V, G693S, and Y702x, and/or (iii) at least one point mutation in a NTRK3 gene that results in the expression of a TrkC kinase polypeptide comprising a mutation at one or more amino acid position(s) selected from the group consisting of: G545R, A570V, Q596x, F617L, G623R, D624V, F628x, R630x, F675x, C685Y, C685F, L686V, G696A, and Y705x.

20. The method of claim 16, wherein the Trk-associated cancer is selected from the group consisting of: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, leukemia lymphocytic, liver cholangiocarcinoma, liver hepatocellular carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, non-Hodgkin's lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma.

* * * * *

SEQUENCE LISTING

<160> NUMBER OF SEQ ID NOS: 9

<210> SEQ ID NO 1
<211> LENGTH: 796
<212> TYPE: PRT
<213> ORGANISM: Homo sapiens

<400> SEQUENCE: 1

Met Leu Arg Gly Gly Arg Arg Gly Gln Leu Gly Trp His Ser Trp Ala
1 5 10 15

Ala Gly Pro Gly Ser Leu Leu Ala Trp Leu Ile Leu Ala Ser Ala Gly
20 25 30

Ala Ala Pro Cys Pro Asp Ala Cys Cys Pro His Gly Ser Ser Gly Leu
35 40 45

Arg Cys Thr Arg Asp Gly Ala Leu Asp Ser Leu His His Leu Pro Gly
50 55 60

Ala Glu Asn Leu Thr Glu Leu Tyr Ile Glu Asn Gln Gln His Leu Gln
65 70 75 80

His Leu Glu Leu Arg Asp Leu Arg Gly Leu Gly Glu Leu Arg Asn Leu
85 90 95

Thr Ile Val Lys Ser Gly Leu Arg Phe Val Ala Pro Asp Ala Phe His
100 105 110

Phe Thr Pro Arg Leu Ser Arg Leu Asn Leu Ser Phe Asn Ala Leu Glu
115 120 125

Ser Leu Ser Trp Lys Thr Val Gln Gly Leu Ser Leu Gln Glu Leu Val
130 135 140

Leu Ser Gly Asn Pro Leu His Cys Ser Cys Ala Leu Arg Trp Leu Gln
145 150 155 160

Arg Trp Glu Glu Glu Gly Leu Gly Gly Val Pro Glu Gln Lys Leu Gln
165 170 175

Cys His Gly Gln Gly Pro Leu Ala His Met Pro Asn Ala Ser Cys Gly
180 185 190

Val Pro Thr Leu Lys Val Gln Val Pro Asn Ala Ser Val Asp Val Gly
195 200 205

Asp Asp Val Leu Leu Arg Cys Gln Val Glu Gly Arg Gly Leu Glu Gln
210 215 220

Ala Gly Trp Ile Leu Thr Glu Leu Glu Gln Ser Ala Thr Val Met Lys
225 230 235 240

Ser Gly Gly Leu Pro Ser Leu Gly Leu Thr Leu Ala Asn Val Thr Ser
245 250 255

Asp Leu Asn Arg Lys Asn Val Thr Cys Trp Ala Glu Asn Asp Val Gly
260 265 270

Arg Ala Glu Val Ser Val Gln Val Asn Val Ser Phe Pro Ala Ser Val
275 280 285

Gln Leu His Thr Ala Val Glu Met His His Trp Cys Ile Pro Phe Ser
290 295 300

```
Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
        435                 440                 445

Gly Ile Asn Arg Pro Ala Val Leu Ala Pro Glu Asp Gly Leu Ala Met
    450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
        515                 520                 525

Cys His Asn Leu Leu Pro Glu Gln Asp Lys Met Leu Val Ala Val Lys
    530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
    610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
        675                 680                 685

Leu Pro Ile Arg Trp Met Pro Pro Glu Ser Ile Leu Tyr Arg Lys Phe
    690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
```

```
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
    770                 775                 780

Ala Gln Ala Pro Pro Val Tyr Leu Asp Val Leu Gly
785                 790                 795


<210> SEQ ID NO 2
<211> LENGTH: 2663
<212> TYPE: DNA
<213> ORGANISM: Homo sapiens

<400> SEQUENCE: 2

tgcagctggg agcgcacaga cggctgcccc gcctgagcga ggcgggcgcc gccgcgatgc      60

tgcgaggcgg acggcgcggg cagcttggct ggcacagctg ggctgcgggg ccgggcagcc     120

tgctggcttg gctgatactg gcatctgcgg gcgccgcacc ctgccccgat gcctgctgcc     180

cccacggctc ctcgggactg cgatgcaccc gggatggggc cctggatagc ctccaccacc     240

tgcccggcgc agagaacctg actgagctct acatcgagaa ccagcagcat ctgcagcatc     300

tggagctccg tgatctgagg ggcctggggg agctgagaaa cctcaccatc gtgaagagtg     360

gtctccgttt cgtggcgcca gatgccttcc atttcactcc tcggctcagt cgcctgaatc     420

tctccttcaa cgctctggag tctctctcct ggaaaactgt gcagggcctc tccttacagg     480

aactggtcct gtcggggaac cctctgcact gttcttgtgc cctgcgctgg ctacagcgct     540

gggaggagga gggactgggc ggagtgcctg aacagaagct gcagtgtcat gggcaagggc     600

ccctggccca catgcccaat gccagctgtg gtgtgcccac gctgaaggtc caggtgccca     660

atgcctcggt ggatgtgggg gacgacgtgc tgctgcggtg ccaggtggag gggcggggcc     720

tggagcaggc cggctggatc ctcacagagc tggagcagtc agccacggtg atgaaatctg     780

ggggtctgcc atccctgggg ctgaccctgg ccaatgtcac cagtgacctc aacaggaaga     840

acgtgacgtg ctgggcagag aacgatgtgg gccgggcaga ggtctctgtt caggtcaacg     900

tctccttccc ggccagtgtg cagctgcaca cggcggtgga gatgcaccac tggtgcatcc     960

ccttctctgt ggatgggcag ccggcaccgt ctctgcgctg gctcttcaat ggctccgtgc    1020

tcaatgagac cagcttcatc ttcactgagt tcctggagcc ggcagccaat gagaccgtgc    1080

ggcacgggtg tctgcgcctc aaccagccca cccacgtcaa caacggcaac tacacgctgc    1140

tggctgccaa ccccttcggc caggcctccg cctccatcat ggctgccttc atggacaacc    1200

ctttcgagtt caaccccgag gaccccatcc ctgtctcctt ctcgccggtg gacactaaca    1260

gcacatctgg agacccggtg gagaagaagg acgaaacacc ttttggggtc tcggtggctg    1320

tgggcctggc cgtctttgcc tgcctcttcc tttctacgct gctccttgtg ctcaacaaat    1380

gtggacggag aaacaagttt gggatcaacc gcccggctgt gctggctcca gaggatgggc    1440

tggccatgtc cctgcatttc atgacattgg gtggcagctc cctgtccccc accgagggca    1500

aaggctctgg gctccaaggc cacatcatcg agaacccaca atacttcagt gatgcctgtg    1560

ttcaccacat caagcgccgg gacatcgtgc tcaagtggga gctgggggag ggcgcctttg    1620

ggaaggtctt ccttgctgag tgccacaacc tcctgcctga gcaggacaag atgctggtgg    1680

ctgtcaaggc actgaaggag gcgtccgaga gtgctcggca ggacttccag cgtgaggctg    1740
```

```
agctgctcac catgctgcag caccagcaca tcgtgcgctt cttcggcgtc tgcaccgagg   1800

gccgcccccct gctcatggtc tttgagtata tgcggcacgg ggacctcaac cgcttcctcc   1860

gatcccatgg acctgatgcc aagctgctgg ctggtgggga ggatgtggct ccaggccccc   1920

tgggtctggg gcagctgctg gccgtggcta gccaggtcgc tgcggggatg gtgtacctgg   1980

cgggtctgca ttttgtgcac cgggacctgg ccacacgcaa ctgtctagtg ggccagggac   2040

tggtggtcaa gattggtgat tttggcatga gcagggatat ctacagcacc gactattacc   2100

gtgtgggagg ccgcaccatg ctgcccattc gctggatgcc gcccgagagc atcctgtacc   2160

gtaagttcac caccgagagc gacgtgtgga gcttcggcgt ggtgctctgg gagatcttca   2220

cctacggcaa gcagccctgg taccagctct ccaacacgga ggcaatcgac tgcatcacgc   2280

agggacgtga gttggagcgg ccacgtgcct gcccaccaga ggtctacgcc atcatgcggg   2340

gctgctggca gcgggagccc cagcaacgcc acagcatcaa ggatgtgcac gcccggctgc   2400

aagccctggc ccaggcacct cctgtctacc tggatgtcct gggctagggg gccggcccag   2460

gggctgggag tggttagccg gaatactggg gcctgccctc agcatccccc atagctccca   2520

gcagccccag ggtgatctca aagtatctaa ttcaccctca gcatgtggga agggacaggt   2580

gggggctggg agtagaggat gttcctgctt ctctaggcaa ggtcccgtca tagcaattat   2640

atttattatc ccttgaaaaa aaa                                          2663
```

<210> SEQ ID NO 3
<211> LENGTH: 760
<212> TYPE: PRT
<213> ORGANISM: Homo sapiens

<400> SEQUENCE: 3

```
Met Lys Glu Ala Ala Leu Ile Cys Leu Ala Pro Ser Val Pro Pro Ile
1               5                   10                  15

Leu Thr Val Lys Ser Trp Asp Thr Met Gln Leu Arg Ala Ala Arg Ser
            20                  25                  30

Arg Cys Thr Asn Leu Leu Ala Ala Ser Tyr Ile Glu Asn Gln Gln His
        35                  40                  45

Leu Gln His Leu Glu Leu Arg Asp Leu Arg Gly Leu Gly Glu Leu Arg
    50                  55                  60

Asn Leu Thr Ile Val Lys Ser Gly Leu Arg Phe Val Ala Pro Asp Ala
65                  70                  75                  80

Phe His Phe Thr Pro Arg Leu Ser Arg Leu Asn Leu Ser Phe Asn Ala
                85                  90                  95

Leu Glu Ser Leu Ser Trp Lys Thr Val Gln Gly Leu Ser Leu Gln Glu
            100                 105                 110

Leu Val Leu Ser Gly Asn Pro Leu His Cys Ser Cys Ala Leu Arg Trp
        115                 120                 125

Leu Gln Arg Trp Glu Glu Glu Gly Leu Gly Gly Val Pro Glu Gln Lys
    130                 135                 140

Leu Gln Cys His Gly Gln Gly Pro Leu Ala His Met Pro Asn Ala Ser
145                 150                 155                 160

Cys Gly Val Pro Thr Leu Lys Val Gln Val Pro Asn Ala Ser Val Asp
                165                 170                 175

Val Gly Asp Asp Val Leu Leu Arg Cys Gln Val Glu Gly Arg Gly Leu
            180                 185                 190

Glu Gln Ala Gly Trp Ile Leu Thr Glu Leu Glu Gln Ser Ala Thr Val
        195                 200                 205
```

```
Met Lys Ser Gly Gly Leu Pro Ser Leu Gly Leu Thr Leu Ala Asn Val
    210                 215                 220

Thr Ser Asp Leu Asn Arg Lys Asn Val Thr Cys Trp Ala Glu Asn Asp
225                 230                 235                 240

Val Gly Arg Ala Glu Val Ser Val Gln Val Asn Val Ser Phe Pro Ala
                245                 250                 255

Ser Val Gln Leu His Thr Ala Val Glu Met His His Trp Cys Ile Pro
            260                 265                 270

Phe Ser Val Asp Gly Gln Pro Ala Pro Ser Leu Arg Trp Leu Phe Asn
        275                 280                 285

Gly Ser Val Leu Asn Glu Thr Ser Phe Ile Phe Thr Glu Phe Leu Glu
    290                 295                 300

Pro Ala Ala Asn Glu Thr Val Arg His Gly Cys Leu Arg Leu Asn Gln
305                 310                 315                 320

Pro Thr His Val Asn Asn Gly Asn Tyr Thr Leu Leu Ala Ala Asn Pro
                325                 330                 335

Phe Gly Gln Ala Ser Ala Ser Ile Met Ala Ala Phe Met Asp Asn Pro
            340                 345                 350

Phe Glu Phe Asn Pro Glu Asp Pro Ile Pro Asp Thr Asn Ser Thr Ser
        355                 360                 365

Gly Asp Pro Val Glu Lys Lys Asp Glu Thr Pro Phe Gly Val Ser Val
    370                 375                 380

Ala Val Gly Leu Ala Val Phe Ala Cys Leu Phe Leu Ser Thr Leu Leu
385                 390                 395                 400

Leu Val Leu Asn Lys Cys Gly Arg Arg Asn Lys Phe Gly Ile Asn Arg
                405                 410                 415

Pro Ala Val Leu Ala Pro Glu Asp Gly Leu Ala Met Ser Leu His Phe
            420                 425                 430

Met Thr Leu Gly Gly Ser Ser Leu Ser Pro Thr Glu Gly Lys Gly Ser
        435                 440                 445

Gly Leu Gln Gly His Ile Ile Glu Asn Pro Gln Tyr Phe Ser Asp Ala
    450                 455                 460

Cys Val His His Ile Lys Arg Arg Asp Ile Val Leu Lys Trp Glu Leu
465                 470                 475                 480

Gly Glu Gly Ala Phe Gly Lys Val Phe Leu Ala Glu Cys His Asn Leu
                485                 490                 495

Leu Pro Glu Gln Asp Lys Met Leu Val Ala Val Lys Ala Leu Lys Glu
            500                 505                 510

Ala Ser Glu Ser Ala Arg Gln Asp Phe Gln Arg Glu Ala Glu Leu Leu
        515                 520                 525

Thr Met Leu Gln His Gln His Ile Val Arg Phe Phe Gly Val Cys Thr
    530                 535                 540

Glu Gly Arg Pro Leu Leu Met Val Phe Glu Tyr Met Arg His Gly Asp
545                 550                 555                 560

Leu Asn Arg Phe Leu Arg Ser His Gly Pro Asp Ala Lys Leu Leu Ala
                565                 570                 575

Gly Gly Glu Asp Val Ala Pro Gly Pro Leu Gly Leu Gly Gln Leu Leu
            580                 585                 590

Ala Val Ala Ser Gln Val Ala Ala Gly Met Val Tyr Leu Ala Gly Leu
        595                 600                 605

His Phe Val His Arg Asp Leu Ala Thr Arg Asn Cys Leu Val Gly Gln
    610                 615                 620
```

```
Gly Leu Val Val Lys Ile Gly Asp Phe Gly Met Ser Arg Asp Ile Tyr
625                 630                 635                 640

Ser Thr Asp Tyr Tyr Arg Val Gly Gly Arg Thr Met Leu Pro Ile Arg
                645                 650                 655

Trp Met Pro Pro Glu Ser Ile Leu Tyr Arg Lys Phe Thr Thr Glu Ser
            660                 665                 670

Asp Val Trp Ser Phe Gly Val Val Leu Trp Glu Ile Phe Thr Tyr Gly
        675                 680                 685

Lys Gln Pro Trp Tyr Gln Leu Ser Asn Thr Glu Ala Ile Asp Cys Ile
    690                 695                 700

Thr Gln Gly Arg Glu Leu Glu Arg Pro Arg Ala Cys Pro Pro Glu Val
705                 710                 715                 720

Tyr Ala Ile Met Arg Gly Cys Trp Gln Arg Glu Pro Gln Gln Arg His
                725                 730                 735

Ser Ile Lys Asp Val His Ala Arg Leu Gln Ala Leu Ala Gln Ala Pro
            740                 745                 750

Pro Val Tyr Leu Asp Val Leu Gly
        755                 760


<210> SEQ ID NO 4
<211> LENGTH: 2581
<212> TYPE: DNA
<213> ORGANISM: Homo sapiens

<400> SEQUENCE: 4

gcaccctggt catctgcgga ctcagcctga gcttccagag ggcctaggag cagtaaggga      60

gtgagtgggc aactcggcgc atgaaggagg ccgccctcat ctgcctggca ccctctgtac     120

ccccgatctt gacggtgaag tcctgggaca ccatgcagtt gcgggctgct agatctcggt     180

gcacaaactt gttggcagca agctacatcg agaaccagca gcatctgcag catctggagc     240

tccgtgatct gaggggcctg ggggagctga gaaacctcac catcgtgaag agtggtctcc     300

gtttcgtggc gccagatgcc ttccatttca ctcctcggct cagtcgcctg aatctctcct     360

tcaacgctct ggagtctctc tcctggaaaa ctgtgcaggg cctctcctta caggaactgg     420

tcctgtcggg gaaccctctg cactgttctt gtgccctgcg ctggctacag cgctgggagg     480

aggagggact gggcggagtg cctgaacaga agctgcagtg tcatgggcaa gggcccctgg     540

cccacatgcc caatgccagc tgtggtgtgc ccacgctgaa ggtccaggtg cccaatgcct     600

cggtggatgt gggggacgac gtgctgctgc ggtgccaggt ggaggggcgg ggcctggagc     660

aggccggctg gatcctcaca gagctggagc agtcagccac ggtgatgaaa tctgggggtc     720

tgccatccct ggggctgacc ctggccaatg tcaccagtga cctcaacagg aagaacgtga     780

cgtgctgggc agagaacgat gtgggccggg cagaggtctc tgttcaggtc aacgtctcct     840

tcccggccag tgtgcagctg cacacggcgg tggagatgca ccactggtgc atccccttct     900

ctgtggatgg gcagccggca ccgtctctgc gctggctctt caatggctcc gtgctcaatg     960

agaccagctt catcttcact gagttcctgg agccggcagc caatgagacc gtgcggcacg    1020

ggtgtctgcg cctcaaccag cccacccacg tcaacaacgg caactacacg ctgctggctg    1080

ccaacccctt cggccaggcc tccgcctcca tcatggctgc cttcatggac aaccctttcg    1140

agttcaaccc cgaggacccc atccctgaca ctaacagcac atctggagac ccggtggaga    1200

agaaggacga aacacctttt ggggtctcgg tggctgtggg cctggccgtc tttgcctgcc    1260

tcttcctttc tacgctgctc cttgtgctca acaaatgtgg acggagaaac aagtttggga    1320
```

```
tcaaccgccc ggctgtgctg gctccagagg atgggctggc catgtccctg catttcatga   1380
cattgggtgg cagctccctg tcccccaccg agggcaaagg ctctgggctc caaggccaca   1440
tcatcgagaa cccacaatac ttcagtgatg cctgtgttca ccacatcaag cgccgggaca   1500
tcgtgctcaa gtgggagctg gggagggcg cctttgggaa ggtcttcctt gctgagtgcc    1560
acaacctcct gcctgagcag gacaagatgc tggtggctgt caaggcactg aaggaggcgt   1620
ccgagagtgc tcggcaggac ttccagcgtg aggctgagct gctcaccatg ctgcagcacc   1680
agcacatcgt gcgcttcttc ggcgtctgca ccgagggccg cccccctgctc atggtctttg  1740
agtatatgcg gcacggggac ctcaaccgct tcctccgatc ccatggacct gatgccaagc   1800
tgctggctgg tggggaggat gtggctccag gccccctggg tctggggcag ctgctggccg   1860
tggctagcca ggtcgctgcg gggatggtgt acctggcggg tctgcatttt gtgcaccggg   1920
acctggccac acgcaactgt ctagtgggcc agggactggt ggtcaagatt ggtgattttg   1980
gcatgagcag ggatatctac agcaccgact attaccgtgt gggaggccgc accatgctgc   2040
ccattcgctg gatgccgccc gagagcatcc tgtaccgtaa gttcaccacc gagagcgacg   2100
tgtggagctt cggcgtggtg ctctgggaga tcttcaccta cggcaagcag ccctggtacc   2160
agctctccaa cacggaggca atcgactgca tcacgcaggg acgtgagttg gagcggccac   2220
gtgcctgccc accagaggtc tacgccatca tgcggggctg ctggcagcgg gagccccagc   2280
aacgccacag catcaaggat gtgcacgccc ggctgcaagc cctggcccag gcacctcctg   2340
tctacctgga tgtcctgggc tagggggccg gcccaggggc tgggagtggt tagccggaat   2400
actggggcct gccctcagca tcccccatag ctcccagcag ccccagggtg atctcaaagt   2460
atctaattca ccctcagcat gtgggaaggg acaggtgggg gctgggagta gaggatgttc   2520
ctgcttctct aggcaaggtc ccgtcatagc aattatattt attatccctt gaaaaaaaaa   2580
a                                                                   2581
```

<210> SEQ ID NO 5
<211> LENGTH: 822
<212> TYPE: PRT
<213> ORGANISM: Homo sapiens

<400> SEQUENCE: 5

```
Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140
```

-continued

```
Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
        515                 520                 525

Phe Val Gln His Ile Lys Arg His Asn Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
```

```
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
    610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820


<210> SEQ ID NO 6
<211> LENGTH: 3194
<212> TYPE: DNA
<213> ORGANISM: Homo sapiens

<400> SEQUENCE: 6

ggaaggttta aagaagaagc cgcaaagcgc agggaaggcc tcccggcacg ggtgggggaa      60

agcggccggt gcagcgcggg gacaggcact cgggctggca ctggctgcta gggatgtcgt     120

cctggataag gtggcatgga cccgccatgg cgcggctctg gggcttctgc tggctggttg     180

tgggcttctg gagggccgct ttcgcctgtc ccacgtcctg caaatgcagt gcctctcgga     240

tctggtgcag cgacccttct cctggcatcg tggcatttcc gagattggag cctaacagtg     300

tagatcctga gaacatcacc gaaattttca tcgcaaacca gaaaaggtta gaaatcatca     360

acgaagatga tgttgaagct tatgtgggac tgagaaatct gacaattgtg gattctggat     420

taaaatttgt ggctcataaa gcatttctga aaaacagcaa cctgcagcac atcaatttta     480

cccgaaacaa actgacgagt ttgtctagga aacatttccg tcaccttgac ttgtctgaac     540

tgatcctggt gggcaatcca tttacatgct cctgtgacat tatgtggatc aagactctcc     600

aagaggctaa atccagtcca gacactcagg atttgtactg cctgaatgaa agcagcaaga     660
```

-continued atattcccct ggcaaacctg cagataccca attgtggttt gccatctgca aatctggccg 720
cacctaacct cactgtggag gaaggaaagt ctatcacatt atcctgtagt gtggcaggtg 780
atccggttcc taatatgtat tggatgttg gtaacctggt ttccaaacat atgaatgaaa 840
caagccacac acagggctcc ttaaggataa ctaacatttc atccgatgac agtgggaagc 900
agatctcttg tgtggcggaa aatcttgtag gagaagatca agattctgtc aacctcactg 960
tgcattttgc accaactatc acatttctcg aatctccaac ctcagaccac cactggtgca 1020
ttccattcac tgtgaaaggc aacccaaaac cagcgcttca gtggttctat aacggggcaa 1080
tattgaatga gtccaaatac atctgtacta aaatacatgt taccaatcac acggagtacc 1140
acggctgcct ccagctggat aatcccactc acatgaacaa tggggactac actctaatag 1200
ccaagaatga gtatgggaag gatgagaaac agatttctgc tcacttcatg ggctggcctg 1260
gaattgacga tggtgcaaac ccaaattatc ctgatgtaat ttatgaagat tatggaactg 1320
cagcgaatga catcggggac accacgaaca gaagtaatga aatcccttcc acagacgtca 1380
ctgataaaac cggtcgggaa catctctcgg tctatgctgt ggtggtgatt gcgtctgtgg 1440
tgggattttg ccttttggta atgctgtttc tgcttaagtt ggcaagacac tccaagtttg 1500
gcatgaaagg cccagcctcc gttatcagca atgatgatga ctctgccagc ccactccatc 1560
acatctccaa tgggagtaac actccatctt cttcggaagg tggcccagat gctgtcatta 1620
ttggaatgac caagatccct gtcattgaaa atccccagta ctttggcatc accaacagtc 1680
agctcaagcc agacacattt gttcagcaca tcaagcgaca taacattgtt ctgaaaaggg 1740
agctaggcga aggagccttt ggaaaagtgt tcctagctga atgctataac ctctgtcctg 1800
agcaggacaa gatcttggtg gcagtgaaga ccctgaagga tgccagtgac aatgcacgca 1860
aggacttcca ccgtgaggcc gagctcctga ccaacctcca gcatgagcac atcgtcaagt 1920
tctatggcgt ctgcgtggag ggcgaccccc tcatcatggt ctttgagtac atgaagcatg 1980
gggacctcaa caagttcctc agggcacacg gccctgatgc cgtgctgatg gctgagggca 2040
acccgcccac ggaactgacg cagtcgcaga tgctgcatat agcccagcag atcgccgcgg 2100
gcatggtcta cctggcgtcc cagcacttcg tgcaccgcga tttggccacc aggaactgcc 2160
tggtcgggga gaacttgctg gtgaaaatcg gggactttgg gatgtcccgg gacgtgtaca 2220
gcactgacta ctacagggtc ggtggccaca caatgctgcc cattcgctgg atgcctccag 2280
agagcatcat gtacaggaaa ttcacgacgg aaagcgacgt ctggagcctg ggggtcgtgt 2340
tgtgggagat tttcacctat ggcaaacagc cctggtacca gctgtcaaac aatgaggtga 2400
tagagtgtat cactcagggc cgagtcctgc agcgaccccg cacgtgcccc caggaggtgt 2460
atgagctgat gctggggtgc tggcagcgag agccccacat gaggaagaac atcaagggca 2520
tccataccct ccttcagaac ttggccaagg catctccggt ctacctggac attctaggct 2580
agggcccttt tccccagacc gatccttccc aacgtactcc tcagacgggc tgagaggatg 2640
aacatctttt aactgccgct ggaggccacc aagctgctct ccttcactct gacagtatta 2700
acatcaaaga ctccgagaag ctctcgaggg aagcagtgtg tacttcttca tccatagaca 2760
cagtattgac ttctttttgg cattatctct ttctctcttt ccatctccct tggttgttcc 2820
tttttctttt tttaaatttt ctttttcttc ttttttttcg tcttccctgc ttcacgattc 2880
ttaccctttc ttttgaatca atctggcttc tgcattacta ttaactctgc atagacaaag 2940
gccttaacaa acgtaatttg ttatatcagc agacactcca gtttgcccac cacaactaac 3000

```
aatgccttgt tgtattcctg cctttgatgt ggatgaaaaa aagggaaaac aaatatttca   3060

cttaaacttt gtcacttctg ctgtacagat atcgagagtt tctatggatt cacttctatt   3120

tatttattat tattactgtt cttattgttt ttggatggct taagcctgtg tataaaaaaa   3180

aaaaaaaatc taga                                                       3194


<210> SEQ ID NO 7
<211> LENGTH: 839
<212> TYPE: PRT
<213> ORGANISM: Homo sapiens

<400> SEQUENCE: 7

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Asn Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Pro Thr Leu His Trp Leu
                325                 330                 335
```

-continued

```
His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
        355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Tyr Val Gln His Ile Lys Arg Arg Asp Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
        595                 600                 605

Asp Gly Asp Pro Leu Ile Met Val Phe Glu Tyr Met Lys His Gly Asp
    610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
    690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
```

```
        755                 760                 765

Gln Pro Trp Phe Gln Leu Ser Asn Thr Glu Val Ile Glu Cys Ile Thr
    770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                805                 810                 815

Ile Lys Glu Ile Tyr Lys Ile Leu His Ala Leu Gly Lys Ala Thr Pro
            820                 825                 830

Ile Tyr Leu Asp Ile Leu Gly
        835


<210> SEQ ID NO 8
<211> LENGTH: 2715
<212> TYPE: DNA
<213> ORGANISM: Homo sapiens

<400> SEQUENCE: 8

ggatccgcgt cggagatgga tgtctctctt tgcccagcca agtgtagttt ctggcggatt     60

ttcttgctgg gaagcgtctg gctggactat gtgggctccg tgctggcttg ccctgcaaat    120

tgtgtctgca gcaagactga gatcaattgc cggcggccgg acgatgggaa cctcttcccc    180

ctcctggaag ggcaggattc agggaacagc aatgggaacg ccaatatcaa catcacggac    240

atctcaagga atatcacttc catacacata gagaactggc gcagtcttca cacgctcaac    300

gccgtggaca tggagctcta caccggactt caaaagctga ccatcaagaa ctcaggactt    360

cggagcattc agcccagagc ctttgccaag aacccccatt tgcgttatat aaacctgtca    420

agtaaccggc tcaccacact ctcgtggcag ctcttccaga cgctgagtct tcgggaattg    480

cagttggagc agaacttttt caactgcagc tgtgacatcc gctggatgca gctctggcag    540

gagcaggggg aggccaagct caacagccag aacctctact gcatcaatgc tgatggctcc    600

cagcttcctc tcttccgcat gaacatcagt cagtgtgacc ttcctgagat cagcgtgagc    660

cacgtcaacc tgaccgtacg agagggtgac aatgctgtta tcacttgcaa tggctctgga    720

tcacccttc ctgatgtgga ctggatagtc actgggctgc agtccatcaa cactcaccag     780

accaatctga actggaccaa tgttcatgcc atcaacttga cgctggtgaa tgtgacgagt    840

gaggacaatg gcttcaccct gacgtgcatt gcagagaacg tggtgggcat gagcaatgcc    900

agtgttgccc tcactgtcta ctatcccca cgtgtggtga gcctggagga gcctgagctg     960

cgcctggagc actgcatcga gtttgtggtg cgtggcaacc ccccaccaac gctgcactgg   1020

ctgcacaatg ggcagcctct gcgggagtcc aagatcatcc atgtggaata ctaccaagag   1080

ggagagattt ccgagggctg cctgctcttc aacaagccca cccactacaa caatggcaac   1140

tataccctca ttgccaaaaa cccactgggc acagccaacc agaccatcaa tggccacttc   1200

ctcaaggagc cctttccaga gagcacggat aactttatct tgtttgacga agtgagtccc   1260

acacctccta tcactgtgac ccacaaacca gaagaagaca cttttggggt atccatagca   1320

gttggacttg ctgcttttgc ctgtgtcctg ttggtggttc tcttcgtcat gatcaacaaa   1380

tatggtcgac ggtccaaatt tggaatgaag ggtcccgtgg ctgtcatcag tggtgaggag   1440

gactcagcca gcccactgca ccacatcaac cacggcatca ccacgccctc gtcactggat   1500

gccgggcccg acactgtggt cattggcatg actcgcatcc ctgtcattga gaaccccccag  1560

tacttccgtc agggacacaa ctgccacaag ccggacacgt atgtgcagca cattaagagg   1620
```

-continued

```
agagacatcg tgctgaagcg agaactgggt gagggagcct ttggaaaggt cttcctggcc   1680

gagtgctaca acctcagccc gaccaaggac aagatgcttg tggctgtgaa ggccctgaag   1740

gatcccaccc tggctgcccg gaaggatttc cagagggagg ccgagctgct caccaacctg   1800

cagcatgagc acattgtcaa gttctatgga gtgtgcggcg atggggaccc cctcatcatg   1860

gtctttgaat acatgaagca tggagacctg aataagttcc tcagggccca tgggccagat   1920

gcaatgatcc ttgtggatgg acagccacgc caggccaagg gtgagctggg gctctcccaa   1980

atgctccaca ttgccagtca gatcgcctcg ggtatggtgt acctggcctc ccagcacttt   2040

gtgcaccgag acctggccac caggaactgc ctggttggag cgaatctgct agtgaagatt   2100

ggggacttcg gcatgtccag agatgtctac agcacggatt attacaggct ctttaatcca   2160

tctggaaatg atttttgtat atggtgtgag gtgggaggac acaccatgct ccccattcgc   2220

tggatgcctc ctgaaagcat catgtaccgg aagttcacta cagagagtga tgtatggagc   2280

ttcggggtga tcctctggga gatcttcacc tatggaaagc agccatggtt ccaactctca   2340

aacacggagg tcattgagtg cattacccaa ggtcgtgttt tggagcggcc ccgagtctgc   2400

cccaaagagg tgtacgatgt catgctgggg tgctggcaga gggaaccaca gcagcggttg   2460

aacatcaagg agatctacaa aatcctccat gctttgggga aggccacccc aatctacctg   2520

gacattcttg gctagtggtg gctggtggtc atgaattcat actctgttgc ctcctctctc   2580

cctgcctcac atctcccttc cacctcacaa ctccttccat ccttgactga agcgaacatc   2640

ttcatataaa ctcaagtgcc tgctacacat acaacactga aaaaaggaaa aaaaaagaaa   2700

aaaaaaaaaa accgc                                                     2715
```

```
<210> SEQ ID NO 9
<211> LENGTH: 720
<212> TYPE: PRT
<213> ORGANISM: Artificial Sequence
<220> FEATURE:
<223> OTHER INFORMATION: Sequence from Alignment of Wildtype TrkA
      Protein Isoform A and Wildtype TrkA Protein Isoform B

<400> SEQUENCE: 9

Leu Tyr Ile Glu Asn Gln Gln His Leu Gln His Leu Glu Leu Arg Asp
1               5                   10                  15

Leu Arg Gly Leu Gly Glu Leu Arg Asn Leu Thr Ile Val Lys Ser Gly
            20                  25                  30

Leu Arg Phe Val Ala Pro Asp Ala Phe His Phe Thr Pro Arg Leu Ser
        35                  40                  45

Arg Leu Asn Leu Ser Phe Asn Ala Leu Glu Ser Leu Ser Trp Lys Thr
    50                  55                  60

Val Gln Gly Leu Ser Leu Gln Glu Leu Val Leu Ser Gly Asn Pro Leu
65                  70                  75                  80

His Cys Ser Cys Ala Leu Arg Trp Leu Gln Arg Trp Glu Glu Glu Gly
                85                  90                  95

Leu Gly Gly Val Pro Glu Gln Lys Leu Gln Cys His Gly Gln Gly Pro
            100                 105                 110

Leu Ala His Met Pro Asn Ala Ser Cys Gly Val Pro Thr Leu Lys Val
        115                 120                 125

Gln Val Pro Asn Ala Ser Val Asp Val Gly Asp Asp Val Leu Leu Arg
    130                 135                 140

Cys Gln Val Glu Gly Arg Gly Leu Glu Gln Ala Gly Trp Ile Leu Thr
145                 150                 155                 160
```

```
Glu Leu Glu Gln Ser Ala Thr Val Met Lys Ser Gly Gly Leu Pro Ser
                165                 170                 175

Leu Gly Leu Thr Leu Ala Asn Val Thr Ser Asp Leu Asn Arg Lys Asn
            180                 185                 190

Val Thr Cys Trp Ala Glu Asn Asp Val Gly Arg Ala Glu Val Ser Val
        195                 200                 205

Gln Val Asn Val Ser Phe Pro Ala Ser Val Gln Leu His Thr Ala Val
    210                 215                 220

Glu Met His His Trp Cys Ile Pro Phe Ser Val Asp Gly Gln Pro Ala
225                 230                 235                 240

Pro Ser Leu Arg Trp Leu Phe Asn Gly Ser Val Leu Asn Glu Thr Ser
                245                 250                 255

Phe Ile Phe Thr Glu Phe Leu Glu Pro Ala Ala Asn Glu Thr Val Arg
            260                 265                 270

His Gly Cys Leu Arg Leu Asn Gln Pro Thr His Val Asn Asn Gly Asn
        275                 280                 285

Tyr Thr Leu Leu Ala Ala Asn Pro Phe Gly Gln Ala Ser Ala Ser Ile
    290                 295                 300

Met Ala Ala Phe Met Asp Asn Pro Phe Glu Phe Asn Pro Glu Asp Pro
305                 310                 315                 320

Ile Pro Asp Thr Asn Ser Thr Ser Gly Asp Pro Val Glu Lys Lys Asp
                325                 330                 335

Glu Thr Pro Phe Gly Val Ser Val Ala Val Gly Leu Ala Val Phe Ala
            340                 345                 350

Cys Leu Phe Leu Ser Thr Leu Leu Leu Val Leu Asn Lys Cys Gly Arg
        355                 360                 365

Arg Asn Lys Phe Gly Ile Asn Arg Pro Ala Val Leu Ala Pro Glu Asp
    370                 375                 380

Gly Leu Ala Met Ser Leu His Phe Met Thr Leu Gly Gly Ser Ser Leu
385                 390                 395                 400

Ser Pro Thr Glu Gly Lys Gly Ser Gly Leu Gln Gly His Ile Ile Glu
                405                 410                 415

Asn Pro Gln Tyr Phe Ser Asp Ala Cys Val His His Ile Lys Arg Arg
            420                 425                 430

Asp Ile Val Leu Lys Trp Glu Leu Gly Glu Gly Ala Phe Gly Lys Val
        435                 440                 445

Phe Leu Ala Glu Cys His Asn Leu Leu Pro Glu Gln Asp Lys Met Leu
    450                 455                 460

Val Ala Val Lys Ala Leu Lys Glu Ala Ser Glu Ser Ala Arg Gln Asp
465                 470                 475                 480

Phe Gln Arg Glu Ala Glu Leu Leu Thr Met Leu Gln His Gln His Ile
                485                 490                 495

Val Arg Phe Phe Gly Val Cys Thr Glu Gly Arg Pro Leu Leu Met Val
            500                 505                 510

Phe Glu Tyr Met Arg His Gly Asp Leu Asn Arg Phe Leu Arg Ser His
        515                 520                 525

Gly Pro Asp Ala Lys Leu Leu Ala Gly Gly Glu Asp Val Ala Pro Gly
    530                 535                 540

Pro Leu Gly Leu Gly Gln Leu Leu Ala Val Ala Ser Gln Val Ala Ala
545                 550                 555                 560

Gly Met Val Tyr Leu Ala Gly Leu His Phe Val His Arg Asp Leu Ala
                565                 570                 575

Thr Arg Asn Cys Leu Val Gly Gln Gly Leu Val Val Lys Ile Gly Asp
```

-continued

```
            580                 585                 590

Phe Gly Met Ser Arg Asp Ile Tyr Ser Thr Asp Tyr Tyr Arg Val Gly
        595                 600                 605

Gly Arg Thr Met Leu Pro Ile Arg Trp Met Pro Pro Glu Ser Ile Leu
    610                 615                 620

Tyr Arg Lys Phe Thr Thr Glu Ser Asp Val Trp Ser Phe Gly Val Val
625                 630                 635                 640

Leu Trp Glu Ile Phe Thr Tyr Gly Lys Gln Pro Trp Tyr Gln Leu Ser
                645                 650                 655

Asn Thr Glu Ala Ile Asp Cys Ile Thr Gln Gly Arg Glu Leu Glu Arg
            660                 665                 670

Pro Arg Ala Cys Pro Pro Glu Val Tyr Ala Ile Met Arg Gly Cys Trp
        675                 680                 685

Gln Arg Glu Pro Gln Gln Arg His Ser Ile Lys Asp Val His Ala Arg
    690                 695                 700

Leu Gln Ala Leu Ala Gln Ala Pro Pro Val Tyr Leu Asp Val Leu Gly
705                 710                 715                 720
```